US012629683B2

(12) United States Patent
Vijayan et al.

(10) Patent No.: US 12,629,683 B2
(45) Date of Patent: May 19, 2026

(54) OLIGONUCLEOTIDE ENCODED CHEMICAL LIBRARIES

(71) Applicant: Plexium, Inc., San Diego, CA (US)

(72) Inventors: Kandaswamy Vijayan, San Diego, CA (US); Andrew Boyd Macconnell, San Diego, CA (US); Joseph Franklin Rokicki, Del Mar, CA (US); Michael Van Nguyen, San Diego, CA (US)

(73) Assignee: Plexium, Inc., San Diego, CA (US)

( * ) Notice: Subject to any disclaimer, the term of this patent is extended or adjusted under 35 U.S.C. 154(b) by 183 days.

(21) Appl. No.: 17/200,538

(22) Filed: Mar. 12, 2021

(65) Prior Publication Data

US 2022/0025358 A1    Jan. 27, 2022

Related U.S. Application Data

(62) Division of application No. 16/870,809, filed on May 8, 2020, now Pat. No. 10,981,170, which is a division of application No. 16/139,831, filed on Sep. 24, 2018, now abandoned.

(60) Provisional application No. 62/562,912, filed on Sep. 25, 2017, provisional application No. 62/562,905, filed on Sep. 25, 2017.

(51) Int. Cl.
| | |
|---|---|
| *C40B 60/02* | (2006.01) |
| *B01L 3/00* | (2006.01) |
| *C12N 15/10* | (2006.01) |
| *C12Q 1/6869* | (2018.01) |
| *C12Q 1/6876* | (2018.01) |
| *C40B 30/04* | (2006.01) |
| *C40B 30/06* | (2006.01) |
| *C40B 50/04* | (2006.01) |
| *C40B 50/14* | (2006.01) |
| *C40B 50/16* | (2006.01) |

(52) U.S. Cl.
CPC ...... *B01L 3/50853* (2013.01); *C12N 15/1034* (2013.01); *C12N 15/1065* (2013.01); *C12N 15/1068* (2013.01); *C12N 15/1075* (2013.01); *C12Q 1/6869* (2013.01); *C12Q 1/6876* (2013.01); *C40B 30/04* (2013.01); *C40B 30/06* (2013.01); *C40B 50/04* (2013.01); *C40B 50/14* (2013.01); *C40B 50/16* (2013.01); *B01L 2300/0829* (2013.01); *C12Q 2600/16* (2013.01)

(58) Field of Classification Search
CPC ......... B01L 3/50853; B01L 2300/0829; C12N 15/1034; C12N 15/1065; C12N 15/1068; C12N 15/1075; C12N 15/10; C12Q 1/6869; C12Q 1/6876; C12Q 2600/16; C12Q 2563/179; C40B 30/04; C40B 30/06; C40B 50/04; C40B 50/14; C40B 50/16
See application file for complete search history.

(56) References Cited

U.S. PATENT DOCUMENTS

| | | | |
|---|---|---|---|
| 6,001,579 | A | 12/1999 | Still et al. |
| 8,551,737 | B2 | 10/2013 | Gumbrecht et al. |
| 8,632,975 | B2 | 1/2014 | Vander Horn et al. |
| 8,853,185 | B2 | 10/2014 | Barany et al. |
| 9,347,092 | B2 | 5/2016 | Roesler et al. |
| 9,902,950 | B2* | 2/2018 | Church .................. C40B 50/16 |
| 10,266,874 | B2 | 4/2019 | Weissleder et al. |
| 10,946,383 | B2 | 3/2021 | Vijayan et al. |
| 10,981,170 | B2 | 4/2021 | Vijayan et al. |
| 2004/0009583 | A1 | 1/2004 | Benn et al. |
| 2005/0260101 | A1 | 11/2005 | Nauck et al. |
| 2006/0134595 | A1 | 6/2006 | Rapp et al. |
| 2007/0003442 | A1* | 1/2007 | Link ................ B01F 25/45211 |
| | | | 422/400 |
| 2007/0065844 | A1 | 3/2007 | Golub et al. |
| 2012/0021940 | A1 | 1/2012 | Guthold et al. |
| 2014/0378345 | A1 | 12/2014 | Hindson et al. |
| 2015/0105553 | A1 | 4/2015 | Barany et al. |
| 2016/0060687 | A1 | 3/2016 | Zhu et al. |
| 2016/0067705 | A1 | 3/2016 | Gehrig et al. |
| 2019/0085324 | A1 | 3/2019 | Regev et al. |
| 2019/0093103 | A1 | 3/2019 | Vijayan et al. |

(Continued)

FOREIGN PATENT DOCUMENTS

| | | |
|---|---|---|
| CN | 1108249 A | 9/1995 |
| CN | 1134156 A | 10/1996 |

(Continued)

OTHER PUBLICATIONS

Sharma (Med. Chem. Commun., 2014,5, 1454-1471).*
Ebert et al., An Erythroid Differentiation Signature Predicts Response to Lenalidomide in Myelodysplastic Syndrome PLoS Medicine , 2008, 5(2), 1-11. (Year: 2008).*

(Continued)

*Primary Examiner* — Amy M Bunker

(74) *Attorney, Agent, or Firm* — Sheppard Mullin Richter & Hampton LLP

(57) ABSTRACT

This application provides a bead with a covalently attached chemical compound and a covalently attached DNA barcode and methods for using such beads. The bead has many substantially identical copies of the chemical compound and many substantially identical copies of the DNA barcode. The compound consists of one or more chemical monomers, where the DNA barcode takes the form of barcode modules, where each module corresponds to and allows identification of a corresponding chemical monomer. The nucleic acid barcode can have a concatenated structure or an orthogonal structure. Provided are method for sequencing the bead-bound nucleic acid barcode, for cleaving the compound from the bead, and for assessing biological activity of the released compound.

16 Claims, 39 Drawing Sheets

(56) References Cited

U.S. PATENT DOCUMENTS

Figure 1:
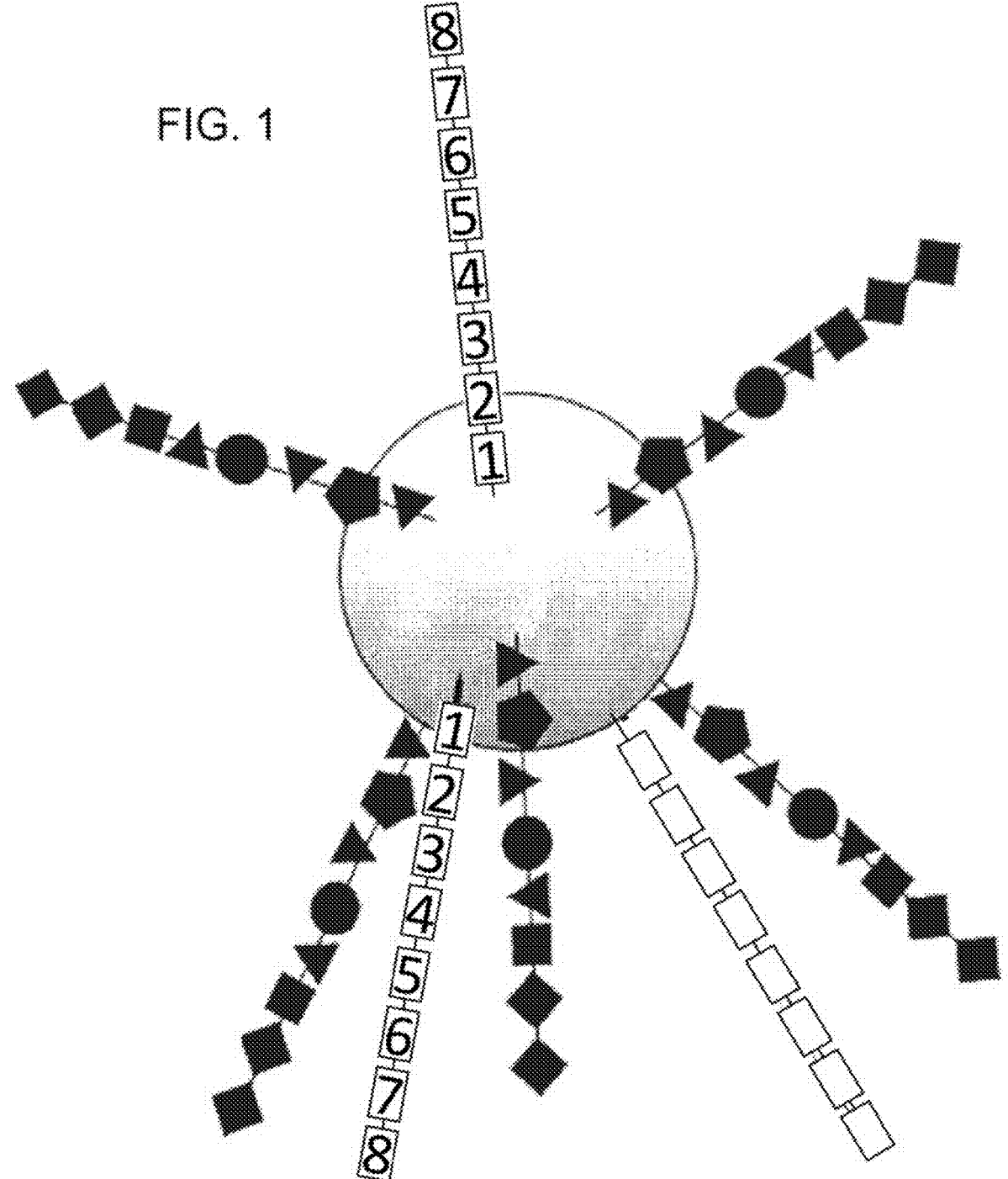

| | | | | |
|---|---|---|---|---|
| 2019/0210018 A1 | 7/2019 | Vijayan et al. | | |
| 2019/0358629 A1 | 11/2019 | Vijayan et al. | | |
| 2020/0001295 A1 | 1/2020 | Vijayan et al. | | |
| 2020/0199662 A1* | 6/2020 | Strauss | ................. | C07K 1/042 |
| 2020/0324287 A1 | 10/2020 | Vijayan et al. | | |

FOREIGN PATENT DOCUMENTS

| | | | | |
|---|---|---|---|---|
| CN | 1193357 A | 9/1998 | | |
| CN | 1940088 A | 4/2007 | | |
| CN | 101505875 A | 8/2009 | | |
| CN | 101838696 A | 9/2010 | | |
| CN | 102485979 A | 6/2012 | | |
| JP | 2011516547 A | 5/2011 | | |
| JP | 2016525344 A | 8/2016 | | |
| WO | WO-93/20242 A1 | 10/1993 | | |
| WO | WO9512608 A1 | 5/1995 | | |
| WO | WO-2009/063462 A2 | 5/2009 | | |
| WO | WO-2010151776 A2 * | 12/2010 | ......... | B01F 33/3031 |
| WO | WO-2012/120514 A2 | 9/2012 | | |
| WO | WO-2014/200767 A1 | 12/2014 | | |
| WO | WO-2014/210353 A2 | 12/2014 | | |
| WO | WO-2015164212 A1 * | 10/2015 | .......... | C12Q 1/6869 |
| WO | WO-2016/138184 A1 | 9/2016 | | |
| WO | WO-2016/183029 A1 | 11/2016 | | |
| WO | WO-2017/048975 A1 | 3/2017 | | |
| WO | WO-2017/075294 A1 | 5/2017 | | |
| WO | WO-2018/064640 A1 | 4/2018 | | |
| WO | WO-2018/089641 A2 | 5/2018 | | |
| WO | WO-2019/060830 A1 | 3/2019 | | |
| WO | WO-2019/060857 A1 | 3/2019 | | |
| WO | WO-2019/060830 A9 | 5/2019 | | |

OTHER PUBLICATIONS

Mendes et al., High-Throughput Identification of DNA-Encoded IgG Ligands that Distinguish Active and Latent Mycobacterium Tuberculosis Infections, ACS Chemical Biology, 2016, 12, 234-243. (Year: 2016).*

Itchaki et al., Lenalidomide in the Treatment of Chronic Lymphocytic Leukemia, Expert Opinion on Investigational Drugs, 2017, 26(5), 633-650. (Year: 2017).*

Halford, Bethany, How DNA-Encoded Libraries are Revolutionizing Drug Discovery, Chemical & Engineering News, 2017, 95(25), 1-20. (Year: 2017).*

U.S. Appl. No. 16/534,886, "Non-Final Office Action", Oct. 21, 2019, 10 pages.

U.S. Appl. No. 16/534,922, "Non-Final Office Action", Dec. 9, 2019, 9 pages.

Akerblom et al., "Six new photolabile linkers for solid-phase synthesis. 1. Methods of preparation", Molecular Diversity, 3, 1998, pp. 137-148.

Akuffo et al., "Ligand-mediated protein degradation reveals functional conservation among sequence variants of the CUL4-type E3 ligase substrate receptor cereblon", J. Biol. Chem. 293, 2018, pp. 6187-6200.

Alam et al., "DNA-binding peptides searched from the solid-phase combinatorial library with the use of the magnetic beads attaching the target duplex DNA", Bioorg. Med. Chem. 8, 2000, pp. 465-473.

Angell et al., "Peptidomimetics via copper-catalyzed azide-alkyne cycloadditions", Chem. Soc. Rev. 36, 2007, pp. 1674-1689.

Anton et al., "Optimization of radiation controlled gene expression by adenoviral vectors in vitro", Cancer Gene Therapy 12, 2005, pp. 640-646.

Appell et al., "Biological screening of a large combinatorial library", J. Biomolecular Screening 1(1), 1996, pp. 27-31.

Avital et al., "Seeing is believing: new methods for in situ single-cell transcriptomics", Genome Biology. 15(110), 2014. 4 pages.

Baird et al., "Topoisomerase II drives DNA transport by hydrolyzing one ATP", Proc. Nat'l. Acad. Sci. 96(24), 1999, pp. 13685-13690.

Baner et al., "Signal amplification of padlock probes by rolling circle replication", Nucleic Acids Res. 26(22), 1998, pp. 5073-5078.

Banks et al., "L2DTL/CDT2 and PCNA Interact with p53 and Regulate p53 Polyubiquitination and protein stability through MDM2 and CUL4A/DDB1 Complexes", Cell Cycle 5, 2006, pp. 1719-1729.

Baruch et al., "Enzyme activity â€" it's all about image", Trends Cell Biology 14(1), 2004, pp. 29-35.

Bayer et al., "Biocytin hydrazide—a selective label for sialic acids, galactose, and other sugars in glycoconjugates using avidin-biotin technology", Analyt. Biochem 170, 1988, pp. 271-281.

Bindels et al., "mScarlet: a bright monomeric red fluorescent protein for cellular imaging", Nature Methods. 14(1), 2017, pp. 53-56.

Bohl et al., "Multi-layer SU-8 lift-off technology for microfluidic devices", J. Micromechanics Microengineering. 15, 2005, pp. 1125-1130.

Bose et al., "Scalable microfluidics for single-cell RNA printing and sequencing", Genome Biology 16(120), DOI 10.1186, 2015. 16 pages.

Boyer et al., "Adenovirus E4 34k and E4 11k inhibit double strand break repair and are physically associated with the cellular DNA-dependent protein kinase", Virology 263, 1999, pp. 307-312.

Brenner et al., "Encoded combinatorial library", Proc. Nat'l. Acad. Sci. 89, 1992, pp. 5381-5383.

Brouzes et al., "Droplet microfluidic technology for single-cell high-throughput screening", Proc. Natl. Acad. Sci. 106, 2009, pp. 14195-14200.

Camperi et al., "An efficient strategy for the preparation of one-bead-one-peptide libraries on a new biocompatible solid support", Tetrahedron Letters 46, 2005, pp. 1561-1564.

Carmona et al., "A continuous fluorescence resonance energy transfer angiotensin I-converting enzyme assay", Nature Protocols 1(4), 2006, pp. 1971-1976.

Carr et al., "Reducing DNA context dependence in bacterial promoters", PLoS One 12:e0176013, 2017. 15 pages.

Chamberlain et al., "Structure of the human Cereblon-DDB1-lenalidomide complex reveals basis for responsiveness to thalidomide analogs", Nature Struct. Mol. Biol. 21(9), 2014, pp. 803-809.

Chen et al., "The Cullin 4A/B-DDB1-Cereblon E3 Ubiquitin Ligase Complex Mediates the Degradation of CLC-1 Chloride Channels", Scientific Reports 5(10667), 2015. 13 pages.

Cho et al., "High-Throughput Screening of One-Beadâ€"One-Compound Peptide Libraries Using Intact Cells", ACS Combinatorial Science 15, 2013, pp. 393-400.

Comellas et al., "Exploration of the one-bead one-compound methodology for the design of prolyl oligopeptidase substrates", PLoS One 4(7), 2009, pp. e6222. 12 pages.

Dal Corso et al., "Protease-Cleavable Linkers Modulate the Anticancer Activity of Non-Internalizing Antibody-Drug Conjugates", Bioconjugate Chemistry 28(7), 2017, pp. 1826-1833.

Decurtins, W. et al. (e-published Mar. 17, 2016, 2016). "Automated screening for small organic ligands using DNA-encoded chemical libraries." Nature Protocols, 11(4), 764-780.

Del Campo et al., "SU-8: a photoresist for high-aspect-ratio and 3D submicron lithography", J. Micromechanics Microengineering 17, 2007, pp. R81-R95.

Devaraj et al., "Fast and Sensitive Pretargeted Labeling of Cancer Cells via Tetrazine/Trans-Cyclooctene Cycloaddition", Angew. Chem. Intl. 48(38), 2009, pp. 7013-7016.

Devy et al., "Plasmin-activated doxorubicin prodrugs containing a spacer reduce tumor growth and angiogenesis without systemic toxicity", FASEB J. 18, 2004, pp. 565-567.

Doran et al., "Utility of redundant combinatorial libraries in distinguishing high and low quality screening hits", ACS Combinatorial Science. 16, 2014, pp. 259-270.

Ekici et al., "Profiling the substrate specificity of viral protease VP4 by a FRET-based peptide library approach", Biochemistry 48, 2009, pp. 5753-5759.

El Debs et al., "Functional single-cell hybridoma screening using droplet-based microfluidics", Proc. Natl. Acad. Sci. 109, 2012, pp. 11570-11575.

(56)        References Cited

OTHER PUBLICATIONS

Farzaneh et al., "ADP-ribosylation is involved in the integration of foreign DNA into the mammalian cell genome", Nucleic Acids Res. 16(23), 1988, pp. 11319-11326.

Feng et al., "Fluorescence Logic-Signal-Based Multiplex Detection of Nucleases with the Assembly of a Cationic Conjugated Polymer and Branched DNA", Angew Chem. Int. Ed. Engl. 48, 2009, pp. 5316-5321.

Fernandez Suarez et al., "Redirecting lipoic acid ligase for cell surface protein labeling with small-molecule probes", Nature Biotechnol 25(12), 2007, pp. 1483-1487.

Gadkar et al., "New Developments in Quantitative Real-time Polymerase Chain Reaction Technology", Curr. Issues Mol. Biol. 16, 2014, pp. 1-6.

Gandhi et al., "Measuring cereblon as a biomarker of response or resistance to lenalidomide and pomalidomide requires use of standardized reagents and understanding of gene complexity", Brit. J. Haematol. 164, 2013, pp. 233-244.

Glatthar et al., "A New Photocleavable Linker in Solid-Phase Chemistry for Ether Cleavage", Organic Letters 2, 2000, pp. 2315-2317.

Go et al., "Optimization and direct comparison of the dimerizer and reverse tet transcriptional control systems", J Gene Med 4, 2002, pp. 258-270.

Gordon et al., "Solid phase synthesis â€" designer linkers for combinatorial chemistry: a review", J. Chemical Technology Biotechnology 74, 1999, pp. 835-851.

Guo et al., "Droplet microfluidics for high-throughput biological assays", Lab Chip 12, 2012, pp. 2146-2155.

Han et al., "Fabrication of 3D Microstructures with Single uv Lithography Step", J. Semiconductor Technology Science. 2, 2002, pp. 268-272.

Haun et al., "Bioorthogonal chemistry amplifies nanoparticle binding and enhances the sensitivity of cell detection", Nature Nanotechnol 5(9), 2010, pp. 660-665.

Hilton et al., "An Assay to Monitor HIV-1 Protease Activity for the Identification of Novel Inhibitors in T-Cells", PLoS One 5(6), 2010, e10940. 7 pages.

Holmes et al., "Model Studies for New o-Nitrobenzyl Photolabile Linkers: Substituent Effects on the Rates of Photochemical Cleavage", J. Org. Chem. 62, 1997, pp. 2370-2380.

Holmes et al., "Reagents for Combinatorial Organic Synthesis: Development of a New o-Nitrobenzyl Photolabile Linker for Solid Phase Synthesis", J. Org. Chem. 60, 1995, pp. 2318-2319.

Jenny et al., "A critical review of the methods for cleavage of fusion proteins with thrombin and factor Xa", Protein Expression Purification 31, 2003, pp. 1-11.

Jeon et al., "Hot embossing for fabrication of a microfluidic 3D cell culture platform", Biomed. Microdevices 13(2), 2011, pp. 325-333.

Jewett et al., "Cu-free click cycloaddition reactions in chemical biology", Chem. Soc. Rev. 39(4), 2010, pp. 1272-1279.

Jia et al., "RBX1/ROC1-SCF E3 ubiquitin ligase is required for mouse embryogenesis and cancer cell survival", Cell Division 4(16), D01:10.1186, 2009. 6 pages.

Johansson et al., "Choosing reporter-quencher pairs for efficient quenching", Methods Mol. Biol. 335, 2006, pp. 17-29.

Kim et al., "High cleavage efficiency of a 2A peptide derived from porcine teschovirus-1 in human cell lines, zebrafish and mice", PLoS One 6(4), 2011, e18556. 8 pages.

Klein et al., "Droplet barcoding for single cell transcriptomics applied to embryonic stem cells", Cell. 161, 2015, pp. 1187-1201.

Kohane et al., "Microparticles and nanoparticles for drug delivery", Biotechnol. Bioeng. 96(2), 2007, pp. 203-209.

Kolb et al., "Click Chemistry: Diverse Chemical Function from a Few Good Reaction", Angew. Chem. Int. Ed. 40, 2001, pp. 2004-2021.

Kolb et al., "The growing impact of click chemistry on drug discovery", Drug Discovery Today 8, 2003, pp. 1128-1137.

Koppelhus et al., "Improved cellular activity of antisense peptide nucleic acids by conjugation to a cationic peptide-lipid59 (CatLip) domain", Bioconjug. Chem. 19, 2008, pp. 1526-1534.

Kronke et al., "Lenalidomide induces ubiquitination and degradation of CK1a in del(5q) MDS", Nature 523(7559), 2015, pp. 183-188.

Lam et al., "The One-Bead-One-Compound Combinatorial Library Method", Chem. Rev. 97, 1997, pp. 411-448.

Leriche et al., "Cleavable linkers in chemical biology", Bioorganic Medicinal Chemistry 20, 2011, pp. 571-582.

Leslie et al., "The MDM2 Ring Domain and Central Acidic Domain Play Distinct Roles in MDM2 Protein Homodimerization and MDM2-MDMX Protein Heterodimerization", J. Biol. Chem. 290, 2015, pp. 12941-12950.

Li et al., "Typing of Multiple Single-Nucleotide Polymorphisms by a Microsphere-Based Rolling Circle Amplification Assay", Anal. Chem. 79, 2007, pp. 9030-9038.

Liu et al., "Fabrication of SU-8 moulds on glass substrates by using a common thin negative photoresist as an adhesive layer", J. Micromechanics and Microengineering. 24:article ID:035009, 2014. 6 pages.

Liu et al., "High-Throughput Screening of One-Bead-One-Compound Libraries: Identification of Cyclic Peptidyl Inhibitors against Calcineurin/NFAT Interaction", ACS Comb. Sci. 13, 2011, pp. 537-546.

Lood et al., "Determining bacteriophage endopeptidase activity using either fluorophore-quencher labeled peptides combined with liquid chromatography-mass spectrometry (LC-MS) or Forster resonance energy transfer (FRET) assays", PLoS One 12, 2017, e0173919. 11 pages.

Lopez-Girona et al., "Cereblon is a direct protein target for immunomodulatory and antiproliferative activities of lenalidomide and pomalidomide", Leukemia 26, 2012, pp. 2326-2335.

Macconnell et al., "An integrated microfluidic processor for DNA-Encoded combinatorial library functional screening", ACS Comb. Sci. 19, 2017, 181-192.

Macconnell et al., "DNA-Encoded solid-phase synthesis: Encoding language design and complex oligomer library synthesis", ACS Comb. Sci. 17, 2015, pp. 518-534.

Macconnell et al., "Poisson statistics of combinatorial library sampling predict false discovery rates of screening", ACS Comb. Sci. 19, 2017, pp. 524-532.

Maltman et al., "Enzyme-cleavable linkers for peptide and glycopeptide synthesis", Organic Biomolecular Chem. 3, 2005, pp. 2505-2507.

Matyskiela et al., "A novel cereblon modulator recruits GSPT1 to the CRL4(CRBN) ubiquitin ligase", Nature 535, 2016, pp. 252-257.

Meldal et al., "Cu-Catalyzed Azide-Alkyne Cycloaddition", Chem. Rev. 108, 2008, pp. 2952-3015.

Mendes et al., "High-throughput identification of DNA encoded IgG ligands that distinguish active and latent Mycobacterium tuberculosis infections", ACS Chem Biol. 12(1), 2017, pp. 234-243.

Meng et al., "Screening of HIV-1 Protease Using a Combination of an Ultra-High-Throughput Fluorescent-Based Assay and RapidFire Mass Spectrometry", J. Biomolecular Sensing 20(5), 2015, pp. 606-615.

Mikkelsen et al., "Photolabile Linkers for Solid-Phase Synthesis", ACS Combinatorial Science. D01:10.1021, 2018, pp. 377-399.

Minetti et al., "The thermodynamics of template-directed DNA synthesis: base insertion and extension enthalpies", Proc. Natl. Acad. Sci. 100, 2003, pp. 14719-14724.

Nag et al., "Cul4A Physically Associates with MDM2 and Participates in the Proteolysis of p53", Cancer Res. 64, 2004, pp. 8152-8155.

Nilsson et al., "Real-time monitoring of rolling-circle amplification using a modified molecular beacon design", Nucleic Acids Res. 30, 2002, e66. 7 pages.

Oh et al., "Integrated Nanoplasmonic Sensing for Cellular Functional Immunoanalysis Using Human Blood", ACS Nano 8(3), 2014, pp. 2667-2676.

Oldenburg et al., "Assay Miniaturization for Ultra-High Throughput Screening of Combinatorial and Discrete Compound Libraries: A 9600-Well (0.2 Microliter) Assay System", Journal of Biomolecular Screening, vol. 3, No. 1, Feb. 1, 1998, pp. 55-62.

(56)            References Cited

OTHER PUBLICATIONS

Olejnik et al., "Photocleavable peptide-DNA conjugates: synthesis and applications to DNA analysis using MALDI-MS", Nucleic Acids Res. 27(23), 1999, pp. 4626-4631.

Ortiz et al., "Contrasting effects of an Mdm2 functional polymorphism on tumor phenotypes", Oncogene 37, 2018, pp. 332-340.

Ostrander et al., "Construction of small-insert genomic DNA libraries highly enriched for microsatellite repeat sequences", Proc. Natl. Acad. Sci. 89, 1992, pp. 3419-3423.

Pabinger et al., "A survey of tools for the analysis of quantitative PCR (qPCR) data", Biomolecular Detection Quantification 1, 2010, pp. 23-33.

Paulick et al., "Cleavable hydrophilic linker for one-bead-one-compound sequencing of oligomer libraries by tandem mass spectrometry", J. Comb. Chem. 8, 2006, pp. 417-426.

PCT/US2018/052438 "International Search Report and Written Opinion", Feb. 4, 2019, 25 pages.

PCT/US2018/052497 "International Search Report and Written Opinion", Jan. 22, 2019, 29 pages.

Perry et al., "Development of plastic microwell arrays for improved replication fidelity", 18th Int. Conference on Miniaturized Systems for Chemistry and Life Sciences Oct. 26-30, 2014, San Antonio, TX, 2014, pp. 1701-1703.

Price et al., "Discovery in droplets", Analyt. Chem. 88, 2016, pp. 339-353.

Price et al., "hvSABR: Photochemical dose-response bead screening in droplets", Analyt. Chem. 88, 2016, pp. 2904-2911.

Price et al., "Microfluidic bead suspension hopper", Analyt. Chem. 86, 2014, 5039-5044.

Qian et al., "An Isotopically Tagged Azobenzene-Based Cleavable Linker for Quantitative Proteomics", ChemBioChem 14, 2013, pp. 1410-1414.

Rahim et al., "Enhancing Reactivity for Bioorthogonal Pretargeting by Unmasking Antibody Conjugated trans-Cyclooctenes", Bioconjug. Chem. 26(2), 2015, pp. 352-360.

Ramya et al., "Glycoproteomics enabled by tagging sialic acid- or galactose-terminated glycans", Glycobiology 23(2), 2013, pp. 211-221.

Rasooly et al., "Development of an In Vitro Activity Assay as an Alternative to the Mouse Bioassay for Clostridium botulinum Neurotoxin Type A", Appl. Environ. Microbiol. 74(14), 2008, pp. 4309-4313.

Refsland et al., "Quantitative profiling of the full APOBEC3 mRNA repertoire in lymphocytes and tissues: implications for HIV-1 restriction", Nucleic Acids Res. 38(13), 2010, pp. 4274-4284.

Reisfeld et al., "Nonradioactive hybridization probes prepared by the reaction of biotin hydrazide with DNA", Biochem. Biophys. Res. Commun. 142(2), 1987, pp. 519-526.

Renil et al., "Synthesis of fully Protected Peptides on a Tetraethyleneglycol Diacrylate (TTEGDA)-Crosslinked Polystyrene support with a Photolytically Detachable 2-Nitrobenzyl Anchoring group", Tetrahedron Lett. 35(22), 1994, pp. 3809-3812.

Rich et al., "Preparation of a new o-nitrobenzyl resin for solid-phase synthesis of tert- butyloxycarbonyl-protected peptide acids", J. Am. Chem. Soc. 97(6), 1975, pp. 1575-1579.

Rohr et al., "Role of IGF-1 in Primary Ovarian Cancer—A Study of the OVCAD European Consortium", Anticancer Res. 36, 2016, pp. 1015-1022.

Saliba et al., "Single-cell RNA-seq: advances and future challenges", Nucleic Acids Res. 42(14), 2014, pp. 8845-8860.

Saran et al., "A Versatile Photocleavable Bifunctional Linker for Facile Synthesis of Substrate-DNA Conjugates for the Selection of Nucleic Acid Catalysts", Bioconguate Chem. 18, 2007, pp. 275-279.

Satz et al., "DNA Compatible Multistep Synthesis and Applications to DNA Encoded Libraries", Bioconjugate Chemistry 26, 2015, pp. 1623-1632.

Schafer et al., "Cereblon modulator iberdomide induces degradation of the transcription factors Ikaros and Aiolos: immunomodulation in healthy volunteers and relevance to systemic lupus erythematosus", Ann. Rheum. Dis. D01:10.1136, 2018;0:1-8.

Sciambi et al., "Accurate microfluidic sorting of droplets at 30KHz", Lab Chip 15(1), 2015, pp. 47-51.

Sepetov et al., "Library of libraries: approach to synthetic combinatorial library design and screening of "pharmacophore" motifs", Proc. Natl. Acad. Sci. 92, 1995, pp. 5426-5430.

Shearer et al., "Functional Roles of the E3 Ubiquitin Ligase UBR5 in Cancer", Molecular Cancer Res. 13, 2015, pp. 1523-1532.

Shih et al., "A Novel Galectin-1 Inhibitor Discovered through One-Bead Two-Compound Library Potentiates the Antitumor Effects of Paclitaxel in vivo", Mol. Cancer Ther. 16(7), 2017, pp. 1212-1223.

Singh et al., "Microencapsulation: A promising technique for controlled drug delivery", Res Pharm Sci. 5(2), 2010, pp. 65-77.

Song et al., "A novel and rapid encoding method based on mass spectrometry for "one-bead-one-compound" small molecule combinatorial libraries", J. Am. Chem. Soc. 125, 2003, pp. 6180-6188.

Spackova et al., "Optical Biosensors Based on Plasmonic Nanostructures: A Review", Proceedings of the IEEE 104(12), 2016, pp. 2380-2408.

Stefflova et al., "Using molecular beacons for cancer imaging and treatment", Frontiers Bioscience 12, 2007, pp. 4709-4721.

Stockwell et al., "Frontiers in chemical genetics", Trends Biotechnol. 18, 2000, pp. 449-455.

Stope et al., "Drug-induced Modulation of Heat Shock Protein HSPB1 in an Ovarian Cancer Cell Model", Anticancer Res. 36, 2016, pp. 3321-3327.

Szymonifka et al., "The preparation of magnetite-impregnated polymeric supports for use in solid phase organic synthesis is described", Tetrahedron Letters 36(10), 1995, pp. 1597-1600.

Tang et al., "Suppression of artifacts and barcode bias in high-throughput transcriptome analyses utilizing template switching", Nucleic Acids Res. 41(3), 2013, e44 (12 pages).

Tsourkas et al., "Hybridization kinetics and thermodynamics of molecular beacons", Nucleic Acids Res. 15(4), 2003, pp. 1319-1330.

Turner et al., "Cell-penetrating peptide conjugates of peptide nucleic acids (PNA) as inhibitors of HIV-1 Tat-dependent trans-activation in cells", Nucleic Acids Research 33(21), 2005, pp. 6837-6849.

Tyagi et al., "Molecular beacons: probes that fluoresce upon hybridization", Nature Biotechnol 14, 1996, pp. 303-308.

Van Buggenum et al., "A covalent and cleavable antibody-DNA conjugation strategy for sensitive protein detection via immuno-PCR", Scientific Reports. 6:22675, 2016. 12 pages.

Whitehouse et al., "An Improved Synthesis and Selective Coupling of a Hydroxy Based Photolabile Linker for Solid Phase Organic Synthesis", Tetrahedron Lett. 38(45), 1997, pp. 7851-7852.

Wilczewska et al., "Nanoparticles as drug delivery systems", Pharmacological Reports 2012(64), 2012, pp. 1020-1037.

Wollscheid et al., "Mass-spectrometric identification and relative quantification of N-linked cell surface glycoproteins", Nature Biotechnol 27(4), 2009, pp. 378-386.

Wu et al., "Targeting RING domains of Mdm2-MdmX E3 complex activates apoptotic arm of the p53 pathway in leukemia/lymphoma cells", Cell Death Disease 6, 2015, e 2035. 10 pages.

Yang et al., "Cereblon suppresses the lipopolysaccharide-induced inflammatory response by promoting the ubiquitmation and degradation of c-Jun", J. Biol. Chem. 293(26), 2018, pp. 10141-10157.

Yang, "Design of Cleavable Linkers and Applications in Chemical Proteomics. Technische Universitat Munchen Lehrstuhl fur Chemie der Biopolymere", 2014. 132 pages.

Yoo et al., "Synthesis of Oligonucleotides Containing 3'-Alkyl Carboxylic Acids Using Universal, Photolabile Solid Phase Synthesis Supports", J. Org. Chem. 60, 1995, pp. 3358-3364.

Zhu et al., "Detecting cytokine release from single T-cells", Anal. Chem. 81(19), 2009, pp. 8150-8156.

Zhu et al., "Identification of cereblon-binding proteins and relationship with response and survival after IMiDs in multiple myeloma", Blood 124, 2014, pp. 536-545.

Ziegenhain et al., "Comparative analysis of single-cell RNA sequencing methods", Molecular Cell. 65, 2017, pp. 631-643.

Zimmermann et al., "Hartwig-Buchwald Amination on Solid Supports: a Novel Access to a Diverse Set of 1H-Benzotriazoles", J. Comb. Chem. 9, 2007, pp. 1114-1137.

(56) References Cited

OTHER PUBLICATIONS

Chu et al., "Cell Surface Self-Assembly of Hybrid Nanoconjugates via Oligonucleotide Hybridization Induces Apoptosis," ACS Nano, 8(1), 2014, pp. 719-730.

Extended European Search Report, dated Oct. 15, 2021, regarding EP Application No. 18859564.9, 15 pages.

Hahn et al., "Microsystem for Field-Amplified Electrokinetic Trapping Preconcentration of DNA at Poly(ethylene terephthalate) Membranes," Analytical Chemistry, 81(8), 2009, pp. 2904-2911.

Heath et al., "Single-cell analysis tools for drug discovery and development," Nature Reviews Drug Discovery, 15(3), 2016, pp. 204-216.

International Search Report, dated Jun. 9, 2021, regarding International Application No. PCT/US21/15550, 4 pages.

Macosko et al., "Highly Parallel Genome-wide Expression Profiling of Individual Cells Using Nanoliter Droplets," Cell, 161(5), 2015, pp. 1202-1214.

Shembekar et al., "Droplet-based microfluidics in drug discovery, transcriptomics and high-throughput molecular genetics," Lab Chip, 16(8), 2016, pp. 1314-1331.

Wagner et al., "DNA-binding transferrin conjugates as functional gene-delivery agents: synthesis by linkage of polylysine or ethidium homodimer to the transferrin carbohydrate moiety," Bioconjugate Chemistry, 4(1), 1991, pp. 226-231.

* cited by examiner

FIG. 3

Ana Spc

Sigma-Aldrich

Acros

Combi-Blocks

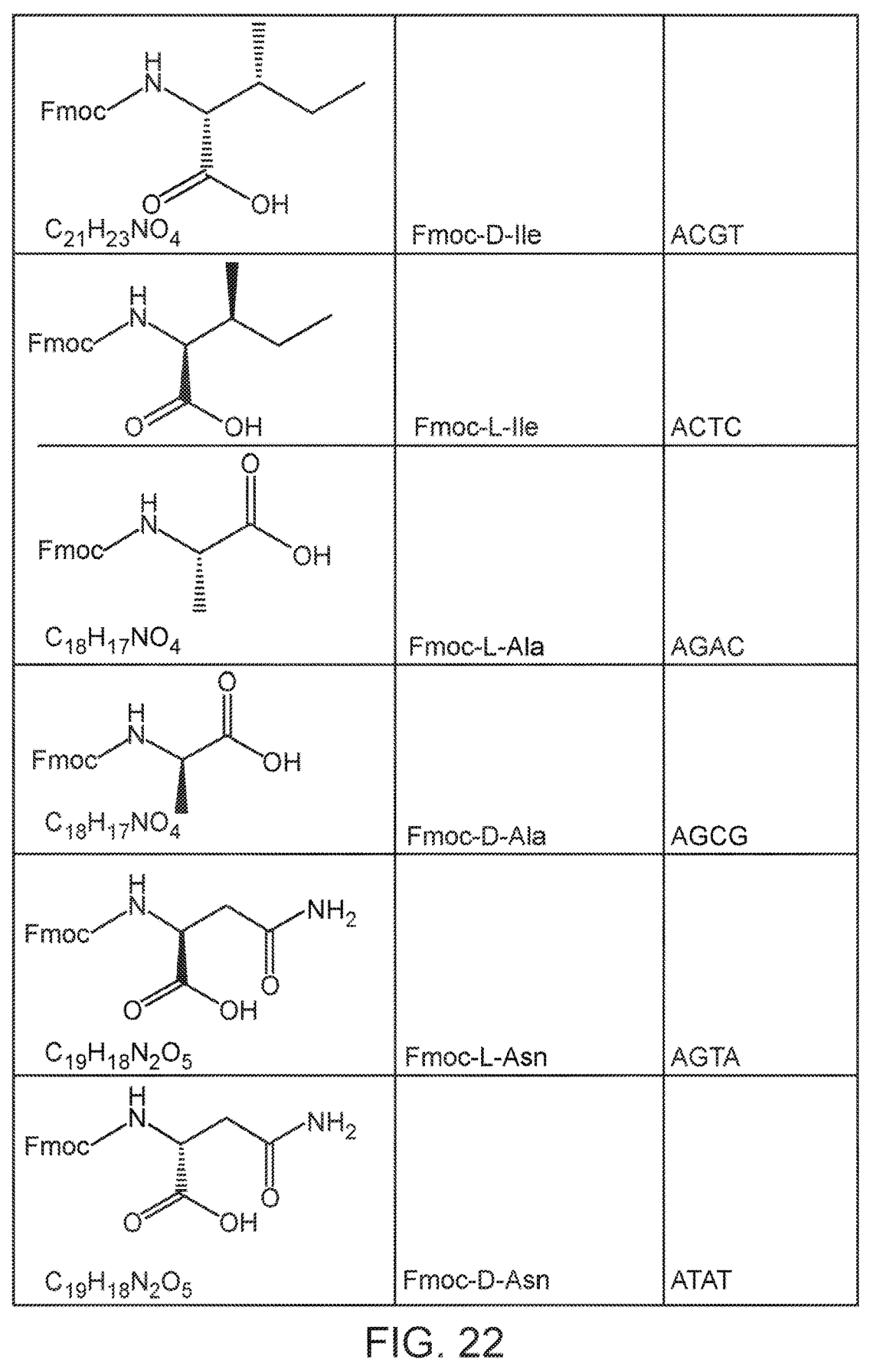

| | | |
|---|---|---|
| $C_{21}H_{23}NO_4$ | Fmoc-D-Ile | ACGT |
| | Fmoc-L-Ile | ACTC |
| $C_{18}H_{17}NO_4$ | Fmoc-L-Ala | AGAC |
| $C_{18}H_{17}NO_4$ | Fmoc-D-Ala | AGCG |
| $C_{19}H_{18}N_2O_5$ | Fmoc-L-Asn | AGTA |
| $C_{19}H_{18}N_2O_5$ | Fmoc-D-Asn | ATAT |

FIG. 22

| | | |
|---|---|---|
| $C_{20}H_{20}N_2O_5$ | Fmoc-L-Gln | ATGA |
| $C_{20}H_{20}N_2O_5$ | Fmoc-D-Gln | CACG |
| $C_{24}H_{21}NO_4$ | Fmoc-L-Phe | CAGC |
| $C_{24}H_{21}NO_4$ | Fmoc-D-Phe | CATA |

FIG. 23

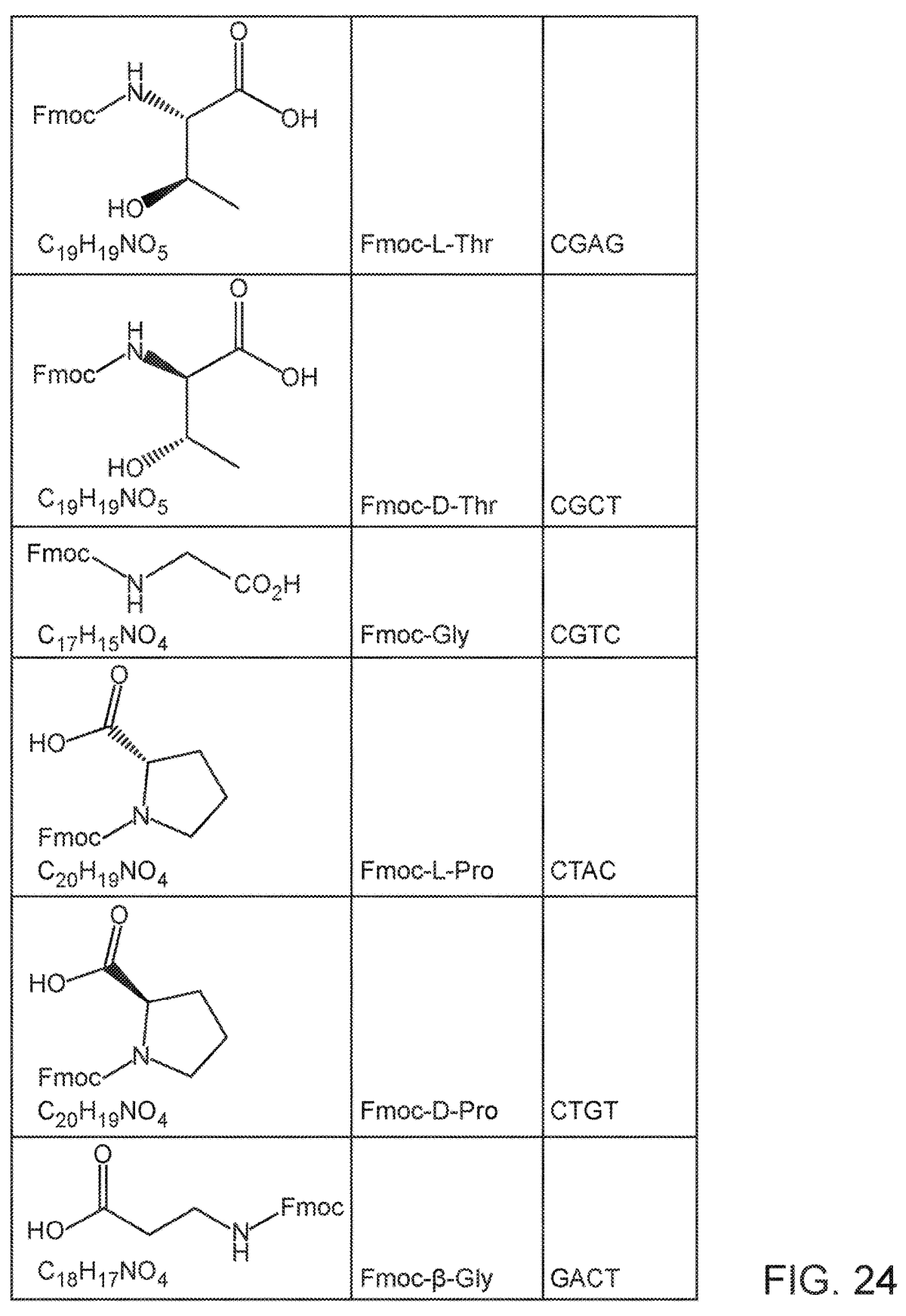

| | | |
|---|---|---|
| $C_{19}H_{19}NO_5$ | Fmoc-L-Thr | CGAG |
| $C_{19}H_{19}NO_5$ | Fmoc-D-Thr | CGCT |
| $C_{17}H_{15}NO_4$ | Fmoc-Gly | CGTC |
| $C_{20}H_{19}NO_4$ | Fmoc-L-Pro | CTAC |
| $C_{20}H_{19}NO_4$ | Fmoc-D-Pro | CTGT |
| $C_{18}H_{17}NO_4$ | Fmoc-β-Gly | GACT |

FIG. 24

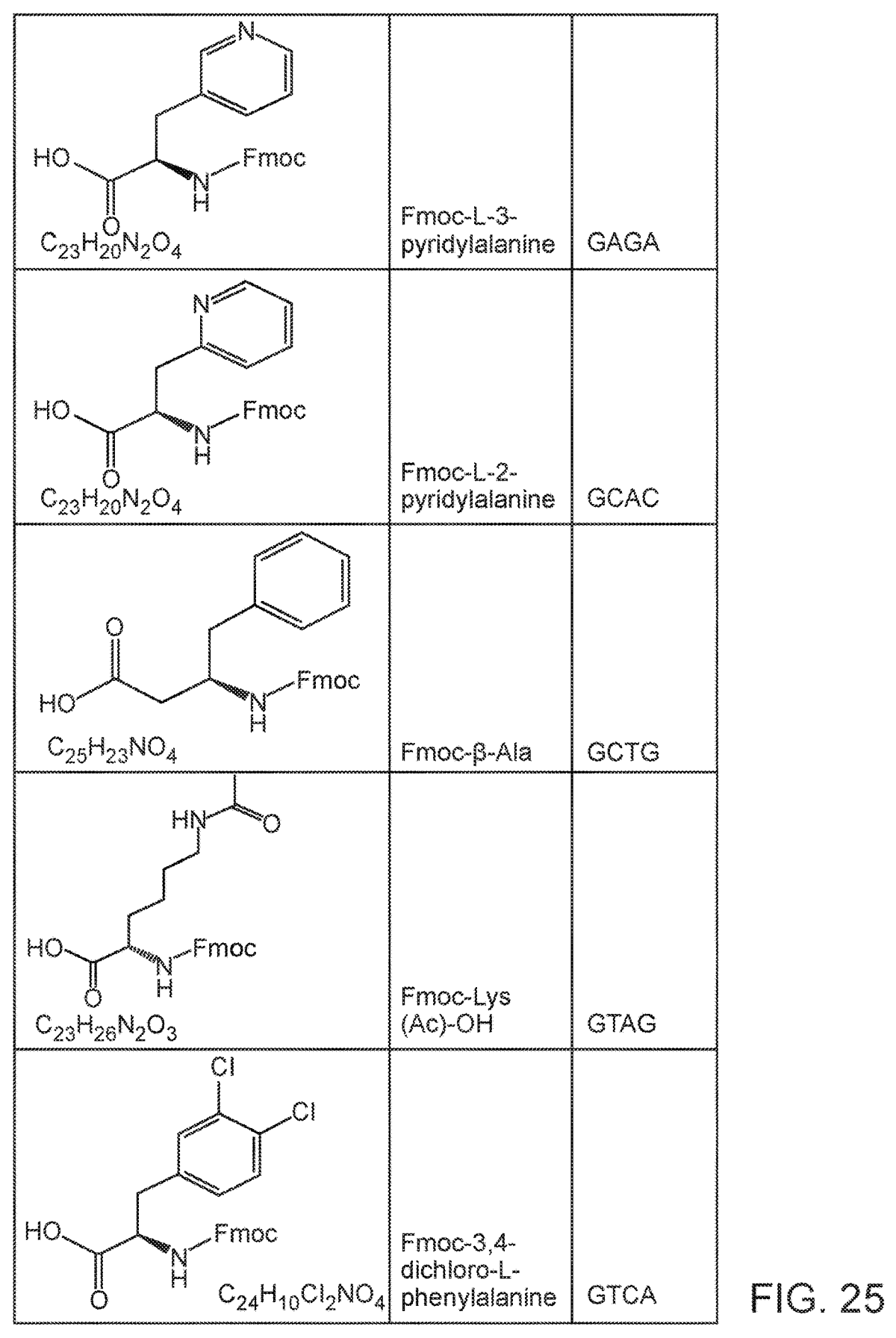

| | | |
|---|---|---|
| $C_{23}H_{20}N_2O_4$ | Fmoc-L-3-pyridylalanine | GAGA |
| $C_{23}H_{20}N_2O_4$ | Fmoc-L-2-pyridylalanine | GCAC |
| $C_{25}H_{23}NO_4$ | Fmoc-β-Ala | GCTG |
| $C_{23}H_{26}N_2O_3$ | Fmoc-Lys (Ac)-OH | GTAG |
| $C_{24}H_{10}Cl_2NO_4$ | Fmoc-3,4-dichloro-L-phenylalanine | GTCA |

FIG. 25

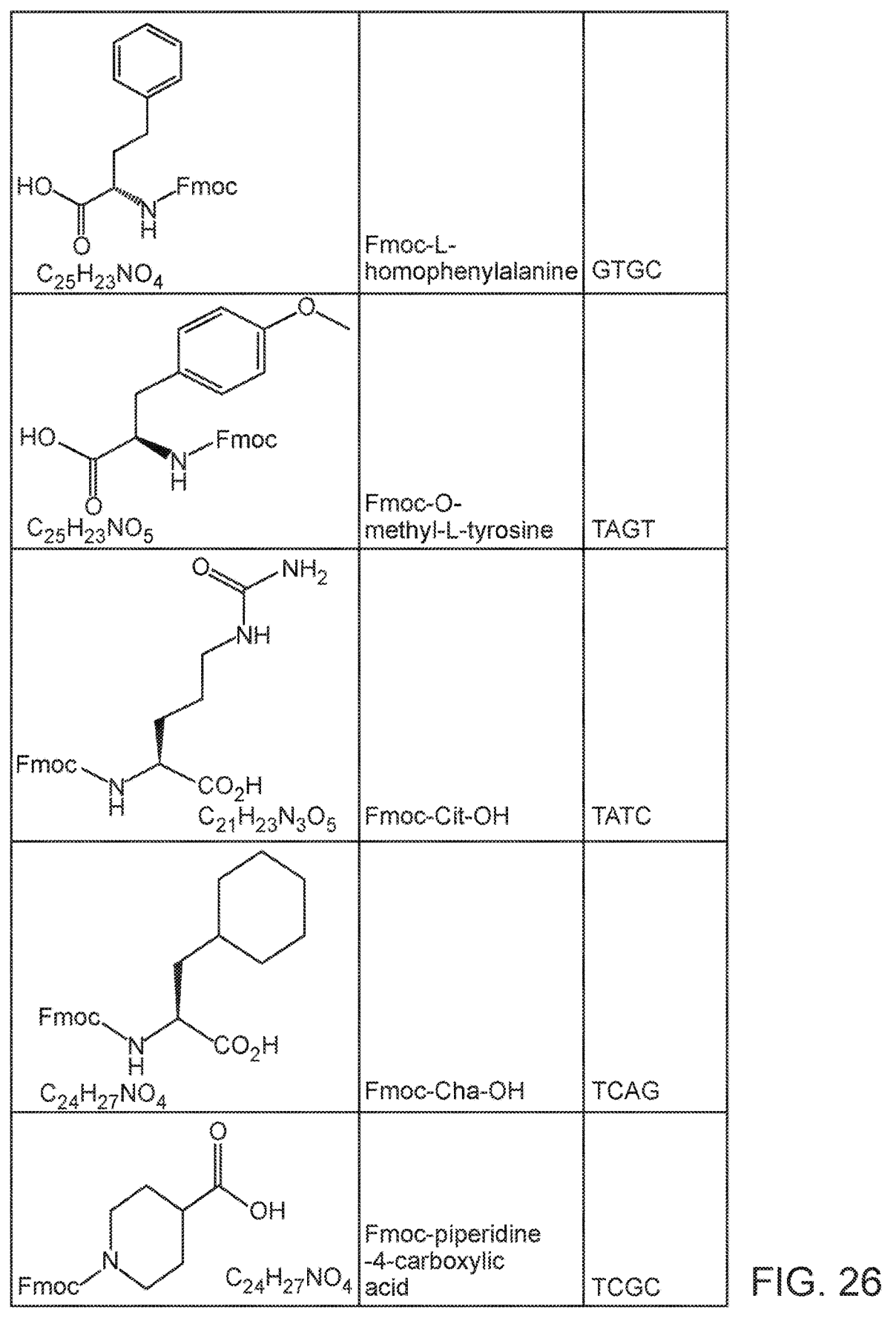

| | | |
|---|---|---|
| $C_{25}H_{23}NO_4$ | Fmoc-L-homophenylalanine | GTGC |
| $C_{25}H_{23}NO_5$ | Fmoc-O-methyl-L-tyrosine | TAGT |
| $C_{21}H_{23}N_3O_5$ | Fmoc-Cit-OH | TATC |
| $C_{24}H_{27}NO_4$ | Fmoc-Cha-OH | TCAG |
| $C_{24}H_{27}NO_4$ | Fmoc-piperidine-4-carboxylic acid | TCGC |

FIG. 26

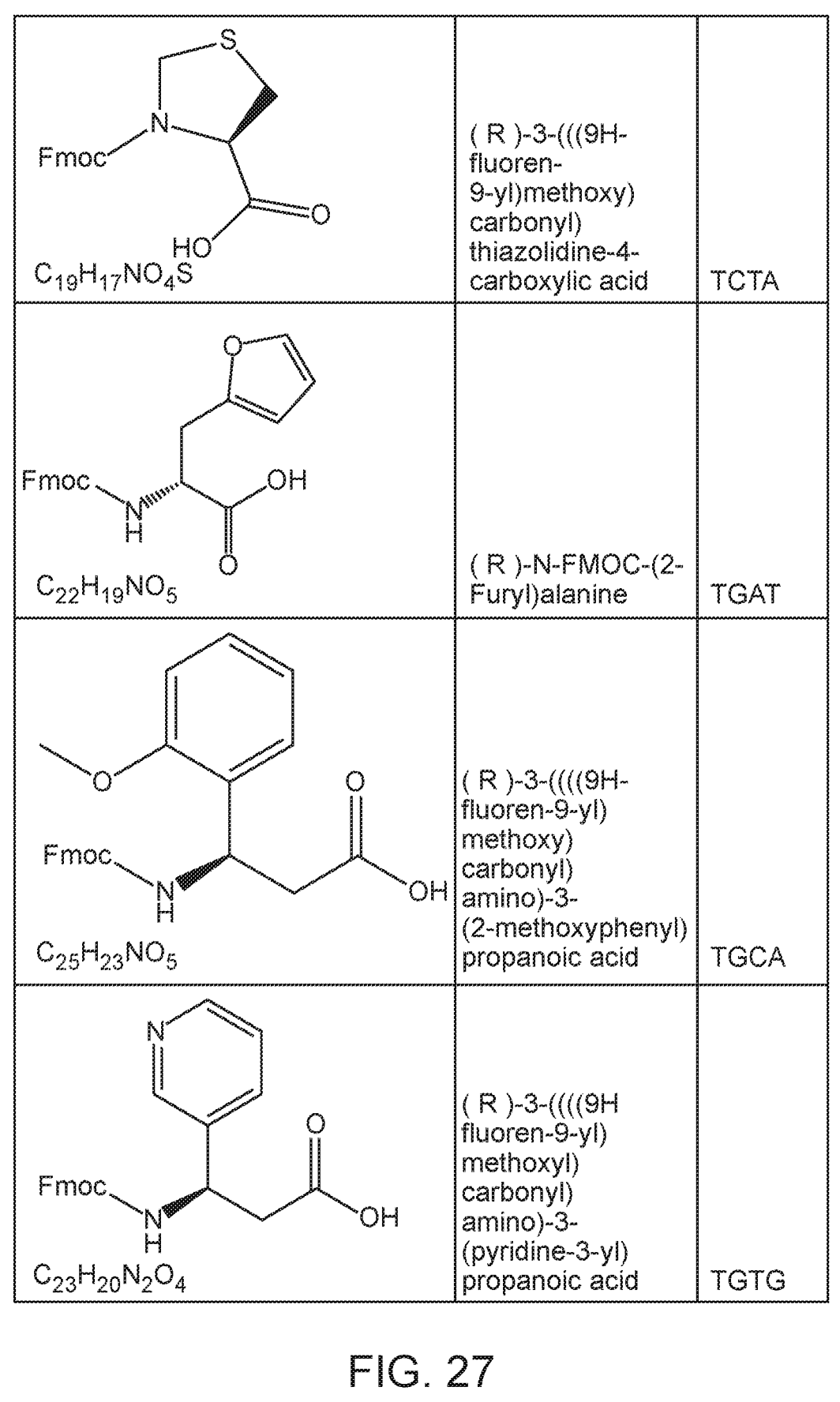

| | | |
|---|---|---|
| $C_{19}H_{17}NO_4S$ | ( R )-3-(((9H-fluoren-9-yl)methoxy)carbonyl)thiazolidine-4-carboxylic acid | TCTA |
| $C_{22}H_{19}NO_5$ | ( R )-N-FMOC-(2-Furyl)alanine | TGAT |
| $C_{25}H_{23}NO_5$ | ( R )-3-((((9H-fluoren-9-yl)methoxy)carbonyl)amino)-3-(2-methoxyphenyl)propanoic acid | TGCA |
| $C_{23}H_{20}N_2O_4$ | ( R )-3-((((9H fluoren-9-yl)methoxyl)carbonyl)amino)-3-(pyridine-3-yl)propanoic acid | TGTG |

FIG. 27

NUCLEOTIDE BEING SEQUENCED

Distance (pixels)

OLIGONUCLEOTIDE ENCODED CHEMICAL LIBRARIES

CROSS REFERENCE TO RELATED CASES

This application is a division of U.S. patent application Ser. No. 16/870,809, filed May 8, 2020, now U.S. Pat. No. 10,981,170; which is a division of U.S. patent application Ser. No. 16/139,831, filed Sep. 25, 2017 and now abandoned; which claims the benefit of, and priority to, U.S. Provisional Patent Application Ser. No. 62/562,905 filed Sep. 25, 2017, and U.S. Provisional Patent Application Ser. No. 62/562,912, also filed Sep. 25, 2017. The content of each is incorporated herein by reference in its entirety.

FIELD OF THE DISCLOSURE

The disclosure relates to high-throughput screening using a library of compounds, where the compounds are bound to beads, or contained within beads, each bead containing multiple copies of one kind of compound, where further, the bead also contains DNA tags that encode the identity or synthetic history of the compound that is contained in or on the bead. The disclosure so relates to high-throughput assays performed in picowells, where the picowells contain compound-laden beads and assay materials. The disclosure further relates to releasing the bead-bound compounds and screening them for biological activity. Broadly, the disclosure contemplates assays where beads are used as delivery-vehicles for compounds, and methods for creating such compound-laden beads.

The disclosure relates bead-bound compounds, where each compound is made of one or more monomers belonging to a chemical library. The disclosure also relates to bead-bound DNA barcodes, that is, to nucleic acids where the sequence of each nucleic acid is a code (not related to the genetic code) refers to one particular chemical library monomer. The disclosure further relates to releasing the bead-bound compounds and then screening the released compounds for biological activity.

The disclosure also pertains generally to methods for perturbing a cell, or a few cells, with a dose-controlled compound, and analyzing the change in the state of the cell by RNA and/or protein analysis. The methods disclosed herein could be applied at the single-cell level, or to a plurality of cells, for the purpose of high throughput screening, target discovery, or diagnostics, and other similar applications.

BACKGROUND OF THE DISCLOSURE

Combinatorial chemistry, for example, involving split-and-pool chemistry, can be used for synthesizing large amounts of compounds. Compounds made in this way find use in the field of medicinal chemistry, where the compounds can be screened for various biochemical activities. These activities include binding to one or more proteins, where the proteins are known at the time the screening test is performed. Alternatively, the proteins that are bound by a compound being tested are identified only after a binding event is detected. Compounds can also be screened for their activity of inhibiting or activating a known protein (this is not merely screening for a "binding" activity). Alternatively, compounds can be screened for their activity of inhibiting or activating a cellular function, and where the molecular targets are not known to the researcher at the time of screening.

The screening of compounds, such as compounds belonging to a huge library of chemicals made by split-and-pool methods, can be facilitated by conducting screening with an array of many thousands of microwells, nanowells, or picowells. Moreover, screening can be facilitated by providing a different compound to each picowell by way of a bead, and where each bead contains hundreds of copies of the same compound, and where the same bead also contains hundreds of copies of a "DNA barcode" that can be used to identify the compound that is attached to the same bead. Moreover, screening of compounds is further facilitated by using cleavable linkers, where the cleavable linker permits controlled release of the compound from the bead, and where the released compound is then used for biochemical assays or cell-based assays in the same picowell.

Assaying compounds in very small, confined volumes, such as droplets, picowells or microfluidic environments is broadly beneficial, for instance, due to the low volumes of assay reagents needed, and therefore need not be limited to combinatorially generated compounds. Any method that can load compounds onto beads, that also allows the compounds to be eluted off the beads at a later time, may be used for delivering bead-bound compounds to assays in small, confined volumes. The addition of nucleic acid barcodes to the beads allows the identity of the compound present within the beads to be carried along to the assay volume. In his manner, very high throughput assays may be performed without needing robotics or spatial indexing of compounds within microtiter plates. Millions to billions of compounds may be held within one small vial, the identity of the compounds tagged on the same bead (with DNA) that contains each individual compound.

A common method for drug discovery involves picking a target of interest and monitoring the interaction of the target protein or enzyme with a large library of chemical compounds. In many cases, a large number of initial hits are found toxic to the body or cross reactive with other proteins in the body, rendering the target-based selection an inefficient method for drug screening. The need for a pre-selected target is also an inherent limitation, since it requires the biological underpinning of disease to be well-known and understood. Screening compounds against an entire organism is a difficult, expensive, and very low-throughput task.

Conventional phenotypic screening on cells has involved creating models of diseased-state cells, contacting the cells with various drug libraries, and monitoring if the disease phenotype is corrected by a measurable assay. Such screening methods are called phenotypic screening, as the underlying biological mechanism is not necessarily understood at the beginning, but a measurable, phenotypic change that is indicative of a curative response is considered the relevant metric. A vast number of cell lines and disease models reflecting various baseline and diseased cell states are available today. Also available are larger numbers of compound libraries and biological drugs candidates. The obvious screening campaign combining different cell models with different drug candidates to look for phenotypic responses is fraught with technical limitations as assays are limited to microtiter plate formats and imaging modalities, both of which are severely limited in throughput.

One method to overcome throughput limitations is to adopt high-throughput single-cell screening approaches to drug discovery (see, e.g., Heath et al., *Nat Rev Drug Discov.* 15:204-216, 2016). In these approaches, single cells are separated and isolated into compartments where individual assays can be performed on each of the cells. Genomic analysis via mRNA sequencing of the single cells, e.g., using droplet encapsulation, is a popular method that reveals intricate details that are hidden in ensemble measurements (see, e.g., Macosko et al., *Cell* 161:1202-1214, 2015 and Ziegenhain et al., *Mol Cell* 65:631-643, 2017, the disclosures of which are incorporated herein by reference in their entireties). Present state of the art single-cell analysis platforms have enabled quantitation of mRNA transcripts with single-cell resolution to characterize and fingerprint cells based on their transcriptional state. This approach allows for comparison between tissue samples, extracted from a subject or prepared in an experiment, and examining single-cell transcription, and therefore, protein expression states. The measurements of single-cell mRNA by transcriptome sequencing and profiling are important approaches to investigate molecular mechanisms of not only genealogic phenotypes of cells during disease progression, but also drug efficacy, resistances, and discovery of therapeutic targets (see, e.g., Chu et al., *Cell Biol and Toxicol* 33:83-97, 2017, Wang, *Cell Biol Toxicol* 32:359-361, 2016, and Wang et al., *Cell Biol Toxicol* 33:423-427, 2017). The application of single-cell RNA sequencing has been used to define intercellular heterogeneity, evidenced by transcriptomic cell-to-cell variation, which is extremely relevant to drug efficacy and specificity, transcriptional stochasticity, transcriptome plasticity, and genome evolution. Encapsulation in picowells has also been demonstrated (see, e.g., Gierahn et al., *Nat Methods* 14:395-398, 2017). Single cell protein measurements are also possible using similar isolation methods (Butnik et al., *BioRxiv, Jan.* 2017, Su et al., *Proteomics* 17:3-4, 2017).

Despite the rapid rise in high-throughput single-cell RNA-sequencing (RNA-seq) methods, including commercialized versions of automated platforms such as the Fluidigm C1, 10×Genomics or 1CellBiO systems, the application of single-cell RNA profiling for target agnostic high-throughput drug screening and target discovery is constrained by the lack of methods that can efficiently partition different drugs to different cells. While incubating cells or tissues under different perturbations within well plates, followed by single-cell analysis and comparisons between transcript profiles can be done, the number of drugs that can be examined is limited by the plate capacity. Further, the need to prepare barcoded mRNA from each sample in isolation and then perform comprehensive RNA profiles for every sample, creates a major bottleneck, as well.

SUMMARY OF THE DISCLOSURE

Briefly stated, the present disclosure provides a system for screening chemical compounds, comprising: (a) A picowell array plate comprising a plurality of picowells, wherein each picowell has a top aperture that defines an opening at the top of the picowell, a bottom that is defined by a floor, wherein the top aperture is separated from the floor, and wherein a wall resides in between the top aperture and the floor; (b) A bead disposed in a picowell, wherein the bead comprises a plurality of substantially identical bead-bound DNA barcodes, and a plurality of substantially identical bead-bound compounds, (c) Wherein the bead comprises a bead-bound DNA barcode that takes the form of either a concatenated DNA barcode or an orthogonal DNA barcode, and wherein if the DNA barcode takes the form of a concatenated DNA barcode the concatenated DNA barcode is made by a method that: (i) Uses click chemistry, or (ii) Uses a repeating cycle of steps, wherein the repeating cycle of steps comprises using a splint oligonucleotide (splint oligo) that is capable of hybridizing to a partially made bead-bound DNA barcode, and wherein the hybridizing is mediated by an annealing site on the splint oligo and a corresponding, complementary annealing site in the partially made bead-bound DNA barcode, wherein the annealed splint oligo is used as a template for extending the partially made DNA barcode using DNA polymerase, and wherein the splint oligo contains bases that are complementary to a DNA barcode module that is to be polymerized to the partially made DNA barcode, (d) Wherein each one of the plurality of substantially identical bead-bound compounds comprises one or more chemical library monomers, and wherein each bead-bound DNA barcode module identifies a corresponding chemical library monomer, wherein the term "compound" is used to refer to a completed product that comprises one or more chemical library members, and wherein the completed DNA barcode identifies the compound.

The floor of a microwell, nanowell, or picowell, need not be flat. The floor may be curved as in the manner of the bottom of a glass test tube or metal centrifuge tube. Also, the floor may be conical-shaped, as in conical centrifuge tubes. The floor may be flat but with notches, for example, notches that facilitate motion of an assay solution or cell culture solution in the vicinity of the bottom of any bead that is sitting in the picowell. In flat-floor embodiments, the present system and methods can require a flat floor.

The concatenated DNA barcode can be made entirely by methods of organic chemistry, for example, by click chemistry. Also, the orthogonal DNA barcode can be made entirely by methods of organic chemistry, for example, comprising click chemistry.

What is also provided is the above system, further comprising a plurality of caps, each cap capable of fitting into the opening of a different picowell, and each cap capable of minimizing or preventing evaporation of fluid that is inside of the picowell, and each capable of minimizing or preventing leakage of fluid that is inside of the picowell.

Moreover, what is embraced is the above system, wherein the concatenated DNA barcode is made by a method that uses: (i) Both click chemistry and the repeating cycle of steps that uses the splint oligo; (ii) Both click chemistry and chemical methods that are not click chemistry methods; (iii) Only click chemistry; or (iv) Only the repeating cycle of steps that uses the splint oligo. For this particular embodiment the "concatenated DNA barcode" in question does not include any chemical coupler that is used to couple a nucleic acid directly to the bead.

In a spherical cap embodiment, what is provided is the above system, further comprising a plurality of spherical caps, wherein each cap is capable of fitting into the aperture of a picowell wherein the aperture is circular, and each cap is capable of minimizing or preventing evaporation of fluid that is inside of the picowell, and each cap is capable of minimizing or preventing leakage of fluid that is inside of the picowell.

In a response element embodiment, what is provided is the above system, wherein the at least one bead disposed in the at least one picowell comprises at least one response capture element that is coupled to said at least one bead. Also, what is contemplated is the above system, wherein the at least one bead disposed in at least one picowell comprises at least one response capture element that is coupled to said at least one bead, wherein the at least one response capture element comprises: (a) Poly(dT) or (b) An exon-targeting RNA probe.

Also contemplated is the above system, wherein the DNA barcode is either a concatenated DNA barcode or an orthogonal DNA barcode, and wherein the DNA barcode comprises one or more DNA barcode modules, wherein each of the one or more DNA barcode modules encodes information that identifies a chemical library monomer, and wherein the concatenated DNA barcode or the orthogonal DNA barcode further includes one or both of: (a) One or more functional nucleic acids; and (b) One or more nucleic acids that encode information of a type other than the identity of a chemical library monomer.

The following discloses "consists of only" embodiments and "comprises" embodiments, as it applies to the number of bead-bound DNA barcode modules that make up a DNA barcode. What is provided is embodiments where the DNA barcode consists of only one DNA barcode module, or only two DNA barcode modules, or contains only three DNA barcode modules, or only four DNA barcode modules, and so on, or where the DNA barcode comprises at least one DNA barcode module, or comprises at least two DNA barcode modules, or comprises at least three DNA barcode modules, or comprises at least four DNA barcode modules, and so on, What is also embraced, is a system wherein the bead-bound concatenated DNA barcode comprises: (i) a $1^{st}$ DNA barcode module; or (i) a $1^{st}$ DNA barcode module, a $1^{st}$ annealing site, and a $2^{nd}$ DNA barcode module; or (ii) a $1^{st}$ DNA barcode module, a $1^{st}$ annealing site, a $2^{nd}$ DNA barcode module, a $2^{nd}$ annealing site, and a $3^{rd}$ DNA barcode module; or (iii) a $1^{st}$ DNA barcode module, a $1^{st}$ annealing site, a $2^{nd}$ DNA barcode module, a $2^{nd}$ annealing site, a $3^{rd}$ DNA barcode module, a $3^{rd}$ annealing site, and a $4^{th}$ DNA barcode module; or (iv) a $1^{st}$ DNA barcode module, a $1^{st}$ annealing site, a $2^{nd}$ DNA barcode module, a $2^{nd}$ annealing site, a $3^{rd}$ DNA barcode module, a $3^{rd}$ annealing site, a $4^{th}$ DNA barcode module, a $4^{th}$ annealing site, and a $5^{th}$ DNA barcode module; or (v) a $1^{st}$ DNA barcode module, a $1^{st}$ annealing site, a $2^{nd}$ DNA barcode module, a $2^{nd}$ annealing site, a $3^{rd}$ DNA barcode module, a $3^{rd}$ annealing site, a $4^{th}$ DNA barcode module, a $4^{th}$ annealing site, a $5^{th}$ DNA barcode module, a $5^{th}$ annealing site, and a $6^{th}$ DNA barcode module.

Moreover, what is contemplated is the above system, further comprising a primer binding site capable of binding a DNA sequencing primer, wherein said primer binding site is capable of directing sequencing of one or more of the $1^{st}$ DNA barcode module, the $2^{nd}$ DNA barcode module, the $3^{rd}$ DNA barcode module, the $4^{th}$ DNA barcode module, the $5^{th}$ DNA barcode module, or the $6^{th}$ DNA barcode module, and wherein the primer binding site is situated 3-prime to the $1^{st}$ DNA barcode module, 3-prime to the $2^{nd}$ DNA barcode module, 3-prime to the $3^{rd}$ DNA barcode module, 3-prime to the $4^{th}$ DNA barcode module, 3-prime to the $5^{th}$ DNA barcode module, or 3-prime to the $6^{th}$ DNA barcode module, or wherein the primer binding site is situated in between the $1^{st}$ and $2^{nd}$ DNA barcode modules, or is situated in between the $2^{nd}$ and $3^{rd}$ DNA barcode modules, or is situated in between the $3^{rd}$ and $4^{th}$ DNA barcode modules, or is situated between the $4^{th}$ and $5^{th}$ DNA barcode modules, or is situated between the $5^{th}$ and $6^{th}$ DNA barcode modules.

Additionally, what is provided is the above system, wherein the primer binding site is situated in between the $1^{st}$ and $2^{nd}$ DNA barcode modules, or is situated in between the $2^{nd}$ and $3^{rd}$ DNA barcode modules, or is situated in between the $3^{rd}$ and $4^{th}$ DNA barcode modules, or is situated between the $4^{th}$ and $5^{th}$ DNA barcode modules, or is situated between the $5^{th}$ and $6^{th}$ DNA barcode modules. In embodiments relating to the position of a primer binding site, relative to upstream DNA barcode modules and relative to downstream DNA barcode modules, what is provided is the above system, wherein a primer binding site is situated in between each and every pair of successive DNA barcode modules.

Furthermore, what is provided is the above system, wherein the bead comprises a DNA barcode that is an orthogonal DNA barcode, wherein the bead comprises an external surface, and wherein the orthogonal DNA barcode comprises: (a) A first nucleic acid that comprises a first DNA barcode module and an annealing site for a sequencing primer, wherein the first nucleic acid is coupled to the bead at a first position, (b) A second nucleic acid that comprises a second DNA barcode module and an annealing site for a sequencing primer, wherein the second nucleic acid is coupled to the bead at a second position, and (c) A third nucleic acid that comprises a third DNA barcode module and an annealing site for a sequencing primer, wherein the second nucleic acid is coupled to the bead at a third position, and wherein the first, second, and third position on the bead are each located at different location on the bead's external surface.

In encoding embodiments, what is provided is the above system, wherein the DNA barcode comprises one or more nucleic acids that do not identify any chemical library monomer but that instead identify: (a) The class of chemical compounds that is cleavably attached to the bead; (b) The step number in a multi-step pathway of organic synthesis; (c) The date that the bead-bound compound was synthesized; (d) The disease that the bead-bound compound is intended to treat; (e) The cellular event that the bead-bound compound is intended to stimulate or inhibit; or (f) The reaction conditions that were used to couple a given chemical library monomer to the bead.

In linker embodiments, what is provided is the above system, wherein each of the plurality of substantially identical bead-bound compounds is coupled to the bead by way of a cleavable linker. Also provided is the above system, wherein each of the plurality of substantially identical bead-bound compounds is coupled to the bead by way of a light-cleavable linker. Also provided is the above system, wherein each of the plurality of substantially identical bead-bound compounds is coupled to the bead by way of a non-cleavable linker.

In TentaGel® embodiments, what is provided is the above system, wherein the at least one bead comprises grafted copolymers consisting of a low crosslinked polystyrene matrix on which polyethylene glycol (PEG) is grafted.

In release-monitor embodiments, the present disclosure provides the above system, wherein at least one picowell contains a release-monitor bead, and does not contain any other type of bead, wherein the release-monitor bead comprises a bead-bound quencher and a bead-bound fluorophore, wherein the bead-bound quencher is quenchingly positioned in the immediate vicinity of the bead-bound fluorophore and capable of quenching at least 50% (or at least 60%, or at least 70%, or at least 80%, or at least 90%, or at least 95%, or at least 99%, or at least 99.5%, or at least 99.9%) of the fluorescence of the bead-bound fluorophore, and wherein the bead-bound fluorophore is bound by way of a first light-cleavable linker, wherein the picowell containing the release-monitor bead is a first picowell, wherein the first picowell contains a first solution, wherein exposing the first picowell to cleaving conditions is capable of severing the light-cleavable linker and releasing the fluorophore into the first solution of the first picowell, wherein the exposing results in the fluorophore diffusing throughout the first solution in the first picowell, and wherein a fluorescent signal acquired by shining light on the first picowell that contains the first solution comprising diffused fluorophore allows the user to use the fluorescent signal to calculate the percent release of the bead-bound fluorophore from the release-monitor bead resulting in a value for the calculated percent release, and wherein a second picowell contains a bead-bound compound coupled with the same type of light-cleavable linker as the first light-cleavable linker, and wherein the second picowell contains a second solution, and wherein the value for the calculated percent release from the release-monitor bead in the first picowell allows calculation of the concentration of the released compound in the second solution of the second picowell.

In embodiments relating to identity of all of the compounds bound to a given bead, or relating to identity of all of the DNA barcodes bound to a given bead, what is provided is the above system, wherein the at least one bead comprises a plurality of substantially identical bead-bound DNA barcodes, wherein the plurality is between 10 million to 100 million copies of the substantially identical bead-bound DNA barcodes. Also provided is the above system, wherein the at least one bead comprises a plurality of substantially identical bead-bound compounds, where wherein the plurality is between 10 million to 100 million copies of the substantially identical bead-bound compounds.

In embodiments relating to cells (e.g., mammalian cells, cancer cells, bacterial cells), what is provided is the above system, wherein at least one picowell comprises at least one cell, wherein the plurality of substantially identical bead-bound compounds are bound to the at least one bead by way of a cleavable linker, and wherein cleaving the cleavable linker releases the bead-bound compound from the bead to produce a released compound, and wherein the released compound is capable of contacting the at least one cell. In other cell embodiments, what is provided is the above system, wherein at least one picowell comprises at least one cell, wherein the plurality of substantially identical bead-bound compounds are bound to the at least one bead by way of a cleavable linker, and wherein cleaving the cleavable linker releases the bead-bound compound from the bead to produce a released compound, and wherein the released compound is capable of contacting the at least one cell, and wherein the at least one cell is: (i) a mammalian cell that is not a cancer cell, (ii) a mammalian cancer cell, (iii) a dead mammalian cell, (iv) an apoptotic mammalian cell, (v) a necrotic mammalian cell, (vi) a bacterial cell, (vii) a plasmodium cell, (vii) a cell that is metabolically active but has a cross-linked genome and is unable to undergo cell division, or (ix) a mammalian cell that is infected with a virus.

In device embodiments, what is provided is the above system, wherein each picowell has a top aperture that defines an opening at the top of the picowell, a bottom that is defined by a floor, wherein the top aperture is separated from the floor, and wherein a wall resides in between the top aperture and the floor, and wherein the aperture is round, wherein the floor is round, and wherein the wall takes the form of a truncated cone, and wherein the aperture has a first diameter, the floor has a second diameter, and wherein the first diameter is greater than the second diameter.

In other device-related embodiments, what is provided is the above system, wherein each picowell has a top aperture that defines an opening at the top of the picowell, a bottom that is defined by a floor, wherein the top aperture is separated from the floor, and wherein a wall resides in between the top aperture and the floor, and wherein the aperture is round, wherein the floor is round, and wherein the wall takes the form of a truncated cone, and wherein the aperture has a first diameter, the floor has a second diameter, and wherein the first diameter is greater than the second diameter, further comprising a cap that snuggly fits into the aperture, wherein the aperture is comprised by a polymer having a greater durometer (harder) and wherein the cap is made of a polymer having a lesser durometer (softer), and wherein the relative durometers of the cap and aperture allow the cap to be reversibly and snuggly fit into the aperture, and wherein the cap is: (i) a cap intended only to plug the picowell and prevent leakage, (ii) a cap that is a passive cap and that is capable of absorbing metabolites that are released by a cell, in the situation where a cell in a cell medium is cultured in the picowell, (iii) a cap that is an active cap, and that takes the form of a bead that comprises a plurality of essentially identical compounds, and wherein each of the plurality of essentially identical compounds is coupled to the bead with a cleavable linker; (iv) a cap that is an active cap, and that takes the form of a bead that comprises a plurality of identical reagents, and wherein each of the plurality of essentially identical reagents is coupled to the bead with a cleavable linker. Also provided is the above system, wherein the cap is spherical, or wherein the cap is non-spherical.

In embodiments, the above system comprises a picowell array plate comprising an upper generally planar surface, a plurality of picowells, wherein each picowell has a top aperture that defines an opening at the top of the picowell, a bottom that is defined by a floor, wherein the top aperture is separated by a wall from the floor, and wherein the wall resides in between the top aperture and the floor, and optionally, a bead disposed in at least one of said plurality of picowells, wherein the bead comprises a plurality of substantially identical bead-bound DNA barcodes, and a plurality of substantially identical bead-bound compounds, wherein the picowell array plate further comprises a mat that is capable of securely covering the opening at the top of at least one or all of the plurality of picowells, or that is actually securely covering the opening at the top of at least one or all of the plurality of picowells, wherein the securely covering is reversible, wherein the mat optionally comprises one or all of: (a) An absorbent surface that, when positioned in contact with the upper generally planar surface of the picowell array plate, is capable of absorbing any metabolites, biochemicals, or proteins that may be comprised by one or more of the plurality of picowells, (b) An adhesive surface that is capable of maintaining reversible adhesion to the top generally planar surface of the picowell array plate.

In biochemical assay embodiments, what is embraced is the above system, that includes at least one picowell, wherein the at least one picowell comprises a bead that comprises a plurality of substantially identical compounds and a plurality of substantially identical barcodes, wherein the at least one picowell comprises an assay medium that includes cereblon E3 ubiquitin ligase, a substrate of cereblon E3 ubiquitin ligase such as Ikaros or Aiolos, and wherein the system is capable of screening for compounds that activate cereblon's E3 ubiquitin ligase activity, and are thereby capable of reducing intracellular concentrations of Ikaros or Aiolos.

In another biochemical assay embodiment, what is contemplated is the above system, that includes at least one picowell, wherein the at least one picowell comprises a bead that comprises a plurality of substantially identical compounds and a plurality of substantially identical barcodes, wherein the at least one picowell comprises an assay medium that includes MDM2 E3 ubiquitin ligase, a substrate of MDM2 E3 ubiquitin ligase such as p53, and wherein the system is capable of screening for compounds that activate MDM2's E3 ubiquitin ligase activity, and thereby capable of increasing the intracellular concentrations of p53.

In more barcoding embodiments, what is provided is the above system, wherein the DNA barcode comprises one or more nucleic acids that do not encode any chemical monomer but that instead identify one or more of: (a) The class of chemical compounds that is cleavably attached to the bead; (b) The step in a multi-step pathway of organic synthesis, wherein a bead-bound nucleic acid corresponds to a given chemical monomer that is used to make a bead-bound compound, and wherein the bead-bound nucleic acid that corresponds to a given chemical monomer identifies that chemical monomer; (c) The date that the bead-bound compound was synthesized; (d) The disease that the bead-bound compound is intended to treat; (e) The cellular event that the bead-bound compound is intended to stimulate or inhibit.

In embodiments that lack any headpiece, what is provided is the above system, wherein the at least one bead comprises a plurality of substantially identical bead-bound compounds and also comprises a plurality of substantially identical bead-bound DNA barcodes, and wherein there does not exist any headpiece that links any of the bead-bound compounds to any of the bead-bound DNA barcodes.

Moreover, what is contemplated is the above system, wherein at least 70%, at least 80%, at least 90%, at least 95%, or at least 98% of the substantially identical bead-bound DNA barcodes have an identical structure. Additionally, what is contemplated is the above system, wherein at least 70%, at least 80%, at least 90%, at least 95%, or at least 98% of the substantially identical bead-bound compounds have an identical structure.

Furthermore, what is supplied is the above system, wherein the concatenated DNA barcode comprises at least one nucleic acid that is a DNA barcode module, or the above system, wherein the concatenated DNA barcode comprises only one nucleic acid that is a DNA barcode module.

In sequencing primer annealing site embodiments, what is provided is the above system, wherein the concatenated DNA barcode comprises at least one nucleic acid that is a DNA barcode module, and at least one functional nucleic acid that: (a) Is capable of being used as an annealing site for a sequencing primer, (b) Is capable of forming a hairpin structure, and wherein the hairpin structure comprises a sequencing primer, an annealing site for the sequencing primer, and a bend in the hairpin structure wherein the bend is 5-prime to the sequencing primer and is 3-prime to the annealing site for the sequencing primer, or (c) Is a spacer nucleic acid.

In other sequencing primer embodiments, what is provided is the above system, wherein the orthogonal DNA barcode contains a plurality of DNA barcode modules, wherein each of the DNA barcode modules is coupled to a different site on the bead either directly or via a linker, and wherein each of the plurality of DNA barcode modules contains at least one functional nucleic acid that: (a) Is capable of being used as an annealing site for a sequencing primer, (b) Is capable of forming a hairpin structure, and wherein the hairpin structure comprises a sequencing primer, an annealing site for the sequencing primer, and a bend in the hairpin structure wherein the bend is 5-prime to the sequencing primer and is 3-prime to the annealing site for the sequencing primer, or (c) Is a spacer nucleic acid.

In embodiments that recite functional language about splint oligos, what is provided is a bead comprising a concatenated DNA barcode, wherein the concatenated DNA barcode comprises: (a) a first DNA barcode module and a first annealing site for a first splint oligonucleotide (splint oligo), wherein the splint oligo comprises three nucleic acids, wherein the three nucleic acids are: a nucleic acid that is a hybridizing complement to the first annealing site, a nucleic acid that is a hybridizing complement to a $2^{nd}$ DNA barcode module, and a nucleic acid that is a $2^{nd}$ annealing site, and (b) a second DNA barcode module and a 2nd annealing site for a second splint oligo, wherein the second splint oligo comprises three nucleic acids, wherein the three nucleic acids are: a nucleic acid that is a hybridizing complement to the 2nd annealing site, a nucleic acid that is a 3rd DNA barcode module, and a nucleic acid that is a 3rd annealing site.

In another embodiment that contains functional language relating to splint oligos, what is provided is the above bead, further comprising: a third DNA barcode module and a 3rd annealing site for a third splint oligo, wherein the third splint oligo comprises three nucleic acids, wherein the three nucleic acids are: a nucleic acid that is a hybridizing complement to the 3rd annealing site, a nucleic acid that is a $4^{th}$ DNA barcode module, and a nucleic acid that is a 4th annealing site.

Moreover, in yet another embodiment containing functional language relating to splint oligos, what is provided is the above bead, further comprising one or more of: (i) a fourth DNA barcode module and a 4th annealing site for a fourth splint oligo, wherein the fourth splint oligo comprises three nucleic acids, wherein the three nucleic acids are: a nucleic acid that is a hybridizing complement to the 4th annealing site, a nucleic acid that is a $5^{th}$ DNA barcode module, and a nucleic acid that is a 5th annealing site, (ii) a response capture element, (iii) a release monitor.

In linker embodiments, what is embraced is the above bead, wherein the concatenated DNA barcode is coupled to the bead, but is: (i) not coupled to the bead by way of any photocleavable linker, (ii) not coupled to the bead by any enzymatically cleavable linker; or (iii) not coupled to the bead by any kind of cleavable linker.

In an embodiment relating to distinct coupling positions, what is provided is the above bead, wherein the concatenated DNA barcode is coupled to a first position on the bead, wherein the bead also comprises a compound that is coupled to a second position on the bead, and wherein the first position is not the same as the second position.

In surface embodiments (interior and exterior surfaces), what is provided is the above bead, wherein the bead comprises an exterior surface and an interior surface, wherein the bead comprises at least 10,000 substantially identical concatenated DNA barcodes that are coupled to the bead, and wherein at least 90% of the at least 10,000 substantially identical concatenated DNA barcodes are coupled to the exterior surface.

In exclusionary embodiments that can distinguish the present disclosure from other embodiments, what is provided is the above bead, that is does not comprise any polyacrylamide, and wherein the concatenated DNA barcode: (i) Does not include any nucleic acid that is a promoter; (ii) Does not include any nucleic acid that is polyA; or (iii) Does not include any nucleic acid that is a promoter and does not include any nucleic acid that is polyA.

In release-monitor bead embodiments, the present disclosure supplies a release-monitor bead that is capable of functioning in an aqueous medium, wherein the release-monitor bead comprises a bead-bound quencher and a bead-bound fluorophore, wherein the bead-bound quencher is quenchingly positioned in the immediate vicinity of the bead-bound fluorophore and capable of quenching at least 50% of the fluorescence of the bead-bound fluorophore, and wherein the bead-bound fluorophore is bound by way of a first light-cleavable linker, wherein the picowell containing the release-monitor bead is a first picowell, wherein the first picowell contains a first solution, wherein exposing the first picowell to cleaving conditions is capable of severing the light-cleavable linker and releasing the fluorophore into the first solution of the first picowell, wherein the exposing results in the fluorophore diffusing throughout the first solution in the first picowell, and wherein a fluorescent signal acquired by shining light on the first picowell that contains the first solution comprising diffused fluorophore allows the user to use the fluorescent signal to calculate the percent release of the bead-bound fluorophore from the release-monitor bead resulting in a value for the calculated percent release, and wherein a second picowell contains a bead-bound compound coupled with the same type of light-cleavable linker as the first light-cleavable linker, and wherein the second picowell contains a second solution, and wherein the value for the calculated percent release from the release-monitor bead in the first picowell allows calculation of the concentration of the released compound in the second solution of the second picowell. In other release-monitor embodiments, what is provided is a release-monitor bead wherein the fluorophore is TAMRA and wherein the quencher is QSY7, and a release-monitor bead that has the structure shown in FIG. 9, and a release-monitor bead of that has the structure shown in FIG. 10, and a release-monitor bead, wherein the capable of quenching is at least 90%, at least 98%, at least 99%, or at least 99.9%.

In a methods of manufacture embodiment, what is embraced is a method for synthesizing a release-monitor bead, wherein the release-monitor bead comprises a bead, a quencher, a fluorophore, and a photocleavable linker that couples the fluorophore to the bead, the method comprising, in this order, (i) Providing a resin, (ii) Coupling a lysine linker to the resin, wherein the reagent containing the lysine linker is L-Fmoc-Lys(4-methyltrityl)-OH, (iii) Removing the Fmoc protecting group, (iv) Coupling the quencher using a reagent that is quencher-N-hydroxysuccinimide (quencher-NHS) as the source of quencher, (v) Removing the 4-methyltrityl protecting group using a reagent comprising trifluoroacetic acid, (vi) Coupling a photocleavable linker to the epsilon amino group of lysine, wherein the photocleavable linker is provided by a reagent that is, Fmoc-photocleavable linker-OH, (vii) Coupling the fluorophore. Also provided is the above embodiment, but without regard to the ordering of steps. In other methods embodiments, what is provided is the above method wherein the fluorophore is TAMRA and wherein the quencher is QSY7.

In methods relating to the utility of release-monitor bead, what is provided is a method for controlling the concentration of a compound in a solution that resides in a picowell, wherein the method is applied to a bead-bound compound in a picowell, wherein the picowell contains a solution, and wherein the bead-bound compound is coupled to the bead by way of a cleavable linker, the method comprising: (a) Exposing the bead-bound compound to a condition that effects cleavage of the cleavable linker and releases the bead-bound compound from the bead to generate a released compound, wherein release is followed by diffusion or dispersion of the released compound in the solution to result in a substantially uniform concentration of the compound in the solution, (b) Wherein the condition comprises light that is capable of cleaving the cleavable linker, (c) Wherein the condition is adjusted to produce a determined concentration of the substantially uniform concentration, and (d) Wherein the determined concentration is made with regard to the concentration of a released fluorophore that is released by from a bead-bound release-monitor. Provided also, is the above method, wherein the condition is adjusted by adjusting one or more of the wavelength of the light, the intensity of the light, and by the duration of light exposure, and the above method, wherein the concentration of a released fluorophore that is released from a bead-bound release-monitor is determined at the same time as effecting release of the bead-bound compound from the bead to generate a released compound, and the above method, wherein the concentration of a released fluorophore that is released from a bead-bound release-monitor is determined at a time substantially before effecting release of the bead-bound compound from the bead to generate a released compound.

The term "determined" can mean a concentration that is predetermined and decided upon as being a desired concentration, prior to exposing the bead to light. Also, the term "determined" can mean a concentration that is decided upon in "real time," that is, a concentration that is decided upon at the same time as the exposing the bead to light.

In cap embodiments, what is embraced is a cap in combination with a picowell plate that comprises a plurality of picowells, wherein the cap is capable of use with the picowell plate that comprises a plurality of picowells, wherein each of the plurality of picowells is definable by an aperture, a floor, and a wall, wherein the wall is defined by the aperture on top and the floor on the bottom, and wherein the aperture is round, wherein the floor is round, and wherein the wall takes the form of a surface of a truncated cone, and wherein the aperture has a first diameter, the floor has a second diameter, and wherein the first diameter is greater than the second diameter, wherein the cap is a spherical cap that is capable of snuggly fitting into the aperture, wherein the aperture is comprised by a polymer having a greater durometer (harder) and wherein the cap is made of a polymer having a lesser durometer (softer), and wherein the relative durometers of the cap and aperture allow the spherical cap to be reversibly and snuggly fit into the aperture, and wherein the cap is: (i) capable of plugging the picowell and preventing leakage, (ii) a passive cap and that is capable of absorbing metabolites that are released by a cell, in the situation where a cell in a cell medium is cultured in the picowell, (iii) an active cap that takes the form of a bead that comprises a plurality of essentially identical compounds, and wherein each of the plurality of essentially identical compounds is coupled to the bead with a cleavable linker, and wherein cleavage of the cleavable linker releases at least some of the plurality of compounds from the bead, (iv) an active cap that takes the form of a bead that comprises a plurality of identical reagents, and wherein each of the plurality of essentially identical reagents is coupled to the bead with a cleavable linker, and wherein cleavage of the cleavable linker releases at least some of the plurality of reagents from the bead.

In porous cap embodiments, what is provided is a plurality of porous caps in combination with a picowell plate and a solid polymer coating, wherein each of the plurality of porous caps comprises an upper surface and a lower surface, wherein the picowell plate comprises a plurality of picowells, wherein at least one porous cap contacts a picowell and reversibly and snuggly fits into the picowell, wherein the picowell plate and each of the upper surfaces of the plurality of porous caps is covered with a solid polymer coating, wherein the solid polymer coating contacts at least some of the upper surface of each cap and is adhesively attached to said at least some of the upper surface, and wherein, (i) Each of the plurality of picowells is capable of holding an aqueous solution, wherein products of a reaction are generated in the solution, and wherein at least some of the products are absorbed by the lower surface of each of the plurality of porous caps, (ii) Wherein a solution of a polymerizable reagent that capable of polymerization is poured over the plurality of porous caps in combination with the picowell plate, and wherein the polymerizable reagent is polymerized to form a substantially planar surface that coats substantially all of the top surface of the picowell plate, thereby fixing the polymerized reagent to each of the plurality of porous caps, and (iii) Wherein all of the plurality of porous caps are removable by the act of peeling from the plurality of picowells, wherein adhesion is maintained between the plurality of porous caps and the polymerized reagent, resulting in an array of adhering caps partly with the upper surface of each cap is embedded in the polymerized reagent and the lower surface of each cap is accessible for analysis of any absorbed reaction product.

This provides a methods of manufacture embodiment, for using splint oligos to guide the enzymatic synthesis of a DNA barcode. What is provided is a method for making a bead-bound concatenated DNA barcode, wherein the bead-bound concatenated DNA barcode comprises a plurality of DNA barcode modules, and optionally one or more functional nucleic acids, and optionally one or more identity-encoding nucleic acids that encode the identity of something other than the identity of a chemical library monomer, the method comprising: (a) The step of providing a bead with a coupled polynucleotide that comprises a $1^{st}$ DNA barcode module and a $1^{st}$ annealing site, wherein the $1^{st}$ annealing site is capable of hybridizing with a first splint oligonucleotide (splint oligo), the first splint oligo being capable of serving as a template for DNA polymerase to catalyze the polymerization to the coupled polynucleotide, nucleotides that are complementary to those of the hybridized first splint oligo, wherein the polymerized nucleotides that are complementary to those of the hybridized first splint oligo following polymerization comprise a bead-bound $2^{nd}$ DNA barcode module and a $2^{nd}$ annealing site; (b) The step of providing said bead with a coupled polynucleotide with said first splint oligo, and allowing said first splint oligo to hybridize with said coupled polynucleotide; (c) The step of adding a DNA polymerase and deoxynucleotide triphosphates (dNTPs) and allowing the DNA polymerase to catalyze polymerization of said dNTPs to the coupled polynucleotide, wherein the coupled polynucleotide has a free 3'-terminus and wherein the polymerization is to the free 3'-terminus, (d) The step of washing away the first splint oligo. Also contemplated is the above method, wherein the first splint oligo comprises a $1^{st}$ annealing site, a $2^{nd}$ DNA barcode module, and a $2^{nd}$ annealing site.

In further methods of manufacture embodiments, what is provided is the above method, wherein the first splint oligo comprises a $1^{st}$ annealing site, a $2^{nd}$ DNA barcode module, a $2^{nd}$ annealing site, and a nucleic acid encoding a $1^{st}$ sequencing primer annealing site, wherein the $1^{st}$ sequencing primer annealing site is capable of hybridizing to a sequencing primer resulting in a hybridized sequencing primer, and wherein the hybridized sequencing primer is capable of directing the sequencing of the $2^{nd}$ DNA barcode module and the $1^{st}$ DNA barcode module.

Moreover, what is contemplated is the above method, wherein the first splint oligo, the DNA polymerase, and the dNTPs are all added at the same time, or wherein the first splint oligo, the DNA polymerase, and the dNTPs are each added at separate times.

Regarding interior versus exterior locations on a bead, what is provided is the above method, wherein the bead comprises an exterior location and an interior location, and wherein the bead-bound concatenated DNA barcode is coupled to the bead at locations that are substantially on the exterior of the bead and sparingly at interior locations of the bead, and wherein the bead also comprises a plurality of coupled compounds wherein all of the plurality of coupled compounds have substantially an identical structure, when compared to each other, and wherein the bead is comprised substantially of a hydrophobic polymer.

In further methods embodiments, what is provided is the above method, further comprising: (a) The step of providing a bead with a coupled first longer polynucleotide that comprises a $1^{st}$ DNA barcode module, a $1^{st}$ annealing site, a $2^{nd}$ DNA barcode, and a $2^{nd}$ annealing site, wherein the $2^{nd}$ annealing site is capable of hybridizing with a second splint oligo, the second splint oligo being capable of serving as a template for DNA polymerase to catalyze the polymeraztion to the coupled first longer polynucleotide, nucleotides that are complementary to those of the hybridized second splint oligo, wherein the polymerized nucleotides that are complementary to those of the hybridized second splint oligo following polymerization comprise a bead-bound $3^{rd}$ DNA barcode module and a $3^{rd}$ annealing site; (b) The step of providing said bead with a coupled polynucleotide with said $2^{nd}$ splint oligo, and allowing said $2^{nd}$ splint oligo to hybridize with said coupled first longer polynucleotide; (c) The step of adding a DNA polymerase and deoxynucleotide triphosphates (dNTPs) and allowing DNA polymerase to catalyze polymerization of said dNTPs to the coupled longer polynucleotide, wherein the coupled longer polynucleotide has a free 3'-terminus and wherein the polymerization is to the free 3'-terminus, (d) The step of washing away the second splint oligo.

This relates to the consecutive numbering of the first DNA barcode module, the second DNA barcode module, the third DNA barcode module, and so on, for the manufacture of the entire DNA barcode. This also relates to repeating the cycle of methods steps, over and over and over, in the manufacture of the entire DNA barcode. What is provided is the above method, wherein each of said plurality of DNA barcode modules is identified or named by a number, the method further comprising reiterating the recited steps, where for a first reiteration, the name of the DNA barcode module is increased by adding one number to the existing name, the name of the annealing site is increased by adding one number to the existing name, and the name of the splint oligo is increased by adding one number to the name o the existing distal terminal DNA barcode module, and the name of the "first longer polynucleotide" is changed by adding one number to the existing name, wherein the comprising reiterating the recited steps is one reiteration, or two reiterations, or three reiterations, or four reiterations, or five reiterations, or more than five reiterations, or more than ten reiterations.

Also contemplated is the above method, that comprises a plurality of splint oligos, wherein each splint oligo comprises a sequencing primer annealing site, wherein the sequencing primer annealing site is capable of hybridizing to a sequencing primer resulting in a hybridized sequencing primer, and wherein the hybridized sequencing primer is capable of directing the sequencing of the at least one bead-bound DNA barcode module and at least one bead-bound DNA barcode module.

This concerns embodiments relating to splint oligos that guides DNA polymerase to synthesize functional nucleic acids and various types of informative nucleic acids. What is provided is the above method, wherein at least one splint oligo comprises a functional nucleic acid, or wherein at least one splint oligo encodes information other than information on a chemical library monomer. What is provided is the above method, further comprising the step of coupling of at least one DNA barcode module by way of click chemistry, wherein the step does not use any splint oligo.

Briefly stated, the present disclosure provides a system for screening chemical compounds, comprising: (a) A picowell array plate comprising a plurality of picowells, wherein each picowell has a top aperture that defines an opening at the top of the picowell, a bottom that is defined by a floor, wherein the top aperture is separated from the floor, and wherein a wall resides in between the top aperture and the floor; (b) At least one bead disposed in at least one picowell, wherein the at least one bead comprises a plurality of substantially identical bead-bound DNA barcodes, and a plurality of substantially identical bead-bound compounds, (c) Wherein the at least one bead comprises a DNA barcode that takes the form of either a concatenated DNA barcode or an orthogonal DNA barcode, and wherein if the DNA barcode takes the form of a concatenated DNA barcode the concatenated DNA barcode is made using a method that: (i) Uses click chemistry, or (ii) Uses a repeating cycle of steps, wherein the steps in the repeating cycle comprise using a splint oligo for annealing to a partially made DNA barcode, wherein the annealed splint oligo is used as a template for extending the partially made DNA barcode using DNA polymerase, and wherein the splint oligo contains bases that are complementary to a DNA barcode module that is to be polymerized to the partially made DNA barcode.

In another aspect, what is provided is the above system, wherein the DNA barcode comprises: (a) One or more DNA barcode modules wherein each of the one or more DNA barcode modules encodes information on the identity of a chemical library monomer, and (b) Optionally one or more functional nucleic acids, and (c) Optionally, one or more nucleic acids that encode information that a type of information other than information on the identity of a chemical library monomer.

Moreover, what is provides is the above system, further comprising a plurality of caps, each capable of fitting into the opening of a different picowell, and each capable of minimizing or preventing evaporation of fluid that is inside of the picowell, and each capable of minimizing or preventing leakage of fluid that is inside of the picowell.

Also embraced is the above system, further comprising a plurality of spherical caps, wherein each is capable of fitting into the aperture of a picowell wherein the aperture is circular, and each capable of minimizing or preventing evaporation of fluid that is inside of the picowell, and each capable of minimizing or preventing leakage of fluid that is inside of the picowell.

Also contemplated is the above system, wherein if the at least one bead comprises a DNA barcode that takes the form of a concatenated DNA barcode, the concatenated DNA barcode comprises: (i) A sequencing primer binding site, (ii) A first DNA barcode module, (iii) A first annealing site that is capable of hybridizing with a first oligonucleotide splint, wherein the first oligonucleotide splint is capable of being used to guide the enzymatic synthesis of a second DNA barcode module, (iv) A second DNA barcode module, (v) A second annealing site that is capable of hybridizing with a second oligonucleotide splint, wherein the second oligonucleotide splint is capable of being used to guide the synthesis of a third DNA barcode, (vi) A third DNA barcode module, (vii) A third annealing site that is capable of hybridizing with a third oligonucleotide splint, wherein the third oligonucleotide splint is capable of being used to synthesize a fourth DNA barcode.

In methods embodiments, what is provided is a method for screening a compound library for compounds having desired properties, comprising: (a) providing a plurality of beads, wherein each bead comprises a plurality of oligonucleotides attached to the bead surface and a plurality of substantially related compounds attached to the bead surface, and wherein the sequence of the oligonucleotides attached to the beads encodes the synthesis history of the plurality of substantially related compounds attached to the bead surface; (b) incorporating the plurality of beads in an assay for desired properties of compounds in the compound library; (c) capturing a signal from at least one bead, wherein the signal reflects the performance of the compounds on the bead in the assay; (d) sequencing the plurality of oligonucleotides attached to the at least one bead for which assay signal was also captured, without removing the oligonucleotides from the bead; and (e) identifying at least one compound from the sequencing readout of step (d) and relating it to its corresponding assay performance captured in the signal of step (c).

In further detail, what is embraced is the above method, wherein the assay comprises a binding assay, or wherein the assay comprises an activity assay, or wherein the assay comprises a competitive binding assay or a competitive inhibition assay, or wherein the assay comprises interaction of untethered compounds with other assay reagents, wherein the untethered compounds are compounds released from the bead surface, or wherein the compounds are released by cleaving a cleavable linker that connects the compounds to the beads, or wherein the assay occurs in a plurality of confined volumes, wherein nominally one bead is dispersed per confined volume.

In another aspect, what is further contemplated, is the above method, wherein the confined volume comprises an aqueous droplet, or wherein the aqueous droplet is suspended in an oil medium or a hydrophobic liquid medium, or wherein the confined volume comprises a picowell, or wherein the picowells are organized in a regular array, or wherein the plurality of confined volumes are organized in a regular array.

Moreover, what is further embraced is the above method, wherein the confined volume comprises a layer of adherent aqueous medium around the bead, wherein the bead is suspended in a hydrophobic medium, and the above method, wherein the assay reagents are washed away before sequencing the oligonucleotides. And the above method wherein the sequencing step (d) is performed before the assay step (b). What is also provided is the above method, wherein the oligonucleotides on the beads are removed after the sequencing step, but before the assay step. Moreover, further contemplated is the above method, wherein the removing of the oligonucleotide comprises an enzymatic digestion, a chemical cleavage, a thermal degradation or a physical shearing, and the above method, wherein the binding assay comprises binding of RNA molecules to the beads, and the above method, wherein the signal from the bead comprises sequencing of the bound RNA molecules.

In yet another aspect, what is provided is the above method, wherein the binding assay comprises a fluorescently labeled binding assay, wherein the molecules binding to the compounds on the beads comprise fluorophores, or the above method, wherein the binding assay comprises nucleic-acid labeled binding assay, wherein the molecules binding to the compounds on the beads comprise nucleic-acid tags, wherein further the signal from the assay comprises sequencing of the nucleic acid tags attached to the molecules binding to the compounds on the beads.

In yet a methods embodiment relating to properties, what is provided is the above method, wherein the desired properties include one or more of: (i) Inhibiting or stimulating the catalytic activity of an enzyme, (ii) Stimulating Th1-type immune response, as measurable by cell-based assays or by in vivo assays, (iii) Stimulating Th2-type immune response, as measurable by cell-based assays or by in vivo assays, (iv) Inhibiting Th1-type immune response, as measurable by cell-based assays or by in vivo assays, (v) Inhibiting Th2-type immune response, as measurable by cell-based assays or by in vivo assays, (vi) Stimulating or inhibiting ubiquitin-mediated degradation of a protein, as measurable by purified proteins, by cell-based assay, or by in vivo assays.

In a system embodiment, what is provided is a system for screening a compound library for a compound having a desired activity, comprising: (a) a sample compartment for receiving a plurality of compound-attached, oligonucle-otide-encoded beads; (b) a plurality of encapsulation compartments within the sample compartment, each encapsulation compartment nominally comprising a single bead dispersed in an assay medium, wherein further the assay medium comprises reagents whose interaction with the compounds on the beads is being assayed resulting in a measurable signal; (c) a detector for measuring signals; (d) a sequencing platform; and (e) a user interface for receiving one or more commands from a user. Also provided is the above system, wherein the encapsulation compartment comprises a liquid droplet. In another aspect, provided is the above system, wherein the encapsulation compartment comprises a picowell, or wherein further the encapsulation compartment comprises assay reagents, or wherein the detector comprises an optical detector, or wherein the sequencer comprises the optical detector.

In one aspect, the disclosure features a method for perturbing a cell by: (a) providing a nucleic-acid encoded perturbation and confining a cell with the nucleic-acid encoded perturbation; (b) contacting the cell with the nucleic-acid encoded perturbation in a confined volume, wherein the perturbation initiation and dose are controlled; (c) incubating the cell with the nucleic-acid encoded perturbation for a specified period of time; and (d) transferring the nucleic acid that encodes the nucleic-acid encoded perturbation to the cell.

In some embodiments of this aspect, the nucleic-acid encoded perturbation is a nucleic acid encoded compound or drug molecule. In some embodiments, the nucleic-acid encoded perturbation is a DNA-encoded library.

In some embodiments, the perturbation and the nucleic acid encoding the perturbation are unattached and free in solution. In some embodiments, the perturbation and the nucleic acid encoding the perturbation are attached to each other. In some embodiments, the perturbation and the nucleic acid encoding the perturbation are attached to the same substrate but not to each other. In some embodiments, the attachment of the perturbation to the substrate and the attachment of the nucleic acid to the substrate are cleavable attachments. In particular embodiments, the cleavable attachment is selected from the group consisting of a pho-tocleavable attachment, a temperature cleavable attachment, a pH sensitive attachment, an acid cleavable attachment, a base cleavable attachment, a sound cleavable attachment, a salt cleavable attachment, a redox sensitive attachment, or a physically cleavable attachment.

In some embodiments of this aspect of the disclosure, confining the cell and the perturbation comprises a droplet encapsulation, an emulsion encapsulation, a picowell encapsulation, a macrowell encapsulation, a physical attachment, a bubble encapsulation, or a microfluidic confinement.

In some embodiments, the control over the perturbation comprises controlling light exposure, controlling temperature exposure, controlling pH exposure, controlling time exposure, controlling sound exposure, controlling salt exposure, controlling chemical or physical redox potential, or controlling mechanical-agitation exposure.

In particular embodiments, the incubation comprises exposing the cell to the perturbation after cleaving the perturbation from the substrate or after cleaving the nucleic acid from the substrate. In some embodiments, the incubation comprises exposing the cell to the perturbation without cleaving the perturbation from the substrate or without cleaving the nucleic acid from the perturbation.

In some embodiments, transferring the nucleic acid that encodes the nucleic-acid encoded perturbation to the cell comprises attaching the nucleic acid to the cell surface of the cell. In particular embodiments, attaching the nucleic acid to the cell surface of the cell comprises intercalating the nucleic acid into the cell membrane. In particular embodiments, attaching the nucleic acid to the cell surface of the cell comprises attaching the nucleic acid to a biomolecule on the cell surface. In particular embodiments, the biomolecule is a protein or a carbohydrate. In other embodiments, attaching the nucleic acid to the cell surface of the cell comprises attaching through an optional tag on the nucleic acid.

In another aspect, the disclosure features a method for perturbing a cell with a perturbation and encoding the cell with the identity of the perturbation. The method includes: (a) providing a bead-bound DNA encoded library; (b) confining a cell with the bead-bound DNA encoded library, wherein the bead-bound DNA encoded library comprises one or more copies of a combinatorially synthesized compound and one or more copies of an encoding nucleic acid tag, wherein the compound and the encoding nucleic acid are attached to a bead, wherein the encoding nucleic acid encodes the identity of the compound, and wherein the bead-bound DNA encoded library and the cell are confined in a confining volume; (c) releasing the compound from the bead and incubating the compound with the cell inside the confining volume; (d) optionally releasing the encoding nucleic acid tag from the bead; and (e) attaching the encoding nucleic acid tag to the cell, thereby preserving the identity of the compound through the encoding nucleic acid tag attached to the cell.

In yet another aspect, the disclosure features a method for perturbing a cell, encoding the cell with the identity of the perturbation, and measuring a response of the cell to the perturbation. The method includes: (a) contacting a cell with a bead-bound DNA encoded library in a first confined volume, wherein the bead-bound DNA encoded library comprises one or more copies of a combinatorially synthe-sized compound and one or more copies of an encoding nucleic acid tag, wherein the compound and the encoding nucleic acid are attached to a bead, and wherein the encoding nucleic acid encodes the identity of the compound; (b)

releasing the compounds in the library from the bead and incubating the compounds in the library with the cell inside the first confined volume; (c) optionally releasing the encoding nucleic acid tag from the bead inside the first confined volume; (d) capturing the encoding nucleic acid tag to the cell surface of the cell, whereby the cell is exposed to the compound in the library and the identity of the compound exposed is captured on to the cell surface; (e) releasing the cell from the first confining volume, wherein the encoding nucleic acid tags are attached to the cell and the encoding nucleic acid tag encodes the identity of the compound the cell is exposed to; (f) capturing a previously perturbed and nucleic acid tagged cell with a response-detection bead in a second confined volume, wherein the cell is exposed to a lysis condition that exposes the cellular content of the cell to the response-capture bead, wherein the response-capture bead comprises capture probes that capture the cellular content and the nucleic acid tag that encodes the perturbation in the previously perturbed and nucleic acid tagged cell; (g) incubating the response-capture bead with the lysed cell in the second confining volume, thereby capturing both cellular content and the nucleic acid tag that encodes the perturbation on to the response-capture bead; (h) optionally converting the response of the cell to the perturbation to a nucleic acid signal, wherein the response of the cell to the perturbation is not a nucleic acid signal; and (i) sequencing the nucleic acid tag attached to the response-capture bead, thereby correlating the identity of the perturbation to the response of the cell to the perturbation.

In still another aspect, the disclosure features a method for perturbing a cell and capturing a response of the cell to the perturbation by: (a) providing an array of picowells and a library of functionalized perturbation beads, wherein the picowells are capable of accommodating a single cell and a single functionalized perturbation bead, wherein each functionalized perturbation bead comprises a different plurality of substantially identical releasable compounds and a plurality of nucleotide barcodes that encodes the compounds, wherein the nucleotide barcodes are functionalized barcodes capable of capturing cellular content of the cell, wherein the cellular content of cell comprises cellular response to the perturbations contained in the functionalized perturbation beads; (b) capturing single cells into each picowell of the picowell array; (c) capturing single functionalized perturbation beads to the picowells containing single cells; (d) releasing the compounds from the functionalized perturbation beads and incubating the cells with the released compounds, wherein the compounds between picowells have minimal diffusion; (e) lysing the cells to release the cellular contents; (f) capturing one or more components of the cellular content onto functionalized oligonucleotides on the functionalized perturbation beads, wherein the capturing comprises hybridization and enzymatic extension to combine nucleotide barcodes with nucleic acid elements of the cellular content, thereby forming a hybrid of the nucleotide barcode and the nucleic acid element of the cellular content; and (g) releasing the hybrid, collecting the hybrid from the library of functionalized perturbation beads, and sequencing the hybrid, thereby relating the perturbation to the cellular response to the perturbation.

BRIEF DESCRIPTIONS OF THE DRAWINGS

FIG. 1. Concatenated-style bead. In concatenated-style bead, the DNA barcode takes the form of all of the DNA barcode modules connected to each other in a single chain, together with any other nucleic acids that have functions, such as primer annealing sites, as a spacer, or information on date of manufacture. The numbers on this figure are not structure numbers. The numbers refer to the sequence of "DNA barcode modules" in the DNA barcode.

Figure 2:
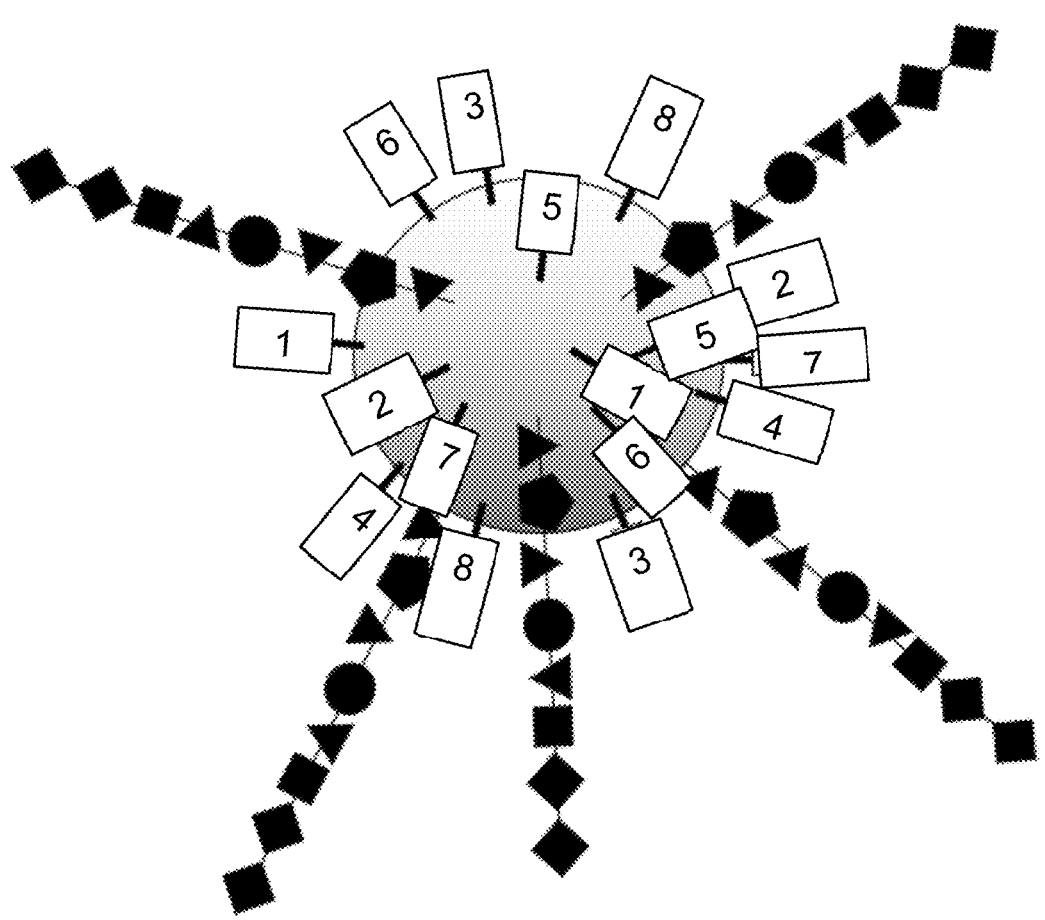

FIG. 2. Orthogonal-style bead. In orthogonal-style bead, the DNA barcode takes the form of all of the DNA barcode modules, where the DNA barcode modules do not occur together in a single chain, but instead occur separately linked to different positions on the bead. The numbers on this figure are not structure numbers. The numbers refer to the sequence of "DNA barcode modules" in the DNA barcode.

Figure 3:
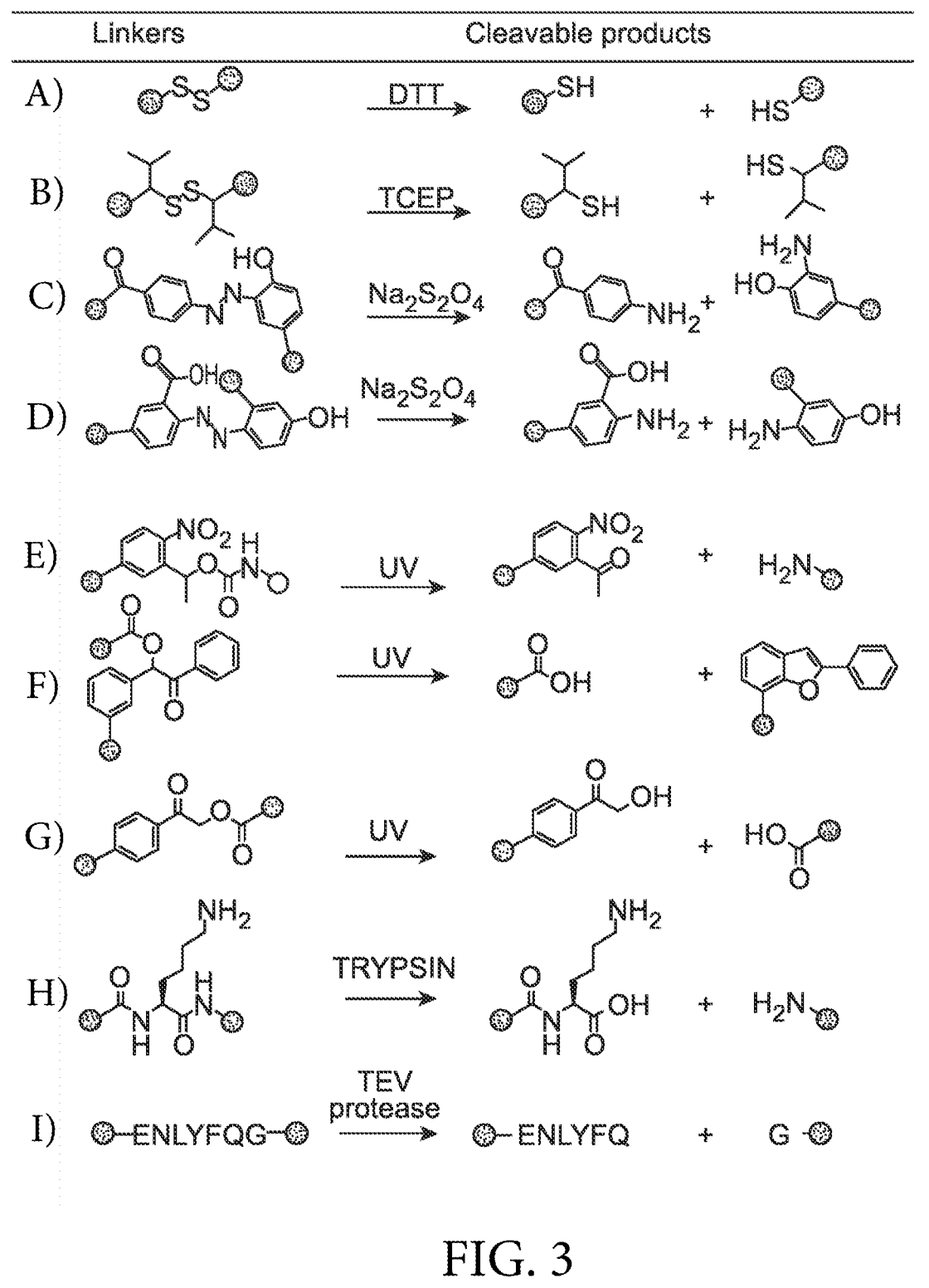

FIG. 3. Cleavable linkers, conditions for cleavage (UV light or chemical), and cleavage products. Information from, Yinliang Yang (2014) Design of Cleavable Linkers and Applications in Chemical Proteomics. Technische Universitat Munchen Lehrstuhl fur Chemie der Biopolymere. The alphabet letter to the left of each linker is from this reference.

Figure 4:
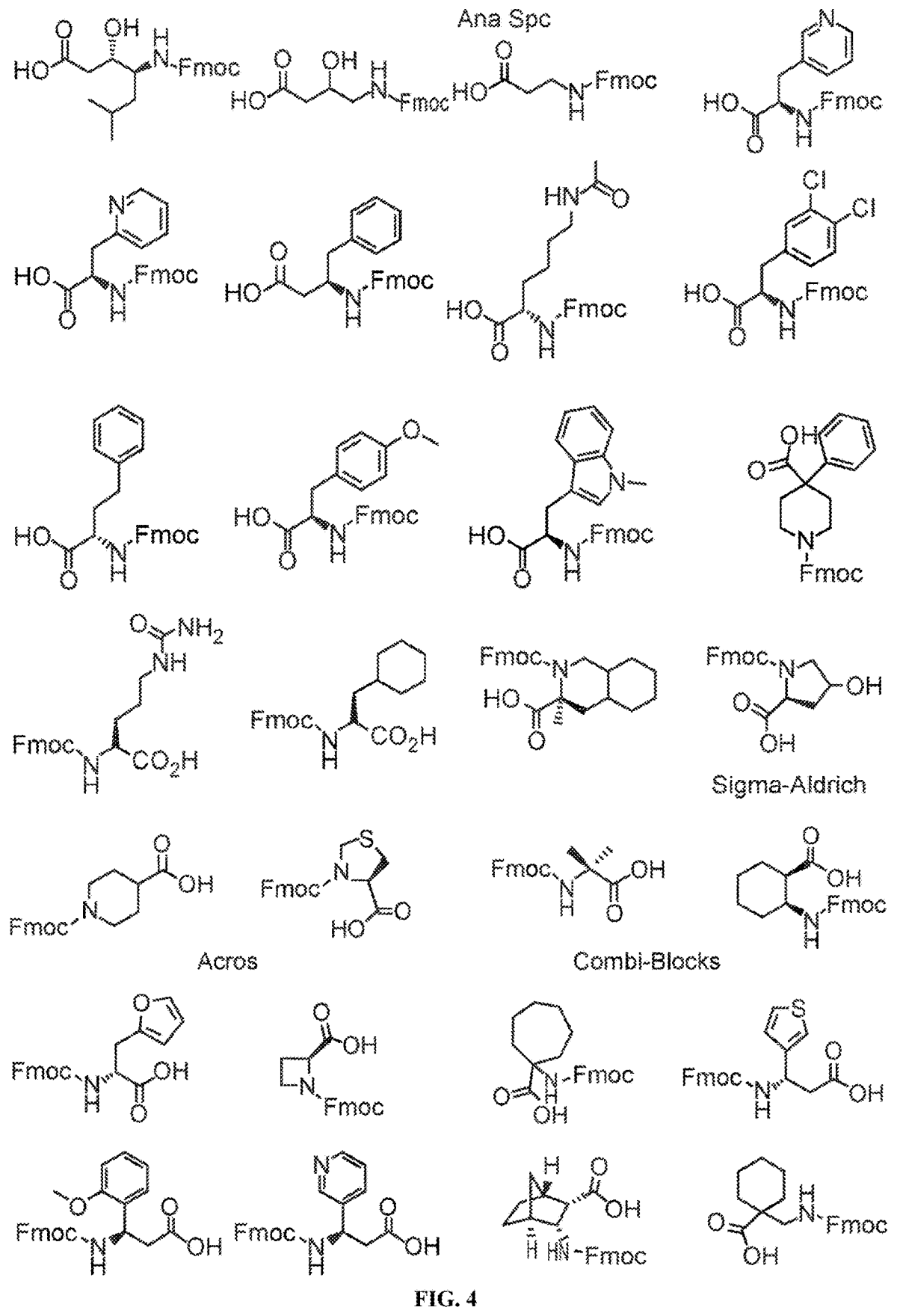

FIG. 4. Exemplary amino acid derivatives for the compositions and methods of the present disclosure.

FIGS. 5A-5H. The photograph discloses increases in degradation of a fusion protein, inside HeLa cells, with increasing concentrations of added lenalidomide. Top: Expression of IKZF1/GFP fusion protein. Bottom: Expression of mScarlett® control. Lenalidomide was added at zero, 0.1, 1.0, or 10 micromolar.

Figure 6:
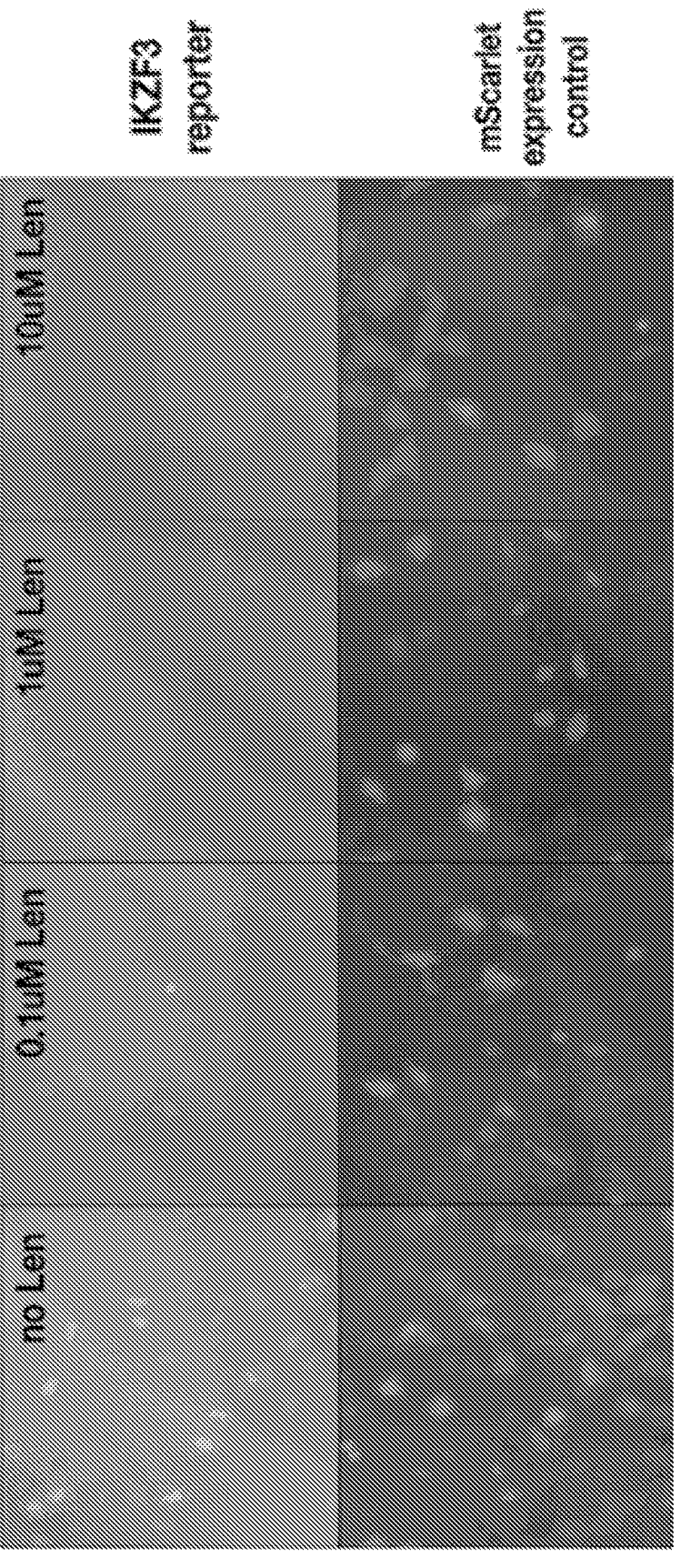

FIG. 6. The photograph discloses increases in degradation of a fusion protein, inside HeLa cells, with increasing concentrations of added lenalidomide. Top: Expression of IKZF3/GFP fusion protein. Bottom: Expression of mScarlett control. Lenalidomide was added at zero, 0.1, 1.0, or 10 micromolar.

Figure 7:
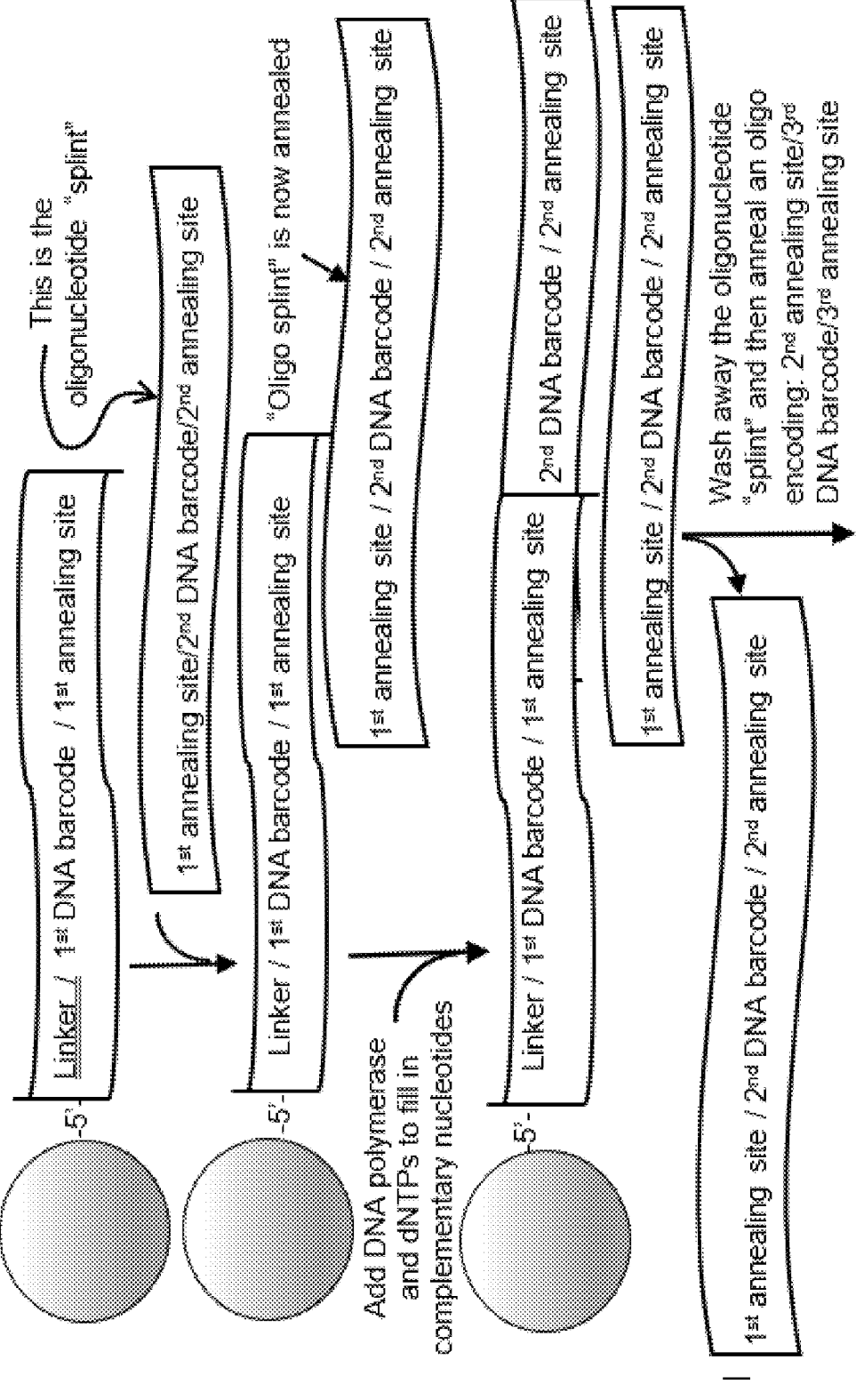

FIG. 7. Methods and reagents for creating bead-bound DNA barcode. The most accurate description of "DNA barcode" is the sum of all of the information that is contained in the sum of all DNA barcode modules. But for convenience, the term "DNA barcode" is used herein to refer to the sum of all of the information of all of the DNA barcode modules plus any additional nucleic acids that provide information such as step number, or general type of chemical monomers that make up the bead-bound compound, and plus any additional nucleic acids that serve a function, such as linker, sequencing primer binding site, hairpin with sequencing primer binding site, or spacer. Where a DNA barcode is made, at least in part, by way of click chemistry, the DNA barcode may include residual chemical groups from the click chemistry reactions.

Figure 8:
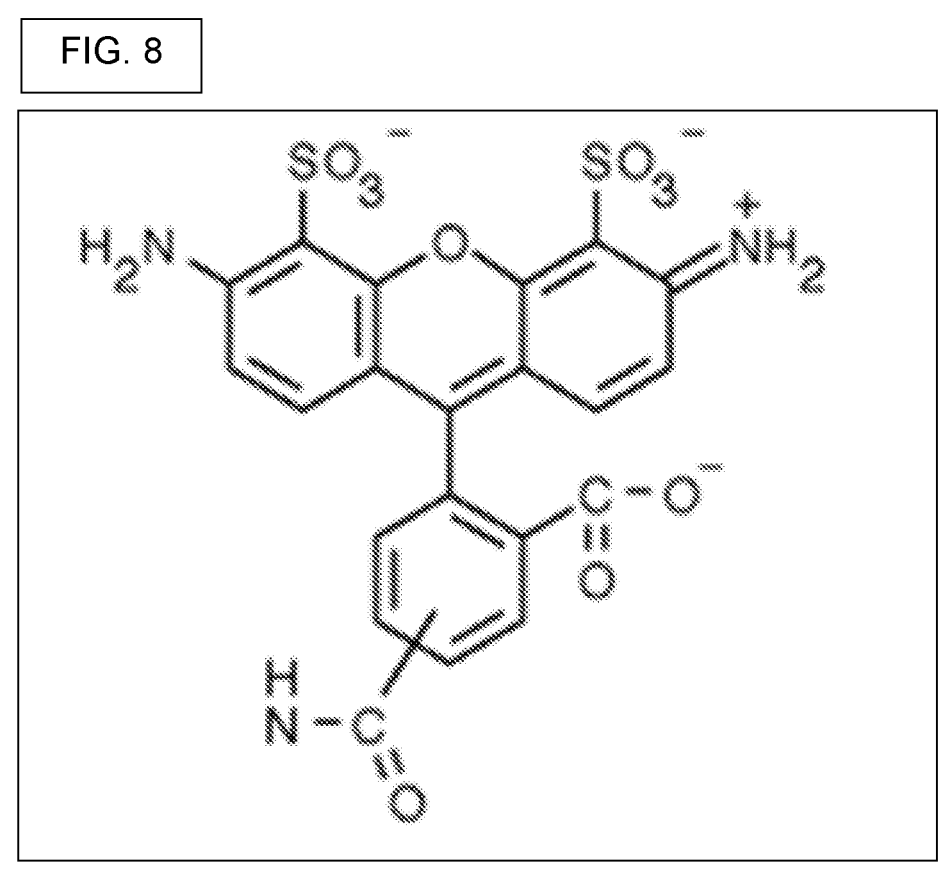

FIG. 8. Structure of Alexa Fluor® 488. A goal of this figure is to identify the compound without having to resort to using the trade name.

Figure 9:
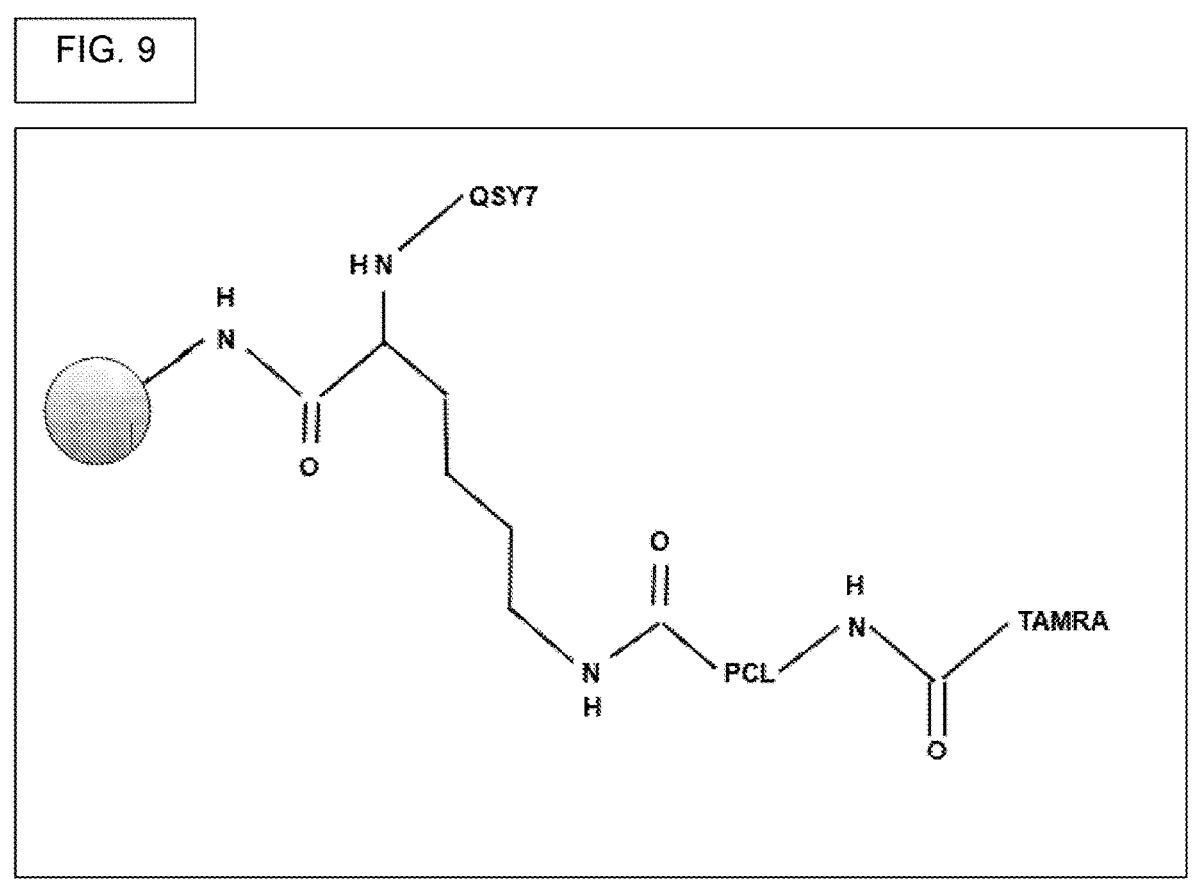

FIG. 9. Simplified diagram of bead-bound release-monitor. The release-monitor provides the user with a measure of the concentration of the soluble compound, following UV-induced release of the compound from the bead. In a preferred embodiment, one type of bead is dedicated to being a release-monitor, that is, this bead does not also contain bead-bound compound and does not also contain bead-bound DNA library. "PCL" is photocleavable linker.

Figure 10:
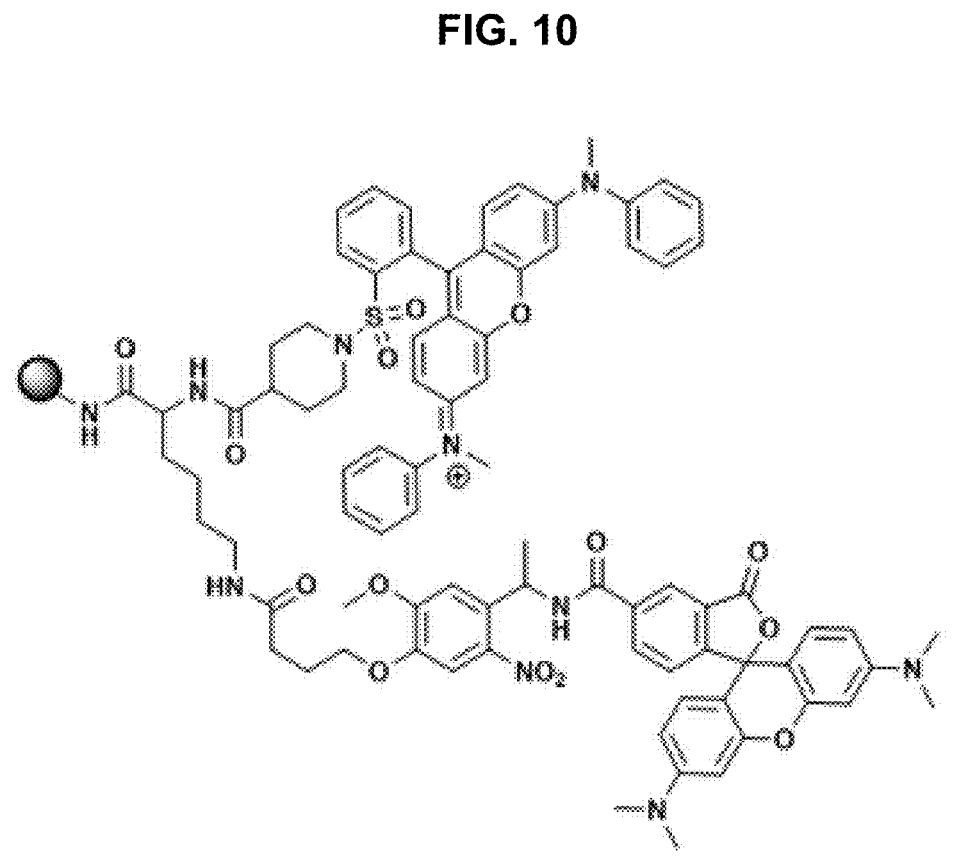

FIG. 10. Detailed diagram of bead release-monitor.

Figure 11:
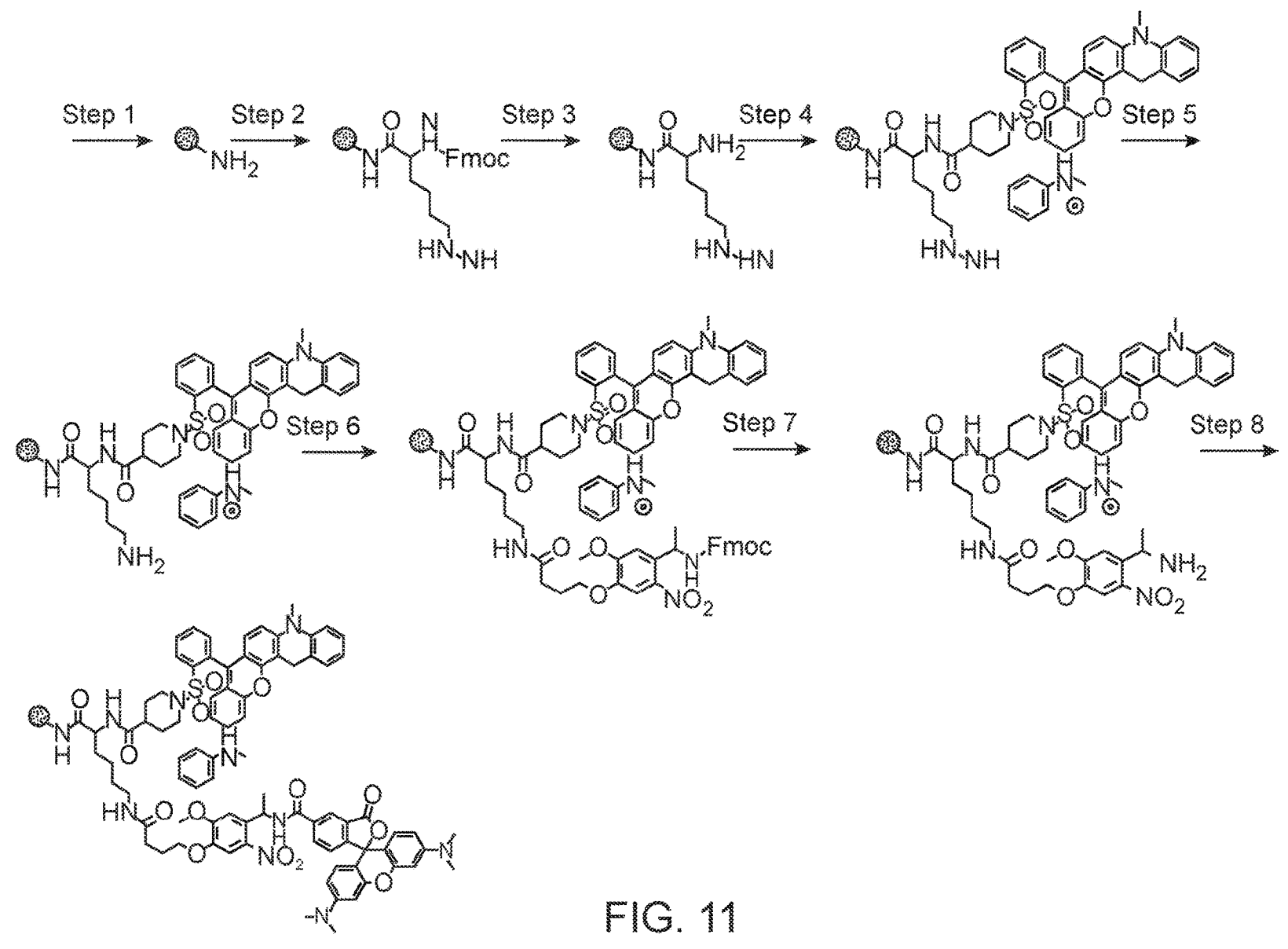

FIG. 11. Chemical synthesis of bead release-monitor.

Figure 12:
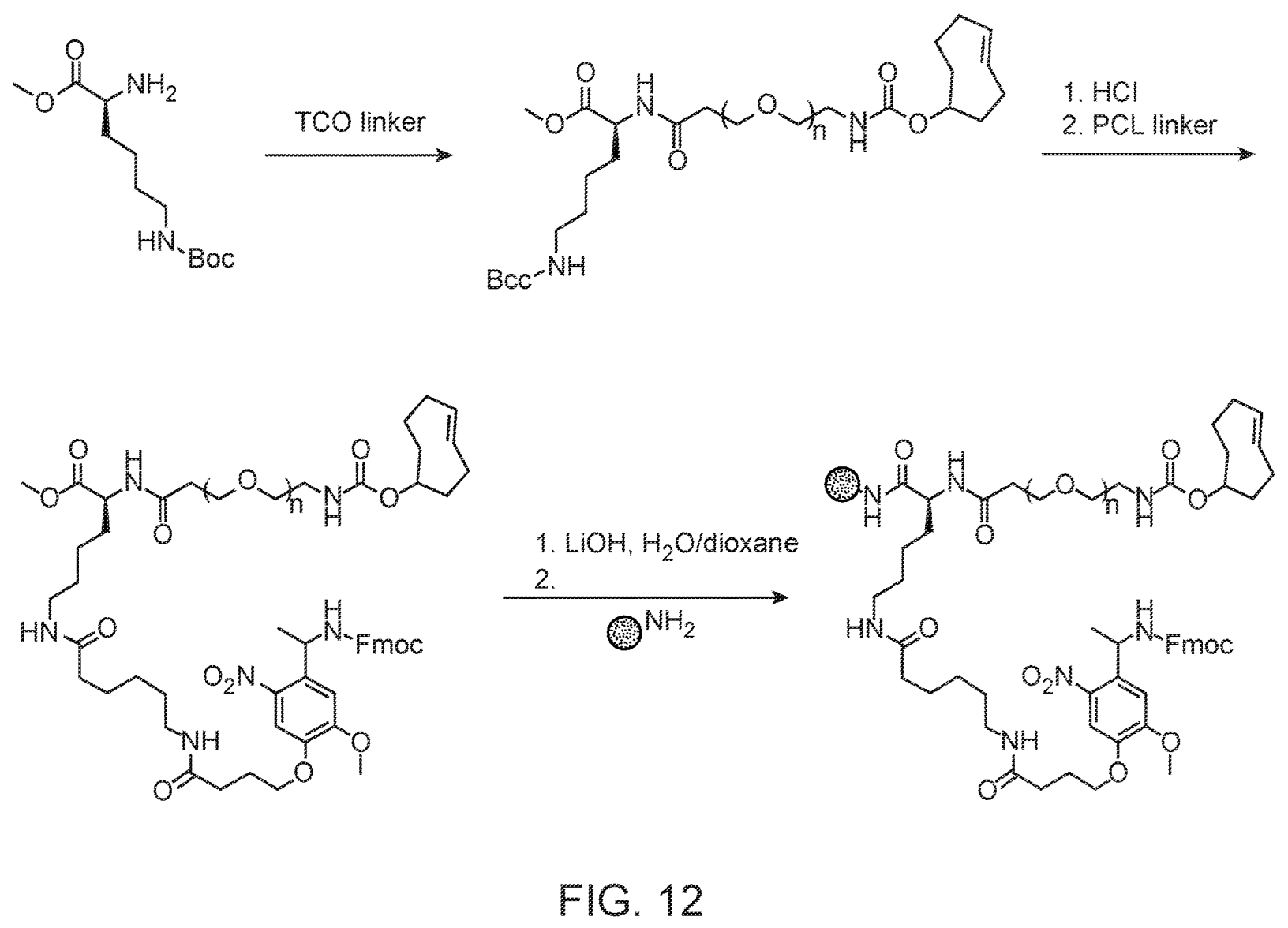

FIG. 12. Amine-functionalized bead with bifunctional linker, where the linker includes a lysine residue.

Figure 13:
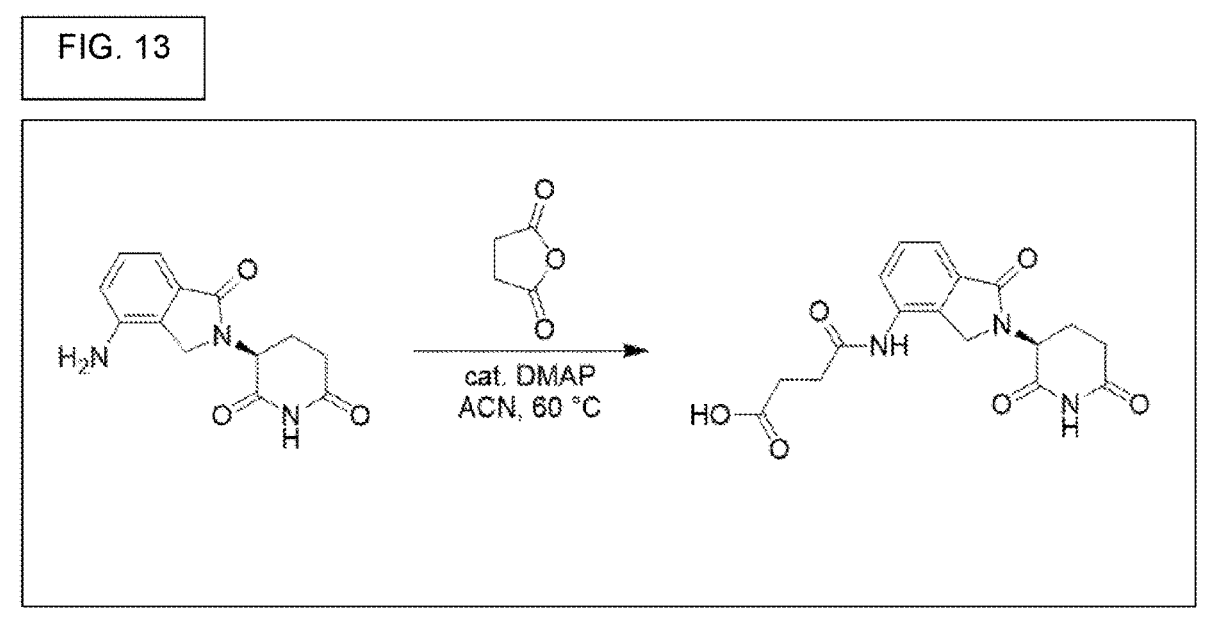

FIG. 13. Steps of chemical synthesis of lenalidomide modified with a first type of carboxyl group.

Figure 14:
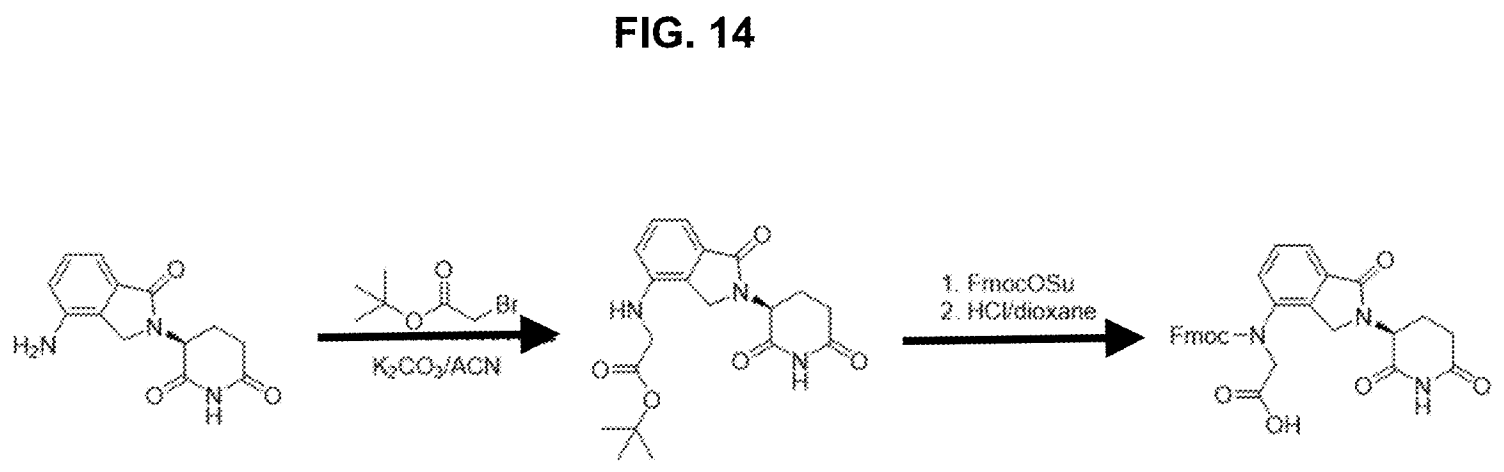

FIG. 14. Steps of chemical synthesis of lenalidomide modified with a second type of carboxyl group.

Figure 15:
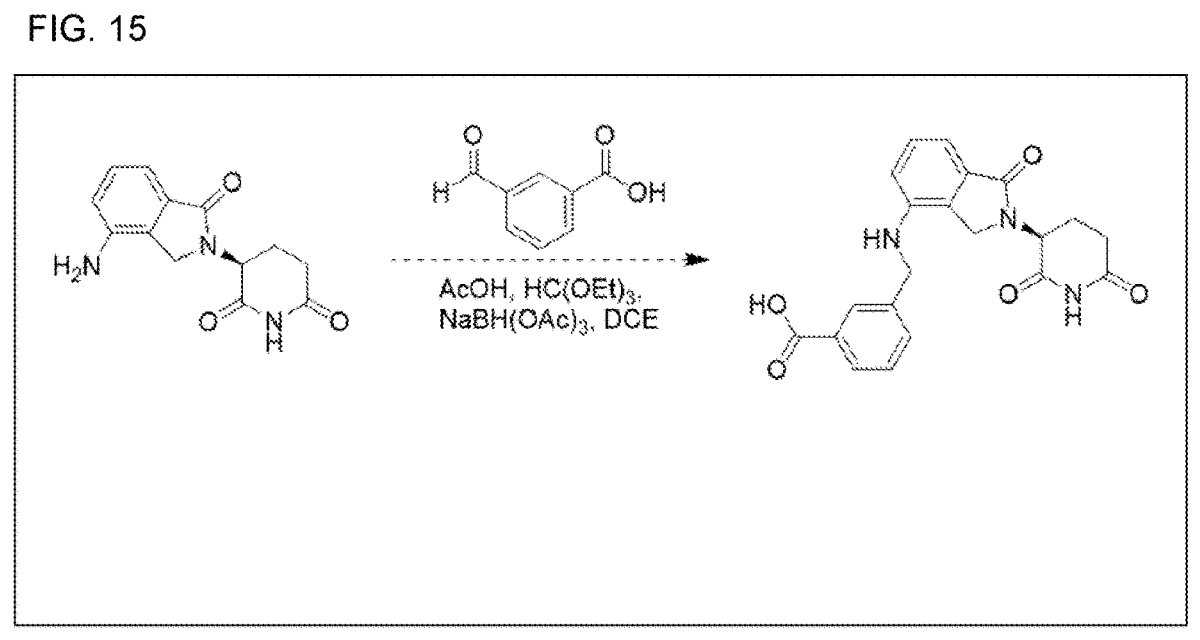

FIG. 15. Steps of chemical synthesis of lenalidomide modified with a third type of carboxyl group.

Figure 16A:
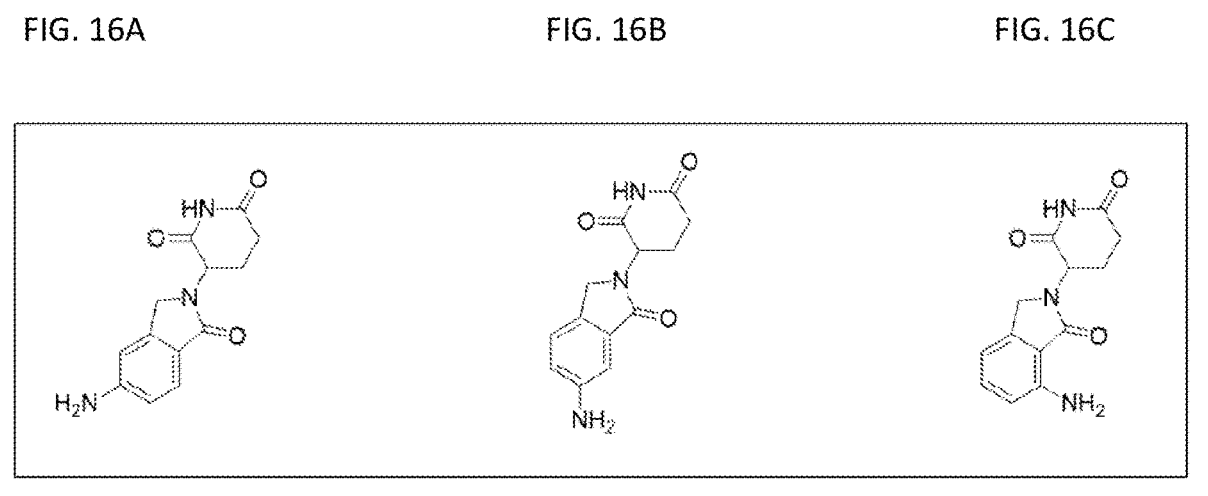

FIG. 16A, FIG. 16B, FIG. 16C. Lenalidomide analogues.

Figure 17:
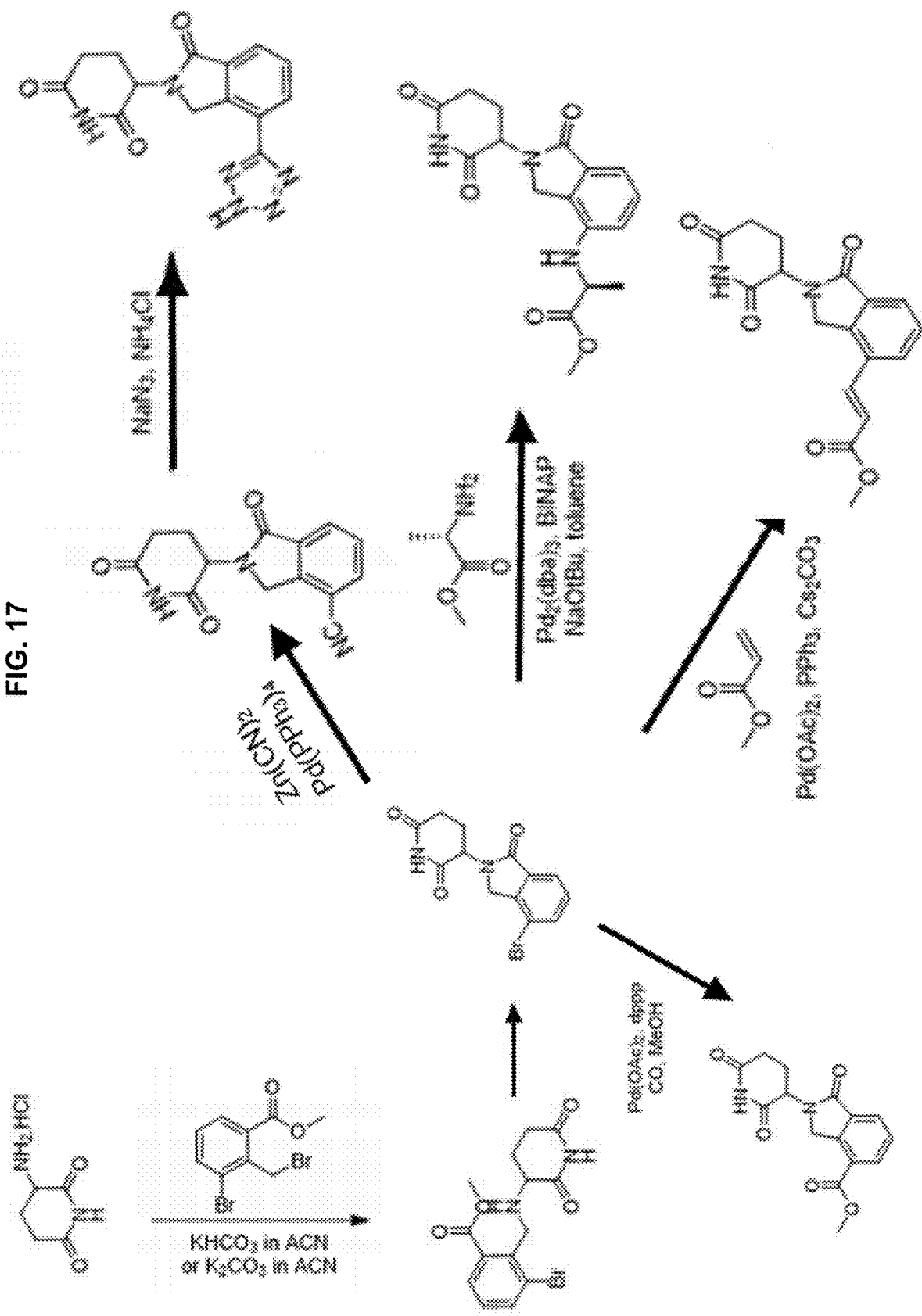

FIG. 17. Steps of chemical synthesis of a deoxycytidine analogue suitable for click-chemistry synthesis of a DNA barcode.

Figures 18A, 18B, 18C:
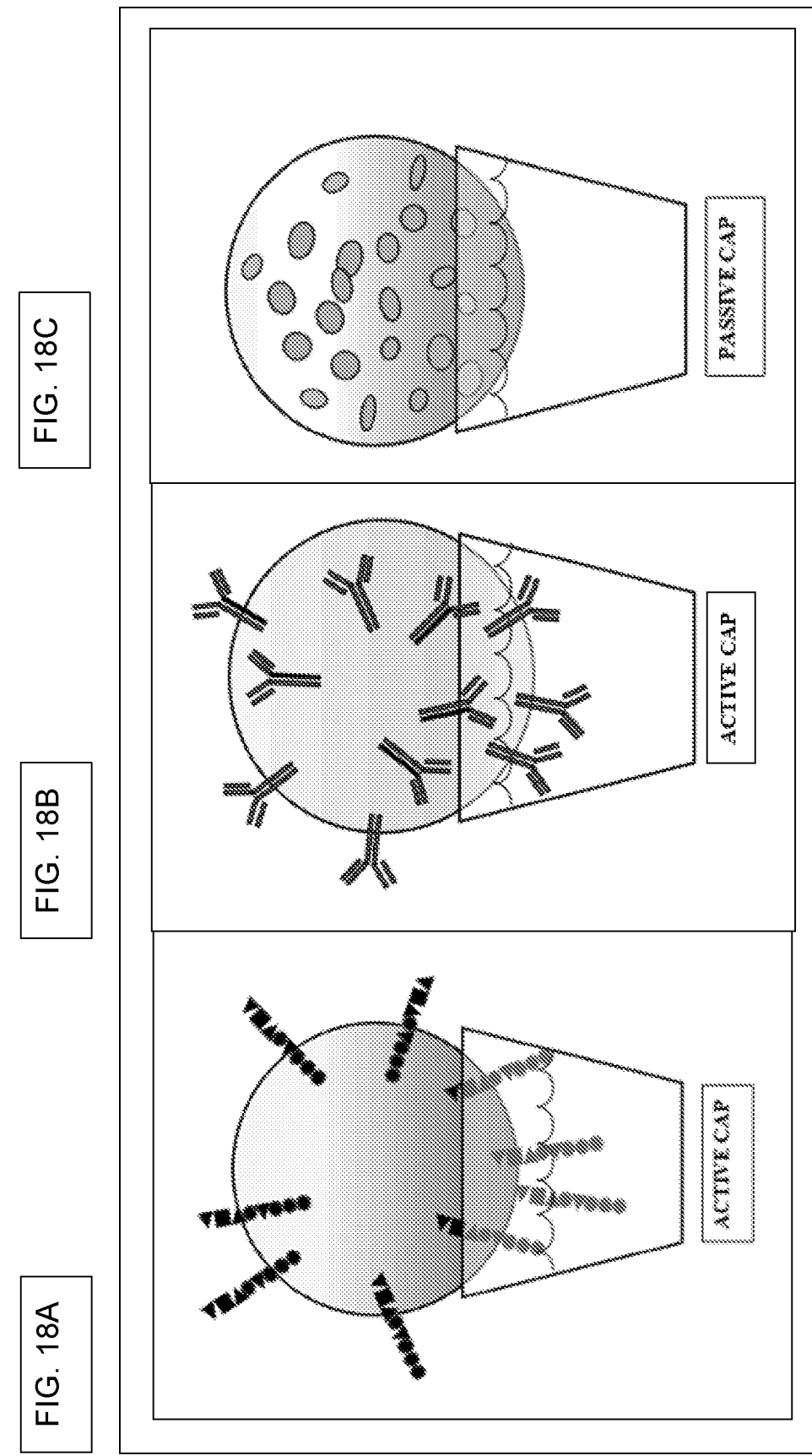

FIGS. 18A, 18B, and 18C. Caps for placing over the top of picowells and for sealing the picowells. FIG. 18A shows active cap, where compound is releasable by way of cleavable linker. FIG. 18B shows another type of active cap, where a reagent such as an antibody is bound. The bound reagent can be permanently linked, it can be linked by a cleavable linker, or it can be bound by way of hydrogen bonds and be releasable merely by exposure to the solution in the picowell followed by diffusion away from the active cap and into this solution. FIG. 18C shows a passive cap, which can be used to absorb, adsorb, collect, or capture metabolites from the solution in the picowell. The absorbed metabolites can subsequently be analyzed.

Figures 19A, 19B:
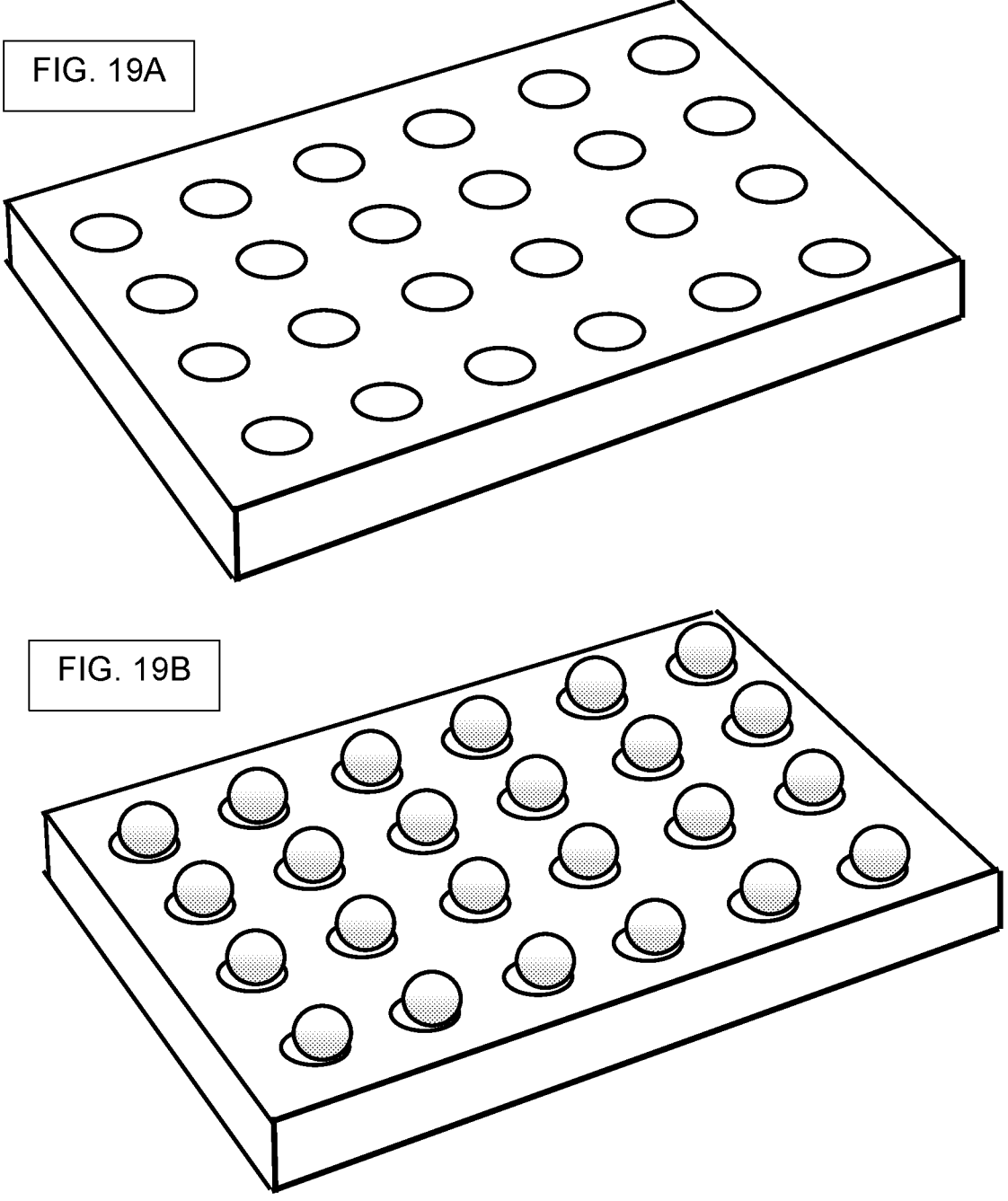
Figure 19C:
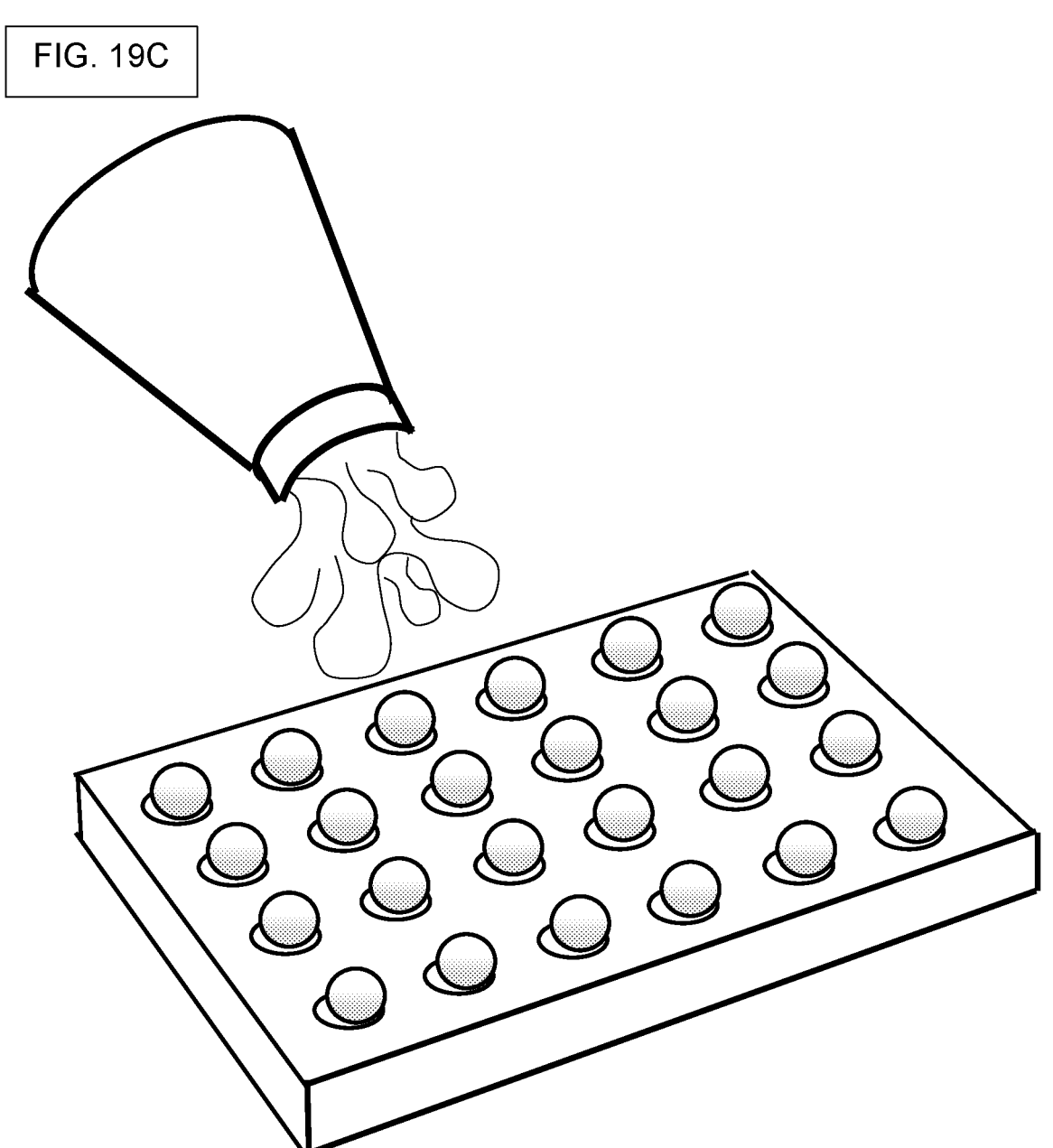
Figure 19D:
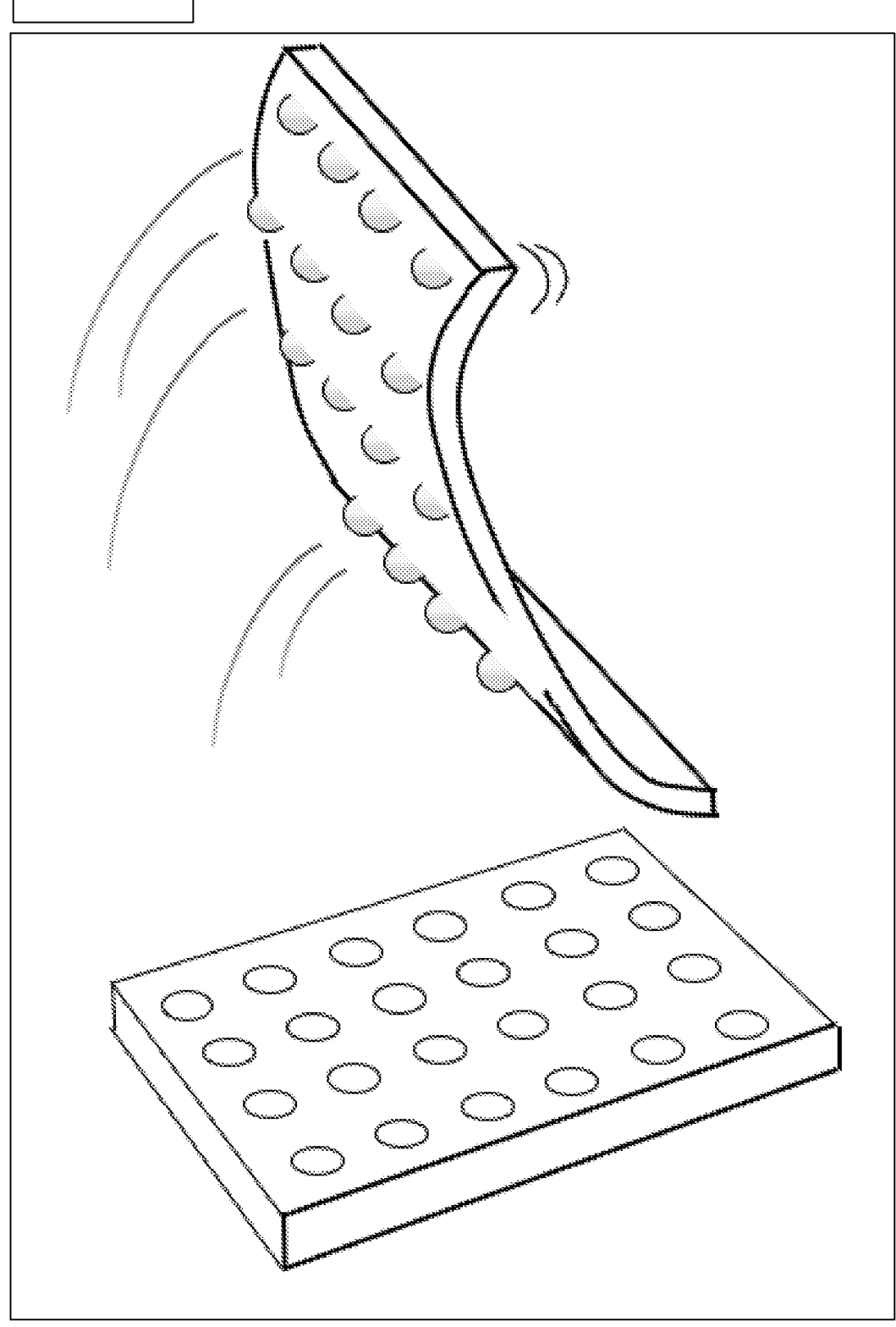

FIGS. 19A, 19B, 19C, and 19D. FIG. 19A Picowell plate without caps over the picowells. FIG. 19B. Picowell plate with a cap over each picowell. FIG. 19C. Polyacrylamide solution being poured over the picowell plate that has one cap securely fastened over each picowell. The polyacrylamide then seeps into the porous cap, solidifies, and forms a stable adhesion to each cap. FIG. 19D. The solidified polyacrylamide "roof" is then peeled off from the picowell plate, bringing with it each cap. The metabolites transferred from the picowell solution and absorbed into each cap can then be analyzed. Preferably, the solution that is poured over the picowell plate and over the bead becomes a hydrogel, and preferably the bead is made from a hydrogel.

In exclusionary embodiments, the present disclosure can exclude a system, microtiter plate, microtiter plate with microwells, nanowells, or picowells, and related methods, where at least one well is capped, and where a liquid polymer solution is poured over the plate and over the capped wells. Also, what can be excluded is the above where the liquid polymer has polymerized to form a solid polymer that adheres to each cap. Also, what can be excluded is the method and resulting compositions, where the solid polymer is torn away, removing with it the adhering caps.

Figure 20:
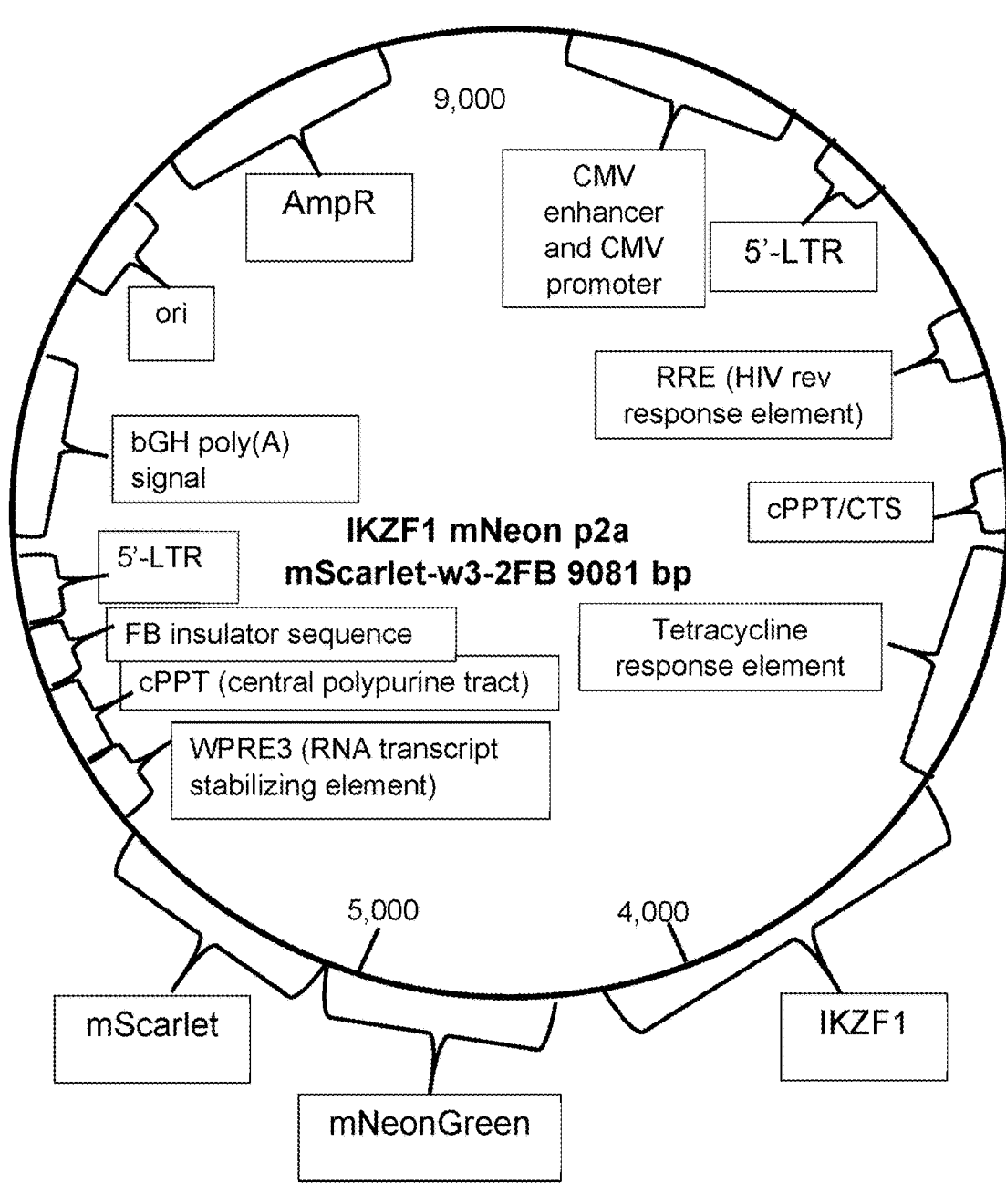

FIG. 20. Map of circular plasmid used for integrating IKZF1 gene into genome of a cell. The plasmid is: IKZF1 mNEON-p2a-mScarlet-w3-2FB (9081 base pairs). IKZF1 encodes the Ikarus protein.

Figure 21:
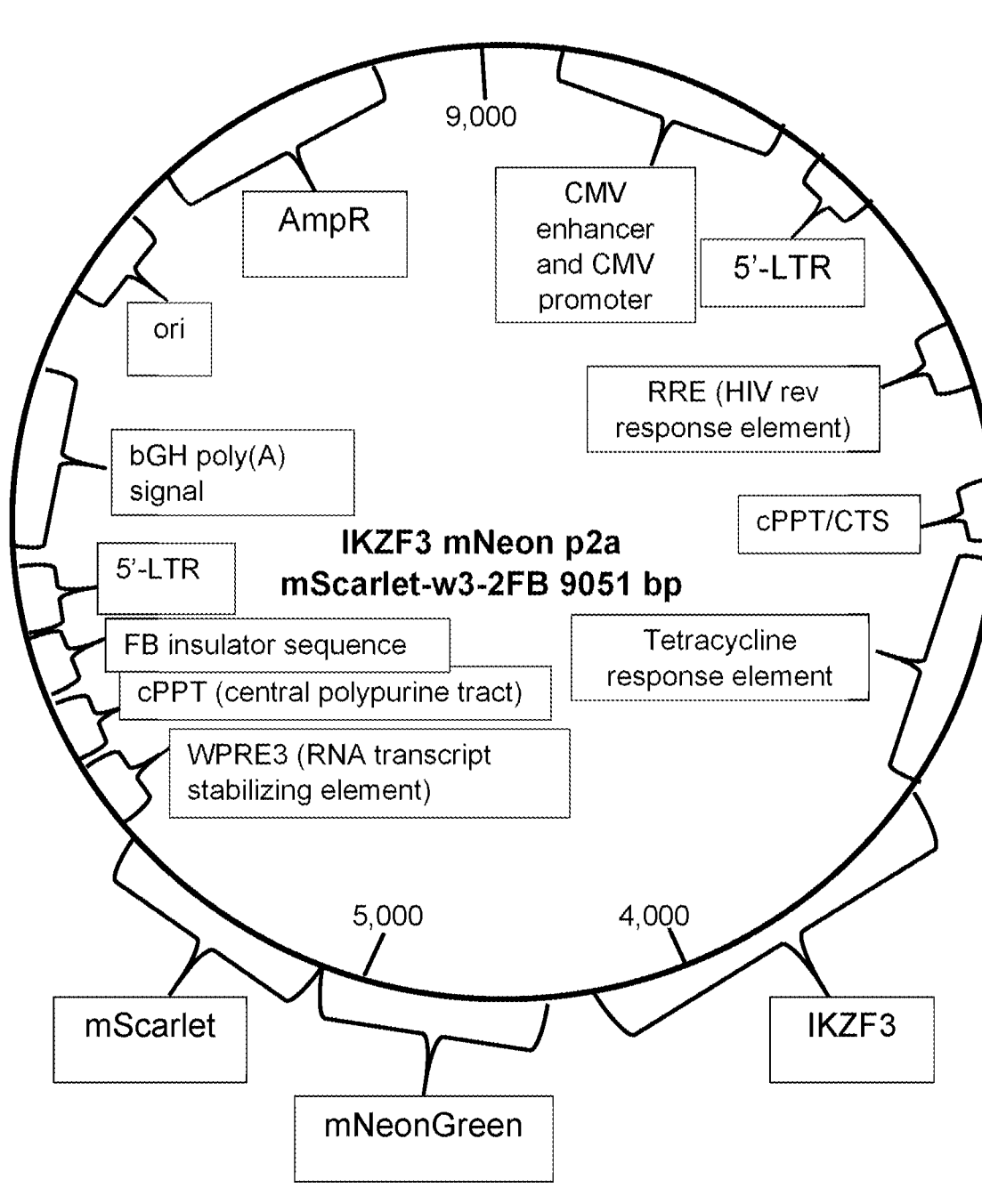

FIG. 21. Map of circular plasmid used for integrating IKZF3 gene into genome of a cell. The plasmid is: IKZF3 mNeon-p2a-mScarlet-w3-2FB (9051 bp). IKZF3 encodes the Aiolos protein.

FIG. 22. Chemical monomers (compounds 1-6) and their DNA barcodes.

Figure 23:
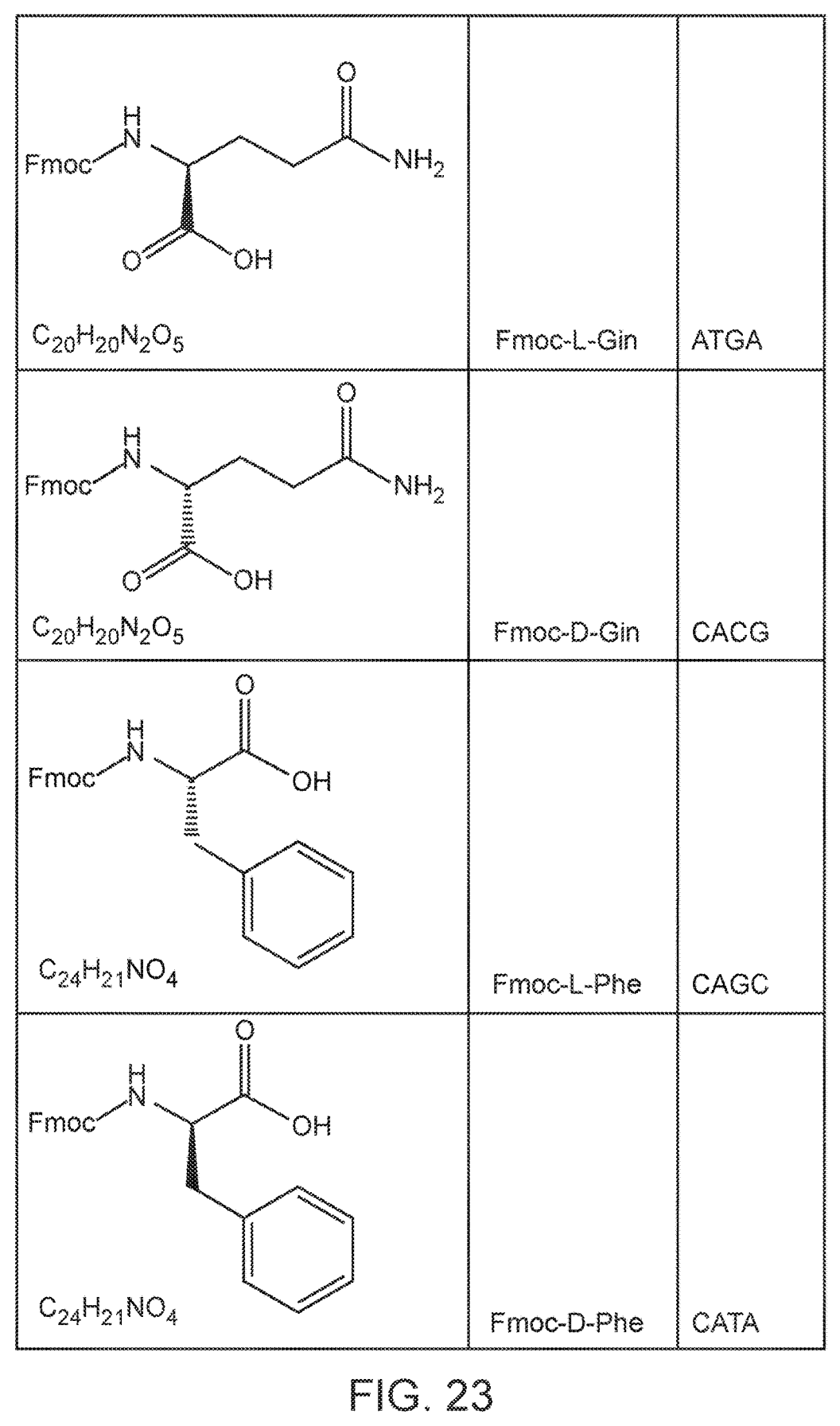

FIG. 23. Chemical monomers (compounds 7-10) and their DNA barcodes.

FIG. 24. Chemical monomers (compounds 11-16) and their DNA barcodes.

FIG. 25. Chemical monomers (compounds 17-21) and their DNA barcodes.

FIG. 26. Chemical monomers (compounds 22-16) and their DNA barcodes.

FIG. 27 Chemical monomers (compounds 27-30) and their DNA barcodes.

Figure 28:
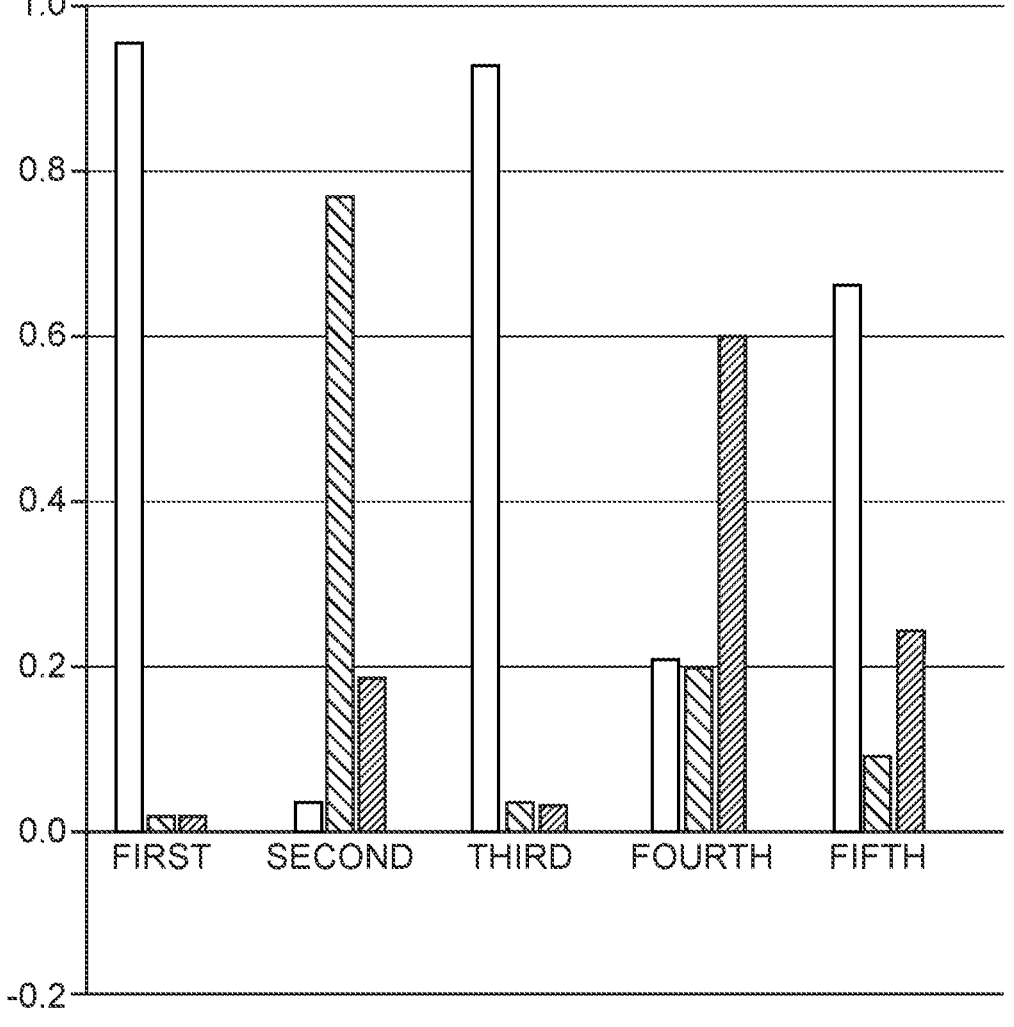

FIG. 28. Sequencing a bead-bound DNA barcode. The figure discloses intensity of fluorescent signal for each of five consecutive bases, where the five consecutive bases are part of a bead-bound DNA barcode.

Figure 29:
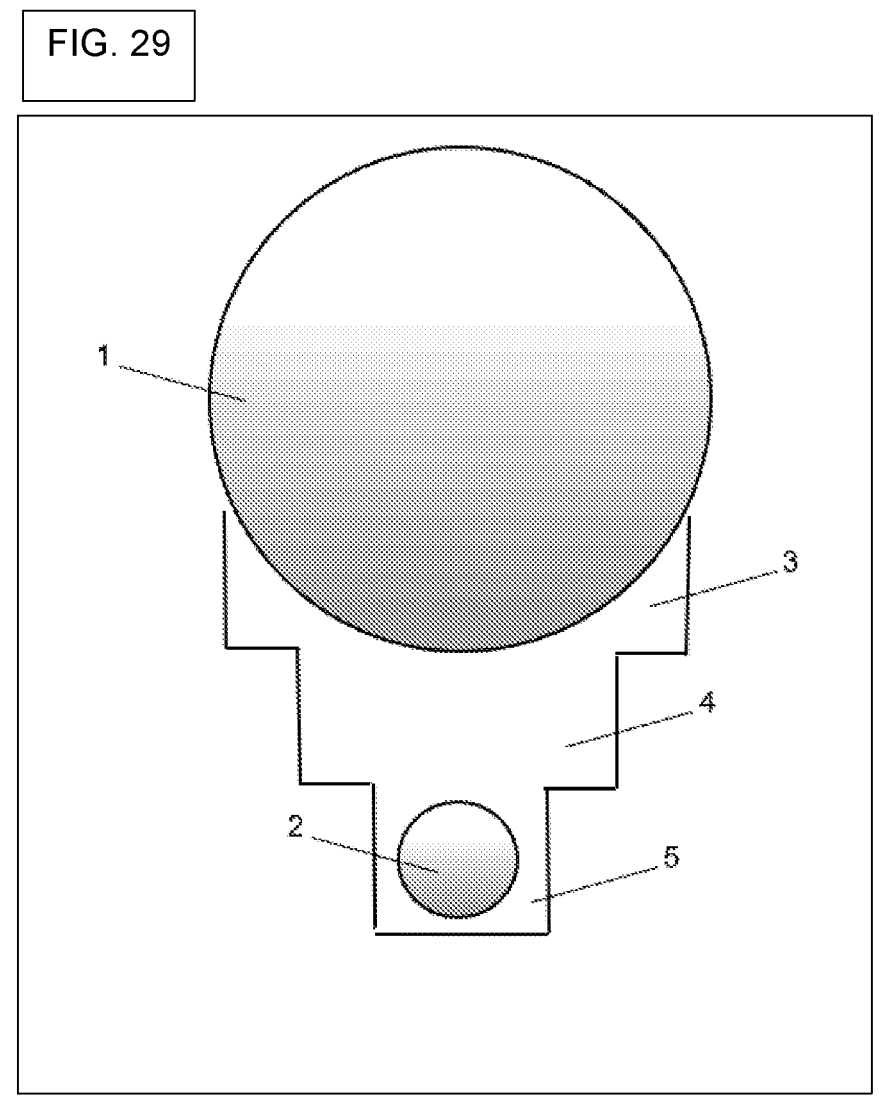

FIG. 29. Stepped picowell.

Figure 30:
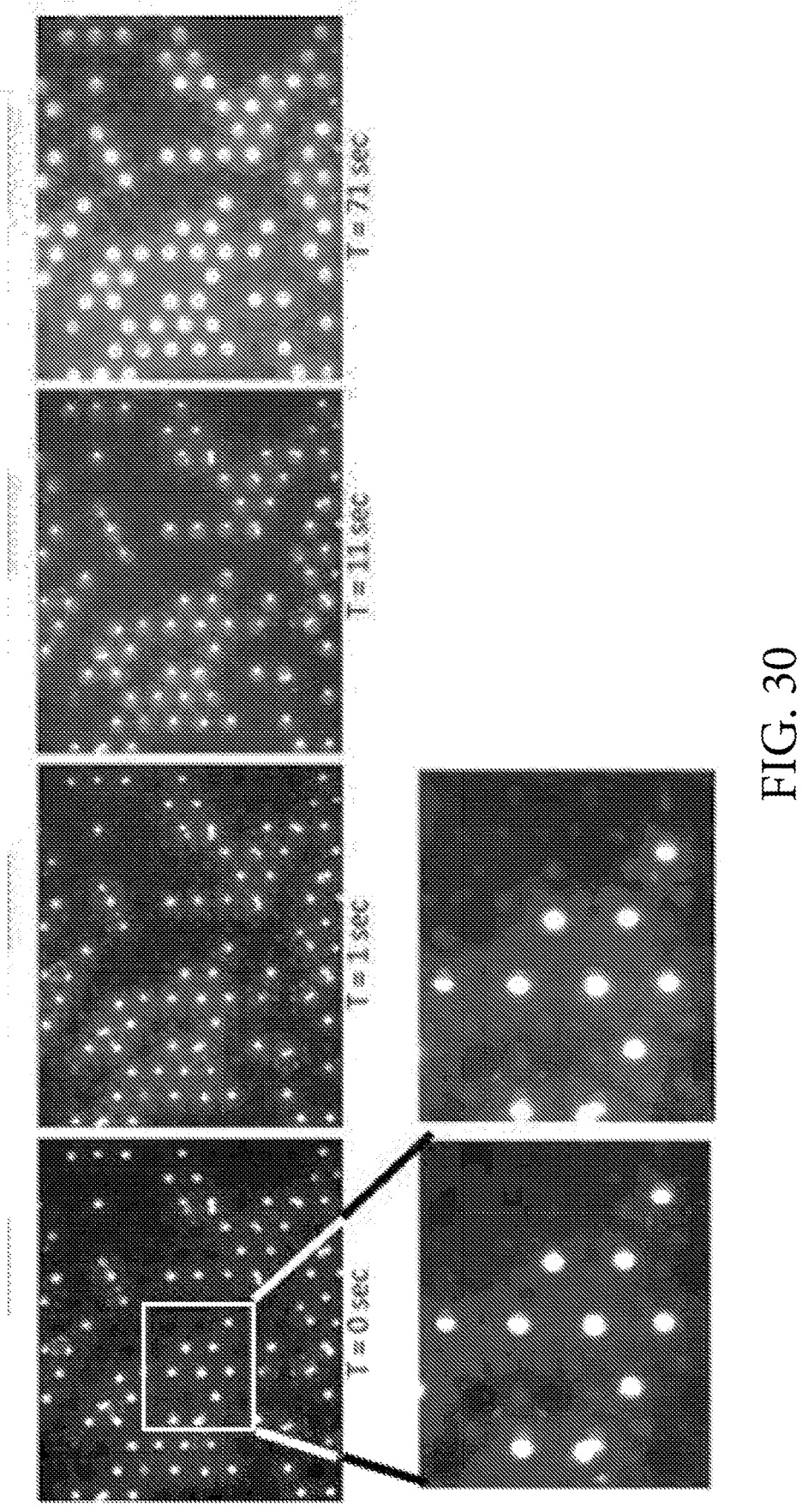

FIG. 30. Time course of release of the fluorophore from the bead. This shows operation of the bead-bound release monitor, acquisition of fluorescent data at t=0 seconds, t=1 seconds, t=11 seconds, and t=71 seconds.

Figure 31A:
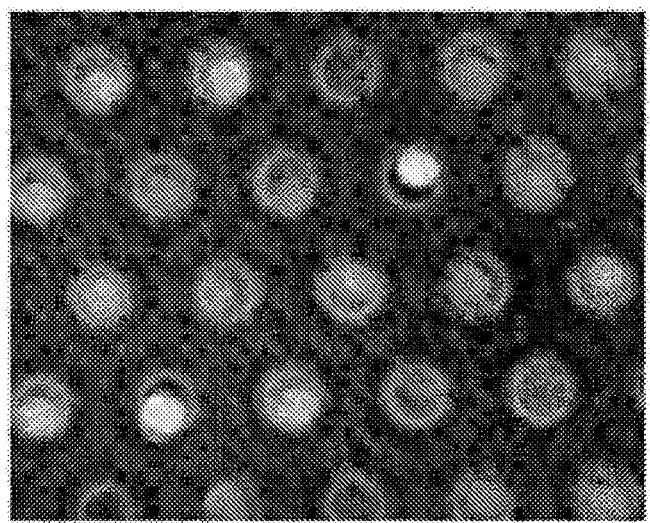
Figure 31B:
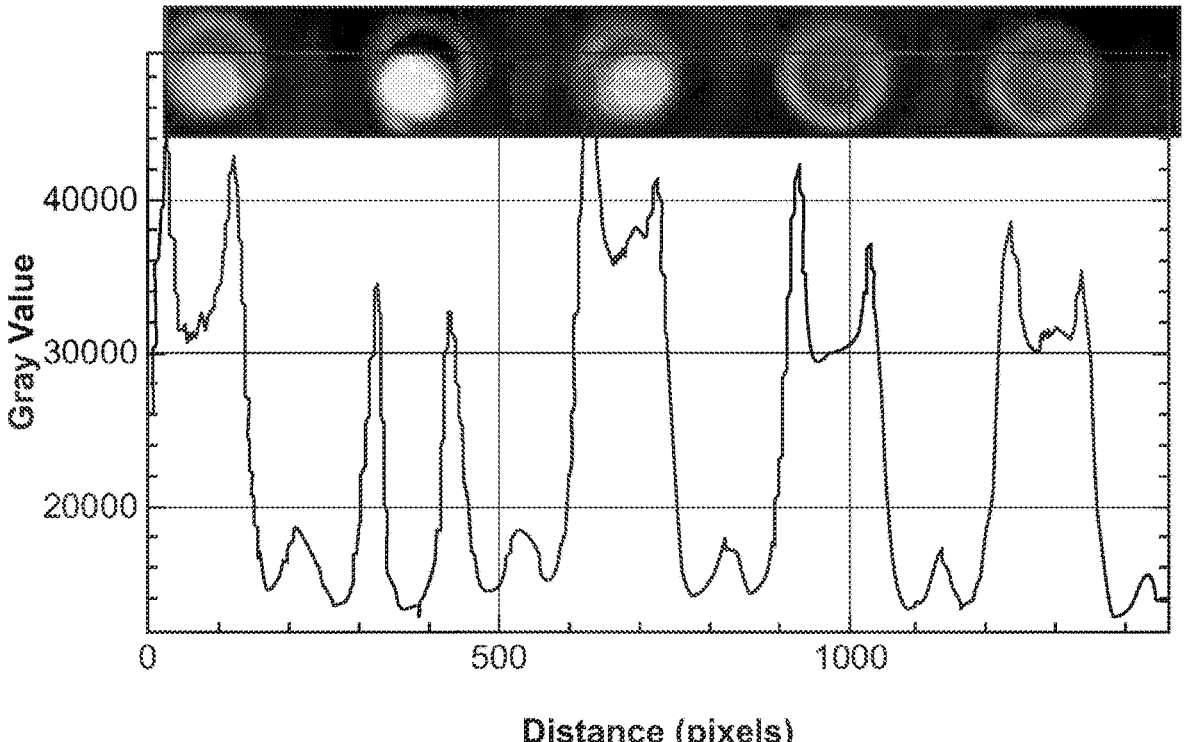

FIGS. 31A-31B. Emission data resulting after catalytic action of aspartyl protease on quencher-fluorophore substrate.

Figure 32:
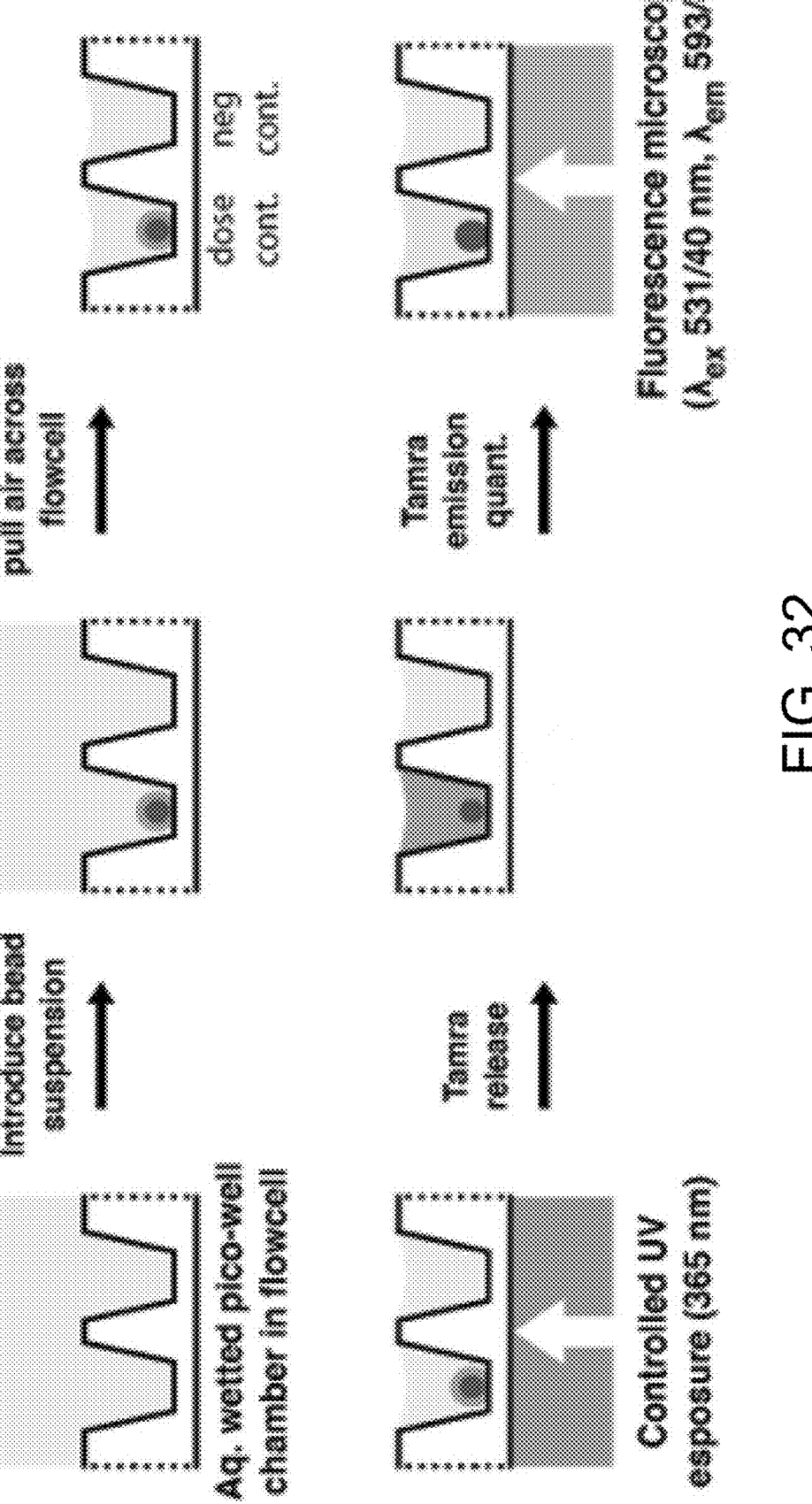
Figure 33:
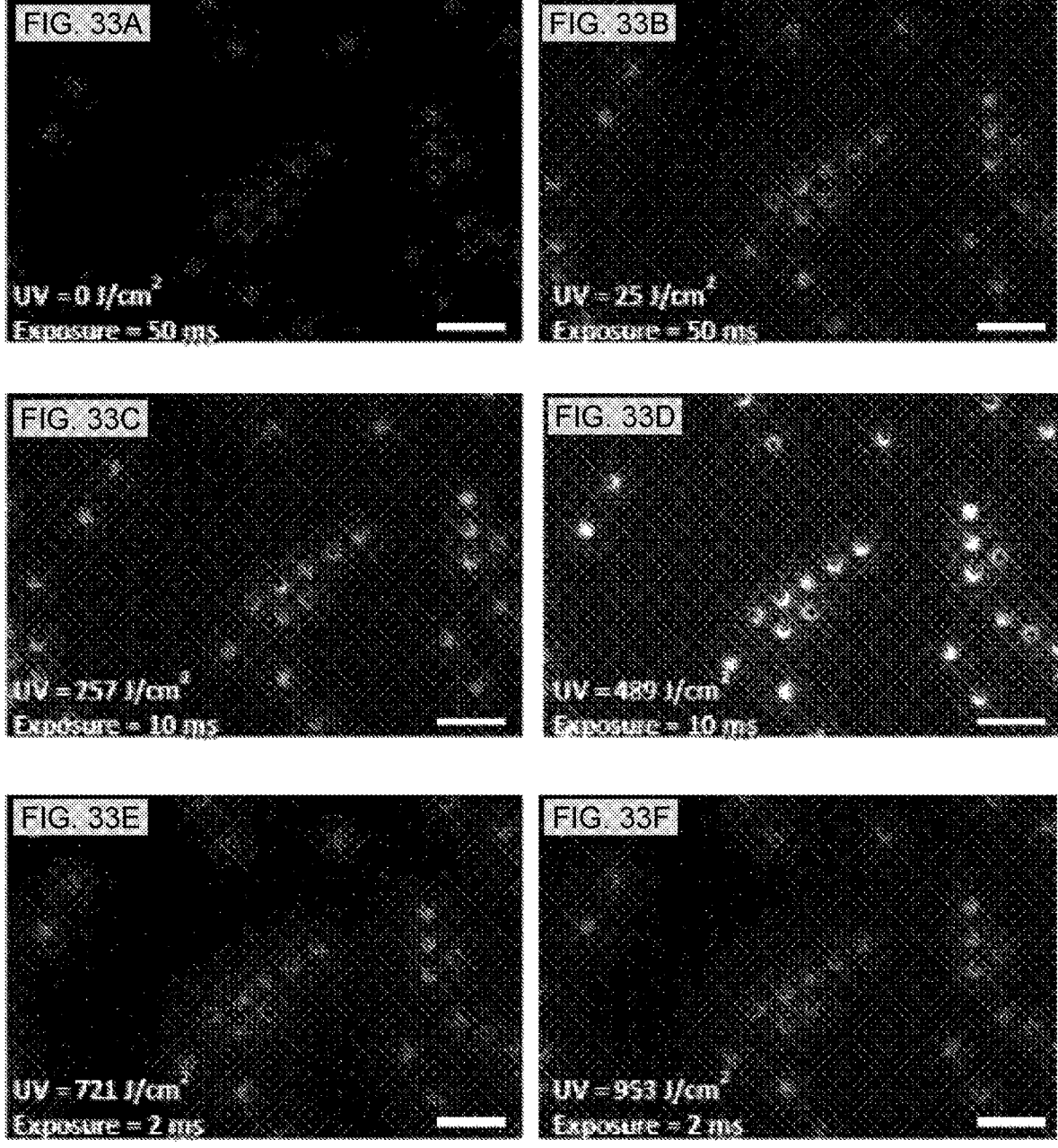

FIG. 32. Drawings of cross-section of picowells, illustrating various steps.

FIGS. 33A-33F. Titration data showing how increase in UV dose results in greater cleavage of fluorophore from the bead. In layperon's terms, this shows how a more powerful swing of the axe influences chopping the fluorophore from the bead (the power of the UV does is measured in Joules per centimeter squared). The notation "Exposure" refers only to a parameter when taking the photograph. It is just exposure time, when taking the photograph (it does not refer to exposure time of the light doing the cleaving, or to the light doing the exciting).

Figure 34:
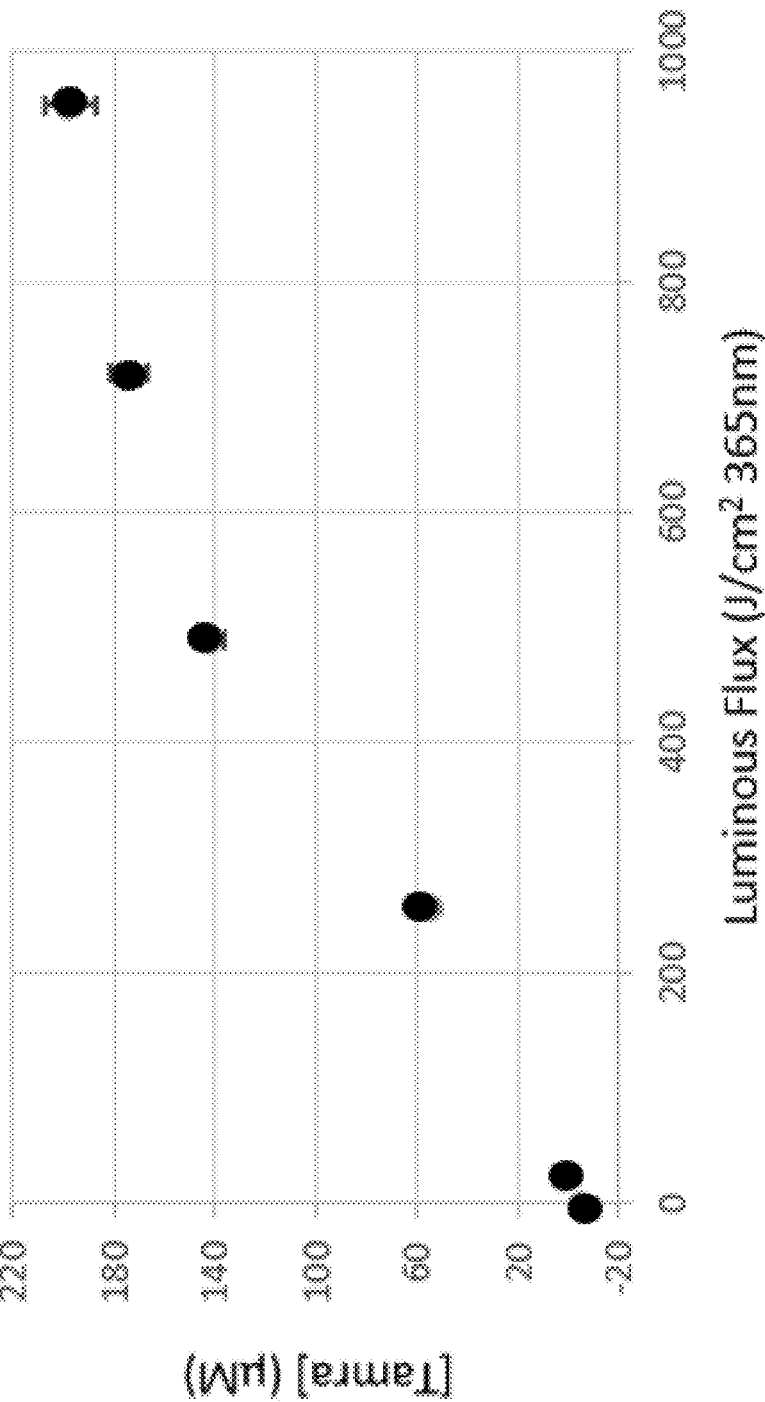

FIG. 34. TAMRA concentration versus luminous flux. What is shown is concentration of free TAMRA, following release after exposure to UV light at 365 nm.

Figure 35:
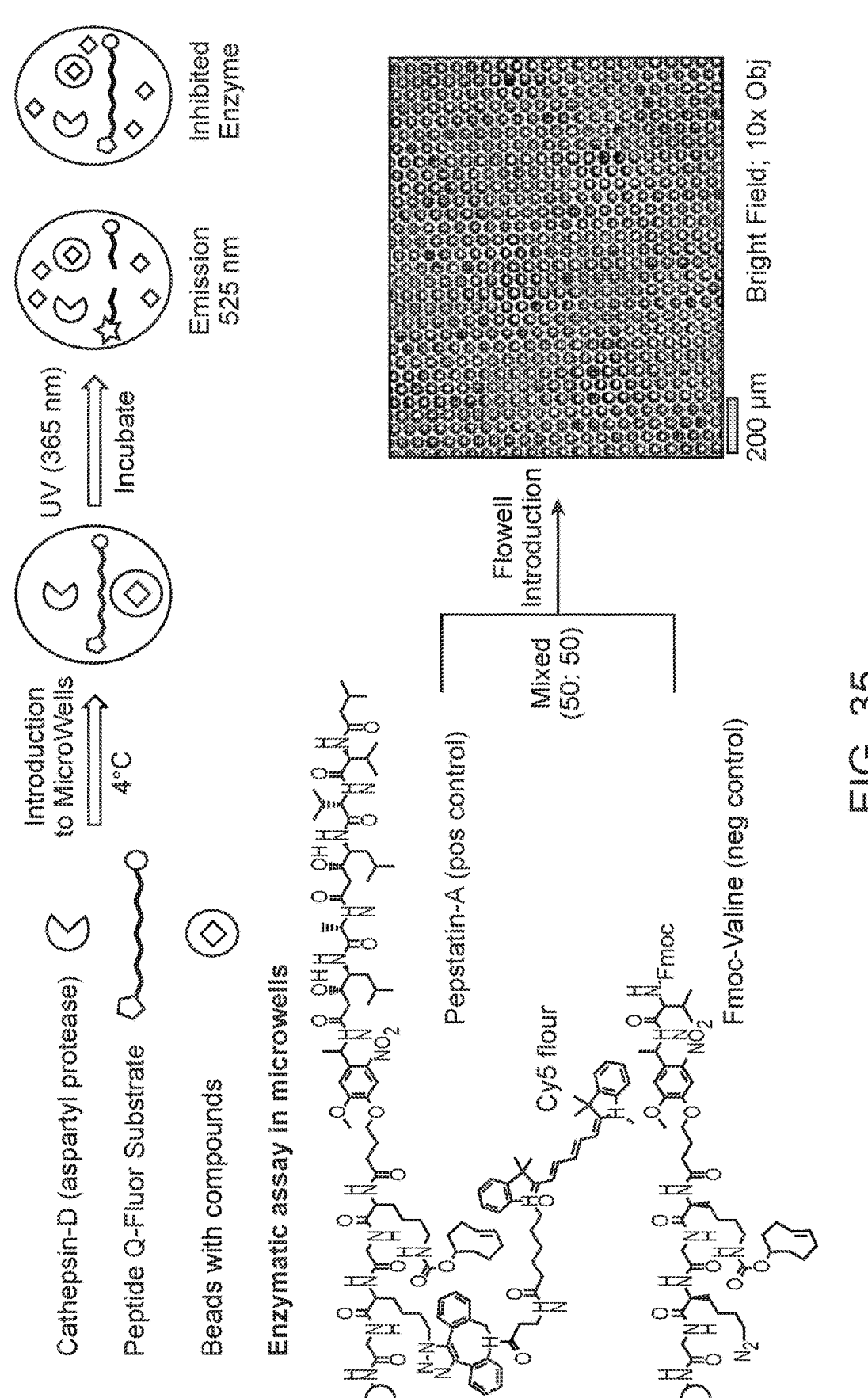

FIG. 35 provides a hand-drawings of the quencher-fluorophore substrate, and of cleavage of this substrate by the enzyme, with consequent inhibition of enzyme. Also shown is the molecular structure of bead-bound pepstatin-A, and bead-bound Fmoc-valine (negative control).

Figure 36:
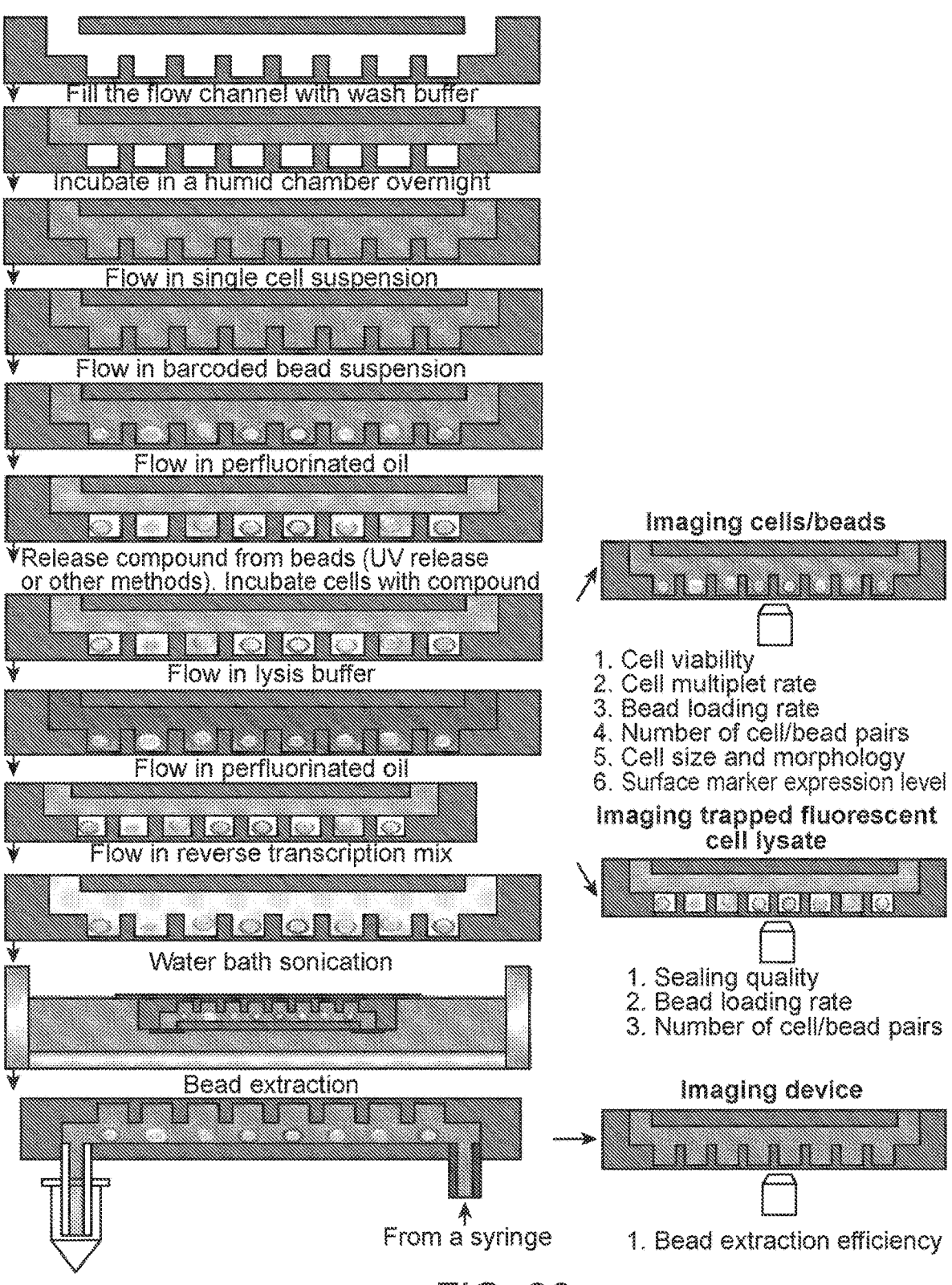

FIG. 36. Steps in preparing beads for use in eventual capture of mRNA from lysed cells, with subsequent manufacture of cDNA library. This figure also occurs in one of the Provisional applications (Compositions and Method for Screening Compound Libraries on Single Cells), from which priority of the present application is claimed.

Figure 37:
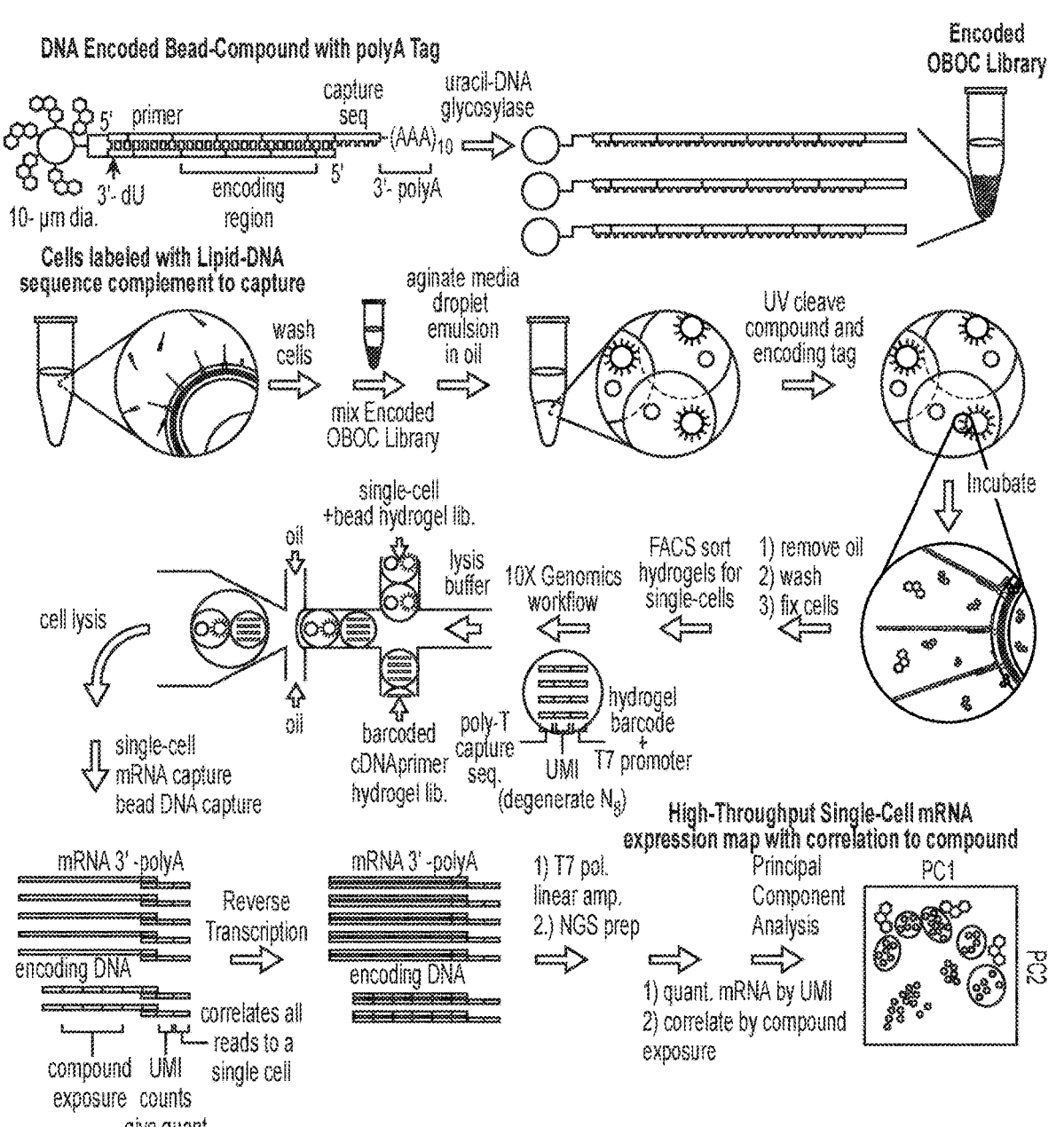

FIG. 37. Tagging cells with DNA barcode, where tagging is by way of a lipid that embeds in the cell membrane. This figure also occurs in one of the Provisional applications (Compositions and Method for Screening Compound Libraries on Single Cells), from which priority of the instant application is claimed.

DETAILED DESCRIPTION OF PREFERRED EMBODIMENTS

As used herein, including the appended claims, the singular forms of words such as "a," "an," and "the" include their corresponding plural references unless the context clearly dictates otherwise. All references cited herein are incorporated by reference to the same extent as if each individual patent, and published patent application, as well as figures, drawings, sequence listings, compact discs, and the like, was specifically and individually indicated to be incorporated by reference.

ABBREVIATIONS

Table 1 provides abbreviations and non-limiting definitions.

TABLE 1

| Abbreviations and non-limiting definitions |
| --- |
| ACN | Acetonitrile |
| AMPSO | 3-[(1,1-dimethyl-2-hydroxyethyl) amino]-2-hydroxypropanesulphonic acid. AMPSO is one of the "Good buffers" ((1966). Hydrogen Ion Buffers for Biological Research. Biochemistry. 5: 467-477). |

TABLE 1-continued

| Abbreviations and non-limiting definitions | |
| --- | --- |
| Aperture | As used herein, the term aperture is used herein to refer to a physical substance that defines an opening and, more specifically, to the minimal amount of physical substance that is capable of defining an opening. Without implying any limitation, this minimal amount of physical substance preferably takes the form of a ring-shaped section of a wall. Without limitation, the aperture can be considered to be a ring-shaped section of a wall, where the thickness of the section is about 0.2 nm, about 0.5 nm, about 10 nm, about 20 nm, about 50 nm, about 100 nm, about 200 nm, about 500 nm, about 1 micrometer (um), about 2 um, about 5 um, and so on, where this thickness measurement is in the radial direction extending away from an axis, and where the axis is defined by the opening. |
| 1-AP | 1-Azidopyrene |
| ATB | Active tuberculosis |
| Barcode | The term "DNA barcode" can refer to a polynucleotide that identifies a chemical compound in its entirety while, in contrast, "DNA barcode module" can refer to only one of the monomers that make up the chemical compound. A short definition of a "DNA barcode module" is that it identifies a chemical library monomer. However, a "DNA barcode module" can be used to identify the history of making that particular monomer. A longer definition of a "DNA barcode module" is as follows. Each of the following chemical library monomers need to be identified by a different "DNA barcode module." Even the first reaction and the second reaction have the same reactants (A and B), a different DNA barcode module is used, because the products are different (the products being either C or D). Also, even though the first reaction and the third reaction result in the same product (the product being "C"), a different DNA barcode module is used, because the reactants are different (the reactants being either A + B, or X + Y). |

| Reaction Condition | |
| --- | --- |
| A + B → C | Reaction condition A, for example, with methane solvent |
| A + B → D | Reaction condition A, for example, with methylene chloride solvent |
| X + Y → C | |

| | |
| --- | --- |
| BiNAP | BiNAP takes the form of two naphthalene groups attached to each other by way of a carbon-carbon bond between the 1-carbon of the first naphthalene and the 1-carbon of the second naphthalene. Each naphthalene group also contains an attached $PPh_2$ group, where the $PPh_2$ group is attached to the naphthalene's 2-carbon. $PPh_2$ takes the form of a phosophate group, to which is attached two phenyl groups. In BiNAP, the phosphate is situated in between the naphthalene and the $PPh_2$. |
| BTPBB | Bis-Tris propane breaking buffer |
| BTPLB | Bis-Tris propane ligation buffer |
| BTPWB | Bis-Tris propane wash buffer |
| Cap | A cap is an object that can serve as a plug, a stopper, a seal, and the like, for placing in stable contact with a microwell, nanowell, or picowell. The cap can be spherical, ovoid, cubical, cubical with rounded edges, pyramidal, pyramidal with rounded edges, and so on. Unless specified otherwise, the stated shape is the shape prior to partial insertion or prior to full insertion into the picowell. Preferably, when in use the cap is partially inserted into the picowell to form a seal. In some embodiments, the cap may be loosely set on top of the picowell without any partial insertion. |
| Compound | The term "compound" is used here, without implying any limitation, to refer to a completed chemical that is synthesized by connecting a plurality of chemical monomers to each other, by way of solid phase synthesis on a bead. Generally, the term "compound" refers to the completed chemical that is to be tested for activity by way of an assay. The term "compound" is not intended to include any linkers that mediate binding of the completed chemical to the bead, and is not intended to include any protecting groups that are to be cleaved off, though it is understood that a "compound" that has a protecting group may have pharmaceutical activity. The term "compound" is NOT used to refer to bead-bound chemicals where not all of the chemical monomers have been connected. If the term "compound" is used in some other context herein, the skilled artisan will be able to determine if this description is relevant or not. |
| COMU | 1-Cyano-2-ethoxy-2-oxoethylidenaminooxy) dimethylamino-morpholino-carbenium hexafluorophosphate (CAS no. 1075198-30-9) |
| Concatenated nucleic acid barcode | A DNA barcode that is "concatenated," takes the form where all of the DNA barcode modules are part of the same polymer. When a bead contains a DNA barcode taking the concatenated form, all of the information from all of the constituent DNA barcode modules are present on the polymer that is attached to a single attachment site on the bead. Concatenated DNA refers to "end-to-end ligation" or "end-to-end joining" (Farzaneh (1988) Nucleic Acids Res. 16: 11319-11326; Boyer (1999) Virology. 263: 307-312). In contrast, the word "catenated" refers to two circles of DNA that are linked to each other as in a chain (Baird (1999) Proc. Nat'l. Acad. Sci. 96: 13685-13690). |
| CuAAC | Copper-catalyzed azide-alkyne cycloaddition |
| CRB | Click reaction buffer |
| DAF | Diazofluorene |
| DBCO | Dibenzocyclooctyne |
| DBU | 1,8-diazabicyclo [5.4.0] undec-7-ene |
| DCE | 1,2-Dichloroethane |

TABLE 1-continued

| | Abbreviations and non-limiting definitions |
|---|---|
| DCM | Dichloromethane |
| DESPS | DNA encoded solid-phase synthesis |
| DIC | Diisopropyl carbodiimide |
| DIEA | N,N'-diisopropylethylamine |
| DMA | Dimethylacetamide |
| DMAP | 4-Dimethylaminopyridine |
| DMF | Dimethylformamide |
| DI | Deionized |
| DTT | Dithiothreitol |
| EDC | Ethyl-dimethylaminopropyl-carbodiimide |
| ELISA | Enzyme linked immunosorbent assay |
| FMOC | 9-Fluorenylmethoxycarbonyl |
| FMOC-PCL-OH | 4-[4-[1-(9-Fluorenylmethyloxycarbonylamino)ethyl]-2-methoxy-5-nitrophenoxy] butanoic acid (CAS No. 162827-98-7) |
| Functional nucleic acid | In the context of a bead-bound DNA barcode, and in the context of manufacturing a bead-bound DNA barcode, the term "functional nucleic acid" refers to nucleic acids with an active biochemical function (a function that takes advantage of hydrogen bonds, of hydrophobic interactions, of hydrophilic interactions, of interactions with enzymes, etc.). The function can be a spacer that establishes a distance between a hydrophobic bead and a primer binding site. The primer binding site preferably occurs in a hydrophilic environment for supporting activity of DNA polymerase. Also, the function can be a primer binding site, a hairpin bend, or the annealing site for a "splint oligo." This is in contrast to "informational nucleic acids," which store information (which "encode") information on the identity of a corresponding chemical monomer. |
| HDNA | Headpiece DNA |
| HTS | High throughput screening |
| INA | 5-Iodonaphthalene-1-azide |
| LC | Liquid chromatography |
| LTB | Latent tuberculosis |
| MDM2 | Murine Double Minute 2 |
| Mtt | 4-Methyltrityl |
| NCL hits; NCL pool | NCL refers to a mixture of sera from latent tuberculosis patients (this accounts for the letter "L") and sera from negative control, healthy human subjects (this accounts for the letter "NC") |
| NHS | N-Hydroxysuccinimide. NHS chemistry can be used to attach tetrazine to free amino groups of, for example, antibodies (van Buggenum, Gerlach, Mulder (2016) Scientific Reports. 6: 22675. |
| Nucleic acid | The term "nucleic acid" can refer to a single nucleic acid molecule, or to modified nucleic acids, such as a nucleic acid bearing a fluorescent tag. Also, the term "nucleic acid" can be used to refer individual contiguous stretches of nucleotides within a longer polynucleotide. Here, the term "nucleic acid" makes it more convient to refer to these individual stretches within a longer polynucleotide, for example, as when the polynucleotide comprises a first nucleic acid that is a primer-binding site, a second nucleic acid that is a DNA barcode module, and a third nucleic acid that identifies the step number in a multi-step pathway of synthesis. |
| OP | Oligo pair. Oligo pair can refer to a reagent that takes the form of a slipped heteroduplex, for example, an aqueous solution of a slipped heteroduplex. |
| Orthogonal nucleic acid barcode | A DNA barcode that is "orthogonal," takes a form where each of the DNA barcode modules occupies a different attachment site on the bead. When a bead contains a DNA barcode taking the orthogonal form, the acquisition of all of the information of a compound's DNA barcode requires separately sequencing each of the attached DNA barcode modules. In other words, with an "orthogonal" nucleic acid barcode, each and every one of the DNA barcode modules that makes up the DNA barcode is dispersed over different attachment sites on the same bead. |
| OSu (OSu is the same as NHS) | N-Hydroxysuccinimide |
| OXYMA | Ethyl 2-cyano-2-(hydroxyamino)acetate |
| Parallel | The term "parallel" refers to the situation where chemical monomers are covalently attached to a bead, one by one, to create a bead-bound compound, and where nucleic acid barcode modules are also covalently attached to the same bead, one by one, to create a bead-bound nucleic acid barcode. The chemical reaction that attaches each chemical monomer is not carried out at exactly the same time as the reaction (chemical or enzymatic) that attaches each nucleic acid barcode module. Instead, these two reactions are staggered, so that the parallel synthesis involves first attaching the chemical monomer, and then attaching the corresponding nucleic acid barcode module. Alternately, the staggered reaction can involve first attaching the nucleic acid and then attaching the corresponding chemical monomer. What is corresponding in this situation, is that each nucleic acid barcode module serves to identify the chemical monomer that is attached in the same round of parallel synthesis. |

TABLE 1-continued

| | Abbreviations and non-limiting definitions |
|---|---|
| PCL | Photocleavable linker |
| PEG | Polyethylene glycol |
| PDMS | Polydimethylsiloxane |
| qPCR | Quantitative polymerase chain reaction |
| Picowell | Without implying any limitation on the presend disclosure, the term "picowell" can be used to refer to a well or cavity in a plate that contains an array of picowells, for example, over 50,000 picowells, over 100,000 picowells, over 200,000 picowells, over 500,000 picowells, and so on. Typically, the volume of a picowell (not including the volume of any beads that might be in the picowell), is about 0.2 picoliters (pL), about 0.5 pL, about 1.0 pL, about 2.0 pL, about 5.0 pL, about 10 pL, about 20 pL, about 30 pL, about 40 pL, about 50 pL, about 75 pL, about 100 pL, about 200 pL, about 300 pL, about 400 pL, about 500 pL, about 600 pL, about 700 pL, about 800 pL, about 1000 pL, about 10,000 pL, about 100,000 pL, about 1,000,000 pL, or in a volume range defined by any of the above two values, for example, about 0.5 to 2.0 pL. The volumes for any "nanowell" and "microwell" can be set as above (except with the term "pico" replaced by nano or micro). Unless specified otherwise, explicitly or by context, the present disclosure refers to picowells (rather than to nanowells or microwells). |
| RAM | Rink Amide |
| RCA | Rolling circle amplification |
| RT | Room temperature |
| SPS | Solid phase synthesis |
| Slipped heteroduplex structure | Slipped heteroduplex structure takes the form of a first strand of ssDNA and a second strand of ssDNA, where a dozen nucleotides at the 5'-end of the first strand of ssDNA are complementary to a dozen nucleotides at the 5'-end of the second strand of ssDNA, and where the first strand of ssDNA is binds to the second strand of ssDNA by way of a dozen complementary base pairings that involve the respective 5'-termini. The number "dozen" is purely exemplary and is not limiting. Alternatively, the slipped heteroduplex structure could be maintained as a hybridized duplex, by way of complementary base pairing at the 3'-end of the first strand of ssDNA and the 3'-end of the second strand of ssDNA. The term "slipped heteroduplex structure" can alternatively be called a "staggered heteroduplex structure." The term "slipped" does not imply that the heteroduplex is slippery (can shift position0 as might be the case with a duplex formed when oligo[C] hybridizes to oligo[G], or when oligo[A] hybridizes to oligo[T]. |
| TB | Tuberculosis |
| TBE | Tris borate EDTA |
| TBAI | Tetrabutyl ammonium iodide. |
| TBTA | Tris[(1-benzyl-1H-1,2,3-triazol-4-yl) methyl] amine |
| TCEP | Tris(2-carboxyethyl)phosphine. Reducing agent that can cleave disulfide bonds. |
| TCO | Trans-cyclooctene |
| TEAA | Triethylammonium acetate |
| TEV protease | Tobacco Etch Virus protease |
| TFA | Trifluoroacetic acid |
| TID | 3-(trifluoromethyl)-3-(m-iodophenyl) diazirine |
| TIPS | Triisopropyl silane |
| TM | Temperature of melting |
| TMP | 2,4,6-Trimethylpyridine |
| QSY7 | Xanthylium, 9-[2-[[4-[[2,5-dioxo-1-pyrrolidinyl)oxy] carbonyl]-1-piperidinyl] sulfonyl]phenyl]-3,6-bis(methylphenylamino)-, chloride (CAS No. 304014-12-8) |
| TAMRA | 5(6)Carboxytetramethyl rhodamine |

Reagents, kits, enzymes, buffers, living cells, instrumentation, and the like, can be acquired. See, for example, Sigma-Aldrich, St. Louis, MO; Oakwood Chemical, Estill, SC; Epicentre, Madison, WI; Invitrogen, Carlsbad, CA; ProMega, Madison, WI; Life Technologies, Carlsbad, CA; ThermoFisher Scientific, South San Francisco, CA; New England BioLabs, Ipswich, MA; American Type Culture Collection (ATCC), Manassas, VA; Becton Dickinson, Franklin Lakes, NJ; Illumina, San Diego, CA; 10× Genomics, Pleasanton, CA Barcoded gel beads, non-barcoded gel beads, and microfluidic chips, are available from 1CellBio, Cambridge, MA Guidance and instrumentation for flow cytometry is available (see, e.g., FACSCalibur®, BD Biosciences, San Jose, CA, BD FACSAria II® User's Guide, part no. 643245, Rev.A, December 2007, 344 pages).

A composition that is "labeled" is detectable, either directly or indirectly, by spectroscopic, photochemical, fluorometric, biochemical, immunochemical, isotopic, or chemical methods, as well as with methods involving plasmonic nanoparticles. For example, useful labels include, $^{32}$P, $^{33}$P, $^{35}$S, $^{14}$C, $^{3}$H, $^{125}$I, stable isotopes, epitope tags, fluorescent dyes, Raman tags, electron-dense reagents, substrates, or enzymes, e.g., as used in enzyme-linked immunoassays, or fluorettes (Rozinov and Nolan (1998) Chem. Biol. 5:713-728).

TABLE OF CONTENTS FOR DETAILED DESCRIPTION (I) Beads
(II) One bead one compound (OBOC)
(III) Coupling nucleic acids to beads
(IV) DNA barcodes
(V) Coupling chemical compounds to beads
(VI) Coupling chemical monomers to each other to make a compound
(VII) Split and pool synthesis and parallel synthesis
(VIII) Fabricating picowells
(IX) Deposit beads into picowells
(X) Sequencing bead-bound nucleic acids in picowells
(XI) Releasing bead-bound compounds from the bead
(XII Biochemical assays for compounds
(XIII) Cell-based assays for compounds (I) BEADS The methods and compositions of the present disclosure use beads, such as monosized TentaGel® M NH$_2$ beads (10, 20, 30, etc., micrometers in diameter)-, standard TentaGel® amino resins (90, 130, etc. micrometers in diameter), Tenta-Gel Macrobeads® (280-320 micrometers in diameter) (all of the above from Rapp Polymere, 72072 Tubingen, Germany). These have a polystyrene core derivatized with polyethylene glycol (Paulick et al (2006) J. Comb. Chem. 8:417-426). TentaGel® resins are grafted copolymers consisting of a low crosslinked polystyrene matrix on which polyethylene glycol (PEG) is grafted. Thus, the present disclosure provides beads or resins that are modified to include one or both of a DNA barcode and a compound, where the unmodified beads take the form of grafted copolymers consisting of a low crosslinked polystyrene matrix on which polyethylene glycol (PEG) is grafted.

TentaGel® is characterized as, "PEG chains of molecular masses up to 20 kilo Dalton have been immobilized on functionalized crosslinked polystyrenes. Graft copolymers with PEG chains of about 2000-3000 Dalton proved to be optimal in respect of kinetic rates, mobility, swelling and resin capacity." (Rapp Polymere, Germany). Thus, the present disclosure provides beads or resins that take the form of graft copolymers with PEG chains of about 2000-3000 Daltons. Regarding swelling, Comellas et al provides guidance for measuring the ability of a bead to swell, for example, when soaked in DCM, DMF, methyl alcohol, water, or a buffer used in enzyme assays (Comellas et al (2009) PLoS ONE. 4:e6222 (12 pages)). The unit of swelling is milliliters per gram of bead.

In an alternate bead embodiment, the present disclosure uses a resin with a PEG spacer is attached to the polystyrene backbone via an alkyl linkage, and where the resin is microspherical and monosized (TentaGel® M resin).

In yet an alternate bead embodiment, the present disclosure uses a resin with a PEG spacer attached to the polystyrene backbone via an alkyl linkage, where the resin type exists in two bifunctional species: First, surface modified resins: the reactive sites on the outer surface of the beads are protected orthogonally to the reactive sites in the internal volume of the beads, and second, hybrid resins: cleavable and noncleavable ligands are present in this support—developed for sequential cleavage (TentaGel® B resin).

Moreover, in another embodiment, the present disclosure uses a resin where a PEG spacer is attached to the polystyrene backbone via an alkyl linkage, and where the macrobead resin shows very large particle diameters and high capacities (TentaGel® MB resin). Also, the present disclosure uses a resin where the PEG spacer is attached to the polystyrene backbone via a benzyl ether linkage. This resin can be used for immunization procedures or for synthesizing PEG modified derivatives (PEG Attached PEG-modified compounds) (TentaGEl® PAP resin).

Moreover, the beads can be, HypoGel® 200 resins. These resins are composites of oligoethylene glycol (MW 200) grafted onto a low cross-linked polystyrene matrix (Fluka Chemie GmbH, CH-9471 Buchs, Switzerland).

In some embodiments amino functionalized polystyrene beads, without PEG linkers, may be used, for instance, monosized polystyrene M NH$_2$ microbeads (5, 10, 20 etc., micrometers in diameter, also from Rapp Polymere, 72072 Tubingen, Germany).

In some embodiments, compounds may be encapsulated within pores or chambers or tunnels within the beads, without covalent attachment to the beads. Compounds may be diffused into or forced within such pores of the beads by various means. In some embodiments the compounds may be loaded within the beads by diffusion. In some embodiments, high temperature may be used to swell the beads and load compounds within the beads. In some embodiments, high pressure may be used to force compounds into the beads. In some embodiments, solvents that swell the beads may be used to load compound within the beads. In some embodiments, vacuum or low pressure may be used to partition compounds into beads. In some embodiments mild, or vigorous physical agitation may be used to load compounds into beads.

In such embodiments where the compounds are loaded onto beads without covalent attachment, compounds may be unloaded from the bead by way of diffusion. In some embodiments, in a non-limiting fashion, temperature, pressure, solvents, pH, salts, buffer or detergent or combinations of such conditions may be used to unload compounds out of such beads. In some embodiments the physical integrity of the beads, for instance by uncrosslinking polymerized beads, may be used to release compounds contained within such beads.

In exclusionary embodiments, the present disclosure can exclude any bead, and bead-compound complex, or any method, that involves one of the above beads.

Beads of the present disclosure also include the following. Merrifield resin (chloromethylpolystyrene); PAM resin (4-hydroxymethylphenyl acetamido methyl polystyrene); MBHA resin (4-methylbenzhydrylamine); Brominated Wang resin (alpha-bromopriopiophenone); 4-Nitrobenzophenone oxime (Kaiser) resin; Wang resin (4hydroxymethyl phenoxymethyl polystyrene; PHB resin (p-hydroxybenzyl alcohol; HMPA resin (4-hydroxymethyl phenoxyacetic acid); HMPB resin (4-hydroxymethyl-3-methoxy phenoxyl butanoic acid); 2-Chlorotrityl resin; 4-Carboxytrityl resin; Rink acid resin (4-[(2,4-dimethoxypehenyl) hydroxymethyl) phenoxymethyl]; Rink amide (RAM) resin "Knorr" resin (4-((2,4-dimethylphenyl) (Fmox-amino)methyl) phenoxyalkyl); PAL resin (5-[4-(Fmoc-amino) methyl-3,5-dimethoxyphenoxy] valeramidomethyl polystyrene); Sieber amide resin (9-Fmox-amino-xanthan-3-yl-oxymethyl); HMBA resin (hydroxymethyl benzoic acid); 4-Sulfamoylbenzoyl resin "Kenner's safety catch" resin (N-(4-sulfamoylbenzoyl) aminomethyhl-polystyrene); FMP-resin (4-(4-formyl-3-methoxyphenoxy)-ethyl) (see, ChemFiles Resins for Solid-Phase Peptide Synthesis Vol. 3 (32 pages) (Fluka Chemie GmbH, CH-9471 Buchs, Switzerland).

Beads of the present disclosure further include the above beads used as passive encapsulants of compounds (passively hold compounds without covalent linkage to the compound), and further comprising the following: unfunctionalized polystyrene beads; silica beads; alumina beads; porous glass beads; polyacrylamide beads; titanium oxide beads; alginate beads; ceramic beads; PMMA (polymethylmethacrylate) beads; melamine beads; zeolite beds; polylactide beads; deblock-copolymer micelles; dextran beads, and others. Many of the beads listed in this paragraph may be purchased from vendors such as Microspheres-Nanospheres, Cold Spring, NY 10516, USA.

In addition to beads, vesicles or droplets may also be used as vehicles for delivering compounds for some embodiments of the present disclosure. Lipids, deblock-copolymers, triblock copolymers or other membrane forming materials may be used to form an internal volume into which compounds may be loaded. Compounds may be released from these encapsulated volumes by addition of detergent, mechanical agitation, temperature, salt, pH or other means. Water-in-oil droplet emulsions or oil-in-water droplet emulsions are yet other means to passively encapsulate compounds that may be delivered to assay volumes.

In all embodiments where passive encapsulation is used to deliver compounds, DNA tags may also be loaded passively, or alternatively, the DNA tags may be covalently attached to the beads, vesicles or droplets.

In exclusionary embodiments, the present disclosure can exclude any beads or resins that are made of any one the above chemicals, or that are made of derivatives of one any one of the above chemicals.

In embodiments, the beads can be spheroid and have a diameter of about 0.1-1 micrometers, about 1-5 micrometers, about 1-10, about 5-10, about 5-20, about 5-30, about 10-20, about 10-30, about 10-40, about 10-50, about 20-30, about 20-40, about 20-50, about 20-60, about 50-100, about 50-200, about 50-300, about 50-400, about 100-200, about 100-400, about 100-600, about 100-800, about 200-400, about 200-600, about 200-800 micrometers, and so on.

Non-spheroid beads that are definable in terms of the above values and ranges are also provided. For example, one of the axes, or one of the primary dimensions (for example, a side) or one of the secondary dimensions (for example, a diagonal) may comprise values in the above ranges. In exclusionary embodiments, the present disclosure can exclude any reagent, composition, system, or method, that encompasses spheroid beads (or non-spheroid beads) falling into one or more of the above values or ranges.

Chains of beads. In one embodiment, what is provided is a plurality of bead dimers, where the bead-dimer takes the form of two beads that are attached to each other, and where one bead contains a plurality of attached nucleic acid barcodes (either orthogonal nucleic acid modules, or concatenated nucleic acid modules), and the other bead contains a plurality of attached compounds, where all of the compounds are substantially related to each other (or where all of the compounds are substantially identical in chemical structure to each other). The bead dimer may be synthesized by preparing the first bead that has the attached compounds, separately preparing the second bead that has attached nucleic acid barcodes, and then linking the two beads together. In one aspect, the beads are attached to each other by a reversible linker, and in another aspect, the beads are attached to each other by a non-reversible linker.

Bead permeability. In embodiments, the present disclosure provides beads with various ranges or degrees of permeability. Permeability can be measured as the percentage of the volume of the bead that is accessible by a solvent, where the unit of measurement is percentage of the bead's surface that takes the form or pores, or where the unit of measurement is percentage of the bead's interior that takes the form of channels, networks, or chambers that are in fluid communication with the surface (and exterior medium) of the bead. The present disclosure can encompass porous beads or, alternatively, can exclude porous beads.

Figure 5:
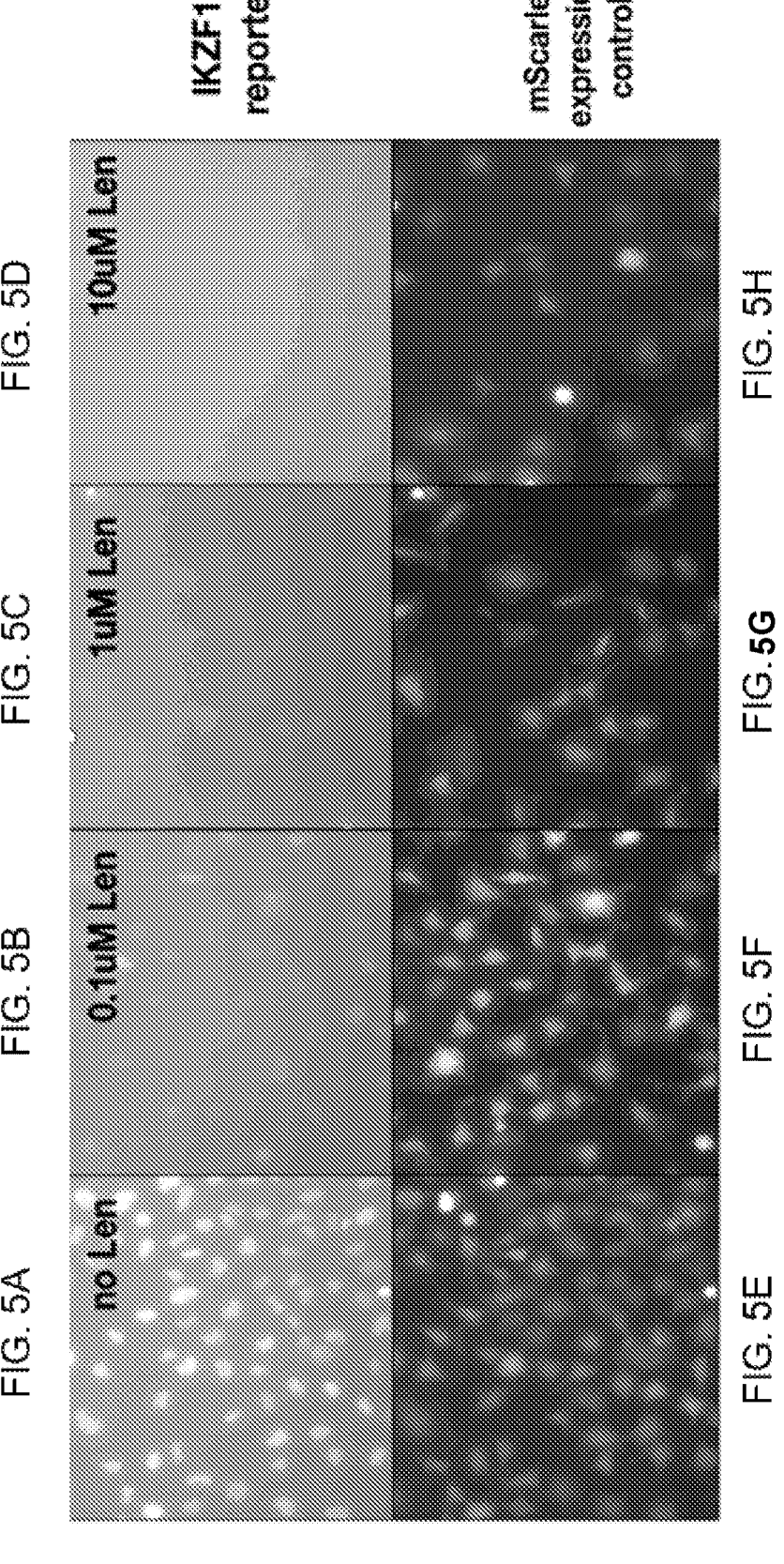

U.S. Pat. No. 9,062,304 of Rothberg discloses a bead with an exterior and with interior regions. What is shown is "internal surfaces (pore surfaces)," and that "suitable pores will . . . exclude larger molecules," and the option of "exploiting differential functionalization of interior and exterior surfaces," and various pore diameters, and polymers such as poly(styrene sulfonic acid) and polystyrene. FIG. 1 of Rothberg provides pictures of surface of bead and pores of bead. U.S. Pat. No. 9,745,438 of Bedre provides transmission electron microscope image of porous bead. U.S. Pat. No. 5,888,930 of Smith provides scanning electron micrograph of cross-section of porous bead. What is shown is sphereical bead with small pores on surface and large pores inside, where bead is made from, e.g., polystyrene, polyacrylonitrile, polycarbonate, cellulose, or polyurethane. U.S. Pat. No. 5,047,437 of Cooke discloses sphereical poly (acrylonitrile) copolymer pore morphology with skinless surface (FIG. 1) and bead that has exterior skin on surface (FIG. 5). U.S. Pat. No. 4,090,022 of Tsao discloses porous openings and internal void spaces, of cellulose beads.

Each of the above-identified patents, including all of the figures, is incorporated herein in its entirety, as though each was individually incorporated by reference in its entirety.

Without implying any limitation, exterior surface of a bead or microparticle can be determined by tightly wrapping the entire bead or microparticle with an elastic film. The bead or microparticle can be wrapped by way of a thought-experiment, or the wrapped bead can be depicted by a drawing or photograph, or the bead can be wrapped in reality. Without implying any limitation, the exterior surface of the bead is that part of the bead that physically contacts the wrapping.

For example, the present disclosure provides a bead with pores accounting for at least 1%, at least 2%, at least 5%, at least 10%, at least 15%, at least 20%, at least 30%, at least 40%, of the surface area. Also, the present disclosure provides a bead where the volume of the internal channels or networks accounts for at least 1%, at least 2%, at least 5%, at least 10%, at least 15%, at least 20%, at least 30%, at least 40%, at least 50%, at least 60%, at least 70%, at least 80%, of the total volume of the bead, and where the internal channels or networks are in fluid communication with the outside surface (and exterior medium) of the bead.

Moreover, the present disclosure provides a bead with pores accounting for less than 1%, less than 2%, less than 5%, less than 10%, less than 15%, less than 20%, less than 30%, less than 40%, of the surface area. Also, the present disclosure provides a bead where the volume of the internal channels or networks accounts for less than 1%, less than 2%, less than 5%, less than 10%, less than 15%, less than 20%, less than 30%, less than 40%, less than 50%, less than 60%, less than 70%, less than 80%, of the total volume of the bead, and where the internal channels or networks are in fluid communication with the outside surface (and exterior medium) of the bead.

Iron-core beads. The present disclosure encompasses iron-core beads or magnetic beads. These beads can be manipulated with magnets to move them from one reaction vessel to another reaction vessel, or from one container to another container. Manipulations by robotics can be enhanced by using these beads. Methods of manufacture and use of magnetic beads are available (Szymonifka and Chapman (1994) Tetrahedron Letters. 36:1597-1600; Liu, Qian, Xiao (2011) ACS Comb. Sci. 13:537-546; Alam, Maeda, Sasaki (2000) Bioorg. Med. Chem. 8:465-473).

In exclusionary embodiments, the present disclosure can exclude any bead, or any population of beads, where the bead or population meets one of the above values or ranges.

Compound Loading into Beads

In many experiments it is advantageous to load pre-synthesized compounds into beads, where the beads may be used as vehicles for delivering the compounds to an assay. Many of the standard techniques used for drug delivery to biological specimens may be adapted to deliver compounds to assays (see, Wilczewska et al (2012) Nanoparticles as drug delivery systems. Pharmacological Reports. 64:1020-1037, Kohane DS (2007) Microparticles and nanoparticles for drug delivery. Biotechnol. Bioeng. 96: 203-209, Singh et al (2010) Microencapsulation: A promising technique for controlled drug delivery. Res Pharm Sci. 5: 65-77).

In such embodiments where pre-synthesized compounds are loaded into beads, the compounds may be held in traditional 96,385 or 1536 well microtiter plates. To these plates, beads may be added, into which the compounds get loaded by diffusion or by other active loading methods. In preferred embodiments, the beads chosen for impregnation have pore sizes or percolation geometries that prevent immediate emptying of the compounds when removed from the mother solution. The diffusion out of the beads may be enhanced by heat, pressure, additives or other stimulants, if needed. In some embodiments, the compound-laden beads may be capped in a manner that prevents leakage of the internal contents until triggered by an external impulse. One method for capping the exteriors of porous beads involves adding lipids or amphiphilic molecules to the bead-compound solution, such that the cavities exposed to the surface of the beads get sealed by a bilayer formed by the amphiphilic molecules. In some embodiments preformed vesicles may be mixed with the drug laden beads, such that upon agitating, the vesicles rupture and the membranes reform over the surface of the drug-laden beads, thereby sealing them. Methods to perform such bead sealing are described (see, Tanuj Sapra et al (2012) Nature Scientific Reports volume 2, Article No.: 848). Further experimental protocols to seal silica beads are available in the report release by Sandia Laboratories by Ryan Davis et al, Nanoporous Microbead Supported Bilayers: Stability, Physical Characterization, and Incorporation of Functional Transmembrane Proteins, SAND2007-1560, and the method bSUM, described by Hui Zheng et al (bSUM: A bead-supported unilamellar membrane system facilitating unidirectional insertion of membrane proteins into giant vesicles) in J. Gen. Physiol. (2016) 147: 77-93.

In some embodiments utilizing pre-synthesized compounds, beads are generated from the compounds by addition of appropriate reagents, for instance by adding lipids or di-block copolymers followed by agitation, whereby vesicles are formed containing the compounds in their interior or within the bilayer membrane. In some embodiments, the compounds may be pushed through a microfluidic T junction to create aqueous phase droplets in an oil phase, where the compounds are contained within the aqueous phase or at the interface between the aqueous phase and the oil phase. In some embodiments, the droplets formed may further be polymerized, creating hydrogels, that are more rugged and stable to handling than unpolymerized aqueous phase droplets. Droplet-based encapsulation and assays are disclosed by, Oliver et al (2013) Droplet Based Microfluidics, SLAS Discovery Volume: 19 issue: 4, page(s): 483-496. Sol-gel encapsulation process may also be employed to encapsulate compounds within beads. Formation of sol-gel beads is described in, Sol-gel Encapsulation of Biomolecules and Cells for Medicinal Applications, Xiaolin Wang et al (2015) Current Topics in Medicinal Chemistry. 15: 223.

One Bead One Compound (OBOC)

Methods used to manufacture combinatorial libraries involve three steps, (1) Preparing the library; (2) Screening the compounds in the library, and (3) Determining the structure of the compounds, for example, of all of the compounds or only of the compounds that provided an interesting result with screening (see, Lam et al (1997) The One-Bead-One-Compound Combinatorial Library Method. Chem. Rev. 97:411-448). An advantage of synthesizing compounds by way of a bead-bound synthesis, is that the compound can be made rapidly by the "split-and-pool" method.

OBOC combined with an encoding strategy. Another feature of OBOC is that each bead can include, not only a compound but also an encoding strategy. Where bead-bound nucleic acids are used for encoding a compound that is bound to the same bead, the term "encoding" does NOT refer to the genetic code. Instead, the term "encoding" means that the user possesses a legend, key, or code, that correlates each of many thousands of short nucleic acid sequences with a single bead-bound compound.

A dramatic variation of using a bead that bears bead-bound compounds and bead-bound nucleic acids, where the nucleic acids encode the associated compounds, is as follows. The dramatic variation is to manufacture a library of conjugates, where each member of the library takes the form of a conjugate of a small molecule plus a DNA moiety, where the DNA moiety encodes the small molecule). This conjugate is soluble and is not bead-bound. After screening with a cell or with a purified protein, the conjugate remains bound to the cell or purified protein, thereby enabling isolation of the conjugate and eventual identifying the compound by sequencing the conjugated nucleic acid (see, Satz et al (2015) Bioconjugate Chemistry. 26:1623-1632).

Here, as in most of this patent document, the term "encode" does not refer to the genetic code, but instead it refers to the fact that the researcher uses a specific nucleic acid sequence to indicate a specific, known structure of a compound that is attached to it.

As an alternative to using an encoding strategy, such as the use of a DNA barcode, a bead that screens positive (thereby indicating a compound that screens positive) can be subjected to Edman degradation or to mass spectrometry to identify the bead-bound compound (see, Shih et al (2017) Mol. Cancer Ther. 16:1212-1223). If the bead-bound compounds are peptides, then MALDI mass spectrometry can be used for direct determination of the sequence of a positively-screening peptide compound. Direct sequencing is possible, because simultaneous cleavage and ionization occur under laser irradiation (Song, Lam (2003) J. Am. Chem. Soc. 125:6180-6188).

One fine point in performing split-and-pool synthesis of a combinatorial library, is that the compound can be manufactured so that all of the compounds share a common motif. This strategy has been described as the, "generation of a library of motifs rather than a library of compounds" (see, Sepetov et al (1995) Proc. Natl. Acad. Sci. 92:5426-5430; Lam et al, supra, at 418).

To provide a typical example of a large bead, the bead can be 0.1 mm in diameter and it can hold about $10^{13}$ copies of the same compound (Lam et al, supra). Following preparation of a library of bead-bound compounds, each bead can be used in individual assays, where the assays measure biochemical activity or, alternatively, a binding activity. Assays can be "on-bead" assays or, alternatively, the compound can be severed from the bead and used in solution-phase assays (Lam et al, supra).

Parameters of any type of bead include its tendency to swell in a given assay medium, whether the bead's polymer is hydrophobic or hydrophilic, the identity of the attachments sites on the bead for attaching each compound, the issue of whether a spacer such as polyethylene glycol (PEG) is used to provide some separation of each compound from the bead's surface, and the internal volume of the bead.

Regarding the need to attach compounds to the bead, but at a distance far away from the bead's hydrophobic surface, Lam et al, supra, discloses that polyoxyethylene-grafted styrene (TentaGel®) has the advantage that the functionalizable group is at the end of a polyoxyethylene chain, and thus far away from the hydrophobic polystyrene. Beads that possess a water-soluble linker include TentaGel and polydimethylacrylamide bead (PepSyn® gel, Cambridge Research Biochemicals, Northwitch, UK).

The parameter of internal volume can provide an advantage, where there is a need to prevent interactions between the bead-bound DNA barcode and the target of the bead-bound compound. To exploit this advantage, the bead can be manufactured so that the DNA barcode is situated in the inside of the bead while, in contrast, the compound that is being screened is attached to the bead's surface (Lam et al, supra, at pages 438-439). This advantage of internal volume may be irrelevant, where the bead-bound compound is attached by a cleavable linker, and where assays of the compound are conducted only on compounds that are cleaved and released.

Appell et al, provide a non-limiting example of spit-and-pool method for synthesizing a chemical library followed by screening to detect active compounds (Appell et al (1996) J. Biomolecular Screening. 1:27-31). Library beads are placed, one into each well, in an array of wells on a first microwell plate, nanowell plate, or picowell plate. Beads are exposed to light, in order to cleave about 50% of the bead-bound compounds, releasing them into solution in the well. Released compound is then transferred to a second microwell plate, and subjected to assays for detecting wells that contain active compounds, thereby identifying which beads in the first plate contain bead-bound compounds that are active. Then, "[o]nce an active [compound] is identified from a single bead, the bead is recovered and decoded, thus yielding the synthetic history and . . . structure of the active compound" (Appell et al, supra).

For cell-based screening assays that screen for bead-bound compounds, Shih et al provide a novel type of bead (Shih et al (2017) Mol. Cancer Ther. 16:1212-1223). This novel type of bead contains a bead-bound compound that is a member of a library of "synthetic death ligands against ovarian cancer." The bead is also decorated with biotin, where two more chemicals are added that create a sandwich, and where the sandwich maintains adhesion of the cell to the bead. The sandwich includes a streptavidin plus biotin-LXY30 complex. This sandwich connects the bead to LXY30's receptor, which happens to be a well-known protein on the cell surface, namely, an integrin. The method of Shih et al, supra, resulted in the discovery of a new molecule ("LLS2") that can kill cancer cells. The above method uses bead-bound compounds, where the compounds bind to cells (even though the compound is still bead-bound). Cho et al created a similar one-bead-one-compound library, where the compound being screened was sufficient to bind to cells (without any need for the above-described sandwich) (Cho et al (2013) ACS Combinatorial Science. 15:393-400). The goal of the Cho et al, report was to discover RGD-containing peptides that bind to integrin that is expressed by cancer cells. The above-disclosed reagents and methods are useful for the present disclosure.

Coupling Nucleic Acids to Beads (Orthogonal Style; Concatenated Style)

One way to get oriented to the topic of concatenated barcodes and orthogonal barcodes, is to note advantages that one has over the other. An advantage of orthogonal barcoding over concatenated barcoding, is as follows. With attachment of each monomer of a growing chemical compound, what is attached in parallel is a DNA barcode module. With concatenated barcoding, if attachment of any given module is imperfect (meaning, that not all of the attachments sites was successfully coupled with a needed module), then the sequence of the completed barcode will not be correct. The statement "not be correct" means that imperfect coupling means that chunks may be missing from wad was assumed to be the completed, correct DNA barcode. Here, the completed barcode sequence will contain a mistake, due to failure of attachment of all of the modules. In contrast, with orthogonal barcoding each individual module gets covalently bound to its own unique attachment site on the bead. And where once a module gets attached to a given site on the bead, no further modules will be connected to the module that is already attached.

The present disclosure provides reagents and methods for reducing damage to bead-bound DNA barcodes, and for reducing damage to to partially synthesized bead-bound DNA barcodes. Each DNA barcode module, prior to attaching to a growing bead-bound DNA barcode, can take the form of double stranded DNA (dsDNA), where this dsDNA is treated with a DNA cross-linker such as mitomycin-C. After completion of the synthesis of the DNA barcode in its dsDNA form, this dsDNA is converted to ssDNA. Conversion of dsDNA to ssDNA can be effected where one of the DNA strands has a uracil (U) residue, and where cleavage of the DNA at the position of the uracil residue is catalyzed by uracil-N-glycosidase (see, FIG. 5 of Ser. No. 62/562,905, filed Sep. 25, 2017. Ser. No. 62/562,905 is incorporated herein by reference in its entirety). The above refers to damage that is inflicted on the growing DNA barcode by reagents used to make the bead-bound chemical compound.

Another method for reducing damage to bead-bound DNA barcodes, and for reducing damage to partially synthesized DNA barcodes, is by synthesizing the DNA barcode in a double stranded DNA form, where each of the DNA barcode modules that are being attached to each other takes the form of dsDNA, and where each of the two strands is stabilized by way of a DNA headpiece. For eventual sequencing of the completed DNA barcode, one of the strands is cleaved off from the DNA headpiece and removed. The above refers to damage that is inflicted on the growing DNA barcode by reagents used to make the bead-bound chemical compound (where this chemical compound is a member of the chemical library).

Yet another method for reducing damage to bead-bound DNA barcodes, is to synthesize the DNA barcode in a way that self-assembles to form a hairpin, and where this DNA barcode self-assembles to that the first prong of the hairpin anneals to the second prong of the hairpin.

Where the DNA barcode being synthesized takes the form of double stranded DNA (dsDNA), solvents such as DCM, DMF, and DMA can denature the DNA barcode. The above methods and reagents can prevent denaturation.

As stated above, the term "DNA barcode" can refer to a polynucleotide that identifies a chemical compound in its entirety while, in contrast, "DNA barcode module" can refer to only one of the monomers that make up the chemical compound.

Another method for reducing damage to bead-bound DNA barcodes, and for reducing damage to partially synthesized DNA barcodes, is to use double stranded DNA (dsDNA) and to seal the ends of this dsDNA by way of 7-aza-dATP and dGTP.

In alternate embodiments, the method can use an intermediate between "concatenated DNA barcoding" and "orthogonal DNA barcoding," where this intermediate involves blocks of DNA barcodes, that is, where each block contains two DNA modules, or contains three DNA modules, or contains four DNA modules, or contains five DNA modules, and the like (but does not contain all of the DNA modules that identify the full-length compound).

FIG. 1 discloses an exemplary and non-limiting diagram of the CONCATENATED structured bead. The bead contains a plurality of DNA barcodes (each made of DNA barcode modules) and a plurality of compounds (each made of chemical library monomers). For ease in speaking, the term "DNA barcode" may be used to refer to the polymer that includes all of the nucleic acids that are a "DNA barcode module," as well as all of the nucleic acids that provide some function. The function can be an annealing site for a sequencing primer, or the function can be used to identify a step in chemical synthesis of the bead-bound compound. FIG. 1 also shows bead-bound compounds, where each compound is made of several chemical library members, and where each chemical library member is represented by a square, circle, or triangle. FIG. 1 shows that each DNA barcode module is numbered, consecutively, from 1 to 8, where these numbers correspond to the respective eight shapes (squares, circles, triangles). For clarity, nucleic acids that serve a function (and do not represent or "encode" any particular chemical unit) are not shown in the figure.

FIG. 2 discloses an exemplary and non-limiting embodiment of the ORTHOGONAL structured bead. The bead contains a plurality of DNA barcodes (each made of DNA barcode modules), but each DNA barcode module is attached to a separate linking site on the bead. The entire DNA barcode consists of eight DNA barcode modules, which in the figure are numbered 1-8. When the information from a particular DNA barcode is read, and then used to identify the chemical compound that is bound to the same bead, one must perform DNA sequencing on each of the separately attached DNA barcode modules. In FIG. 2, the bead also contains a plurality of attached chemical compounds, each with eight units, as shown by the eight shapes (circles, squares, triangles).

In FIG. 2, for clarity, functional nucleic acids that are attached to each DNA barcode module is not shown. Of course, each of the DNA barcode modules needs to have a nucleic acid that identifies the position of the chemical library monomer in the completed, full-length compound. For the example shown in FIG. 2, the position needs to be first, second, third, fourth, fifth, sixth, seventh, or eighth.

In one embodiment, the chemical monomer is first attached and then, after that, the corresponding DNA barcode module is attached. In an alternative embodiment, the DNA barcode module is first attached, and then the corresponding chemical monomer is attached. Also, a procedure of organic synthesis can be followed that sometimes uses the "one embodiment" and sometimes uses the "alternative embodiment." In yet another alternative embodiment, the present method provides block-wise addition of a block of several chemical monomers which is attached to the bead, in parallel with attachment of a block of several DNA barcode modules.

In exclusionary embodiments, what can be excluded is reagents, compositions, and methods that used block-wise addition of chemical monomers, of DNA barcode modules, or of both chemical monomers and DNA barcode modules, to a bead.

This concerns nucleic acids that may be present in the bead-bound polynucleotide, including nucleic acids that "encode" or serve to identify monomers of a bead-bound compound. In exclusionary embodiments, the present disclosure can exclude a nucleic acid that encodes a "step-specific DNA sequencing primer site." In this situation, for each chemical monomer that is present in a compound, there is a corresponding DNA barcode module, where each DNA barcode module is flanked by at least one corresponding primer-binding site, that is, "a step-specific DNA sequencing primer site." Also, what can be excluded is a nucleic acid that encodes or designates a particular step in the chemical synthesis of a compound, such as step 1, step 2, step 3, or step 4.

Moreover, the present disclosure can include a nucleic acid that functions as a spacer. For example, as spacer can create a distance, along a polynucleotide chain, between a first site that is a sequencing primer annealing site and a second site that identifies a chemical monomer. Also, the present disclosure can use a nucleic acid that reiterates or confirms the information provided by another nucleic acid. Also, the present disclosure can use a nucleic acid that encodes a PCR primer binding site. A PCR primer binding site can be distinguished from a sequencing primer, because a polynucleotide with a PCR primer binding site has two PCR primer binding sites, and because both of these sites are designed to have the same melting point (melting point when the PCR primer is annealed to PCR primer binding site).

In exclusionary embodiments, the present disclosure can exclude a nucleic acid that functions as a spacer, or solely as a spacer. Also, the present disclosure can exclude a nucleic acid that reiterates or confirms the info provided by another nucleic acid. Moreover, the present disclosure can exclude a nucleic acid that serves as a PCR primer binding site, and can exclude a nucleic acid that serves as a binding site for a primer that is not a PCR primer.

Additionally, the present disclosure can exclude a nucleic acid that identifies the date that a chemical library was made, or that identifies a step in chemical synthesis of a particular compound, or that serves as a primer annealing sequence.

Dedication of sequencing primers to a particular DNA barcode module. The present disclosure provides a DNA barcode that contains DNA barcode modules and one or more sequencing primer annealing sites. Each DNA barcode module may have its own, dedicated, sequencing primer binding site. Alternatively, one particular sequencing primer binding site may be used for sequencing two, three, four, five, 6, 7, 8, 9, 10, or more consecutive DNA barcode modules, as may exist on the bead-bound DNA barcode.

The following describes the situation where each DNA barcode module has its own dedicated sequencing primer binding site. The present disclosure provides a bead-bound concatenated barcode comprising a primer binding site capable of binding a DNA sequencing primer, wherein said primer binding site is capable of directing sequencing of one or more of the $1^{st}$ DNA barcode module, the $2^{nd}$ DNA barcode module, the $3^{rd}$ DNA barcode module, the $4^{th}$ DNA barcode module, the $5^{th}$ DNA barcode module, and the $6^{th}$ DNA barcode module, and wherein the primer binding site is situated 3-prime to the 1st DNA barcode module with no other DNA barcode module in between the $1^{st}$ DNA barcode module and the primer binding site, 3-prime to the $2^{nd}$ DNA barcode module with no other DNA barcode module in between, 3-prime to the $3^{rd}$ DNA barcode module with no other DNA barcode module in between, 3-prime to the $4^{th}$ DNA barcode module with no other DNA barcode module in between, 3-prime to the $5^{th}$ DNA barcode module with no other DNA barcode module in between, or 3-prime to the $6^{th}$ DNA barcode module with no other DNA barcode module in between.

Encoding sequences and sequences complementary to encoding sequences. The present disclosure can encompass any one, any combination of, or all of the encoding sequences disclosed above, or elsewhere, in this document. In exclusionary embodiments, what can be excluded are any one, any combination of, or all of the encoding sequences disclosed above, or elsewhere, in this document. What can also be included or can be excluded are double stranded nucleic acids that encode any one, any combination of, or all of the encoding sequences described above, or elsewhere, in this document.

Orthogonal-Style DNA Barcode (Each DNA Barcode Module Attached to Separate Location on Bead)

Synthesis of orthogonal-style bead. With orthogonal synthesis, each DNA module gets covalently attached to a separate site on the bead, and where the result is that the entire DNA barcode is contributed by a plurality of DNA modules. Where the DNA barcode has the orthogonal structure, none of the DNA barcode modules are attached to each other —instead each and every one of the DNA barcode molecules has its own bead-attachment site that is dedicated to that particular DNA barcode module.

Nucleic acid identifying the synthesis step number for each DNA barcode module. In embodiments, the orthogonal DNA barcode includes a short nucleic acid that identifies the first step of compound synthesis. For this embodiment, with the parallel attachment of the first chemical monomer and the first DNA barcode module, the first DNA barcode module actually takes the form of this complex of two nucleic acids: [SHORT NUCLEIC ACID THAT MEANS "STEP ONE"] connected to [FIRST DNA BARCODE MODULE]. All of the nucleotides of this complex are in-frame with each other and can be read in a sequencing assay, but the first short nucleic acid may optionally be attached to the first DNA barcode module by way of a spacer nucleic acid.

The following continues the above description of the orthogonal DNA barcode. The orthogonal DNA barcode includes a short nucleic acid that identifies the second step of compound synthesis. For this embodiment, with the parallel attachment of the second chemical monomer and the second DNA barcode module, the second DNA barcode module actually takes the form of this complex of two nucleic acids: [SHORT NUCLEIC ACID THAT MEANS "STEP TWO"] connected to [SECOND DNA BARCODE MODULE]. All of the nucleotides of this complex are in-frame with each other and can be read in a sequencing assay, but the second short nucleic acid may optionally be attached to the second DNA barcode module by way of a spacer nucleic acid.

The above-described method is repeated for the third, fourth, fifth, sixth, seventh, eighth, ninth, tenth, and up to the last of the DNA barcode modules and up to the last of the chemical monomers, for any given bead. The above-method can be followed when using split-and-pool synthesis, for creating DNA barcodes and chemical compounds that are bead-bound.

The orthogonal structure provides the following advantage over the concatenated structure. With concatenated synthesis (all DNA barcode modules attached to each other in one, continuous polymer) it is the case that failure to achieve synthesis any of the intermediates coupling steps can ruin the meaning of the concatenated DNA barcode that is eventually completed. In contrast, with orthogonal synthesis (each and every one of the DNA barcode modules attached to a dedicated site on the bead), failure to attach any of the DNA barcode modules will only result in an empty attachment site on the bead, and will not ruin the meaning of any of the other attached DNA barcode modules. In a preferred embodiment, each attached DNA barcode module includes an attached, second nucleic acid, where this second nucleic acid identifies the step (the step during the parallel synthesis of DNA barcode and chemical compound).

For orthogonal synthesis, it is acceptable for all of the attachment sites on the bead to be used up (sites for attaching the growing chemical library member). However, for orthogonal synthesis, the chemical reaction needs to be designed so that the entire population of attachment sites on the bead is only partly used up, with attachment of the first of many DNA barcode modules. The following provides optional limits for using up sites during chemical synthesis of an orthogonal barcode. For the non-modified bead, the total number of sites available for attaching a DNA barcode module is 100%.

Extent of using up attachment sites on a given bead, with synthesis of an orthogonal-configured bead (regarding the $1^{st}$ DNA barcode). The following concerns attaching the first DNA barcode module. In embodiments, with attachment of the first DNA barcode module, about 5%, about 10%, about 20%, about 30%, about 40%, or about 50% of the DNA barcode attachments sites on the bead are used up. In other embodiments, less than about 2%, less than about 5%, less than about 10%, less than about 20%, less than about 30%, less than about 40%, or less than about 50% of the DNA barcode attachments sites on the bead are used up. In still other embodiments, with attachment of the first DNA barcode module, between 2-4%, between 2-6%, between 2-8%, between 2-10%, between 2-12%, between 2-14%, between 2-16%, between 2-18%, between 2-20%, between 10-20%, between 10-25%, between 10-30%, between 10-35%, between 10-40%, of the DNA barcode attachment sites are used up.

Regarding limits, with attaching the last of the DNA barcode modules that make up a particular DNA barcode, less than 20% of the sites are used up, less than 30%, less than 40%, less than 50%, less than 60%, less than 70%, less than 80%, less than 90%, less than 95%, or less than 98% of the sites are used up.

Exclusionary embodiments can exclude beads or methods that match any of the above values or ranges. Also, exclusionary embodiments can exclude beads or methods that fail to match any of the above values or ranges.

The following concerns polymers that comprises one or more nucleic acids, each being a DNA barcode, as well as polymers that comprise two or more nucleic acids, where some of the nucleic acids have a biochemical function such as serving as a primer-annealing site or as a spacer, and where other nucleic acids have an informational function and are DNA barcodes. In exclusionary embodiments, the present disclosure can exclude a DNA barcode that includes a DNA crosslinking agent such as psoralen. Also, what can be excluded is a DNA barcode with a primer binding region with a higher melting temperature (or a lower melting temperature) than a DNA barcode module. This temperature can be merely "higher" or "lower" or it can be at least 2 degrees C. higher, at least 4 degrees C. higher, at least 6 degrees C. higher, at least 8 degrees higher, or at least 2 degrees C. lower, at least 4 degrees C. lower, at least 6 degrees C. lower, at least 8 degrees lower.

Also what can be excluded is a method for making a DNA barcode that uses DNA ligase. Also, what can be excluded is a DNA barcode and methods for making, that comprise a hairpin (ssDNA bent in a loop, so that one portion of the ssDNA hybridizes to another portion of the same ssDNA). Additionally, what can be excluded is a composition with a nucleic acid hairpin, where the nucleic acid hairpin is covalently closed, for example, with a chemical linker.

Moreover, what can be excluded is a DNA barcode that is covalently linked, either directly to a "headpiece," or indirectly to "headpiece" (indirectly by way of covalent binding to one or more chemicals that reside in between DNA barcode and the headpiece).

In other exclusionary embodiments, what can be excluded is a bead-bound DNA barcode, where the completed DNA barcode does not comprise any double stranded DNA (dsDNA), but only comprises single stranded DNA (ssDNA).

Extent of using up attachment sites on a given bead, with synthesis of an orthogonal-configured bead (regarding the $2^{nd}$ DNA barcode). The following concerns attaching the second DNA barcode module. In embodiments, with attachment of the second DNA barcode module (for the creation of the orthogonal configured bead), about 5%, about 10%, about 20%, about 30%, about 40%, or about 50% of the remaining free DNA barcode attachments sites on the bead are used up. In other embodiments, less than about 5%, less than about 10%, less than about 20%, less than about 30%, less than about 40%, or less than about 50% of the remaining free DNA barcode attachments sites on the bead are used up. In still other embodiments, with attachment of the first DNA barcode module, between 2-4%, between 2-6%, between 2-8%, between 2-10%, between 2-12%, between 2-14%, between 2-16%, between 2-18%, between 2-20%, between 10-20%, between 10-25%, between 10-30%, between 10-35%, between 10-40%, of the remaining free DNA barcode attachment sites are used up.

Exclusionary embodiments can exclude beads or methods that match any of the above values or ranges. Also, exclusionary embodiments can exclude beads or methods that fail to match any of the above values or ranges.

The above embodiments, as well as the above exclusionary embodiments, can also be applied to a method with attaching a third DNA module barcode, or with attaching a fourth DNA module barcode, or with attaching a fifth DNA barcode module, and so on.

Concatenated-style DNA barcode (all DNA barcode modules reside in one chain or polymer, where the entire chain or polymer is attached to one location on the bead).

Synthesis of bead-bound concatenated-style DNA barcode. The present disclosure provides a bead-bound concatenated-style DNA barcode, where the bead contains a plurality of concatenated-style DNA barcodes, and where most or nearly all of the plurality of concatenated-style DNA barcodes have essentially the same structure. The concatenated-style DNA barcode can contain one or more DNA barcode modules, where the ordering of these DNA barcode modules (from the bead-attachment terminus to the distal terminus) along the entire DNA barcode, takes the same order as the time that the bead-bound concatenated-style DNA barcode is synthesized. Also, the ordering of these DNA barcode modules along the entire DNA barcode, takes the same order as the time that a corresponding chemical library monomer is coupled to the growing bead-bound compound.

The concatenated-style DNA barcode can comprise, in this order, a linker that is used to couple the entire concatenated-style DNA barcode to the bead. Also, it can comprise, in this order, a $1^{st}$ DNA barcode module, a $1^{st}$ annealing site, a $2^{nd}$ DNA barcode module, a $2^{nd}$ annealing site, a $3^{rd}$ DNA barcode module, and a $3^{rd}$ annealing site.

One ordering of sequencing primer hybridizing site in a bead-bound DNA barcode. In sequencing primer hybridizing site embodiments, the concatenated-style DNA barcode can comprise, in this order, a linker, a $1^{st}$ DNA barcode module, a $1^{st}$ annealing site, a $1^{st}$ sequencing primer binding site, a $2^{nd}$ DNA barcode module, a $2^{nd}$ annealing site, a $2^{nd}$ sequencing primer binding site, a $3^{rd}$ DNA barcode module, a $3^{rd}$ annealing site, and a $3^{rd}$ sequencing primer binding site, and so on.

Another ordering of the sequencing primer hybridizing site, as it occurs in a bead-bound DNA barcode. In another sequencing primer hybridizing site embodiment, the concatenated-style DNA barcode can comprise, in this order, a linker, a $1^{st}$ DNA barcode module, a $1^{st}$ sequencing primer binding site, $1^{st}$ annealing site, a $2^{nd}$ DNA barcode module, a $2^{nd}$ sequencing primer binding site, a $2^{nd}$ annealing site, a $3^{rd}$ DNA barcode module, a $3^{rd}$ sequencing primer binding site, and $3^{rd}$ annealing site, and so on.

The term "annealing site." The term "annealing site" is used to refer to an annealing site that is part of a splint oligonucleotide (splint oligo) and also to refer to the corresponding bead-bound annealing site that resides on a growing bead-bound DNA barcode. The skilled artisan understands that the "annealing site" on the splint oligo does not possess the same DNA sequence as the corresponding "annealing site" on the growing bead-bound DNA barcode. In other words, the skilled artisan understands that one sequence is complementary to the other sequence. Therefore, it is of no consequence that, for the descriptions herein, both annealing sites have the same name. In other words, it is of no consequence that the $2^{nd}$ annealing site on a splint oligo is disclosed as one that hybridizes to the $2^{nd}$ annealing site on growing bead-bound DNA barcode.

Synthesis in blocks. In an alternative embodiment, the growing compound and the growing sequence of DNA barcode modules can be synthesized in blocks. For example, a block consisting of 2-chemical library units can be attached to a bead in parallel with attaching a block consisting of corresponding 2-DNA barcode modules. Similarly, a block consisting of 3-chemical library units, can be attached to a bead in parallel with attaching a block consisting of a corresponding 3-DNA barcodes. Block synthesis involving blocks of four, blocks of five, blocks of six, blocks of seven, blocks of eight, blocks of nine, blocks of ten, and so on, are also provided. Each of these block transfer embodiments can also be excluded by the present disclosure. The blockwise transfer of DNA barcode monomers can be done orthogonally, with unique attachment points for receiving each of successive blocks of DNA barcode momers. Alternatively, blockwise transfer of DNA barcode monomers can be done to produce a concatemer structure (all DNA barcode modules occurring as only one continuous, linear polymer).

Also, during split-and-pool synthesis in parallel of the bead-bound DNA barcode and the bead-bound compound, synthesis of can occur in blocks. The block can take the form of two or more chemical library monomers, and the block can take the form of two or more DNA barcode modules.

Location of split-and-pool synthesis. Split-and-pool synthesis can be used for the parallel synthesis of bead-bound compounds and bead-bound concatenated DNA barcode. Also, split-and-pool synthesis can be used for the parallel synthesis of bead-bound compounds and bead-bound orthogonal DNA barcode. The concatenated DNA barcode can be made by way of the "splint oligo" method. Alternatively, concatenated DNA barcode can be made by way of click chemistry. Also, a combination of the "splint oligo" method and click chemistry can be used. Split-and-pool synthesis can occur in a 96 well plate, where each well has a floor made of a 0.25 micrometer filter. Under normal gravity conditions, aqueous solutions do not flow through this filter. However, suction can be applied to remove any aqueous solutions from all of the 96 wells, for example, where there is a need to replace a first aqueous solution with a second aqueous solution. This suction method is used when the bead is exposed to a first set of reagents, or when the first set of reagents needs to be rinsed out, or when the first set of reagents needs to be replaced by a second set of reagents. A manifold is used to hold the 96 well plate (Resprep VM-96 manifold) and a pump can be used to draw fluid out the bottom of every filter (BUCHI Vac V-500 pump). The 96 well plate with the filter bottom was, Acro-Prep Advance 96 well, 350 uL, 0.45 um, REF 8048 (Pall Corp., Multi-Well Plates, Ann Arbor, MI).

Distance from primer annealing site to a DNA barcode module. For the purpose of sequencing a bead-bound DNA barcode, that is, for the goal of sequencing all of the DNA barcode modules that form the DNA barcode, a polynucleotide comprising a first nucleic acid that is an annealing site for a sequencing primer, and a second nucleic acid that is a DNA barcode module, the first nucleic acid can be immediately upstream of the second nucleic acid. Alternatively, the first nucleic acid can be upstream of the second nucleic acid, where the first and second nucleic acids are separated from each other by one, two, three, four, five, 6, 7, 8, 9, 10, 11, 12, 13, 14, 15, or more nucleotides, or by about one, about two, about three, about about four, about five, about 6, about 7, about 8, about 9, about 10, about 11, about 12, about 13, about 14, or about 15 nucleotides. The separation can be with nucleic acids that merely serve as a spacer or, alternatively, the separation can be with a third nucleic acid that encodes information, such as step number in a multi-step pathway of organic synthesis, or the nume of a class of chemical compounds, or a disease that might be treatable by the bead-bound compound, or the date, or a lot number, and so on.

Synthesis of Bead-Bound Concatenated DNA Barcode Using Click Chemistry

Click chemistry can be used for the step-by-step synthesis of a DNA barcode. Here, what can be coupled is a first DNA barcode module directly to a bead, or a first DNA barcode module to a bead-bound linker.

Also, what can be coupled is a polynucleotide taking the form of a first nucleic acid that is a $1^{st}$ DNA barcode module attached to a second nucleic acid that is a $1^{st}$ sequencing primer binding site. This sequencing primer binding site allows the operator to determine the sequence of the $1^{st}$ DNA barcode module.

To provide another example, what can be coupled is a $2^{nd}$ DNA barcode module directly to a bead-bound $1^{st}$ DNA barcode module. Alternatively, what can be coupled is a polynucleotide taking the form of a first nucleic acid that is a $2^{nd}$ DNA barcode module attached to a second nucleic acid that is a $2^{nd}$ sequencing primer binding site. This sequencing primer binding site allows the operator to determine the sequence of the $2^{nd}$ DNA barcode module. If there is read-through to the $1^{st}$ DNA barcode module, then what can be determined is the sequence of both of these DNA barcode modules.

To provide yet another example, what can be coupled is a polynucleotide comprising a first nucleic acid that is a $1^{st}$ DNA barcode module, and a second nucleic acid that identifies the step in a multi-step parallel synthesis of the DNA barcode and of the compound. Also, or alternatively, the second nucleic acid can identify the general class of compounds that are being made by the split-and-pool synthesis. Also, or alternatively, the second nucleic acid can identify a disease that is to be treated by the compounds to be screened. Also, the second nucleic acid can identify the date, or the name of the chemist, and so on.

A preferred method for synthesizing the DNA barcode is shown below, where the same cycle of reactions is used with progressive attachment of each DNA barcode module.

Step 1. Provide a bead with an attached TCO group. In actual practice, the bead will have hundreds or thousands of identically attached TCO groups, where each TCO group is attached to a different site on the bead. Also, in actual practice, a large number of beads will be simultaneously modified by click chemistry, with employment of the split-and-pool method.

Step 2. Add [tetrazine]-[first DNA barcode module]-[azide] to the bead, and allow the TCO group condense with the tetrazine group. The result is the following construct: BEAD-TCO-tetrazine-first DNA barcode module-azide. In actual practice, this construct does not include any TCO or tetrazine, but instead has the condensation product that is created when TCO condenses with tetrazine.

Step 3. Optional wash.

Step 4. Add DBCO-TCO in order to cap the azide and to create a TCO terminus The result is the following structure: BEAD-TCO-tetrazine-first DNA barcode module-azide-DBCO-TCO Step 5. Optional wash.

Step 6. Add the following reagent, which attaches the second DNA barcode module. Attachment is to the distal terminus of the growing DNA barcode. The reagent is:

[tetrazine]-[second DNA barcode module]-[azide] to the bead, and allow the TCO group condense with the tetrazine group. The result is the following construct:

BEAD-TCO-tetrazine-first DNA barcode module-azide-DBCO-TCO-[tetrazine]-[second DNA barcode module]-[azide]

The above scheme includes a cycle of steps for the stepwise addition of more and more DNA barcode modules, where these additions are in parallel with additions of more and more chemical monomers. As stated elsewhere, this "parallel" synthesis can involve attaching a chemical monomer followed by attaching a DNA barcode module that identifies that monomer or, alternatively, attaching a DNA barcode module followed by attaching a chemical monomer that is identified by that particular chemical monomer.

Compounds for Click-Chemistry Synthesis of DNA Barcode

FIG. 17 discloses the chemical synthesis of a compound suitable for connecting a deoxycytidine reside (dC) during the synthesis of a DNA barcode module and, ultimately, the entire DNA barcode. The starting material is N4-acetyl-2'-deoxy-5'-O-DMT cytidine. The abbreviation "DMT" stands for 4,4-dimethoxytrityl. The final product of this multi-step pathway of organic synthesis bears a cytosine moiety, a triphosphate group, and a propargyl group that is attached to the 3'-position of the ribose group. The propargyl group is used for click chemistry, where it condenses with an azide group to produce a covalent bond. After condensing, the result is that a residual chemical (never naturally present in nucleic acids), occurs as a "scar" from the click chemistry that had been performed. What is available is DNA polymerases that can be used for sequencing-by-synthesis of DNA barcodes made by click chemistry, and where the DNA polymerases can move across the scars, and where the scars do not cause sequencing errors. TBAI is tetrabutyl ammonium iodide.

Synthesis of Concatenated Configuration DNA Barcode

In the following description, DNA barcode modules are assembled in a row in order to create the DNA barcode. However, in the in-text diagrams that are shown below, the term "DNA barcode" is used instead of "DNA barcode module," in order to make the in-text diagrams fit on the page. FIG. 7 illustrates the same steps as shown here, but with additional details, such as diagrams of beads. A reiterated sequence of reactions can be used for adding each additional DNA barcode module.

Option of creating a DNA barcode that includes a terminal nucleic acid that encodes DNA hairpin. This concerns a DNA barcode that includes, at the 3-prime end, a nucleic acid that possesses an annealing site for a sequencing primer, a bend taking the form of about four bases that are not base-paired, and a sequencing primer that is capable of bending around and forming base pairs with the sequencing primer annealing site. To repeat, the sequencing primer anneals to the sequencing primer annealing site, where the actual sequencing reaction begins at the 3'-terminus of the annealed sequencing primer.

When it is time to perform a final step in synthesizing a DNA barcode, and when the final DNA barcode module is to be coupled to the growing bead-bound DNA barcode, the "splint oligo" can include a sequence that encompasses a DNA hairpin (the DNA hairpin including, in this order, an annealing site for the sequencing primer, several nucleotides that do not base pair with each other or with any nearby sequences of bases, and a sequencing primer). After annealing the "splint oligo," then DNA polymerase and dNTPs are added, where polymerization occurs at the 3'-end of the growing DNA barcode, where what gets polymerized using the splint oligo as a template is, in order: (1) Annealing site for sequencing primer; (2) Bend in the hairpin taking the form of four or five deoxyribonucleotides that do not base pair with teach other; and (3) Sequencing primer.

Reversible terminator group at the 3'-end of the hairpin sequencing primer. The present disclosure provides reagents, compositions, and methods, for attaching a preformed complex of a nucleotide/reversible terminator group, to the 3'-terminus of the annealed sequencing primer. Reversible terminator group is an optional component of the hairpin sequencing primer, where it is to be part of a bead-bound DNA barcode.

STEP 1. At the start, we have a bead situated in a picowell, where the bead bears a coupled polynucleotide, and where the 5'-end of the polynucleotide is coupled to the bead, optionally, with a linker. FIG. 7 shows that the bead-bound polynucleotide comprises a $1^{st}$ DNA barcode and a $1^{st}$ annealing site. The linker can be made of a nucleic acid, or it can be made of some other chemically. Preferrably, the linker is hydrophobic, and preferably the linker separates the bead-bound DNA barcode from the hydrophobic polystyrene bead, for example, a TentaGel® bead.

For convenience in writing, a $1^{st}$ annealing site that is part of a bead-bound DNA barcode and a $1^{st}$ annealing site that is part of a soluble "splint oligo" are both called "$1^{st}$ annealing site," even though they do not have the same sequence of bases (instead, the sequence of bases are complementary to each other, where the result is that the splint oligo can hybridize to the $1^{st}$ annealing site on the bead-bound growing DNA barcode, thereby serving as a template for DNA polymerase to extend the bead-bound DNA barcode by copying what is on the splint oligo.

Also, for convenience in writing, a $2^{nd}$ annealing site that is part of a bead-bound DNA barcode and a $2^{nd}$ annealing site that is part of a soluble "splint oligo" are both called, "$2^{nd}$ annealing site," even though they do not have the same sequence (but instead have complementary bases).

The bead-bound growing DNA barcode, from the 5'-end to the 3'-end, may contain the nucleic acids in the following order:

Bead-/$1^{st}$ DNA Barcode/$1^{st}$ Annealing Site/

Alternately, the bead-bound growing DNA barcode, from the 5'-end to the 3'-end, may include a nucleic acid that encodes the step number, where the bead-bound growing DNA barcode has nucleic acids in the following order:

Bead-/$1^{st}$ DNA Barcode/Nucleic Acid Encoding Step Number/$1^{st}$ Annealing Site/

Alternatively, the bead-bound growing DNA barcode can include a nucleic acid that is a functional nucleic acid (a sequencing primer annealing site), as shown below:

Bead-/$1^{st}$ DNA Barcode/Sequencing Primer Annealing Site/$1^{st}$ Annealing Site/

What is not shown in these in-text diagrams is an optional linker that mediates coupling of the DNA barcode to the bead. The linker can take the form of a nucleic acid, or it can be made of some other organic chemical.

STEP 2. Add a soluble splint oligonucleotide (splint oligo), where this splint oligo comprises a 1st annealing site and a $2^{nd}$ DNA barcode module, and a $2^{nd}$ annealing site.

FIG. 7 also illustrates the step where the hybridized splint oligo is used as a template, where DNA polymerase catalyzes the attachment to the bead-bound growing DNA barcode of the $2^{nd}$ DNA barcode module and the $2^{nd}$ annealing site. FIG. 7 shows the enzymatic product where DNA polymerase catalyzes uses the splint oligo as a template, resulting in the bead-bound DNA barcode growing by a bit longer (growing by covalent attachment of the $2^{nd}$ DNA barcode and the $2^{nd}$ annealing site. What is shown immediately below in the text, is the complex of the splint oligo that is hybridized to the bead-bound growing DNA barcode:

Bead-/$1^{st}$ DNA Barcode/$1^{st}$ Annealing Site/

. . . $1^{st}$ annealing site/$2^{nd}$ DNA barcode/$2^{nd}$ annealing site

To reiterate some information shown in FIG. 7, what is shown immediately below is the splint oligo:

"$1_{st}$ Annealing Site/$2^{nd}$ DNA Barcode/$2^{nd}$ Annealing Site"

STEP 3. DNA polymerase and dNTPs are added to extend the bead-bound DNA barcode. Shown below is the bead-bound growing DNA barcode, with the splint oligo still hybridized to it, and where the bead-bound growing barcode is longer than before, because what is now attached to it is a nucleic acid that is the "$2^{nd}$ DNA barcode module" and a nucleic acid that is the "$2^{nd}$ annealing site." FIG. 7 also illustrates this step. The splint oligo is shown underneath the bead-bound growing barcode:

Bead-/$1^{st}$ DNA Barcode/$1^{st}$ annealing site/$2^{nd}$ DNA Barcode/$2^{nd}$ Annealing Site . . . $1^{st}$ annealing site/$2^{nd}$ DNA barcode/$2^{nd}$ Annealing Site Step 4. Wash away the splint oligo. The splint oligo can be encouraged to dissociate from the bead-bound growing barcode by heating, that is, by heating the entire picowell plate, for example, to about 60 degrees C., about 65 degrees C., about 70 degrees C., about 75 degrees C., about 80 degrees C., for about ten minutes or, alternatively, by adding dilute NaOH to the picowell array, and then neutralizing.

Step 5. Add a second splint oligo which, after hybridizing to the bead-bound growing splint oligo, can be used as a template for mediating DNA polymerase-catalyzed attachment of a $3^{rd}$ DNA barcode and a $3^{rd}$ annealing site. This second splint oligo, which is a soluble reagent, is shown below (but it is not shown in FIG. 7):

$2^{nd}$ annealing site/$3^{rd}$ DNA barcode/$3^{rd}$ annealing site/

Step 6. Allow this oligonucleotide to anneal to the corresponding bead-bound "$2^{nd}$ annealing site," and allow DNA polymerase to extend the bead-bound oligonucleotide, so that it contains a complement to the: "$3^{rd}$ DNA barcode/$3^{rd}$ annealing site/

Step 7. Wash away the second splint oligo.

Step 4. Add the following splint oligo (this particular addition is not shown in FIG. 7).

3rd annealing site/4th DNA barcode/4th annealing site/

This soluble oligonucleotide has a nucleic acid that can anneal to the "$3^{rd}$ annealing site" of the bead-bound oligonucleotide. Once annealed, DNA polymerase with four dNTPs are employed and used for extending the bead-bound oligonucleotide to encode yet another DNA barcode module (the $4^{th}$ DNA barcode). The above cycle of steps is repeated, during the entire split-and-pool procedure that creates, in parallel, the library of chemical compounds and the associated DNA barcodes, where each DNA barcode is associated with a given compound (where each DNA barcode informs us of the history of chemical synthesis of the associated compound). The above cycle of steps is stopped, when the chemical synthesis of the library of compounds has been completed. With the completed bead-bound, DNA barcoded chemical library in hand, the beads can then be dispensed into microwells of a microwell array.

The DNA barcode for each bead also constitutes a DNA barcode that associated with each microwell. The DNA barcode allows identification of the bead-bound compound. The sequencing method of the present disclosure occurs inside the microwell while the bead is still inside the microwell. In exclusionary embodiments, the present disclosure can exclude any sequencing method and can exclude exclude any reagents used for sequencing, where sequencing is not performed on a DNA tempate that is bead-bound, or where sequencing is not performed on a bead-bound DNA template that is situated inside a microwell.

Annealing sites for sequencing primer. In one embodiment, each DNA barcode module in a completed DNA barcode is operably linked and in frame with its own sequencing primer annealing site, thus providing the operator with the ability to conduct separate sequencing procedures on each DNA barcode module (in this embodiment, it is preferred that each DNA barcode module is also operably linked with its own nucleic acid that identifies (encodes) the step in synthesis of the entire DNA barcode.

In another embodiment, each DNA barcode has only one sequencing primer annealing site, where this can be situated at or near the 3'-terminus of the bead-bound DNA barcode, and where the sequencing primer itself can be soluble, added to the picowell, and then hybridized to the sequencing primer annealing site. Alternatively, where the sequencing primer is to be part of a DNA hairpin, this DNA hairpin is added by way of a "splint oligo" at the final step in creating the bead-bound DNA barcode. FIG. 7 does not show any annealing sites for any sequencing primers.

Nucleic Acids Coupled to Beads by Way of the 3'-Terminus of the Nucleic Acid

While various embodiments disclosed in this invention pertain to coupling DNA to a bead by way of the DNA's 5'-end, in other embodiments, DNA such as a DNA barcode or a DNA tag, can be coupled to the bead by way of their 3'-end. The 3'-hydroxyl group of DNA might be reactive under certain chemical synthesis conditions (e.g. Mitsunobu transformations), rendering the 3'-end damaged and unable to participate in extension, ligation or other steps. Thus DNA tags may be attached to beads via their 3'-ends to prevent unwanted chemical reactions and to prevent damage to the DNA barcodes.

Exclusionary embodiments regarding bead-bound DNA barcodes of the present disclosure. What can be excluded is any bead, microparticle, microsphere, resin, or polymeric composition of matter, wherein the concatenated DNA barcode is linked to the bead by way of a photocleavable linker or by way of a cleavable linker.

What can be excluded is any bead, microparticle, microsphere, resin, or polymeric composition of matter, that does not include both of the following: (1) Concatenated DNA barcode that is coupled to a first position on the bead, (2) A compound that is coupled to a second position on the bead, and wherein the first position is not the same as the second position. In a preferred embodiment, this "compound" is made of a plurality of chemical library monomers.

What can be excluded is any bead, microparticle, microsphere, resin, or polymeric composition of matter, that does not have an exterior surface (or exterior surfaces) and also an interior surface (or interior surfaces, or interior regions), and where the bead does not comprise at least 10,000 substantially identical concatenated DNA barcodes that are coupled to the bead, and wherein at least 90% of the at least 10,000 substantially identical concatenated DNA barcodes are coupled to the exterior surface. In other words, what can be excluded is any bead where at least 90% of the coupled concatenated DNA barcodes are not coupled to the exterior surface.

What can be excluded is any bead, microparticle, microsphere, resin, or polymeric composition of matter, that is made substantially of polyacrylamide or that contains any polyacrylamide.

What can be excluded is any bead, microparticle, microsphere, hydrogel, resin, or polymeric composition of matter, that contains a promoter, such as a T7 promoter, or that contains a polyA region, or that contains a promoter and also a polyA region.

Method with only one cycle of annealing/polymerization, to produce a bead-bound DNA barcode with two DNA barcode modules. The present disclosure encompasses systems, reagents, and methods, where the bead-bound DNA barcode includes only one annealing/polymerization step. This embodiment is represented by the following diagrams, where the first diagram shows annealing of the splint oligo, and the second diagram shows filling-in using DNA polymerase. The end-result is a bead-bound DNA barcode that contains two DNA barcode modules. In this particular procedure, the bead-bound starting material can optionally include linker (but preferably not any cleavable linker), optionally a nucleic acid that encodes information other than identifying a chemical compound, and optionally a functional nucleic acid, such as a sequencing primer or a DNA hairpin. The two diagrams are shown in the text (see, immediately below):

Bead-/$1^{st}$ DNA barcode/$1^{st}$ annealing site/

... $1^{st}$ annealing site/$2^{nd}$ DNA barcode/$2^{nd}$ annealing site

Bead-/$1^{st}$ DNA barcode/$1^{st}$ annealing site/$2^{nd}$ DNA barcode/$2^{nd}$ annealing site ... $1^{st}$ annealing site/$2^{nd}$ DNA barcode/$2^{nd}$ annealing site Method with two cycles of annealing/polymerization, to produce a bead-bound DNA barcode that has three DNA barcode modules. The present disclosure encompasses bead-bound compositions, systems, and methods, where two different split oligos are used (first splint oligo; second splint oligo). In this situation, the first splint oligo comprises the structure: $1^{st}$ annealing site/$2^{nd}$ DNA barcode/$2^{nd}$ annealing site, and where the second splint oligo comprises the structure: $2^{nd}$ annealing site/$3^{rd}$ DNA barcode/$3^{rd}$ annealing site.

Method with three cycles of annealing/polymerization, to produce a bead-bound DNA barcode that has four DNA barcode modules. The present disclosure encompasses bead-bound compositions, systems, and methods, where three different split oligos are used (first splint oligo; second splint oligo, third splint oligo). In this situation, the first splint oligo comprises the structure: $1^{st}$ annealing site/$2^{nd}$ DNA barcode/2nd annealing site, and where the second splint oligo comprises the structure: $2^{nd}$ annealing site/$3^{rd}$ DNA barcode/$3^{rd}$ annealing site, and where the third splint oligo comprises the structure: $3^{rd}$ annealing site/$4^{th}$ DNA barcode/$4^{th}$ annealing site.

Method with four cycles of annealing/polymerization, to produce a bead-bound DNA barcode that has five DNA barcode modules. The present disclosure encompasses bead-bound compositions, systems, and methods, where four different split oligos are used (first splint oligo; second splint oligo, third splint oligo, fourth splint oligo). In this situation, the first splint oligo comprises the structure: $1^{st}$ annealing site/$2^{nd}$ DNA barcode/$2^{nd}$ annealing site, and where the second splint oligo comprises the structure: $2^{nd}$ annealing site/$3^{rd}$ DNA barcode/$3^{rd}$ annealing site, and where the third splint oligo comprises the structure: $3^{rd}$ annealing site/$4^{th}$ DNA barcode/$4^{th}$ annealing site, and where the fourth splint oligo comprises the structure: 4th annealing site/$5^{th}$ DNA barcode/$5^{th}$ annealing site, Embodiments with a plurality of steps of annealing/polymerization, to produce a bead-bound DNA barcode that has a plurality of DNA barcode modules. The present disclosure encompasses bead-bound compositions, systems, and methods, relating to concatenated barcodes, that uses only one splint oligo (making a 2-module DNA barcode), that uses only two splint oligos (making a 3-module DNA barcode), that uses only three splint oligos (making a 4-module DNA barcode), that uses only four splint oligos (making a 5-module DNA barcode), that uses only five splint oligos (making a 6-module DNA barcode), that uses only six splint oligos (making a 7-module DNA barcode), and so on.

What is encompassed is bead-bound compositions, systems, and methods, that uses at least one splint oligo, at least two splint oligos, at least three splint oligos, at least four splint oligos, at least five splint oligos, at least 6, at least 7, at least 8, at least 9, at least 10, at least 11, at least 12, at last 13, at least 14, at least 20 splint oligos, or less than 20, less than 15, less than 10, less than 8, less than 6, less than 4, less than 3, less than 2 splint oligos. These numbers refer to the splint oligo itself, as well as to the number of the step of adding the splint oligo, and also to the numbering of the DNA module that is added to the growing bead-bound DNA barcode.

Reducing Damage to DNA Barcodes

Reducing damage by using orthogonal DNA barcodes (instead of concatenated DNA barcodes). One way to get oriented to the topic of concatenated DNA barcodes and orthogonal DNA barcodes, is to note advantages that one has over the other. An advantage of orthogonal barcoding over concatenated barcoding, is as follows. With attachment of each monomer of a growing chemical compound, what is attached in parallel are chemical library monomers to create a chemical library, and DNA barcode modules to create a completed and full-length DNA barcode.

With concatenated barcoding, if attachment of any given module is imperfect (meaning, that not all of the attachments sites were successfully coupled with a needed module), then the sequence of the completed barcode will not be correct. The statement "not be correct" means that imperfect coupling resulted in chunks that were missing, where the user had assumed that the completed product was a completed and correct DNA barcode. Here, the completed DNA barcode sequence will contain a mistake, due to failure of attachment of all of the DNA modules. In contrast, with orthogonal barcoding each individual DNA module gets covalently bound to its own unique attachment site on the bead. And where once a DNA module gets attached to a given site on the bead, no further DNA modules need to get coupled to the DNA modules that are already coupled to the bead.

Reducing damage by using cross-linkers. The present disclosure provides reagents and methods for reducing damage to bead-bound DNA barcodes, and for reducing damage to to partially synthesized bead-bound DNA barcodes. Each DNA barcode module, prior to attaching to a growing bead-bound DNA barcode, can take the form of double stranded DNA (dsDNA), where this dsDNA is treated with a DNA cross-linker such as mitomycin-C. After completion of the synthesis of the DNA barcode in its dsDNA form, this dsDNA is converted to ssDNA. Conversion of dsDNA to ssDNA can be effected where one of the DNA strands has a uracil (U) residue, and where cleavage of the DNA at the position of the uracil residue is catalyzed by uracil-N-glycosidase (see, FIG. 5 of Ser. No. 62/562,905, filed Sep. 25, 2017. Ser. No. 62/562,905 is incorporated herein by reference in its entirety). The above refers to damage that is inflicted on the growing DNA barcode by reagents used to make the bead-bound chemical compound.

Reducing damage by using double stranded DNA (dsDNA) for making DNA barcodes. Another method for reducing damage to bead-bound DNA barcodes, and for reducing damage to partially synthesized DNA barcodes, is by synthesizing the DNA barcode in a double stranded DNA form, where each of the DNA barcode modules that are being attached to each other takes the form of dsDNA, and where each of the two strands is stabilized by way of a DNA headpiece. For eventual sequencing of the completed DNA barcode, one of the strands is cleaved off from the DNA headpiece and removed. The above refers to damage that is inflicted on the growing DNA barcode by reagents used to make the bead-bound chemical compound (where this chemical compound is a member of the chemical library).

Reducing damage by including a hairpin. Yet another method for reducing damage to bead-bound DNA barcodes, is to synthesize the DNA barcode in a way that self-assembles to form a hairpin, and where this DNA barcode self-assembles to that the first prong of the hairpin anneals to the second prong of the hairpin.

Where the DNA barcode being synthesized takes the form of double stranded DNA (dsDNA), solvents such as DCM, DMF, and DMA can denature the DNA barcode. The above methods and reagents can prevent denaturation.

Reducing damage by using sealed ends of dsDNA. Another method for reducing damage to bead-bound DNA barcodes, and for reducing damage to partially synthesized DNA barcodes, is to use double stranded DNA (dsDNA) and to seal the ends of this dsDNA by way of 7-aza-dATP and dGTP.

Reducing damage by avoiding proteic solvents, avoiding strong acids and basis, avoiding strong reducing agents and oxidants. The type of chemistry that is compatible with the presence of deoxyribonucleic acids (DNA), whether bead-bound DNA or DNA that is not bead-bound, may require absence of proteic solvents, avoiding strong acidic conditions, avoiding strong basis such as t-butyl lithium, avoiding strong reducing agents such as lithium aluminum hydride, avoiding reagents that react with DNA bases, such as some alkyl halides, and avoiding some oxidants (see, Luk and Sats (2014) DNA-Compatible Chemistry (Chapter 4) in A Handbook for DNA-Encoded Chemistry, $1^{st}$ ed. John Wiley and Sons, Inc.).

As stated elsewhere, the term "DNA barcode" can refer to a polynucleotide that identifies a chemical compound in its entirety while, in contrast, "DNA barcode module" can refer to only one of the monomers that make up the chemical compound.

Reducing damage to nucleic acids by using DNA-compatible chemistry. Satz et al, disclose various chemistries that are compatible with bead-bound nucleic acids (Satz et al (2015) Bioconjugate Chemistry. 26:1623-1632; correction in Satz et al (2016) Bioconjugate Chem. 27:2580-2580). Although the descriptions in Satz et al, supra, concern chemical reactions that are performed on DNA/chemical library member conjugates, the types of DNA-compatible chemistries that are described are also relevant, where the organic chemistry is to be performed on a bead that contains bead-bound compounds and bead-bound DNA.

DNA-compatible reactions for the formation of benzimidazole compounds, imidazolidinone compounds, quinazolinone compounds, isoindolinone compounds, thiazole compounds, and imidazopyridine compounds are disclosed (see, Satz et al, Table 1, entries 1-6).

Moreover, DNA-compatible protecting groups are disclosed as including, alloc deprotection, BOC deprotection, t-butyl ester hydrolysis, methyl/ethyl ester hydrolysis, and nitro reduction with hydrazine and Raney nickel (see, Satz et al, Table 1, entries 7-11).

Furthermore, methods for coupling reagents to DNA are disclosed, where the coupling occurs with a functional group that is already attached to the DNA. The methods include Suzuki coupling, an optimized procedure for the Sonogashira coupling between an alkyne and an arylhalide, the conversion of aldehydes to alkynes using dimethyl-1-diazo-2-oxopropylphosphonate, a new method for triazole cyclo addition directly from purified alkyne, an improved method for reaction of isocyanate building blocks with an amine functionalized DNA where the improved reaction occurs with isocyanate reagent at pH 9.4 buffer (see, Satz, et al, Table 1, entries 12-15).

Additional methods for coupling reagents to DNA are disclosed, where the coupling occurs to a functional group already attached to the DNA. These include a method where a primary amine is conjugated to DNA, an optimized procedure to form DNA-conjugated thioureas, a method to alkylate secondary amines and the bis-alkylation of aliphatic primary amindes, monoalkylation of a primary amine DNA-conjugate, using hetarylhalides as building blocks that can be reacted with amine-functionalized DNA-conjugate, and methods for Wittig reactions (see, Satz et al, Table 1, entries 16-20).

Reducing damaged DNA by way of DNA repair enzymes. Various proteins, including enzymes, DNA-damage binding proteins, and helicases, are available for repairing DNA damage. What is commercially available is DNA repair proteins that can repair oxidative damage, radiation-induced damage, UV light-induced damage, damage from formaldehyde adducts, and damage taking the form of alkyl group adducts. Glycoside enzyme, which remove damaged bases (but do not cleave ssDNA or dsDNA) are available to repair 5-formyluracil, deoxyuridine, and 5-hydroxymethyluracil. T4PDG is available to repair pyrimidine dimers. hNEIL1 as well as Fpg are available to repair oxidized pyrimidines, oxidized purines, apurinic sites, and apyrimidinic sites. EndoVIII is available to repair oxidized pyrimidine and apyrimidinic sites. EndoV is available for repairing mismatches. HaaG is a glycosylase that is available for repairing alkylated purines. Where a DNA repair enzyme leaves a gap, where double stranded DNA has a gap where one or more continuous deoxyribonucleotides are missing in one of the strands, then various DNA polymerases are available for filling in the gap (see, Catalog (2018) New England Bio-Labs, Ipswich, MA).

A variety of DNA repair enzymes and DNA repair systems have been isolated from mammals, yeast, and bacteria. These include those that mediate nucleotide excision repair (NER), direct repair, base excision repair, transcription-coupled DNA repair, and recombinational repair. Interstrand DNA cros slinks can be repaired by combined use of NER and homologous recombination. Direct repair includes repair of cyclobutane pyrimidine dimers and 6-4 products, by way of photolyase enzymes. Direct repair also includes removal of $O^6$-methyl from $O^6$-methylguanine by DNA methyltarnsferase. See, Sancar et al (2004) Ann. Rev. Biochem. 73:39-85; Hu, Sancar (2017) J. Biol. Chem. 292:15588-15597.

The present disclosure provides systems, reagents, and methods for repairing damage to bead-bound DNA barcodes by treating with a DNA repair enzyme, or by a complex of DNA repair proteins, and the like.

Reducing damage via coupling DNA to beads via their 3'-end. Certain chemical transformation may damage exposed 3'-hydroxyl groups of nucleic acids. For instance Mitsunobu reactions allow the conversion of primary and secondary alcohols to esters, phenyl ethers, thioethers and various other compounds, which might render exposed 3'-ends unreactive to subsequent processing steps, or cause the now modified 3'-end to participate in further chemical reactions. In some embodiments, the DNA tags may be attached to beads via their 3'-end, so only the 5'-end is exposed to solution.

The reagents, systems, and methods of the present disclosure encompass bead-bound nucleic acids, such as a bead-bound DNA or a bead-bound DNA tags, where coupling to the bead involves the 3'-terminus (or the 3'-end) of the DNA. Where ssDNA that comprises a DNA barcode is coupled by way of the 3'-end, of the ssDNA, sequencing can be initiated by hybridizing only one sequencing primer, where this sequencing primer hybridizes upstream of the entire DNA barcode, and where this hybridizing is at or near the bead-bound end of the coupled ssDNA. As an alternative to using only one sequencing primer, a plurality of sequencing primers can be used, where each sequencing primer hybridizes upstream to a particular DNA barcode module. For example, if a given DNA barcode contains five DNA barcode modules, and where the DNA is coupled to a bead by way of its 3'-end, the DNA barcode can include five different primer annealing sites, where each primer annealing site is located just upstream, or immediately upstream, of a given DNA barcode module.

Double stranded DNA (dsDNA) coupling embodiments. In other embodiments, what is coupled to the bead is dsDNA, where the 3'-terminus of only one of the strands in the dsDNA are coupled to the bead. In a 5'-coupling embodiment that involves dsDNA, what can be coupled is dsDNA, where the 5'-terminus of only one of the strands of the dsDNA is coupled to the bead.

(V) Coupling Chemical Compounds to Beads

The present disclosure provides: (1) Linkers to attach chemical library member to a substrate, such as a bead; (2) Linkers to attach nucleic acid barcode to a substrate, such as a bead; (3) Cleavable linkers, for example, cleavable by UV light, cleavable by an enzyme such as a protease; (4) Non-cleavable linkers; (5) Bifunctional linkers; (6) Multi-functional linkers; and (7) Plurality of beads used for linking. Available, for example, is 4-hydroxymethyl benzoic acid (HMBA) linker, 4-hydroxymethylphenylacetic acid linker (see, Camperi, Marani, Cascone (2005) Tetrahedron Letters. 46:1561-1564).

A "non-cleavable linker" may be characterized as a linker that cannot be detectably cleaved by any reagent, condition, or environment, that is used during the steps of a given organic chemistry procedure. Alternatively, a "non-cleavable linker" may be characterized as a linker that cannot be cleaved, except by a reagent, condition, or environment that is unacceptably destructive towards other reactants, products, or reagents of a given organic chemistry procedure.

A bifunctional linker, or other multifunctional linker, can take the form of a fork (fork used by humans for consuming food), where the handle of the fork is attached to a bead, and where each tine of the fork are linked to one of a variety of chemicals. For example, one tine can be linked to a chemical library member. Another tine can be linked to a DNA barcode. Yet another tine of the fork can be linked to a metal ion.

Regarding use of a multiplicity of beads, the present disclosure provides multiple-bead embodiments, such as: (1) A first bead containing attached nucleic acid barcode linked to a second bead, where the second bead contains attached chemical library member; (2) A first bead containing an attached nucleic acid barcode linked to a second bead, where the second bead contains an attached chemical library member, and where a third bead is attached (to one or both of the first bead and second bead), and where the third bead contains a covalently attached reagent. The attached reagent can be an enzyme, where the enzyme is used for assaying activity of the attached chemical library member.

(VI) Coupling Monomers Together to Make a Compound

Exemplary chemical monomers. Amino acid derivatives suitable for use as chemical monomers for the compositions and methods of the present disclosure are shown in FIG. 4. The figure indicates a source of the chemicals, for example, AnaSpec EGT Group, Fremont, CA; Sigman-Aldrich, St. Louis, MO; Acros Organics (part of ThermoFisher Scientific), or Combi-Blocks, San Diego, CA Additional chemical monomers are shown in FIGS. 22-27. Each of FIGS. 22-27 provides the structure, chemical name, and an associated DNA module barcode. As disclosed on the figures, compounds 1-6 (FIG. 22), the respective barcodes are ACGT, ACTC, AGAC, AGCG, AGTA, and ATAT. For compounds 7-10 (FIG. 23), the respective barcodes are, ATGA, CACG, CAGC, and CATA. For compounds 11-16 (FIG. 24), the respective barcodes are, CGAG, CGCT, CGTC, CTAC, CTGT, and GACT. For compounds 17-21 (FIG. 25), the respective barcodes are GAGA, GCAC, GCTG, GTAG, and GTCA. For compounds 22-26 (FIG. 26), the respective barcodes are GTGC, TAGT, TATC, TCAG, and TCGC. And for compounds 27-30 (FIG. 27), the respective barcodes are TCTA, TGAT, TGCA, and TGTG. These barcodes are only exemplary. For any given library of compounds, a different collection of DNA barcodes may be used to identify each of the chemical monomers that are used to build the compounds in that library.

Coupling reactions. The following describes coupling chemical monomers to the bead and to each other, that is, where a first step is coupling the first chemical monomer directly to the bead by way of a cleavable linker, and where subsequent chemical monomers are then connected to each other, one by one. The conditions disclosed below are DNA compatible.

This describes methods to make three amino acid compounds on Tentagel® beads. The Fmoc protected resin (1 mg, Rapp polymere GmbH, 10 um, TentaGel M-NH2, 0.23 mmol/g) modified with Fmoc-Photo-Linker, 4-{4-[1-(9-Fluorenylmethyloxycarbonylamino) ethyl]-2-methoxy-5-ni-trophenoxy} butanoic acid) or another appropriate linker with Fmoc protection was suspended inside each well of a reactor plate (Merck Millipore Ltd, 0.45 um hydrophobic PTFE) in DMA (150 uL). The solvent was removed by application of a vacuum to the bottom of the plate with a Resprep VM-96 vacuum manifold. The Fmoc protecting group was removed by suspending the resin in 150 uL of a mixture of 5% piperazine, 2% DBU in DMF. The plate was sealed with an Excel Scientific Alumna Seal and shaken at 40 C for 15 min. The solvent was removed by an applied vacuum and the deprotection procedure repeated for 5 min. After filtration each well was washed with 150 uL each of 2×DMA, 3×DCM, 1×DMA with a vacuum applied between each wash to remove the solvent. Each well of resin was then acylated by the appropriate amino acid by adding 150 uL of a pre-activated mixture of 60 mM Fmoc-amino acid, 80 mM Oxyma, 200 mM DIC and 80 mM 2,4,6-trimethylpyridine that was allowed to sit for 2 min at room temperature. The plate was again sealed and shaken for 1 hr at 40 degrees C. After filtration each well was washed with 150 uL each of 2×DMA and 3×DCM. The beads in each well were re-suspended in 150 ul of DCM and each well's contents combined through pipetting into a single receptacle. The combined beads are thoroughly mixed and redistributed into the plate through pipetting equal amounts in the appropriate wells (1 mg/well). The solvent was removed by an applied vacuum and each well was ready for the next appropriate step. For each additional amino acid coupling, first the Fmoc deprotection step is repeated followed by the coupling step with the desired amino acid. If a split and pool is required, the combining and redistribution method is repeated.

This describes a method for creating 3-mer amino acid by split-pool method on beads. The Fmoc protected resin (1 mg, Rapp polymere GmbH, 10 um, TentaGel M-NH2, 0.23 mmol/g) modified with Fmoc-Photo-Linker, 4-{4-[1-(9-Fluorenylmethyloxycarbonylamino) ethyl]-2-methoxy-5-ni-trophenoxy} butanoic acid) or any other appropriate linker was suspended inside each well of a reactor plate (Merck Millipore Ltd, 0.45 um hydrophobic PTFE) in DMA (150 uL). The solvent was removed by application of a vacuum to the bottom of the plate with a Resprep® VM-96 vacuum manifold. The Fmoc protecting group was removed by suspending the resin in 150 uL of a mixture of 5% pperazine, 2% DBU in DMF. The plate was sealed with an Excel Scientific Alumna Seal and shaken at 40 C for 15 min. The solvent was removed by an applied vacuum and the deprotection procedure repeated for 5 min. After filtration each well was washed with 150 uL each of 2×DMA, 3×DCM, 1×DMA with a vacuum applied between each wash to remove the solvent. Each well of resin was then acylated by the appropriate AA by adding 150 uL of a pre-activated mixture of 60 mM Fmoc-amino acid, 80 mM Oxyma, 200 mM DIC and 80 mM 2,4,6-trimethylpyridine that was allowed to sit for 2 min at room temperature. The plate was again sealed and shaken for 1 hr at 40 C. After filtration each well was washed with 150 uL each of 2×DMA, 3×DCM, 1×DMA. For each additional AA coupling, first the Fmoc deprotection step is repeated followed by the coupling step with the desired AA. To analyze each successive coupling, a 1 mg portion of beads was suspended in 100 uL DMSO and exposed to full power of the 365 nm LED for two hours. The resin is filtered off and the filtrate injected onto an Agilent 1100 series LCMS equipped with a Agilent Poroshell SB-C-18, 3.0×50 mm, 2.7 um column. A gradient of 5% CH3CN in 0.1% TFA in water to 100 CH3CN in 0.1% TFA over 4 min at a flow rate of 1.2 mL/min and monitored at 220 nm was ran.

Experiment to make non-amino acid pendant with lenalidomide (Revlimid®) attached. This would be attached to the last amino acid after deprotection. This was also done in a spin. Each well of resin was acylated (after an Fmoc deprotection) with 150 uL of a 5 min preaged mixture of 40 mM chloro acetic acid, 40 mM Oxyma, 80 mM DIC, and 40 mM TMP in DMA. The plate was sealed and shaken at 40 C for 1 hr. Each well was washed with 150 uL each of 3×DMA, 3×DCM, and 2×DMA. The resin was then re-suspended in a suspension of 100 mM K2CO3 and 100 mM Rev in DMA. The plate was sealed and shaken for 3 hrs at rt. The resin was washed with 150 uL each of 2×50/50 DMA/water, 3×DMA, 3×DCM, and 2×DMA.

Defining the degree of fidelity of synthesis of a chemical compound that is attached to a given bead. This concerns the completed chemical compound, where the chemical compound is a member of a chemical library. Each chemical compound may be made, in part, or in full, from chemical monomers. The following characterizes chemical compounds that are attached to a given bead. This given bead may be the product of split-and-pool based synthesis of a library of chemical compounds, where each bead possesses a unique chemical compound.

Members of a chemical library can be synthesized on a solid support, such as on a bead, by way of solid phase synthesis. Solid phase synthesis of chemicals with peptide bonds is charactized by use of one the following two chemical groups. The first chemical group is, N-alpha-9-fluorenyl-methyloxycarbonyl (Fmoc, base labile). The second chemical group is, tert-butyloxycarbonyl (tBoc, acid labile) (see, Vagner, Barany, Lam (1996) Proc. Natl. Acad. Sci. 93:8194-8199). Fmoc and tBoc are protecting groups that can be used to protect pepide substrates, where the Fmoc group or tBoc group is attached to the alpha-amino group (Sigler, Fuller, Verlander (1983) Biopolymers. 22:2157-2162).

Preferably, at least 99.5%, at least 99.0%, at least 95%, at least 90%, at least 85%, or at least 80% of the member of the chemical library bound to a given bead, following completed synthesis, has exactly the same chemical structure. It is possible that incomplete coupling that might occur at one or more steps in the multi-step synthesis of the chemical library member. For this reason, the compositions of the present disclosure may be characterized and limited by one of the following limits or ranges.

What is also provided by the present disclosure are methods and reagents where at least 5%, at least 10%, at least 20%, at least 30%, at least 40%, at least 50%, at least 60%, or at least 70%, or at least 80%, or at least 90%, or at least 95%, or at least 99%, of the members of the chemical library bound to a given bead has, following completed synthesis, exactly the same chemical structure (these numbers do take into account, and reflect, errors that might occur during solid phase synthesis, for example, failure of one growing compound to receive one of the chemical monomers. Also, these numbers do take into account, and reflect, chemical damage to any of the monomers that might occur during solid phase synthesis).

In exclusionary embodiments, the present disclosure can exclude any method or reagent that does not meet one of the above cut-off values for "exactly the same structure."

In an alternate embodiment, two beads, 3 beads, 4 beads, 5 beads, about 5-10 beads, about 10-20 beads, about 20-40 beads, about 40-80 beads, in a population of beads, contain the same and identical chemical compound (without taking into account any errors in incorporation of chemical monomers during solid phase synthesis, and without taking into account any chemical damage that occurs to a chemical monomer during organic synthesis).

Introduction to click chemistry. According to Jewett et al, "Click reactions are defined . . . as those that . . . [are] selective, high yielding, and having good reaction kinetics. A subclass of click reactions whose components are inert to the surrounding biological milieu is termed biorthogonal" (Jewett and Bertozzi (2010) Chem. Soc. Rev. 39:1272-1279). "Click chemistry" can be used for joining small units together with heteroatom links, such as carbon-X-carbon. Click chemistry can be used alone, or in conjunction with other types of chemical reactions, for the synthesis of drugs or drug candidates. Click chemistry works well with procedures used for combinatorial chemistry. Reactions in click chemistry are characterized by high yields, by being irreversible, by insensitivity to oxygen or water. Classes of chemical reactions used in "click chemistry" include: (1) Cycloaddition reactions, especially from the 1,3-dipolar family and from hetero-Diels Alder reactions; (2) Nucleophilic ring-opening reactions, as with strained heterocyclic molecules such as epoxides, aziridines, and cyclic sulfates; (4) Carbonyl chemistyr of the non-aldol type; and (5) Addition to carbon-carbon multiple bonds, as with oxidation reactions and some Michael addition reactions. Click chemistry reactions are distinguished by their high thermodynamic driving force, often greater than 20 kcal/mol while, in contrast, non-click chemistry reactions involve forming bonds with only a modest thermodynamic driving force (Kolb and Sharpless (2003) Drug Discovery Today. 8:1128-1137, Kolb, Finn, Sharpless (2001) Angew. Chem. Int. Ed. 40:2004-2021).

Tetrazine and trans-cyclooctene (TCO). Tetrazine, such as, 1,2,4,5-tetrazine, can react with trans-cyclooctene (TCO) by way of a Diels-Alder cyclo addition (Devaraj, Haun, Weissleder (2009) Angew. Chem. Intl. 48:7013-7016).

Hartig-Buchwald amination. Hartwig-Buchwald amination reactions can be used in the solid-phase synthesis of pharmaceuticals. This amination reactions is used to synthesize carbon-nitrogen bonds, where the reaction involves: aryl-halide plus amine ($R_1$—NH—$R_2$), as catalyzed by palladium, to produce an aryl product where the amine replaces the halide, and where the nitrogen of the amino group is directly attached to the aromatic ring. The end-result is a product involving a carbon (of aryl group) to nitrogen (of amino group) bond. Stated another way, the reaction converts arylhalides into the corresponding anilines. Hartwig-Buchwald amination is compatible with a variety of amines, and is well-suited for combinatorial chemistry (Zimmermann and Brase (2007) J. Comb. Chem. 9:1114-1137).

Huisgen cycloadditions. Huisgen 1,3-dipolar cycloaddition reactions involve alkynes and organic azides. Alkynes have the structure, R—C≡CH. Azides have the structure, $R—N^+=N=N^-$. Copper catalysts accelerate the rate of the Huisgen cycloaddition reaction. The Huisgen reaction operates by way of "click chemistry" or "click reactions." Huisgen reaction, when catalyzed by copper, can produce a 1,2,3-triazole nucleus suitable for making small molecule drugs. Huisgen reaction is compatible with the presence of amino acid side chains, at least when in a protected form. Molecules made with a 1,2,3-triazole may possess a bond that is similar to the amide bonds of polypeptides, and thus these molecules can be a surrogate for the peptide bond (Angell and Burgess (2007) Chem. Soc. Rev. 36:1674-1689).

Peptide nucleic acids (PNAs). The present disclosure provides the methods of split and pool chemistry, combinatorial chemistry, or solid phase chemistry, for synthesizing peptide nucleic acids. Peptide nucleic acids are analogues of oligonucleotides. They resist hydrolysis by nucleases. They can bind strongly to their target RNA sequences. Uptake of peptide nucleic acids into cells can be enhanced by "cell penetrating peptides" (Turner, Ivanova, Gait (2005) Nucleic Acids Res. 33:6837-6849; Koppelhus (2008) Bioconjug. Chem. 19:1526-1534). Peptide nucleic acids can be made by solid phase synthesis and by combinatorial synthesis (see, Quijano, Bahal, Glazer (2017) Yale J. Biology Medicine. 90:583-598; Domling (2006) Nucleosides Nucleotides. 17:1667-1670).

The present disclosure encompasses bead-bound compounds, where the compound takes the form of only one monomer. For example, this bead-bound compound can take the form of lenalidomide, or it can take the form of lenalidomide with an attached carboxylic acid group, or a form of lenalidomide where the amino group has been modified with a small chemical moiety that bears a carboxylic acid group, or where the compound is a lenalidomide analog that is a stereoisomer or an enantiomer of lenalidomide.

(VII) Split and Pool Synthesis and Parallel Synthesis

This concerns use of the "split and pool" method for synthesizing a library of chemical compounds, and the method where the "split and "pool" method is used for the simultaneous synthesis of bead-bound chemical compounds and bead-bound DNA barcodes. This also describes splitting and pooling to make a mixed set of compounds. At a later point, what is disclosed below is coupling of a non-amino acid, as well as the preparations of beads that are modified by polyethylene glycol (PEG).

The present disclosure provides split and pool synthesis for generating chemical libraries. In one embodiment, this method involves the steps: (a) Split beads into different containers; (b) Add a different building block to each container. For example, where three container are used, add and react Species A to the first containing, Species B to the second container; and Species C to the third container, where the species become covalently bound to attachment sites on whatever bead is in the container; (c) Pool all beads together in one container; (d) Split beads into three containers, (e) Add a different building block to each container, where Species A is added to the first container, Species B is added to the second container, and Species C is added to the third container, where the species become covalently bound to the first species that had been previously attached (see, Stockwell (2000) Trends Biotechnol. 18:449-455).

The split-and-pool synthesis of the present disclosure includes, either before or after each chemical coupling step (making the chemical library member), a DNA-barcode coupling step, where this DNA barcode identifies the chemical that is being coupled in that step.

In exclusionary embodiments, the present disclosure can exclude methods and reagents where, for a given step of parallel synthesis, a barcode is attached prior to attaching a chemical. Conversely, the present disclosure can exclude methods and reagents where, for a given step of parallel synthesis, a chemical is attached prior to attaching a barcode.

One characteristics of a bead-bound chemical library that is prepared by the split and pool method, is that each bead will have only one type of compound attached to it. Where there is incomplete coupling, for example, if for a given split and pool step, only 4,000 out of 5,000 attachment sites was successfully coupled with the desired chemical species, then some heterogeneity will occur.

Parallel synthesis. In a preferred embodiment of the present disclosure, parallel synthesis can be used for organic synthesis of a chemical compound and of the associated DNA barcode. In actual practice, modification of a bead by one more chemical monomers and modification of the same bead by one more DNA barcode modules, is not strictly in parallel. In actual practice, the bead receives one more chemical unit (chemical monomer) followed by receiving a DNA barcode module that encodes that particular chemical unit. The term "parallel" refers to the fact that, as the polymer of chemical library monomers grows, the polymer of DNA barcode module also grows. When all of the DNA barcode modules have been attached to the bead, to form either a CONCATENATED structure or an ORTHOGONAL structure, the full-length DNA barcode is called a "DNA barcode" (and not merely a DNA barcode module).

Ratio of Number of Externally Attached DNA Barcode to Total Number of Attached Chemical Library Member.

This concerns external surfaces and internal surfaces of a bead. For a given bead that has externally attached DNA barcodes (without regard to number of internally attached DNA barcodes) and attached chemical library member (attached to both external surface as well as to internal surfaces), the ratio of number of externally attached DNA barcode number total attached chemical library member number can be, for example, about 0.1:100, about 0.2:100, about 0.5:100, about 1.0:100, about 2:100, about 5:100, about 10:100, about 20:100, about 30:100, about 40:100, about 50:100, about 60:100, about 70:100, about 80:100, about 90:100, about 1:1, about 100:150, about 100:200; about 100:400; about 100:600, and the like. In exclusionary embodiments, the present disclosure can exclude any bead, or any population of beads, that fits into one of the above values.

Homogeneity of DNA Barcode for a Typical Bead; Homogeneity of Chemical Library Member for a Typical Bead The present disclosure provides, for any given bead (or for any population of beads) a "chemical library homogeneity" that is at least 50%, at least 60%, at least 70%, at least 80%, at least 90%, at least 92%, at least 94%, at least 96%, at least 98%, at least 99.5%, and the like.

In less stringent embodiment, the present disclosure provides, for any given bead or, alternatively, for any given population of beads, a "chemical library homogeneity that is at least 10%, at least 20%, at least 30%, at least 40%, or at least 50%.

Similarly, the present disclosure provides the above cutoff values for assessing homogeneity of a barcode, such as a DNA barcode.

Homogeneity for DNA barcode and homogeneity for a chemical library member may be defined, in terms, of percent of total population that conforms to the exact sequence as planned and desired by the methods section of a lab manual or notebook.

In exclusionary embodiments, the present disclosure can exclude any reagent, composition, or method, that does not conform with one or more of the above cut-off values.

Where one assesses homogeneity of a population of beads, one needs to account homogeneity for the sum of bead #1, bead #2, bead #3, bead #4, bead #5, bead #6, bead #7, and so on, for the situation where homogeneity is desired throughout the entire population of beads.

In exclusionary embodiments, the present disclosure can exclude any bead, or any population of beads, where homogeneity of DNA barcode is not at least 50%, at least 60%, at least 70%, at least 80%, at least 90%, at least 92%, at least 94%, at least 96%, at least 98%, at least 99.5%, and the like. Also, in exclusionary embodiments, the present disclosure can exclude any bead, or any population of beads, where homogeneity of chemical library member is not at least 50%, at least 60%, at least 70%, at least 80%, at least 90%, at least 92%, at least 94%, at least 96%, at least 98%, at least 99.5%, and the like.

Ratio of Internally Attached DNA Barcodes to Externally Attached DNA Barcodes

In some embodiments of the present disclosure, it might be desired to manufacture and use beads where DNA barcodes are mainly attached on the exterior surface. One reason to NOT make and use beads with internal DNA barcodes, is the low permeation of DNA oligomers to the interior spaces, and low permeation of DNA ligases to interior spaces (ligases for connecting DNA modules to each other to create the finished DNA barcode). And for sequencing purposes, a reason to NOT make and use internal DNA barcodes, is low permeation of enzymes needed to amplify DNA needed for eventual sequencing of the barcode. Yet another reason NOT to make and use beads with internal DNA barcodes is to fee up interior space for attaching members of the chemical library.

The present disclosure provides beads bearing DNA barcodes, where the ratio of internally attached DNA barcodes to externally attached DNA barcodes is about 0.1:100, about 0.2:100, about 0.4:100, about 0.8:100, about 1:100, about 2:100, about 4:100, about 8:100, about 10:100, about 20:100, about 40:100, about 50:100, about 60:100, about 70:100, about 80:100, about 90:100, about 1:1, and so on.

Also, the present disclosure provides beads bearing DNA barcodes, where the ratio of internally attached DNA barcodes to externally attached DNA barcodes is under 0.1:100, under 0.2:100, under 0.4:100, under 0.8:100, under 1:100, under 2:100, under 4:100, under 8:100, under 10:100, under 20:100, under 40:100, under 50:100, under 60:100, under 70:100, under 80:100, under 90:100, under 1:1, and so on.

A population of beads, in an aqueous suspension, can be contacted to a substrate, such as a microwell array, resulting in beads entering and occupying the microwells. The ratio of the number of beads in the suspension to the number of microwells in the substrate can be adjusted, to arrive at a desired occupancy. For example, if the suspension contains only one bead, then every microwell that contains a bead will contain only one bead, where the remaining microwells will not contain any bead. If the suspension contains 20,000 beads and if the substrate contains 200,000 microwells, then at least 180,000 microwells will be totally empty of beads, and where most of the microwells that contain a bead will contain only one bead. A small percentage of occupied microwells will contain two beads.

In value embodiments, the ratio of bead number in the suspension to microwell number can be about 0.2:100, about 0.4:100, about 0.6:100, about 0.8:100, about 1:100, about 2:100, about 4:100, about 6:100, about 8:100, about 10:100, about 20:100, about 30:100, about 40:100, about 50:100, about 60:100; 80:100, about 100:100 (same as 1:1), about 2:1, about 4:1, about 6:1, about 8:1, about 10:1, and the like.

In exclusionary embodiments, the present disclosure can exclude any method or system, that falls into one of the above values or ranges.

In range embodiments, the ratio of bead number in the suspension to microwell number can be about 0.2:100 to about 0.4:100, about 0.4:100 to about 0.6:100, about 0.6:100 to about 0.8:100, about 0.6:100 to about 1:100, about 1:100 to about 2:100, about 2:100 to about 4:100, about 4:100 to about 6:100, about 0.6:100 to about 8:100, about 8:100 to about 10:100, about 10:100 to about 20:100, about 20:100 to about 30:100, about 30:100 to about 40:100, about 40:100 to about 50:100, about 50:100 to about 60:100, about 60:100 to 80:100; about 80:100 to about 100:100 (same as 1:1), about 100:100 (same as 1:1) to about 2:1, about 2:1 to about 4:1, about 4:1 to about 6:1, about 6:1 to about 8:1, about 8:1 to about 10:1, and the like.

In exclusionary embodiments, the present disclosure can exclude any method or system, that falls into one of the above values or ranges.

(VIII) Fabricating Picowells

Combination of UV light, photomask, and photoresist for manufacturing a picowell array plate. Plates that include many microwells or picowells can be fabricated as follows for use in the present disclosure. In brief, a sandwich of three layers is assembled. The top layer is photoresist. The middle layer is a glass wafer. The bottom layer is a photomask. The picowells will be carved out of the photoresist by UV light. After the picowells are carved out of the flat sheet of photoresist, the photoresist resembles a typical metal pan that contains cups for baking muffins, and where the cups in the pan that are used for holding muffin batter have angled sides. The UV light acts as an "un-cross linker" because it breaks down the photoresist's polymer. After UV treatment, solvent is added to wash out the UV treated photoresist, leaving clean-looking picowells.

Rotating at an angle to create angled walls. Picowells with angled walls are created as follows. The photomask has many apertures, where each aperture corresponds to the desired bottom dimension of the picowell. The bottom dimensions can include a circumference, diameter, and a shape, that is, a round shape. The top dimension of the well is created by directing an angled UV light towards the apertures in the photomask while rotating the light source or rotating the stage that holds the sandwich (photomask/glass wafer/photoresist sandwich). With rotation, the light source is not at a 90 degree angle to the photomask/wafer/photoresist sandwich, but instead is slightly angled away from the 90 degree point, in order to carve out angled walls in each picowell. The resulting picowell array plate that contains many picowells can be used as is. Alternatively, this picowell array plate can be used as a mold for the inexpensive creating of many picowell array plates.

Han et al describes equipment and reagents for manufacturing microwell plates where the microwells have angled walls (see, Han et al (2002) J. Semiconductor Technology and Science. 2:268-272). What is described is a UV source, a contact stage, a tilting stage, and the SU-8 photoresist. Fabrication begins with a single side polished silicon wafer. SU-8 photoresist is coated on the wafer at about 0.10 to 0.15 mm thick. Then, the photoresist is soft baked on a 65 degrees C. hot plate for 10 min and then on a 95 degrees C. hot plate for 30 minutes. The resulting photoresist/wafer sandwich is contacted with a UV mask using a contact stage. The term "Inclined and rotated UV lithography" refers to a method for manufacturing microwell array plates or picowell array plates, where each well has an angled wall. Here, the floor of the well has a smaller diameter and the top of the well (where the top edge of the well meets the flat surface of the plate) has a wider diameter. For exposure with UV light, a turntable is used and where the UV light is inclined (Han et al, supra). The mask is contacted with the photoresist where each of the apertures in the mask are circular. FIG. 8 of Han et al, supra, provides a picture of the direction of UV light, the UV mask, the photoresist structure, the wafer substrate, and the turntable. Han et al describes how to manufacture a truncated cone. A soft material such as PDMS (polydimethylsiloxane) may be poured over the cone array and cured, whereupon peeling the PDMS layer, conical wells are formed.

Creating a mold for use in mass-production of picowell array plates. Where a picowell array plate has been manufactured, epoxy can be poured over the plate resulting in filling all of the picowells and connecting all of the filled picowells with a platform of epoxy. Once the epoxy has solidified, the solid platform with the attached array of picoprotuberances is removed (the picoprotuberance being the reverse of the desired picowell). The solid platform with picoprotuberances is a reusable molding that can be used for the manufacture of many picowell array plates.

The procedure for making replicates from the epoxy mold (or a cone array mold made of any hard material is called, "hot embossing." Briefly, a substrate material is heated to its glass transition temperature or softening temperature, at which point the mold with picoprotrubances is uniformly pressed against the heat-softened material. The mold can be separated from the substrate after the picoprotrubances are transferred as pico-invaginations into the substrate material. This disclosure preferably discloses pico-cones and picowells as the patterns of the mold and substrate, respectively.

Hot embossing, epoxy masters, and photoresist such as the SU-8 photoresist are described (see, Bohl et al (2005) J. Micromechanics and Microengineering. 15:1125-1130, Jeon et al (2011) Biomed Microdevices. 13:325-333; Liu, Song, Zong (2014) J. Micromechanics and Microengineering. 24:article ID:035009; del Campo and Greiner (2007) J. Micromechanics and Microengineering. 17:R81-R95).

Other microwell plate embodiments. Plastic microwell arrays can be manufactured by way of a thermal forming using a silicon mold, where the silicon mold possesses an array of microwells, for example, an array of 800,000 microwells. A high degree of control that results in tapered geometries and smooth sidewalls, and submicron tolerances can be created with use of a non-pulsed dry etch process. In contrast, methods that use a pulsed dry etch process, such as the Bosch process, can result in rough sidewalls and lack of control over lateral dimensions during etching.

Using non-pulsed dry etch process, plastic arrays are fabricated by thermally forming plastic on a silicon master that is created by a non-pulsed isotropic dry etch process using a chrome mask. This process uses three gases, Ar, $SF_6$, and $C_4F_8$. The process is conducted at a RF power between 1200 to 2000 Watts and a bias of 150 Watts. Fine-tuning of the taper of the silicon mold with production of smooth sidewalls can be accomplished by varying the gas flow between the three gases. What is varied is the ratio of SF6 to C4F8, where the result of changing the ratio is, for example, a tapered wall of the mold (the silicon pillar) that resides at an angle of 18 degrees (very slanted walls), 9 degrees (slightly slanted walls), or 2 degrees (walls almost perpendicular to substrate) (see, Perry, Henley, and Ramsey (Oct. 26-30, 2014) Development of Plastic Microwell Arrays for Improved Replication Fidelity. 18th Int. Conference on Miniaturized Systems for Chemistry and Life Sciences. San Antonio, TX (pages 1700-1703).

In embodiments, the present disclosure provides a substrate, an array, a grid, a microfluidic device, and the like, that includes an array of microwells. In one embodiment, all of the microwells have essentially the same volume. This volume can be about 1 femtoliters, about 2, about 4, about 6, about 8, about 10, about 20, about 40, about 60, about 80, about 100, about 200, about 400, about 600 about 800, or about 1,000 femtoliters.

Moreover, the volume can take the form of a range between any of the above two adjacent values, such as, the range of about 40 femtoliters to about 60 femtoliters. Also, the volume can take the form of a range between any of the above two values that are not immediately adjacent to each other in the above list.

Furthermore, the volume can be about 1 picoliters, about 2, about 4, about 6, about 8, about 10, about 20, about 40, about 60, about 80, about 100, about 200, about 400, about 600 about 800, or about 1,000, about 2,000, about 5,000, about 10,000, about 20,000, about 50,000, about 100,000, about 200,000, about 500,000, or about 1,000,000 picoliters. Also, the volume can take the form of a range between any of the above two values that are not immediately adjacent to each other in the above list.

In exclusionary embodiments, the present disclosure can exclude any substrate comprising microwells, or any array comprising microwells, where the volume of each microwell is definable by one of the above values, or is definable by a range of any of the above two values that are adjacent to each other, or is definable by a range of any of the above two values that are not adjacent to each other in the list.

Spherical plug (also known as capping beads) on microwells. The present disclosure provides a spherical plug, or alternatively, a porous spherical plug, for each and every well, or substantially every well of a picowell array. A goal of the plug is to keep drugs, drug candidates, cellular contents, and metabolites, inside of the well. The plug also helps isolate the contents of picowells from each other. The spherical plug may need not be perfectly spherical, as long as the goal of covering the top (or opening, or mouth), of the picowell may be satisfied. The well can have a top diameter and a bottom diameter. Diameter of spherical plug, prior to capping a well, is about 10 micrometers, about 30, about 35, about 40, about 45, about 50, about 55, about 70, about 90, about 120 or about 200 micrometers. The plugs may be added to cover the picowells by simply flowing them over the picowell array. Centrifugation, pressure, agitation or other methods may be used to jam the beads to the tops (or mouths or openings) of the picowells to ensure tight sealing. In some embodiments, solvents may be used to modify the swelling and/or size of the capping beads. In some embodiments, the capping beads may be loaded in a solvent that renders the beads shrunken, and once replaced by assay buffer, or a different solvent, the capping beads are restored to their original sizes, or swell, thereby sealing the picowells tightly. In some embodiments temperature may be used to swell or sharing the capping beads to obtain better seals at the mouths of picowells. Where needed, capping beads may be held in place, and prevented from falling further into the picowell, by one of the steps in a stepped picowell array.

The capping beads may be the same type of beads that carry the compounds of this disclosure, or may be beads of a different type. In some embodiments, the capping beads may actually be the compound bearing beads themselves. The capping beads may serve as passive caps, preventing or slowing diffusion of molecules out of the picowells, or the beads may be active beads, where functional moieties attached to the capping beads may be used to capture reagents from the picowells. In some embodiments, porous capping beads may passively trap metabolites released from cell-based assays performed inside picowells. In some embodiments, capping beads may non-specifically capture cellular materials such as lipid, proteins, carbohydrates and nucleic acids. In some embodiments, the capping beads may be functionalized with antibodies to specifically capture proteins released from healthy, diseased, lysed or fixed cells. In some embodiments, the capping beads may be functionalized with DNA or RNA oligonucleotides that specifically capture cellular nucleic acids. In some embodiments, the DNA or RNA functionalized capping beads may be used to capture microRNA released from cells within the capped picowells. In some embodiments picowells contain two beads, a compound containing bead inside the picowell, and a capping bead covering the mouth of the picowells. In some embodiments, the capping beads are also the compound-bearing beads. In some embodiments, the capping beads capture materials released from the compound beads. In some embodiments, the capping beads capture a sampling of the compounds released from compound-beads. In some embodiments, the capping beads capture DNA barcodes released from the compound-beads. In some embodiments, the capping beads capture different types of analytes released from within the picowells they cap.

Relative hardness of cap and of picowell. A preferred equipment is a microwell plate, where each microwell includes, in its bottom surface, many thousands of picowells. Ability of a cap to seat properly or to seal each picowell can be a function of the hardness of the plastic that makes up the picowell's aperture and the picowell's inner walls, relative to the hardness of the cap.

Hardness of a plastic can be defined in terms of a "durometer" value. Hardness is defined and tested as a material's resistance to indentation. The hardness of the spherical plug, and the hardness of the wall of the microwell can be defined in terms of its "durometer." The hardness can be, for example, about 45, about 50, about 55, about 60, about 65, about 70, about 75, about 80, about 85, about 90, about 95, or about 100. In attributing any of these durometer values to a plastic substance or other substance, one must also state which scale is used. For example, the scale can be ASTM D2240 type A scale, which is used for softer materials, or the ASTM D2240 type D scale, which is used for harder materials (see, Silicon Design Manual, 6th ed., Albright Technologies, Inc., Leominster, MA).

Shapes of picowells. In some embodiments, the picowells may be cylindrical picowells where the diameter of the cylinder is roughly similar at the top and the bottom of the picowell. In some embodiments, the picowells may have a slight taper, with the top of the picowells slightly larger than the bottom of the picowells. In some embodiments, the picowells may be conical picowells, with angles off normal anywhere between 1 degree to 30 degrees. In some embodiments, the picowells are stepped picowells, where the picowells have discontinuous steps from the top diameter to the bottom diameter (as opposed to conical picowells whose diameter change smoothly from the top to the bottom). In some embodiments, the stepped picowells have a broad cylinder near the opening of the picowell and a narrower cylinder near the bottom of the picowells. In some embodiments, the stepped picowells may have multiple discontinuous steps from the top to the bottom. In some embodiments of multi-stepped picowells, the diameter at every rung may be larger than the diameter of the rung below it. In some embodiments a small bead may be deposited at the bottom of the stepped picowell, and a capping bead may be deposited at the topmost opening of the stepped-picowell. In some embodiments picowells may contain more than 2 beads.

Methods to make stepped-picowells. FIG. 29 disclosed stepped picowell. The embodiment shown has three compartments and two steps. Top compartment is widest and is configured for accepting cap where most of the top compartment is occupied by the cap in the situation where the picowell is capped. Middle compartment is configured for being occupied mainly by, or solely by, reagents. Reagents can include buffer, enzyme substrates, one or more salts, and a preservative or stabilizer such as dithiothreitol, RNAse inhibitor, glycerol, or DMSO. Lowest compartment is configured for being occupied by bead, that is, a bead with coupled both a DNA library and with releasable compounds. In addition to bearing DNA barcode and releasable compounds, the same bead can also bear a "response capture element." Capping beads may be held in place, and prevented from falling further into the picowell, by one of the steps in a stepped picowell. In FIG. 29, structure 1 is cap., structure 2 is bead., and structure 3 is top region, which is situated immediately above first step. Structure 4 is middle region, which can be used for placing assay reagents. Middle region is immediately above second step. Assay reagents in middle region can diffuse into lowest region. Structure 5 is lowest region, which can be used for placing a bead and for placing one or more cells.

Regarding the space of the lowest compartment that is taken up by the bead (assuming that only one bead is present in picowell), the diameter of the bead can be about 25%, about 30%, about 35%, about 40%, about 45%, about 50%, about 55%, about 60%, about 65%, about 70%, about 75%, about 80%, about 85%, about 90%, about 95%, or about 98%, of the diameter of the lowest compartment (assuming that the picowell is a circular well). If picowell is not a circular well, the above values can refer to widest dimension of the well. In exclusionary embodiments, the present disclosure can exclude any system or bead that does not meet any of the above parameters.

Further regarding space taken up by the bead (assuming that only one bead is present in picowell), about 50% of bead is in lowest compartment and about 50% of same bead is in middle compartment, where these parameters can also be: about 55% lowest and about 65% middle; about 60% lowest and about 40% middle; about 65% lowest and about 45% middle; about 70% lowest and about 30% middle, about 75% lowest and about 25% middle, about 80% lowest and about 20% middle, about 85% lowest and about 15% middle, about 90% lowest and about 10% middle, about 95% lowest and about 5% middle, and about 100% lowest. For making these calculations the space taken up by bead assumes (hypothetically) that the bead is not porous. In exclusionary embodiments, the present disclosure can exclude any system or bead that does not meet any of the above parameters.

As with conical and cylindrical picowell, using a molding system is one preferred embodiment to create stepped picowells. For this purpose, a mold containing arrays of multilayered pillars is desired, whereupon stamping into a thermoplastic or other curable polymer substrate, an impression of stepped picowells may be formed. A layered pillar array with multiple steps, each step of a different diameter (smaller as it goes up) may be formed by a multilayer lithography process. Briefly, a first layer of photoresist is exposed, via a first mask, to cros slink the first layer of the micropillar array. A second layer of photoresist may be deposited directly on the (previously exposed) first layer, and a second photomask may be used to crosslink a second pattern in the second photoresist later, and so on. At the end of the multiple-layer patterning, the stack of resist may be developed to wash away the uncrosslinked regions, leaving an array of multilayered pillars. Detailed protocols for creating multilayered pillar arrays may be found in Francisco Perdigones et al., (Jan. 8, 2011). Microsystem Technologies for Biomedical Applications, Biomedical Engineering, Trends in Electronics Anthony N. Laskovski, IntechOpen. Once an array of multilayered pillars array is created, standard processes may be used to imprint stepped picowell arrays using the mold.

Removing the capping beads. In many embodiments it is advantageous to sample the capping beads to study reactions, analytes or cellular response to the chemical perturbations within picowells. In some embodiments, the capping beads may be dislodged from the mouths of the picowells by inverting the picowell array and using mechanical agitation. In some embodiments solvents may be used to shrink the picowells, rendering them easier to dislodge from the mouths of picowells. In some embodiments, liquids of higher density than the capping beads may be added on top of the picowell array, causing the capping beads to raise by buoyancy and float atop the high-density medium.

In some embodiments, the capping beads may be cross-linked to each other, converting the capping beads to a capping sheet that can be peeled off the top of the picowell array. In some embodiments, a crosslinking gel may be poured over the capped picowells, where the crosslinking gel crosslinks to the capping beads, and to themselves, causing the capping beads to be embedded into a crosslinked sheet that can be peeled off.

Preserving relative locations of picowells, in the form of the peeled-off layer. It should be appreciated that in such embodiments as when the capping beads are enmeshed into a gel layer that can be peeled off, the relative locations of capping beads with respect to each other and with respect to the picowells are preserved in the peeled-off layer. This allows direct connection between picowells, assays in picowells, the beads in the picowells, and any materials captured in the capping beads.

In some embodiments, fiducial markers may be used to orient the relative features of the picowell arrays to the capping beads in the peeled-off-layer.

Fiducial markers to enable registration and alignment of picowells. Arranging picowells in irregular arrays allows easy identification of shifts and drifts during imaging of the picowell arrays. In some embodiments, the picowells are arranged in an irregular order to facilitate detection of optical and mechanical drifts during imaging. In some embodiments, the picowell arrays contain fiducial markers to help identify shifts and drifts during imaging. In some embodiments, the fiducial markers are easily identifiable shapes, patterns or features that are interspersed between the picowells of the picowell array. In some embodiments, a small number of picowells may themselves be arranged in an easily identifiable pattern to allow easy registration in case of optical or mechanical drifts during imaging. In some embodiments, external marker, such as fluorescent beads, may be drizzled on the picowell array to provide fiducial patterns.

Cap-free mat embodiments. Cap-free mat embodiment, at least in some forms or examples, can take the form of a "capless film." Instead of sealing openings at the top of picowells, for example, for preventing evaporation of any cell culture medium or enzyme assay medium that may be in the picowell, sealing can be accomplished by way of a mat. Preferably, the mat is sized to cover all of the picowells in a given picowell array. Alternatively, the mat can be sized to cover a predetermined fraction of the picowells in the array. The mat can be secured to the top of the picowell plate, covering picowells and also covering the generally planar top surface of the picowell plate that resides in between the picowells. Secure contact can be achieve by one or more of: (i) Maintaining constant pressure, for example, by a hard rubber platen that sits on top of and serves as a weight on top of the matt; (ii) Using a mat that is connected to a weight, such as hard rubber platen; (iii) A reversible chemical adhesive, that can be applied to the entire mat (in the situation where the mat is not be be an absorbant mat). Where the mat is to be an absorbent mat, the mat contains circular absorbent pads that are surrounded by the reversible chemical adhesive. Here, the mat is contacted with the picowell array and aligned so that the circular absorbent pads cover only the openings of each picowell, and do not "spill out" over the opening to contact the planar surface of the picowell plate.

Membranes for use as mat for contacting substantially planar surface of picowell plate, and for use in capless-sealing of picowells, are available. Flat sheet membranes, such as Dow Film Tex, GE Osmonics, Microdyn Nadir, Toray, TriSep, Synder, Novamem, Evonik, and Aquaporin flatt sheet membreans are available from Sterlitech Corp, Kent, WA These include membranes made of polyamide-TFC, cellulose acetate, polyamide-urea-TFC, cellulose acetate blend, polypiperazine-amide-TFC, PES, composite polyamide-TFC, PES, PAN, PVDF, PSUH, RC, PESH, polyether ether ketone, polyimide, and so on. Pore size in terms of molecular weight cutoffs include, 150 Da, 200 Da, 300 Da, 500 Da, 900 Da, 600 Da, 1,000 Da, 2,000 Da, 3,000 Da, 5,000 Da, 10,000 Da, 50,000 Da, 20,000 Da, 30,000 Da 70,000 Da, 100,000 Da, 200,000 Da, 300,000 Da, 400,000 Da, 500,000 Da, 800, 000 Da, 3500 Da, 0.005 micrometers, 0.030 micrometers, 0.05 micrometers, 0.10 micrometers, 0.20 micrometers, and so on. Regarding the system, compositions, reagents, and methods of the present disclosure, these cutoff values can allow selective collection of certain classes of compounds with exclusion of other classes of compounds. For example, some of the above membranes can allow small molecule metabolites to pass through and be absorbed by an absorbable mat, while excluding proteins and other macromolecules. Flat sheet membranes that are impermeable to all molecules, including water, metal ions, salts, metabolites, proteins, and nucleic acids, are also available for use in the systems, compositions, and methods of the present disclosure.

Reversible adhesion can be mediated by "molecular velcro," for example, metalloporphyrin containing polymers with pyridine-containing polymers (Sievers, Namyslo, Lederle, Huber (2018) eXPRESS Polymer Letters. 12:556-568). Other molecular velcro adhesives involve, L-3,4-dihydroxyphenyl alanine, complementary strands of ssDNA (one type of ssDNA covalently attached to flat upper surface of picowell plate, and other type of ssDNA covalently attached to mat), copolymers containing catechol side chains, and so on (see, Sievers, et al, supra). Also, reversible adhesion can be mediated by a gallium adhesive, where degree of adhesion can be controlled by slight changes in temperature (Metin Sitti (May 18, 2016) Switch and Stick. The chemical element gallium could be used as a new reversible adhesive that allows its adhesive effect to be switched on and off with ease. Max-planck-Gesellschaft). Yet another reversible adhesive is available from DSM-Niaga Technology, Zwoll, The Netherlands.

Absorbent substances (non-specific absorbents; specific absorbents). Absorbent substances, which can be incorporated into a mat to provide absorbent characteristics include "molecule sieve" beads, such as Sepharose®, Sephadex®, Agarose®, as well as ion exchange beads made of DEAE cellulose, carboxymethylcellulose, phosphocellulose, or any combination of the above, all combined into one absorbent mat. Absorbent ligands include those that are used in high pressure liquid chromatography (HPLC) (see, BioRad catalog, Hercules, CA). Specific absorbents include response-capture elements, such as poly(dT), which can capture mRNA by way of hybridizing with polyA tail. Also, response capture elements include exon-targeting RNA probs, antibodies, and aptamers. Each or any combination of these can be covalently attached to mat, to create an absorbent mat, where contacting absorbent mat to top surface of picowell enables capture of aqueous assay medium or aqueous cell culture medium that might be inside picowells.

(IX) Depositing Beads into Picowells

Plates with picowells can take the form of a 96-well plate where each of these 96 wells contains many thousands of picowells. Also, plates with picowells can take the form of a 24-well plate, where each of these 24 wells contains many thousands of picowells. For the 96-well plate, each well can be filled using 0.1-0.2 mL of a suspension of beads in water or in an aqueous solution. For the 24-well plate, each well can be filled using about 0.5 mL of a suspension of beads in water or in an aqueous solution. Suspension can be added using an ordinary pipet with a disposable tip. The number of beads that are in the suspension can be that resulting in about one third of the picowells containing only one bead, about one third of the picowells containing two beads, and about one third of the beads containing either no beads or more than two beads. Also, the number of beads in the suspension can be that resulting in the situation where, of the wells that do contain one or more beads, at least 70%, at least 80%, at least 85%, at least 90%, at least 95%, or at least 98% of these wells contain only one bead.

After the beads have settled, any excess liquid can be removed by touching a pipet tip to the wall of each well of the 96 well plate, or by touching a pipet tip to the wall of each well of the 24 well plate, and drawing off the excess liquid.

Regarding assay reagents, where the picowells are to be used for carrying out reactions, for example, DNA sequencing, biochemical assays, or assays of cultured cells, assay reagents can be added to the picowells that already contain settled beads. Adding the assay reagents is with a pipet, as described above for initial addition of the bead suspensions. After the assay reagents have equilibrated with the solution that is already in each picowell, any excess solution that is in each of the 96 wells of the 96-well plate, or any excess solution that is in each of the 24 wells of the 24-well plate, can drawn off with a pipet tip that touches the wall of each of the 96 wells of the 96-well plate, or that touches the wall of each of the 24 wells of the 24-well plate.

Flow-cell embodiment of picowell array. Picowell array may be part of a flow-cell, where a fluidic chamber with an inlet and an outlet are mounted on top of the picowell array. In such embodiments, beads of this disclosure, cells, and other assay materials may be flowed in from the inlet and out through the outlet. Gravity or centrifugal force may be used to lodge the beads into the picowells as they are flowed through the flowcell.

(X) Sequencing Bead-Bound Nucleic Acids in Picowells

Bead-bound nucleic acids can be sequenced while still attached to beads. Alternatively, or in addition, bead-bound nucleic acids can be sequenced following cleavage of the DNA barcode from the bead.

Cleaving the DNA barcode from the bead before sequencing. In some embodiments, the present disclosure can encompass a method where bead-bound DNA barcode is cleaved from the bead, thereby releasing the DNA barcode in a soluble form, prior to amplification, or prior to sequencing, or prior to any type of sequence identification technique such as hybridizing with a nucleic acid probe.

Exclusionary embodiments. In embodiments, the present disclosure can exclude any method, associated reagents, system, compositions, or beads, where a bead-bound DNA barcode is cleaved prior to amplification, or prior to sequencing, or prior to any type of sequence identification technique such as hybridizing with a nucleic acid probe. Also, the present disclosure can exclude any method where a polynucleotide comprising a DNA barcode is cleaved, or where a nucleic acid comprising only part of a DNA barcode is cleaved, prior to amplification, prior to sequencing, or prior to any type of sequence identification technique such as hybridizing with a nucleic acid probe.

Polymerase chain reaction (PCR); Quantitative PCR (qPCR). The PCR method, as well as the qPCR method, depend on the 3-step method involving: (1) Denaturing the DNA template at a high temperature, annealing primers at a reduced temperature, and finally extending the primer by way of DNA synthesis, as catalyzed by DNA polymerase (Gadkar and Filion (2014) Curr. Issues Mol. Biol. 16:1-6). qPCR is also called, "real time PCR" (Kralik and Ricchi (2017) Frontiers Microbiology. 8 (9 pages).

Recent modifications or improvements in the PCR method and qPCR method include, using helicase-dependent (HDA) amplification, using an internal amplification control, using locked nucleic acids (LNA), and using additives that bind to inhibitors (Gadkar and Filion (2014) Curr. Issues Mol. Biol. 16:1-6). Locked nucleic acids provide the advantage of recognizing and binding its target with extreme precision.

qPCR allows the simultaneous amplification and quantification of a targeted DNA molecule. The qPCR method compares the number of amplification cycles required for the response curvecs to reach a particular fluorescence threshold (Pabinger, Rodiger, Kriegner (2014) Biomolecular Detection Quantification. 1:23-33). Refsland et al provide a concise account of apparently typical conditions for conducting qPCR (Refsland, Stenglein, Harris (2010) Nucleic Acids Res. 38:4274-4284).

Guidance is available for designing and validating PCR primers, and on variables such annealing temperature (Ta), melting temperature (Tm), temperature of elongation step, type of buffer (Bustin and Huggett (2017) Biomolecular Detection Quantification. 14:19-28).

Rolling circle amplification (RCA). DNA can be amplified while attached to a bead. DNA in amplified form is easier to sequence that non-amplified DNA. In the rolling circle amplification method, DNA tags (the DNA barcode) is made single stranded. Once single stranded, a splint oligo is added to bridge the ends of the tag DNA, and this is followed by extension and ligation of the splint oligo. Using DNA polymerase (minus 5'→3'exonuclease activity) ensures a ligatable junction after the DNA catalyzes extension of the splint oligo. The circularized DNA can then be subjected to rolling circle amplification by adding a strand-displacing DNA polymerase, such as phi29 DNA polymerase. The ability to perform rolling circle amplification (RCA) on the DNA barcode tag permits the use of synthesis chemistries that may be damaging to DNA, as any surviving DNA molecules can be thermally amplified to sufficient quantities to be easily sequenced. DNA can be made single-stranded by exonuclease digestion, nicking, and melting at high temperature, or by treating with sodium hydroxide.

Further details of rolling circle amplification (RCA) are revealed by the following steps that can be used for conducting RCA.

Step One: Start with bead-bound ssDNA. If the bead-bound DNA is initially in a double stranded from (dsDNA), the strand that is not to be used for RCA can be prepared so that a residue of thymine (T) is replaced, at or very close to the bead-attachment terminus, with a residue of uracil (U). If the dsDNA is prepared in this way, uracil-N glycosidase can be used to cleave the uracil residue, thereby leaving an unstable sugar phosphate (as part of the DNA backbone), where this unstable location can be cleaved by nuclease-treatment (Ostrander et al (1992) Proc. Natl. Acad. Sci. 89:3419-3423).

Step Two: Add a "splint oligo" to the bead-bound ssDNA. The splint oligo is designed so that it hybridizes to about 10-20 base pairs at the end (the 5'-end) of the ssDNA that is covalently coupled to the bead, and so that it also hybridizes to about 10-20 base pairs at the free end (the 3'-end) of the bead-bound ssDNA. The splint oligo does not need to bring the bead-bound end of the ssDNA in close proximity to the free end of the bead-bound ssDNA. All that is needed is for the far ends of the bead-bound ssDNA sequence be tethered together, in order to form a huge loop.

Step Three: Add sulfolobus DNA polymerase IV, so that this polymerase uses the huge loop of ssDNA as a template, for creating a complementary huge loop that is covalently attached at one end to the splint oligo.

Step Four: Use DNA ligase to covalently close the complementary huge loop, where the result is circular ssDNA. It is this closed circle of ssDNA that does the "rolling," during RCA.

Step Five: Add DNA polymerase that has a strand displacement activity, and add dNTPs. The added DNA polymerase covalently attaches dNTPs to the bead-bound ssDNA, and the distal terminus of the bead-bound ssDNA is extended to create a complementary copy of what is on the "rolling circle," and then further extended to create yet another complementary copy of what is on the "rolling circle," and even more extended to create still another complementary copy of what is on the "rolling circle." During this process of potentially infinite amplification, continued activity of DNA polymerase is made possible by the strand displacement activity of the DNA polymerase.

Optionally, the method of the present disclosure includes real-time monitoring of rolling circle amplification (RCA) by way of fluorescent molecular beacons (Nilsson, Gullberg, Raap (2002) Nucleic Acids Res. 30:e66 (7 pages)). Reagents for RCA are available from Sigma-Aldrich (St. Louis, MO), Sygnis TruePrime Technology (TruePrime® RCA kit), Heidelberg, Germany, and GE Healthcare (TempliPhi 500® amplification kit). Fluorophores and quenchers are available from ThermoFisher Scientific (Carlsbad, CA), Molecular Probes (Eugene, OR), Cayman Chemical (Ann Arbor, MI), and Sigma-Aldrich (St. Louis, MO).

Step Six. Use the ssDNA that was amplified by RCA as a template for PCR amplification, where primers are added, where thermostable DNA polymerase is added, and where the PCR products are subsequently sequenced by Next Generation Sequencing.

In one aspect of the present disclosure, the RCA-amplified ssDNA is cleaved from the bead prior to PCR amplification that makes PCR products. In another aspect of the present disclosure, the PCR amplification that makes PCR products can be made without cleaving the RCA-amplified ssDNA from the bead.

As described by Baner et al, "Through the RCA reaction, a strand can be generated that represents many tandem copies of the complement to the circularized molecule" (Baner, Nilsson, Landegren (1998) Nucleic Acids Res. 26:5073-5078). *Bacillus subtilis* phase phi29 DNA polymerase is a suitable enzyme, because of its strand displacement activity and high processivity. RCA is similarly characterized by Li et al as, "In RCA, a circular template is amplified isothermally by a DNA polymerase phi29 with . . . strand displacement properties. The long single-stranded DNA products contain thousands of sequence repeats: (Li and Zhong (2007) Anal. Chem. 79:9030-9038).

Sequencing of DNA barcodes of the present disclosure can be, without implying any limitation, with methods of Vander Horn U.S. Pat. No. 8,632,975, which is incorporated herein by reference in its entirety. Also, the DNA barcodes of the present disclosure can be sequenced, for example, by methods that use sequencing-by-synthesis, such as the Sanger sequencing method, or by methods that use "Next Generation sequencing."

Illumina method for DNA sequencing. Illumina method for DNA sequencing is as follows. DNA can be fragmented to a size range of 100-400 base pairs (bp) by sonication (Hughes, Magrini, Demeter (2014) PLoS Genet. 10:e1004462). In the Illumina method, DNA libraries are made, where fragments of DNA from a cell or from cells are modified by DNA adaptors (attached to termini of the fragments). The The reaction product takes the form of a sandwich, where the DNA to be sequenced is in the center of the sandwich. The reaction product takes the form: (first adaptor)-(DNA to be sequenced)-(second adaptor). The adaptor-DNA-adaptor complex is then associated with yet another adaptor, where this other adaptor is covalently attached to a solid surface. The solid surface can be a flat plate. The solid surface has a lawn of many adaptors that stick out of the flat surface. The adaptor has a DNA sequence that is complementary to one of the adaptors that is in the sandwich. Actually, the lawn contains two type of adaptors, where one adaptor binds (hybridizes) to one of the adaptors in the complex, and non-covalently tethers the complex to the plate. These may be called the, "first lawn-bound adaptor" and the "second lawn-bound adaptor." The first task of DNA polymerase, is to create a daughter strand, using the tethered (but non-covalently bound) DNA as a template and, when DNA polymerization occurs, the daughter strand is in a form that is covalently attached to the "first lawn-bound adaptor." This covalent link was generated by the catalytic action of DNA polymerase. After the daughter strand is completely synthesized, the distal end (the end that sticks out into the medium) contains a DNA sequence that is complementary to the second adaptor in the above-named sandwich. This DNA sequence that is complementary, allows the distal end of the newly synthesized daughter DNA to bend over and to hybridize to the "second lawn-bound adaptor." What has been described above, is how both adaptors of the sandwich are used, and how both the "first lawn-bound adaptor" and the "second lawn-bound adaptor" are used.

A cycle of reactions is then performed many times, where the result is a cluster of amplified versions of the original dsDNA. Actually, the cluster takes the form of covalently attached (tethered) ssDNA molecules, where all of these ssDNA molecules correspond to only one of the strands of the original dsDNA (dsDNA isolated from a living cell or tissue). This cluster of tethered ssDNA molecules is called a "polony." The generation of the polony is by a technique called, "bridge amplification." Finally, after bridge amplification and the creation of polonies, the reverse strands that are covalently attached to the solid suface are cleaved from its tetherings, washed away, and discarded, leaving only the forward strands.

Information on the Illumina® method is available from Goodwin, McPherson, McCombie (2016) Nature Rev. Genetics. 17:333-351, Gierahn, Wadsworth, Hughes (2017) Nature Methods. 14:395-398, Shendure and Hanlee (2008) Nature Biotechnology. 26:1135-1145; Reuter, Spacek, Snyder (2015) Molecular Cell. 58:586-597; Illumina Sequencing by Synthesis (5 minute video on YouTube).

Sequencing by oligonucleotide ligation and detection (SOLiD sequencing). SOLiD measures fluorescence intensities from dye-labeled molecules to determine the sequence of DNA fragments. A library of DNA fragments is prepared from the sample to be sequenced and used to prepare clonal bead populations (with only one species of fragment on the surface of each magnetic bead). The fragments attached to the heads are given a universal P1 adapter sequence attached so that the starting sequence of every fragment is both known and identical. PCR is conducted and the resulting PCR products that are attached to the beads are then covalently bound to a slide.

Then, primers hybridize to the P1 adapter sequence within the library template. A set of four fluorescently labelled di-base probes compete for ligation to the sequencing primer. Specificity of the di-base probe is achieved by interrogating every 1st and 2nd base in each ligation reaction. Multiple cycles of ligation, detection and cleavage are performed with the number of cycles determining the eventual read length. Following a series of ligation cycles, the extension product is removed and the template is reset with a primer complementary to the n–1 position for a second round of ligation cycles (see, Wu et al (2010) Nature Methods. 7:336-337).

pH-based DNA sequencing. pH-Based DNA sequencing is a system and method where, base incorporations are determined by measuring hydrogen ions that are generated as byproducts of polymerase-catalyzed extension reactions. DNA templates each having a primer and polymerase operably bound are loaded into reaction chambers or microwells, after which repeated cycles of deoxynucleoside triphosphate (dNTP) addition and washing are carried out. The DNA template is templates are attached as clonal populations to a solid support. With each such incorporation a hydrogen ion is released, and collectively a population of templates releasing hydrogen ions causing detectable changes to the local pH of the reaction chamber (see, Pourmand (2006) Proc. Nat'l. Acad. Sci. 103:6466-6470). The present disclosure can exclude pH-based DNA sequencing.

Regarding the concatenated DNA barcode, the entire concatenated DNA barcode can be sequenced in one run (where sequencing of the entire concatenated DNA barcode requires only one sequencing primer). Alternatively, some or all of the DNA barcode modules that make up the concatenated DNA barcode can be subjected to individual sequencing (where each of the individually-sequenced DNA barcode modules gets its own sequencing primer). Regarding orthogonal DNA barcodes, each of the DNA barcode modules that make up the orthogonal DNA barcode needs its own, dedicated sequencing primer, because of the fact that each DNA barcode module is attached to its own site on the bead.

Exclusionary embodiments. In embodiments, the present disclosure can exclude any system, device, combination of devices, and method, that involves microfluidics, aqueous droplets that reside in an oil medium, and aqueous droplets that are created where a first channel containing aqueous reagents is joined with a second channel containing an oil to create aqueous droplets that move through an oil medium through a third channel that starts at the joining area. Microfluidics devices and reagents are described (see, e.g., Brouzes, Medkova, Savenelli (2009) Proc. Natl. Acad. Sci. 106:14195-14200; Guo, Rotem, Hayman (2012) Lab Chip. 12:2146-2155; Debs, Utharala, Balyasnikova (2012) Proc. Natl. Acad. Sci. 109:11570-11575; Sciambi and Abate (2015) Lab Chip. 15:47-51).

In other exclusionary embodiments, what can be excluded is any reagent, composition, nucleic acid, or bead, that comprises a "DNA headpiece" or an reagent, composition, nucleic acid, or bead, that is covalently attached to a "DNA headpiece." MacConnell, Price, Paegel (2017) ACS Combinatorial Science. 19:181-192, provide an example of a DNA headpiece, where beads are functionalized with azido DNA headpiece moieties.

Additional exclusionary embodiments relating to sequencing methods and sequencing reagents. In embodiments, the present disclosure can exclude reagents, systems, or methods that do not involve use of a "reversible terminator" in DNA sequencing. Also, what can be excluded is any reagent, system, or method, that do not include methoxy blocking group. Moreover, what can be excluded is any reagent, system, or method, that involves DNA sequencing, but where the DNA being sequenced is not covalently bound to a bead at the time at the time that information on the order of polynucleotides is being detected and collected. Furthermore, what can be excluded is any reagent, system, or method that amplifies a DNA template prior to conducting sequencing reactions, for example, amplification by PCR technique or by rolling circle technique. In embodiments, what can be excluded is any method of barcoding, for example, nucleic acid barcoding, that is concatenated (all information on synthesis of a member of the chemical library residing on one single nucleic acid). In another aspect, what can be excluded is any method of barcoding, for example, nucleic acid barcoding, that is orthogonal (information on synthesis of a given monomer of a chemical library being dispersed on a plurality of attachment positions on the bead). In an exclusionary embodiment relating to DNA ligase, the present disclosure can exclude any reagent, system, or method, that uses DNA ligase for connecting modules of a nucleic acid barcode.

Fluorophores, quenchers, and FRET-based assays. The present disclosure provides fluorophores and quenchers for screening members of a chemical library, or for characterizing an isolated member of a chemical library. FRET is Förster resonance energy transfer.

Assays can be performed on bead-bound chemical libraries. Also, assays can be performed on free chemical library members shortly after cleavage from a bead, that is, performed in the same microwell as the bead or performed in the same vicinity of a hydrogel matrix as the bead. Moreover, assays can be performed on a soluble chemical library member that had never been attached to any bead, or that had been cleaved from a bead and then purified.

Fluorophores suitable as reagents of the present disclosure include Alexa 350, Alexa 568, Alexa 594, Alexa 633, A647, Alexa 680, fluorescein, Pacific Blue, coumarin, Alexa 430, Alexa 488, Alexa 532, Alexa 546, Alexa 660, ATTO655, ATTO647n, Setau-665 (SETA Biochemicals, Urbana, IL), Cy2, Cy3, Cy3.5, Cy5, Cy5.5, tetramethylrhodamine (TMR), Texas red, tetrachlorofluorescein (TET), hexachlorofluorescein (HEX), and Joe dye (4'-5'-dichloro-2',7'-dimethoxy-6-carboxyfluorescein), SYBR green I (absorb 497 nm, emit 520 nm), 6-carboxyfluorescein (6-FAM) (absorbs 492 nm, emits 518 nm), 5-carboxyfluorescein (5-FAM) (absorbs 492 nm, emits 518 nm), FITC, and rhodamine. Quenchers include TAMRA quencher, black hole quencher-1 (BHQ1), and black hole quencher-2 (BHQ2), and DABCYL quencher. Please note, as disclosed elsewhere in this patent document, that TAMRA can be a fluorophore and it can also be a quencher.

Guidance is available on reagents for FRET-based assays, where the FRET reagent includes a fluorophore and quencher (see, Johansson (2006) Choosing reporter-quencher pairs for efficient quenching. Methods Mol. Biol. 335:17-29). An example of a FRET-based assays including measuring the activity of a signal peptidase (SpsB) with the substrate, "SceD peptide." The FRET-pair attached to the peptide was 4-(4-dimethylaminophenylazo) 5-((2-amino-ethyl) amino)-1-nepthalenesulfonic acid (see, Rao et al (2009) FEBS J. 276:3222-3234). Another example comes from assays of HIV-1 protease, with the peptide substrate, KVSLNFPIL. The donor/acceptor FRET pair was EDANS (donor) and DABCYL (acceptor). EDANS fluorescence can be quenched by DABCYL by way of resonance energy transfer to the nonfluorescent DABCYL (see, Meng et al (2015) J. Biomolecular Screening. 20:606-615). Yet another example comes from assays of botulinum toxin. Activity of SNAP-25 can be measured by using the substrate, BoNT-A. For FRET-based assays, the substrate had an N-terminally linked fluorescein-isothiocyanate (FITC) and the C-terminally linked quencher was, 4-(4-dimethylaminophenyl) diazenylbenzoic acid (DABSYL). The peptide substrate corresponded to amino acids 190-201 of SNAP-25 (see, Rasooly and Do (2008) Appl. Environ. Microbiol. 74:4309-4313).

The present disclosure provides for reagents, compositions, and methods for screening a library of compounds in order to discover and identify enzyme inhibitors, enzyme activators, and to discover compounds that can enhance the rate of in vivo degradation of a given protein. These reagents, compositions, and methods can use FRET-based assays and, alternatively, they can use assays other than FRET-based assays.

Molecular beacons are described (see, Baruch, Jefferey, Bogyo (2004) Trends Cell Biology. 14:29-35). A molecular beacon is a reagent where a fluorophore is bound, by way of a linker, to a quencher. The linker may be cleavable by a nuclease, and thus measure nuclease activity. The present disclosure provides for methods to screen chemical libraries for identifying nuclease inhibitors and, alternatively, for identifying nuclease activators. Feng et al have described the use of molecular beacons and use of FRET-based assays for measuring activity of various nucleases (Feng, Duan, Liu (2009) Angew Chem. Int. Ed. Engl. 48:5316-5321). Feng et al, showed use of FRET-based assays for measuring activity of various restriction enzymes.

(XI) Releasing Bead-Bound Compounds

Cleavable linkers. What is provided is linkers that are not cleavable. Also, what is provided are cleavable linkers (see, Holmes and Jones ((1995) J. Org. Chem. 60:2318-2319; Whitehouse et al (1997) Tetrahedron Lett. 38:7851-7852, and Yoo and Greenberg ((1995) J. Org. Chem. 60:3358-

3364, as cited by Gordon et al (1999) J. Chem. Technology Biotechnology. 74:835-851). Cleavable linkers also include an acyl sulphonamide linkers that reside alkaline hydrolysis, as well as activated N-alkyl derivatives which are cleaved under mild conditions, and also traceless linkers based on aryl-silicon bonds, and traceless linkers based on silyl ether linkages (described on page 839 and 842 of Gordon et al (1999) J. Chemical Technology Biotechnology. 74:835-851). Moreover, what is provided is a linker based on tartaric acid which, upon cleavage, generates a C-terminal aldehyde, where cleavage is by periodate oxidation (see, Paulick et al (2006) J. Comb. Chem. 8:417-426).

FIG. 3 discloses various cleavable linkers that are suitable for the compositions and methods of the present disclosure. FIG. 3 is reproduced from Table 1 of: Yinliang Yang (2014) Design of Cleavable Linkers and Applications in Chemical Proteomics. Technische Universitat Munchen Lehrstuhl fur Chemie der Biopolymere. From FIG. 3, cleavable linkers that are preferred for the present disclosure are linkers A, C, D, E, F, G, and I. Linker E was used in the experimental results disclosed herein. Cleavage conditions for these are DTT (linker A), $Na_2SO_4$ (linker C), $Na_2SO_4$ (linker D), UV light (linker E), UV light (linker F), UV light (linker G), and TEV protease (linker I). These particular cleavage conditions are gentle and are not expected to damage the bead, to damage the bead-bound compound, or to damage any chemical library member (the unit) of the bead-bound compound.

Chemically cleavable linkers that are compatible with click-chemistry. Qian et al (2013) describes a number of cleavable linkers that are compatible with click-chemistry (Qian, Martell, Pace (2013) ChemBioChem. 14:1410-1414). These include linkers with an azo bond, where the azo bond is cleavable with dithionite. This linker has the following structure: $R_1$-benzenel-N=N-benzene2-$R_2$. The first benzene ring has a hydroxy group para to $R_1$, and the second benzene ring has a carbonyl group that links to $R_2$, where this carbonyl group is para to the azo moiety.

Photolabile cleavable linkers. The present disclosure encompasses photocleavable linkers that have an o-nitrobenzyl group. This group can be cleaved by irradiation at 330-370 nm (see, Saran and Burke (2007) Bioconjugate Chem. 18:275-279; Mikkelsen, Grier, Mortensen (2018) ACS Combinatorial Science. DOI:10.1021). A linker with a shorter photolysis time than o-nitrobenzyl linker is 2-(2-nitrophenyl)-propyloxycarbonyl (NPPOC) linker. A variation of o-nitrobenzyl linker is o-nitrobenzylamino linker. When attached to a peptide chain, and when subsequently cleaved, this linker releases an amide. Linker with an o-nitroveratryl group are available, and these have shorter photolysis time and greater release yields than unsubstituted o-nitrobenzyl linkers. Also available are phenacyl linkers, benzoin linkers, and pivaloyl linkers (see, Mikkelsen et al (2018) ACS Combinatorial Science. DOI:10.1021).

Linkers with photocleavable ether bonds are available. This photocleavable linker can be used where the linker is attached to a bead and where the cleavable group is an "R group," and after cleavage, the released group takes the form of ROH (see, Glatthar and Giese (2000) Organic Letters. 2:2315-2317). Also available are linkers with photocleavable ester bonds (see, Rich et al (1975) 97:1575; Renil and Pillai (1994) Tetrahedron Lett. 35:3809-3812; Holmes (1997) J. Org. Chem. 62:2370-2380, as cited by Glatthar and Giese, supra). Ether bonds in linkers can be cleaved by acid, base, oxidation, reduction, and fluoride sensitive silyl-oxygen bond cleavage, and photolysis (Glatthar and Giese, supra).

Another photocleavable linker, which has been used to link a peptide ($R_1$) and a nucleic acid (R2), is as follows. $R_1$ is connected directly to the methylene moiety of a benzyl group. Para to the methylene group is a ring-attached nitro group. Meta to the methylene moiety is a ring-attached ethyl group. The 1-carbon of the ethyl group bears a phosphate. To an oxygen atom of this phosphate is attached the R2 group (Olejnik et al (1999) Nucleic Acids Res. 27:4626-4631).

Akerblom et al, discloses photolabile linkers of the alpha-methyl 2-nitrobenzyl type, containing amino, hydroxyl, bromo, and methylamino groups, and also 4-nitrophenoxy-carbonyl activated hydroxyl and amino groups (see, Akerblom and Nyren (1997) Molecular Diversity. 3:137-148). Cathepsin B can cleava a linker with the target sequence, "valine-citrulline" (Dal Corso, Cazzamalli, Neri (2017) Bioconjugate Chemistry. 28:1826-1833).

Enzyme-cleavable linkers. Linkers that are cleavable by enzymes, such as proteases, are available (see, Leriche, Chisholm, Wagner (2012) Bioorganic Medicinal Chem. 20:571-582). The hydroxymethylphenoxy linker can be cleaved with chymotrypsin (Maltman, Bejugam, Flitsch (2005) Organic Biomolecular Chem. 3:2505-2507). Linkers that are cleavable with tobacco etch virus protease are available (see, Weerapana, Speers, Cravatt (2007) Nature Protocols. 2:1414-1425; Dieterich, Link, Graumann (2006) Proc. Nat'l. Acad. Sci. 103:9482-9487). The linker sequences LVPRG and LVPRGS can be cleaved by thrombin (Jenny, Mann, Lundblad (2003) Protein Expression Purification. 31:1-11). Plasmin-cleavable linkers are available (Devy, Blacher, Noel (2004) FASEB J. 18:565-567).

Bead-bound release-monitor. The present disclosure provides a novel and unique release-monitor that is capable of assessing release of bead-bound compounds. The release-monitor takes the form of a bead-bound complex of fluorophore and quencher, where the fluorophore is connected to the bead by way of a cleavable linker. Preferably, the cleavable linker is a photocleavable linker. Preferably, the bead-bound release-monitor is situated in a dedicated picowell, where that picowell does not contain any other type of bead. With severing of the photocleavable linker, the fluorophore is released from the bead, diffuses into the medium in the picowell, achieves some distance from the bead-bound quencher, where the result is an increase in fluorescence that is proportional to the amount of release. The increase in fluorescence allows the calculation of the concentration of the free fluorophore that is in the picowell and, more importantly, allows calculation of the amount of chemical compounds that are released from other beads that are situated in other wells.

To summarize, the bead-bound release-monitor is situated in its own dedicated well, where other wells contained bead-bound compounds that are drug candidates.

FIG. 8 discloses a simplified version of a preferred and non-limiting example of a bead-bound release-monitor. The release-monitor takes the form of a quencher that is held in the vicinity of a fluorophore, resulting in quenching of the fluorophore. In embodiments, quenching is at least 85%, at least 90%, at least 95%, at least 96%, at least 97%, at least 98%, at least 99%, at least 99.5%, at least 99.8%, at least 99.9%, at least 99.95%, and so on. In a picowell, one bead is dedicated to being a release-monitor, while another bead or beads are used for attaching a compound and for attaching DNA library. Exposure of all of the beads in a picowell to UV light result in simultaneous cleavage of fluorophore and of the compound. QSY7 is a preferred quencher. The structure and CAS number for QSY7 is as follows (see below):

CAS name/number: Xanthylium, 9-[2-[[4-[[(2,5-dioxo-1-pyrrolidinyl)oxy] carbonyl]-1-piperidinyl]sulfonyl]phenyl]-3,6-bis(methylphenylamino)-, chloride 304014-12-8

The increase in fluorescence that results from separation of the fluorophore from the quencher can be used to infer the concentration in the picowell of the simultaneously released compound. Also, the increase in fluorescence that results from separation of the fluorophore from the quencher can be used to infer the number of molecules (molecules taking the form of the compound that was formerly a bead-bound compound) that reside in free form in the picowell. In a more preferred embodiment, the release-monitor comprises a quencher and a fluorophore, where cleavage results in the release of the fluorophore (and not release of the quencher). This embodiment provides lower background noise than the following less preferred embodiment. In a less preferred embodiment, cleavage results in the release of the quencher, where the read-out takes the form of the increase in fluorescence from bead-bound fluorophore.

The release-monitor provides the user with a measure of the concentration of the soluble compound, following UV-induced release of the compound from the bead. In a preferred embodiment, one type of bead is dedicated to being a release-monitor. By "dedicated," what this means is that this bead does not also contain bead-bound compound and does not also contain bead-bound DNA library.

As a general proposition, just because a compound has been released from a bead by cleavage of a photosensitive linker, it should not be inferred that the compound has become a soluble compound. First of all, please note that just because a compound is considered to be "hydrophobic" or is considered to be "water-insoluble" does not mean that none of the molecules are freely moving in the solvent. For example, even cholesterol has a measurable solubility in water (see, Saad and Higuchi (1965) Water Solubility of Cholesterol. J. Pharmaceutical Sciences. 54:1205-1206). Moreover, biochemical efficacy of a bead-bound water-insoluble compound can be increased, by way of surfactants, detergents, additives such as DMSO, or carriers such as human serum albumin. Thus, the release-monitor can be used to assess overall concentration of compounds of limited water-solubility or of no water-solubility, under the condition where the picowell contains one of the above agents or, alternatively, where the water-insoluble compound is released in the vicinity of the plasma membrane of a living cell that is cultured inside of the picowell.

FIG. 9 discloses a simplified version of a preferred embodiment of bead-bound release-monitor, while FIG. 10 discloses a complete and detailed structure of this preferred embodiment of bead-bound release-monitor.

FIG. 30 provide data demonstrating use of bead-release monitor, where bead is in a picowell. The bead-bound fluorophore, which is bound using a light-cleavable linker, was TAMRA (excitation wavelength 530 nm; emission wavelength 570 nm). The figure shows time-course of release of the fluorophore from the bead. This shows operation of the bead-bound release monitor, acquisition of fluorescent data at t=0 seconds, t=1 seconds, t=11 seconds, and t=71 seconds. FIG. 30 also include insets showing blowups of the smaller figures, for two of the four smaller figures. FIG. 30 were obtained from incubation of cathepsin-D, which is an aspartyl protease, with "Peptide Q-Fluor Substrate" and beads. Reagents were placed into wells at 4 degrees C. Ultraviolet light at 365 nm was used to cleave the fluorophore from the bead, thereby releasing the fluorophore and separating it from the quencher. A goal of this assay was to assess the time course of release taking place in a separate well, where the separate well contained a different type of bead. The different type of bead had the same light-cleavable linker, but where this light-cleavable linker was attached to pepstatin-A. Release of pepstatin-A can bind to and inhibit an aspartyl protease that is in the same assay medium. This setup with bead-bound pepstatin-A and the aspartyl protease can serve as a positive control.

UV exposed through 20× objective. Image was obtained with Gain 32. 5; Exposure was 400 Ms. Excite at TAMRA at 530 nm. TAMRA emits at 570 nm.

FIG. 35 discloses further details on enzymatic assays, where bead-bound pepstatin-A is released, and where the released pepstatin-A results in enzyme inhibition. 10 µm TentaGel beads displaying photocleavable Pepstatin-A (positive control) and a covalent Cy5 label, were mixed with 10 µm TentaGel beads displaying photocleavable Fmoc-Valine (negative control) in PBST buffer. This bead population was introduced into picowells, then buffer exchanged into a protease inhibition assay, including Cathepsin-D protease and Peptide Q-Fluor substrate ($\lambda_{ex}$=480 nm, $\lambda_{em}$, =525 nm). Wells were encapsulated by air, and entire slide exposed to UV (365 nm, 77 J/cm$^2$), cleaving the photolabile linker, releasing the compound to reach approximately 13 µM. The flowcell was incubated (30 min, 37° C.). Wells containing positive control beads should inhibit peptide proteolysis by Cathepsin-D, resulting in low fluorescence signal. Wells containing negative control beads should not show any Cathepsin-D inhibition, and should be similar in fluorescence intensity to empty wells.

Terminology for quencher and fluorophore can change, for a given chemical, depending on what other chemicals occur in the immediate vicinity. Although the TAMRA that is used in the laboratory data of the bead-bound release monitor is a fluorophore, in other contexts, TAMRA can be a quencher. TAMRA acts as a quencher in TaqMan® probes that contain FAM and TAMRA.

Additional accounts of experimental setup and laboratory data. The present disclosure provides data on controlled 5(6)-Carboxytetramethylrhodamine (TAMRA) concentrations in phosphate buffer (10 mM phosphate, 154 mM sodium, pH 8.0) within filled pico-wells, compartmentalized by air. Fluorescence images captured (10 ms, 2 ms exposures) and well-area quantitated by mean pixel intensity (n 100) to generate a concentration vs fluorescence intensity calibration curve. The above data take the form of a standard curve, showing fluorescence at various predetermined concentrations of free TAMRA (2, 10, 30, 60, 100 mM TAMRA). This standard curve was prepared under two different conditions, that is, where the photographic image was taken with a 2 millisecond exposure or with a 10 millisecond exposure. The experiment used for preparing the standard curve was conducted in picowells, but there were not any beads used in this experiment (just known amounts of TAMRA). The photographic image is not shown in this patent document, because the data merely take the form of a standard curve, which may also be called a calibration curve.

The experimental setup included the following. For Scheme X), TentaGel-Lys(PCL1-Tamra)-QSY7 bead structure. QSY7 (gray) quenches the Tamra fluorophore (orange) while covalently attached to bead through a photocleavable linker (purple). Irradiation from UV (365 nm) provides quantitative release of compounds in situ FIGS. 31A-31B discloses emission data resulting after catalytic action of aspartyl protease on quencher-fluorophore substrate. Greater fluorescence means that the enzyme is more catalytically active. Lesser fluorescence means that the enzyme is less catalytically active, that is, there the enzyme is more inhibited by a free inhibitor, where the inhibitor was freed from a bead, and where freedom was obtained by cleavage of light-cleavable linker. Images were captured following UV release and Cathepsin-D assay incubation ($\lambda_{ex}$=480 nm, $\lambda_{em}$=525 nm). Wells containing positive control beads could be identified spectrally by Cy5 fluorophore ($\lambda_{ex}$=645 nm, $\lambda_{em}$=665 nm, orange false color). A section was analyzed with a line-plot across open well volume, Wells containing negative control beads elicit no Cathepsin-D inhibition. Assay volume within wells containing positive control beads are dark, indicating strong inhibition. Assay volume within empty wells is comparable to wells containing negative control beads.

FIG. 32 illustrates the following procedure. Further regarding Scheme X), Picowell substrate (46 pL per well) is enclosed in a flowcell, wells wetted under vacuum, a suspension of TentaGel-Lys(PCL1-TAMRA)-QSY7 beads are introduced, and air pulled across flow-cell, compartmentalizing each well (top). Flowcell is irradiated by a UV LED ($\lambda_{mean}$ 365 nm) with controlled luminous flux, allowed to equilibrate (20 min), before fluorescence microscopy images taken to quantitate released compound (TAMRA) concentration (bottom) (FIG. 32). In detail, FIG. 32 shows drawings of cross-section of picowell, illustrating the steps where picowells wetted in a flowcell, the step where beads in a suspension are introduced over the picowells, resulting in one bead per picowell, the step of drawing air across flowcell in order to reduce excessive dispersion solution and resulting in a meniscus dropping below the surface of the planar top surface of the picowell plate, the step of controlled UV exposure (365 nm), resulting in release of some TAMRA, and the step of provoking light emission from TAMRA with detecting fluorescent signal with fluorescent microscopy (excite 531/40 nm) (emit 594/40 nm). The notation, "slash 40" refers to the bandwidth, that is, it means that cut-off filters confined the light to the range of: 531 nm plus 20 nm and minus 20 nm, and to 594 nm, plus 20 nm and minus 20 nm (this slash notation can be used for excitation wavelengths and also to emission wavelengths).

The present inventors acquired photographs showing the following data (see, FIGS. 33A-33F). Fluorescence emission ($\lambda_{ex}$ 531/40 nm, $\lambda_{em}$ 593/40) of fluorophore (TAMRA) released from 10-µm TentaGel-Lys(PCL1-TAMRA)-QSY7 beads after UV LED (365 nm) exposure in pico-well flow cell. A) No significant emission above background prior to UV exposure (0 J/cm$^2$), owed to the FRET quenching effect of QSY7. TAMRA release allowed to reach equilibrium (20 min) following UV exposures of (B) 25 J/cm$^2$, (C) 257 J/cm$^2$, (D) 489 J/cm$^2$, (E) 721 J/cm$^2$, (F) 953 J/cm$^2$ then imaged using appropriate exposure times. Fluorescence emission was measured within the volume surrounding each bead to measure TAMRA concentration (FIGS. 33A-33F) The notation, "slash 40" refers to the bandwidth, that is, it means that cut-off filters confined the light to the range of: 531 nm plus 20 nm and minus 20 nm (this slash notation can be used for excitation wavelengths and also to emission wavelengths).

The following is an interpretation, by the present inventors, of some of the fluorescence data from testing and use of the bead-bound release monitor (see, FIG. 34) Concentration of bead-released TAMRA inside pico-wells (45 pL) after UV exposure (365 nm). Image analysis used mean pixel intensity of the solution surrounding bead-filled wells (n≥14), normalized to image exposure time, then correlated to standard curve of known TAMRA concentrations in pico wells. Error bars represent 1σ, calculated from RSD %. UV released compound concentrations were 1.1 µM (RSD % 8.9), 54.3 µM (RSD % 5.2), 142 µM (RSD % 4.2), 174 µM (RSD % 7.7), 197.3 µM (RSD % 10.1) (FIG. 34)

(XII) Biochemical Assays for Compounds (Assays that are not Cell-Based)

A variety of biochemical assays are possible using beads within picowells. Non-limiting examples include binding assays, enzymatic assays, catalytic assays, fluorescence based assays, luminescence based assays, scattering based assays, and so on. Examples are elaborated below.

Biochemical assays that are sensitive to inhibitors of proteases and peptidases. Where the goal is to detect and then develop a drug that inhibits a protease, screening assay can use a mixture of a particular protease or peptidase, a suitable cleavable substrate, and a color-based assay or a fluorescence-based assay that is sensitive to the degree of inhibition by candidate drug compounds. For example, one reagent can be a bead-bound compound, where the compound has not yet been tested for activity. Another reagent can take the form of bead-bound pepstatin (an established inhibitor of HIV-1 protease) (Hilton and Wolkowicz (2010) PLoS ONE. 5:e10940 (7 pages)). Yet another reagent can be a cleavable substrate of HIV-1 protease, and where cleavage by the HIV-1 protease results in a change in color or a change in fluorescence. Positive-screening drug candidates are identified where a particular assay (in a given microwell) results in a difference in color (or a difference in fluorescence). The cleavable substrate takes the form of a susceptible peptide that is covalently bound to and flanked by a quencher and a fluorescer. Before cleavage, the fluorophore does not fluoresce, because of the nearby quencher, but after cleavage, fluorescence materializes (see, Lood et al (2017) PLoS ONE. 12:e0173919 (11 pages); Ekici et al (2009) Biochemistry. 48:5753-5759; Carmona et al (2006) Nature Protocols. 1:1971-1976). The reagents and methods of the present disclosure encompass the above-disclosed technology.

Enzyme-based screening assay for compounds that inhibit ubiquitin ligases, where the reagents include MDM2 (enzyme) and p53 (substrate). Applicants have conducted working tests based on the following technology. MDM2 regulates the amount of p53 in the cell. MDM2 is overexpressed in some cancers. MDM2 is an enzyme, as shown by the statement that, "In vitro studies have shown that purified MDM2 . . . is sufficient to ubiquitinate . . . p53" (Leslie et al (2015) J. Biol. Chem. 290:12941-12950). Applicant's goal is to discover inhibitors of MDM2, where these inhibitors are expected to reduce ubiquitination of p53 and thus reduce subsequent degradation of p53. In view of the expected increase in p53 in the cell, an inhibitor with the above property is expected to be useful for treating cancer.

Applicants used the following enzyme-based assay for assessing the influence of lenalidomide on ubiquitination of p53, as mediated by MDM2/HDM2. Applicants used reagents from the following kit: MDM2/HDM2 Ubiquitin Ligase Kit -p53 Substrate (Boston Biochem, Cambridge, MA). One of the reagents used in the assay was a bead with a covalently bound antibody. The bead was TentaGel® M NH2 (cat. no. M30102, Rapp Polymere GmbH, Germany) and the antibody was anti-human p53 monoclonal antibody, biosynthesized in a mouse. MDM2 is an E3 ligase that can use p53 as a substrate, where MDM2 catalyzes ubiquitination of the p53.

Goal of activating p53 for reducing cancer. A relation between MDM2, the transcription factor called, "p53," and anti-cancer therapy is suggested by the following description. The description is, "MDM2 is an E3 ubiquitin ligase that ubiquitinates p53, targeting it for proteasomal degradation" (Ortiz, Lozano (2018) Oncogene. 37:332-340). p53 has tumor-suppressing activity. p53 activity can be inhibited by MDM2. According to Wu et al, MDM2 is a, "p53-binding protein" (see, Wu, Buckley, Chernov (2015) Cell Death Disease. 6:e 2035). Where a compound prevents ubiquitination of p53, for example, by blocking interactions between MDM2 and p53, the compound might be expected to function as an anti-cancer drug.

Goal of the screening assay. A purpose of the screening assay is to discover compounds that influence ubiquitination of p53, for example, compounds that stimulate p53 ubiquitination and compounds that inhibit p53 ubiquitination. In detail, the purpose is to discover compounds that are inhibiting or activating, where their effect is via MDM-2 and either E1 ligase, E2 ligase, or E3 ligase. MDM2 means, "murine double minute." MDM2 has been called an, "E3 ubiquitin ligase." When MDM2 occurs in the cell, evidence suggests its activity in catalyzing the ubiquitination of p53 requires a number of other proteins, such as CUL4A, DDB1, and RoC1 (see, Banks, Gavrilova (2006) Cell Cycle. 5:1719-1729; Nag et al (2004) Cancer Res. 64:8152-8155). Banks et al have described a physical interaction involving p53 and MDM2 as, "L2DTL, PCNA and DDB1/CUL4A complexes were found to physically interact with p53 tumor suppressor and its regulator MDM2/HDM2" (Banks, Gavrilova (2006) Cell Cycle. 5:1719-1729). Nag et al have also described a physical interaction involving p53 and MDM2 as, "Cul4A functions as an E3 ligase and participates in the proteolysis of several regulatory proteins through the ubiquitin-proteasome pathway. Here, we show that Cul4A associates with MDM2 and p53" (Nag et al (2004) Cancer Res. 64:8152-8155).

Desired read-out from the bead-based assay for modulators of p53 ubiquitination. Where screening compounds results in a positive-screening hit, that is, where there is more AF488 fluorescence, this means that an ACTIVATOR has been discovered. And where screening compounds results in a positive-screening hit, where there is a REDUCTION in fluorescence, this means that an INHIBITOR has been discovered. A compound that inhibits ubiquitination of p53, suggests that the compound can be used for treating cancer. Also a compound that specifically inhibits ubiquitination of p53, that is, where the compound does not inhibit ubiquitination of other proteins, or where the compound inhibits ubiquitination of other proteins with inhibition that is less severe than for p53, also suggests that the compound can be used for treating cancer.

Materials. Materials included E3 Ligase kit K-200B from Boston Biochem. Boston Biochem catalog describes this kit as: Mdm2/HDM2 Ubiquitin Ligase Kit -p53 Substrate. The following concerns Mdm2, which is part of this kit. This kit does not include cereblon. Lenalidomide and similar compounds can bind to either cereblon or to Mdm2, where the end-result is activation of ubiquitin ligase. Materials also included Diamond White Glass microscope slides, 25 mm×75 mm (Globe Scientific, Paramus, NJ). Corning Stirrer/Hot Plate (settings from zero to ten) 698 Watts, Model PC-420. N-hydroxy-succinimide (NHS). Methyltetrazine (mTET). AlexaFluor488 (AF488) (ThermoFisher Scientific) . TentaGel beads M NH2 (cat. No. M30102) (Rapp Polymere GmbH). Parafilm (Sigma-Aldrich, St. Louis, MO). FIG. 8 shows the structure of Alexa Fluor® 488. The structure of Alexa Fluor 488 (AF488) is shown in Product Information for AlexaFluor488-Nanogold-Streptavidin (Nanoprobes, Inc., Yaphank, NY).

(XIII) Cell-Based Assays for Chemical Compounds

Cell-based assays that are conducted in a picowell can use human cells, non-human cells, human cancer cells, non-human cancer cells, bacterial cells, cells of a parasite such as plasmodium cells. Also, cell-based assays can be conducted with human cells or non-human cells that are "killed but metabolically active," that is, where their genome has been cross-linked to allow metabolism but to prevent cell division (see, U.S. Pat. Publ. No. 2007/0207170 of Dubensky, which is incorporated herein by reference in its entirety). More-over, cell-based assays can be conducted on apoptotic cells, necrotic cells, or on dead cells. Cell-based assays with bacterial cells can be used to screen for antibiotics. Human cells that are infected with a virus can be used to screen for anti-viral agents. Combinations of cells are provided for cell-based assays. For example, combinations of dendritic cells and T cells are provided to screen for and identify compounds that stimulate antigen presentation or, alternatively, that impair antigen presentation.

Cell-based assays can be based on a primary culture of cells, for example, as obtained from a biopsy of normal tissue, a biopsy from a solid tumor, or from a hematological cancer, or from a circulating solid tumor cells. Also, cell-based assays can be based on cells that have been passaged one or more times.

Cell-based assays that are conducted in a picowell can use a culture that contains only one cell, or that contains two cells, three cells, four cells, five cells, or about 2 cells, about 3 cells, about 4 cells, about 5 cells, or a plurality of cells, or less than 3 cells, less than 4 cells, less than 5 cells, and so on.

Applicants have conducted working tests based on the following technology. This describes cell-based assays for screening compound for the exemplary embodiment where lenalidomide (test compound) inhibits ubiquitin-mediated proteolysis of a transcription factor. The transcription factors include Ikaros and Aiolos.

The present disclosure provides a cell-based assay that screens compounds on a bead-bound compounds, and where screening is done with a plate bearing many picowells. The components of the cell-based assay include, a picowell for holding a bead-bound chemical library, where each bead has attached to it substantially only one, uniform type of com-pound. The compounds are released by way of a cleavable linker. Mammalian cells are cultured in the picowell. The picowell also includes culture medium. The presently dis-closed non-limiting example with lenalidomide is a proof-of-principle example that can be used for screening chemical libraries in order to discover other compounds that modulate ubiquitination of a given target protein.

Shorter description of a cell-based assay. Recombinant cells are used as a reagent for detecting and screening for compounds that induce proteolysis of green fluorescent protein (GFP), where the read-out that identifies a positively screening compound is the situation where green-colored cells become colorless cells, or cells with reduced green color. Regarding the mechanism of this cell-based assay, the mechanism of action of lenalidomide in causing green-colored cells become colorless cells, or cells with a reduced green color, is that the lenalidomide binds to a protein called, "cereblon." In the cell, cereblon is part of a complex of proteins called, "E3 ubiquitin ligase." Cereblon is the direct target of the anti-cancer drugs, lenalidomide, thalidomide, and pomalidomide. The normal and constitutive activity of E3 ubiquitin ligase, and its relation to cereblon, has been described as, "cereblon . . . promotes proteosomal degrada-tion [of target proteins] by engaging the . . . E3 ubiquitin ligase" (see, Akuffo et al (2018) J. Biol. Chem. 293:6187-6200). In contrast to the normal activity of E3 ubiquitin ligase, when a drug such as lenalidomide, thalidomide, or pomalidomide is added, the result is that the, "lenalidomide, thalidomide, and pomalidomide . . . promote[s] the ubiq-uitination and degradation of . . . substrates by an E3 ubiquitin ligase . . . each of these drugs induces degradation of transcription factors, IKZF1 and IKZF3" (Kronke et al (2015) Nature. 523:183-188).

Regarding terminology, cereblon has been described as being part of a complex of proteins that is called, "E3 ligase" and also called, "E3 ubiquitin ligase." Generally, cereblon by itself is not called an "E3 ligase. The following excerpts reveal how the word "cereblon" is used. According to Akuffo et al (2018) J. Biol. Chem. 293:6187-6200, "Upon binding to thalidomide . . . the E3 ligase substrate receptor cereblon . . . promotes proteosomal destruction [of the substrate] by engaging the DDB1-CUL4A-Rocl-RBX1 E3 ubiquitin ligase." Consistently, Yang et al (2018) J. Biol. Chem. 293:10141-10157, discloses that, "Cereblon . . . functions as a substrate receptor of the cullin-4 RING E3 ligase to mediate protein [the substrate] ubiquitination." Zhu et al (2014) Blood. 124:536-545, state that, "Thalidomide binds CRBN [cereblon] to alter the function of the E3 ubiquitin ligase complex . . . composed of CRBN, DDB1, and CUL4." Lopez-Girona et al (2012) Leukemia. 26:2326-2335, state that, "studies identified E3 ligase protein cere-blon (CRBN) as a direct molecular target . . . of thalidomide . . . CRBN and . . . DDB1 form a functional E3 ligase complex with Cul4A and Roc 1."

To view the big picture of the cell-based assay devised and used by the Applicants, the first step is that lenalidomide is added to cells. The last step is that IKZF1 and IKZF3 are degraded. Where IKZF1 occurs as a fusion protein with GFP, then the last step is that the entire fusion protein is degraded by the proteasome. Similarly, where IKZF3 occurs as a fusion protein with GFP, then the final step is that this entire fusion protein gets degraded by the proteasome. The result of GFP degradation is that the cell, which was once green-fluorescing cell, is turned into a non-fluorescing cell.

Longer description of a cell-based assay. This concerns names of proteins of E3 ubiquitin ligase (a complex of proteins), names of proteins that bind to this complex, and names of proteins that are the target of this complex. For these names, the published literature is not consistent. Some-times it refers to the protein by the name of the protein, and sometimes it refers to the protein using the name of the gene that encodes the protein. For this reason, the following account uses the protein name together with the gene name, such as "cereblom" (name of protein" and "CRBN" (name of gene). Also, "Ikaros" is the name of a protein, while the gene's name is IKZF1. Also, "Aiolos" is the name of a protein, IKZF3 is the name of the gene. "Cullin-ring finger ligase-4" is the name of a protein, and the gene's name is CRL4. "Regulator of cullin-1" is the name of a protein, and the gene's name is ROC1. ROC1 is also known as, RBX1 (Jia and Sun (2009) Cell Division. 4:16. DOI:10.1186. "Cullin-4A" is the name of a protein and the gene's name is CUL4A. See, Schafer, Ye, Chopra (2018) Ann. Rheum. Dis. DOI:10.1136; Chen, Peng, Hu (2015) Scientific Reports. 5:10667; Matyskiela et al (2016) Nature. 535:252-257; Akuffo et al (2018) J. Biol. Chem. 293:6187-6200).

E3 ubiquitin ligase catalyzes the transfer of a residue of ubiquitin to a target protein, where the consequence is that the target protein gets sent to the proteasome for degrada-tion. The E3 ligase catalyzes attachment of ubiquitin to one or more lysine residues of the target protein. Humans express about 617 different E3 ubiquitin ligase enzymes (see, Shearer et al (2015) Molecular Cancer Res. 13:1523-1532). E3 ubiquitin ligase is a complex of these proteins: DNA damage binding protein-1 (DDB1); Cullin-4 (CUL4A or CUL4B); Regulator of Cullins-1 (RoC1); and RING Box-domain protein (RBX1). As stated above, RoC1 is the same protein as RBX1 (see, Jia and Sun (2009) Cell Division. 4:16. DOI:10.1186). When cereblon (CRBN) joins the E3 ubiquitin ligase complex, the resulting larger complex is called: CRL4$^{CRBN}$ (Matyskiela et al (2016) Nature. 535:252-257). The term "CRL4" means, "Cullin-4 RING Ligase" (Gandhi et al (2013) Brit. J. Haematol. 164:233-244; Chamberlain et al (2014) Nature Struct. Mol. Biol. 21:803-809). The above discrepancies in nomenclature need to be taken into account when reading the literature of cereblon.

The following are longer versions of the short excerpts disclosed above. Shown below is yet another form of nomenclature, namely, the term: "CRL4$^{cRBN}$ E3 ubiquitin ligase." The longer account more fully integrates the various names and cellular events. "The relation between cereblon (CRBN) and E3 ubiquitin ligase complex has been described as, "cereblon (CRBN) promotes proteosomal degradation [of target protein] by engaging the DDB1-CUL4A-Roc1-RBX1 E3 ubiquitin ligase" (Akuffo et al (2018) J. Biol. Chem. 293:6187-6200). Regarding anti-cancer drugs, "lenalidomide, thalidomide, and pomalidomide . . . promote the ubiquitination and degradation of . . . substrates by an E3 ubiquitin ligase. These compounds bind CRBN, the substrate adaptor for the CRL4$^{CRBN}$ E3 ubiquitin ligase . . . each of these drugs induces degradation of . . . transcription factors, IKZF1 and IKZF3" (Kronke et al (2015) Nature. 523:183-188).

This concerns cell-based assays where any given microwell, nanowell, or picowell contains a bead where bead has covalently linked compounds, where the compound is attached via a cleavable linker, and where the well contains one or more cultured mammalian cells. Responses to compounds and to drug candidates of the present disclosure can be assessed by way of one or more biomarkers.

Biomarkers include diagnostic biomarkers, biomarkers that predict if a given patient will respond (get better) to a given drug, and biomarkers that predict if a given patient will experience unacceptable toxicity to a given drug (Brody, T. (2016) Clinical Trials: Study Design, Endpoints and Biomarkers, Drug Safety, and FDA and ICH Guidelines, 2$^{nd}$ ed., Elsevier, San Diego, CA). The present disclosure makes use of yet another kind of biomarker, namely, a biomarker that monitors response of a patient to a given drug, after drug therapy has been initiated. To give an example, the following concerns the biomarker "peroxiredoxin6 (PRDX6) and lung cancer. According to Hughes et al, "PRDX6 levels in cell media from . . . cell lines increased . . . after gefitinib treatment vs. vehicle . . . PRDX6 accumulation over time correlated positively with gefitinib sensitivity. Serum PRDX6 levels . . . increased markedly during the first 24 hours of treatment . . . changes in serum PRDX6 during the course of gefitinib treatment . . . offers . . . advantages over imaging-based strategies for monitoring response to anti-EGFR agents." Please note comment that the biomarker has advantages over a more direct measure of efficacy of response, namely, use of "imaging" to detect decrease in tumor size and numbers (Hughes et al (2018) Cancer Biomarkers. 22:333-344). Other biomarkers that monitor response to anti-cancer drugs include CA125 for monitoring response to platin therapy for ovarian cancer, and serum HSPB1 for monitoring response to chemotherapy with ovarian cancer (see, Rohr et al (2016) Anticancer Res. 36:1015-1022; Stope et al (2016) Anticancer Res. 36:3321-3327).

Cytokine expression. Responses can be assessed by measuring expressed cytokines, such as IL-2, IL-4, IL-6, IL-10, IFN-gamma, and TNF-alpha. These particular cytokines can be simultaneously measured using gold nanostructures bearing antibodies that specifically recognize one of these cytokines, where detection involves plasmon resonance (Spackova, Wrobel, Homola (2016) Proceedings of the IEEE. 104:2380-2408; Oh et al (2014) ACS Nano. 8:2667-2676). Cytokines expressed by single cells, such as a single T cell, can be measured by way of fluorescent antibodies, in a device that includes microwells (Zhu, Stybayeva (2009) Anal. Chem. 81:8150-8156). The above methods are useful as reagents and methods for the present disclosure.

In some embodiments, antibodies to cytokines may be attached to the walls of the picowells, wherein any cytokines released, or differentially released, from cells, as a function of drug exposure can be captured by the antibodies bound to the walls of the picowells. The captured cytokines may be identified by a second set of labeled antibodies. In some embodiments, antibodies for cytokines may be attached to capping beads. The capping beads may then be embedded in a crosslinking hydrogel sheet that may be peeled off and subjected to further analysis, for example, via ELISA, mass spectrometer or other analytical techniques.

Apoptosis. Real-time data on apoptosis, and early events in apoptosis of single cells can be measured with Surface-Enhanced Raman Spectroscopy (SERS) and with Localized Surface Plasmon Resonance (LSPR) (see, Stojanovic, Schasfoort (2016) Sensing Bio-Sensing Res.7:48-54; Loo, Lau, Kong (2017) Micromachines. 8:338. DOI:10.3390). Stajanovic, supra, detects release from cells of cytochrome C, EpCam, and CD49e. Loo et al, supra, measures release from cell of cytochrome C, where detection involves a DNA aptamer (this DNA aptamer works like an antibody). Zhou et al detect early apoptosis in single cells using SERS, where what is measured is phosphatidyl serine on the cell membrane (see, Zhou, Wang, Yuan (2016) Analyst. 141:4293-4298). In addition to collecting data on apoptosis, SERS can be used for assessing drug activity by collecting data on stages of mitosis, release of metabolites, expression of a biomolecule bound to the plasma membrane (see, Cialla-May et al (2017) Chem. Soc. Rev. 46:3945-3961). Plasmon resonance can measure protein denaturation and DNA fragmentation that occurs in apoptosis (see, Kang, Austin, El-Sayed (2014) ACS Nano. 8:4883-4892). Plasmon resonance (SERS) can distinguish between cancer cells and normal cells, by measuring the percentage of mitotic proteins in the alpha helix form versus in beta sheet form (Panikkanvalappil, Hira, E1-Sayed (2014) J. Am. Chem. Soc. 136:159-15968). The above methods are suitable as reagents and methods for the present disclosure.

Apoptosis can also be measured in cultured cells in a method not using plasmonic resonance, but that instead uses immunocytochemistry using anti-cleaved caspase-3 antibody (Shih et al (2017) Mol. Cancer Ther. 16:1212-1223).

General information on cell-based assays. Cell-based assays of the present disclosure can be used to test responses from human cancer cells, cells from a solid tumor, cells from a hematological cancer, human stem cells, human hepatocytes, a pathogenic bacterium, an infectious bacterium, human cells infected with a bacterium, human cells infected with a virus, and so on. The assays can detect morphological response of the cell, such as migration, as well as genetic responses and biochemical responses.

Assays of the present disclosure can be designed to detect response of cells that are situated inside a microwell, or to detect response of cells that are situated outside a microwell, such as in a nutrient medium situated as a layer above the array of microwells. Also, assays of the present disclosure can be designed to detect responses of cells, where cells and beads are situated within a medium, where cells are situated within a medium and beads are above or below the medium, where cells are situated on top of a medium and where beads are situated above or within or below the medium.

The present disclosure provides a population of cells to a microwell array. In embodiments, at least about 5%, at least about 10%, at least about 20%, at least about 40%, at least about 60%, at least about 80%, at least about 90%, at least about 95%, or at least about 100%, of the population of cells resides inside the microwells (and not in any region situated above the microwells). In embodiments, the proportion of cells that resides inside of the wells, with the rest being situated in a layer of nutrient medium residing above the array of wells, can be about 10%, about 20%, about 30%, about 40%, about 50%, about 60%, about 70%, about 80%, about 90%, about 95%, about 100%, or in any range defined by two of these numbers, such as the range of "about 60% to about 90%."

Matrix for cells. For assays of biological activity of cells, and where cells are exposed to compounds released from beads, or where cells are exposed to bead-bound compounds, suitable matrices include those that include one or more of the following: poly-D-lysine (PDL), poly-L-lysine (PLL), poly-L-ornithine (PLO), vitronectin, osteopontin, collagen, peptides that contain RGD sequence, polypeptides that contain RGD sequence, laminin, laminin/fibronectin complex, laminin/entactin complex, and so on. Suitable matrices also include products available from Corning, Inc., such as, PuraMatrix® Peptide Hydrogel®, Cell-Tak® cell and tissue adhesive, Matrigel®, and so on. See, Corning Life Sciences (2015) Corning Cell Culture Surfaces, Tewksbury, MA (20 pages), De Castro, Orive, Pedraz (2005) J. Micro-encapsul. 22:303-315. In exclusionary embodiments, the present disclosure can exclude any composition or method that includes one of the above matrices or one of the above polymers.

In embodiments, the present disclosure provides an array, where individual microwells contain a bead, one or more cells, and either a solution (without any matrix) or a matrix or a combined solution and matrix. The matrix can be a hydrogel, polylysine, vitronectin, MatriGel®, and so on.

Activity of bead-bound compounds or of bead-released compounds can be conducted. Assays to assess activity can include, activating or inhibiting an enzyme, activating or inhibiting a cell-signaling cascade or an individual cell-signaling protein, binding to an antibody (or to a comple-mentarty determining region (CDR) of an antibody, to a variable region of an antibody), inhibiting the binding of a ligand or substrate to an enzyme (or to an antibody, or to a variable region of an antibody).

For the above assays, the readout can be determined with fluorescence assays, for example, involving a fluorophore linked to a quencher (F-Q). The linker can be designed to be cleavable by an endoprotease, DNAse, RNAse, or phosop-holipase (see, Stefflova, Zheng (2007) Frontiers Bioscience. 12:4709-4721). The term "molecular beacon" refers to this type of F-Q molecule, however, "molecular probe" has also been used to refer to constructs where separation of F and Q is induced by hybridization, as in TaqMan® assays (Tyagi and Kramer (1996) Nature Biotechnol. 14:303-308; Tsour-kas, Behlke, Bao (2003) Nucleic Acids Res. 15:1319-1330).

Transcriptional profiling in response to drug exposure. The DNA barcodes of this disclosure may be modified to contain response-capture elements, where the response cap-ture elements capture the response of cells to perturbations encoded by the encoding portions of the barcode. In some embodiments, the DNA barcodes may terminate in a poly-T section (multiple repeats of the thymidne nucloetide), wher the poly-T sequence may be used to capture poly-A termi-nated mRNA molecules released from lysed cells. In some embodiments, the response-capture sequence may be complementary to genes of interest, thereby capturing the expression profile of desired genes via hybridization to the beads of this embodiment. In some embodiments, picowells may contain a single cell picowell whose transcriptional profile is captured on the bead. In some other embodiments, a plurality of cells may be be contained in the picowell whose transcriptional profile is being captured.

In one exemplary workflow, the following procedure may be followed to capture transcriptional response of cells to drugs. (a) Picowells designed to capture single cells per well are provided. (b) A compound-laden, DNA barcoded bead is introduced into the picowells, such that one bead is present per picowell. (c) Compounds are released from the beads in each picowell by appropriate methods (UV treatment for compounds attached via UV cleavable linker, diffusion in case of beads soaked in compounds, acid cleavable, base cleavable, temperature cleavable etc., as appropriate for the beads of the embodiment). (d) The picowells may be iso-lated from each other via a capping bead that retains contents within the picowell or by other means such as an air barrier or an oil barrier on top of the picowells. (e) The cells in the picowells are allowed to incubate in the presence of the compounds released from the beads for a duration. (f) After a suitable amount of time, say 1 hr, 2 hrs, 5 hrs, 9 hrs, 12 hrs, 15 hrs, 18 hrs, one day, 3 days, one week, two weeks, one months, or another appropriate time based on the assay, the cells are lysed by a lysing method. The lysing methods may involve addition of detergents, repeated cycles of freezing and thawing, heating, addition of membrane disrupting peptides, mechanical agitation or other suitable means. (g) once lysed, the contents of the cell are exposed to the bead within the picowell, at which time the response-capture elements on the beads of the picowell are enabled to capture the response they are design for. In some embodiments, the response capture are poly-T sequences which capture the complete mRNA profile of the cell (or cells) within each picowell. In some embodiments, the response-capture ele-ments are designed to capture specific DNA or RNA sequences from the cell. In some embodiments, the tran-scriptional response of the cell may be captured as a function of dosage (or concentration) of compounds.

EXAMPLES

Example 1. First Workflow

The present disclosure provides methods, including that outlined below as "First Workflow" and as "Second Work-flow."

The First Workflow includes the steps: (1) Generate DELB, (2) Beads into picowells, (3) Load assay reagents into picowells, (4) Release bead-bound compounds, (5) Measure assay readout, (6) Rank the assay readout, and (7) Generate a new set of DELBs.

Generate DELB. First, create the DNA encoded library on beads (DELB). Each bead contains a population of the exact, same compound, though slight departures from this may occur where some of the manufactured compounds had incomplete couplings or were suffered chemical damage, such as inadvertent oxidation.

Beads into picowells. Then, deposit beads in picowells. In a preferred embodiment, each picowell gets only one bead. Each picowell can have a round upper edge, a round lower edge, a solid circular bottom, an open top, and a wall. The wall's bottom is defined by the round upper edge and by the round lower edge. In a preferred embodiment, the wall is angled, where the diameter of the round upper edge is greater than the diameter of the round lower edge. In this way, the wall (viewed by itself) resembles a slice of an inverted cone. The picowell array can be prepared, so that there is a redundancy of beads. In other words, the array can be prepared so that two of the beads, out of the many thousands of beads that are placed into the picowells, contain exactly the same compound. The redundancy can be, e.g., 2 beads, 3 beads, 4 beads, 5 beads, 10 beads, 20 beads, 40 beads, 60 beads, 80 beads, 100 beads, and so on, or about 2, about 3, about 4, about 10, about 20, about 40, about 60, about 80, about 100, about 200, about 500, about 1,000 beads, and so on, or more than 2, more than 5, more than 10, more than 20, more than 40, more than 60, more than 80, more than 100, more than 200, more than 500, more than 1,000 beads, and so on.

Load assay reagents into picowells. Introduce reagents into each picowell that can be used to assess biochemical activity of each bead-bound compound. The biochemical activity can take the form of a binding activity, enzyme inhibition activity, enzyme activation activity, activity of a living mammalian cell (where the molecular target is not known), activity of a living mammalian cell (where the molecular target is known), and so on. The reagent can take the form of a FRET reagent plus an enzyme. The FRET reagent can be a fluorophore linked by way of a protease substrate to a quencher. The enzyme can be a substrate of that protease, which is cleavable by the protease. The bead-bound compound is being tested for ability to inhibit the protease.

After loading assay materials, each picowell can be capped by a film, or many or all of the picowells can be capped by one film, or many or all of the picowells can be capped by a film with pimples where each pimple fits into a picowell, or or where each picowell is fitted with a porous sphere. In embodiments, about 5% of the volume about 10% of the volume, about 20% of the volume, about 30% of the volume, or about 40% of the volume of the sphere fits into the picowell (where the remainder is flush with the surface or resides above the surface). In embodiments, about 5%, about 10%, about 20%, about 40%, about 60%, about 80%, about 90%, or about 100% of the pimple fits into the picowell.

Release bead-bound compounds. Perform a step that causes release of the bead-bound compound. In embodiments, the step can cause release of about 0.1%, about 0.2%, about 0.1%, about 0.2%, about 2%, about 5%, about 10%, about 20%, about 40%, about 60%, about 80%, about 99%, or about 100% of the compounds that are attached to a given bead. Release can be effected by light, by a chemical reagent, by an enzyme, by a shift in temperature, by any combination thereof, and so on.

Release can take the form of: (i) Single release, (ii) Multiple release, (iii) Continual release. Multiple release, for example, can take the form of several emissions of ultra-violet light, where each emission is sufficient to cleave about 10% of the bead-bound compound that happens to be attached to the bead at the start of that light emission.

Continual release, for example, can take the form of con-tinual emission of light over the course of one hour, resulting in a steadily increasing concentrations of free compound. In this situation, the steadily increasing concentrations of free compound (cleaved compound) may be for the purpose of titrating the target of that compound. A titration experiment of this kind can be used to assess potency of a given compound. To provide non-limiting examples, with a single release method, a period of light exposure is followed by a subsequent period where readout is taken, and with a con-tinual release method, light exposure continues during some, most, or all of the period where readout is taken.

In exclusionary embodiments, the present disclosure can exclude any method, reagent, composition, or system that uses single release, that uses multiple release, or that uses continual release.

Measure assay readout. Detect the above-disclosed bio-chemical activity, and the influence of the released com-pound on that activity. This biochemical activity can take the form of enzymatic activity, activity of a reporter gene, genetic activity (e.g., rate of transcription or translation), binding activity (e.g., antigen to antibody), cellular activity (e.g., change in migration, change in cell-signaling pathway, change in morphology). Activity can be detected by fluo-rescence, chromogenic activity, luminescence, light micros-copy, TaqMan® assays, molecular beacons, mass spectrom-etry, Raman spectroscopy, Localized Surface Plasmon Resonance (LSPR), Surface Plasmon-Coupled Emission (SPCE), Surface-Enhanced Raman Scattering (SERS), and so on. Detection can be with methods that are totally remote, such as fluorescence detection or light microscopy or, alter-natively, by methods that involve taking a sample from the picowell. In one embodiment, a sample that contains a mixture of reactants and products can be withdrawn for analysis by way of a spherical porous sponge that is partially inserted into one of the picowells.

Rank the assay readout. In this step, assay readouts from a plurality of different compounds (each type of compound associated with one particular bead), are ranked in terms of their ability to activate, inhibit, or in some way to modulate the biochemical activity.

Generate a new set of DELBs. The steps that are described above inform the user of various compounds that exhibit a biochemical activity. The information may take the form of one compound with maximal activity, with the rest having about half maximal activity or less. Alternatively, the infor-mation may take the form of several compounds having a similar maximal activity, with the other compounds having about half maximal activity or less. A new set of DELBs can be created as follows. One or more of the highest-ranking compounds (the lead compounds) can be used as a basis for manufacturing a new set of DELBs, based on one or more of the following non-limiting strategies: (i) Replacing an aliphatic chain with a homolog, such as replacing a propanol side chain with a butanol side chain; (ii) Replacing an aliphatic chain with an isomer, such as replacing a propanol side chain with an isopropanol side chain; (iii) Replacing a peptide bond with an analog of a peptide bond, such as with a bond that cannot be hydrolyzed by peptidases; (iv) Replac-ing one type of charged group with another type of charged group, such as replacing a phosphate group with a phos-phonate, sulfate, sulfonate, or carboxyl group.

Example Two. Second Workflow

The Second Workflow involves picowells that are sealed with caps. The caps can take the form of spheres of slightly greater diameter than the diameter of the picowells, where this diameter is measured at the top rim of the picowell (not measured at the bottom of the picowell). The cap can be made to fit snuggly into the top of the picowell by subjecting the entire picowell plate to mild-gravity centrifugation. In Second Workflow, the caps take the form of beads that contain linkers, where each linker is linked to a compound. The linkers are cleavable linkers, where cleavage released the compounds and allows them to diffuse to the cells. This type of cap is called an "active cap." The Second Workflow includes the steps, (1) Generate DELB, (2) Load assay reagents into picowells, (3) Cap picowells with DELB, (4) Release bead-bound compounds from the bead that acts as a cap, (5) Measure assay readout, (6) Determine sequence of the DNA barcode that is on the bead; (7) Rank the assay readout, and (8) Generate a new set of DELB s.

Example 3. Release Control

This concerns controlling and monitoring release of bead-bound compounds. Applicants devised the following procedure for synthesizing bead-bound release-monitor. See, FIG. 11 and the following text.

FIG. 11 describes steps in the organic synthesis of the above exemplary embodiment of a bead-bound release-monitor.

Step 1. Provide the Resin

TentaGel® resin (M30102, 10 μm NH2, 0.23 mmol/g, 10 mg; MB160230, 160 μm RAM, 0.46 mmol/g, 2 mg) was weighed into a tube (1.5 mL Eppendorf) and swelled (400 μL, DMA).

Resin was transferred into fitted spin-column (MoBiCol® spin column, Fisher Scientific), solvent removed through filter by vacuum, and pendent Fmoc was deprotected (5% Piperazine with 2% DBU in DMA, 400 μL; 2×10 min at 40° C.). The MoBiCol spin column has a 10 micrometer large frit and a luer-lock cap.

Resin was filtered over vacuum, and washed (2× DMA, 400 μL; 3× DCM, 400 μL; 1× DMA, 400 μL).

Step 2. Couple Lysine Linker to Resin

A solution was prepared containing L-Fmoc-Lys(Mtt)-OH (21 moles, 6.6 eq.), DIEA (42 moles, 13.3 eq.), COMU (21 moles, 6.6 eq.) mixed in DMA (350 μL), incubated (1 min, RT), then added to dry resin inside the fritted spin-column, vortexed, and incubated (15 min, 40° C.) to amidate the free amine. Resin was filtered by vacuum, and this reaction was repeated, once.

Resin was filtered over vacuum, and washed (2× DMA, 400 μL; 3× DCM, 400 μL; 1× DMA, 400 μL).

Step 3. Remove the Fmoc Protecting Group

The pendent Fmoc was deprotected (5% Piperazine with 2% DBU in DMA, 400 μL; 2×10 min at 40° C.).

Resin was filtered over vacuum, and washed (2× DMA, 400 μL; 3× DCM, 400 μL; 1× DMA, 400 μL).

Step 4. Couple the Quencher

A solution was prepared containing QSY7-NHS (4.9 moles, 1.55 eq.), Oxyma (9.5 eq, 3.3 eq.), DIC (21 moles, 6.6 eq.), TMP (3.5 moles, 1.1 eq.) mixed in DMA (350 μL), incubated (1 min, RT), then added to dry resin inside the fritted spin-column, vortexed, and incubated (14 hr, 40° C.) to amidate the free amine.

Resin was filtered over vacuum, and washed (2× DMA, 400 μL; 3× DCM, 400 μL; 1× DMA, 400 μL).

A solution was prepared containing Acetic Anhydride (80 moles, 25.3 eq.), TMP (80 moles, 25.3 eq.), mixed in DMA (400 μL), mixed then added to dry resin inside the fitted spin-column, vortexed, and incubated (20 min, RT)

Resin was filtered over vacuum, washed (2× DMA, 400 μL; 3× DCM), and incubated in DCM (1 hr, RT), then filtered over vacuum and dried in vacuum chamber (30 min, 2.5 PSI)

Step 5. Remove the Mtt Protecting Group

Mtt deprotection cocktail was prepared containing TFA (96 μL), Methanol (16 μL), mixed in DCM (1488 μL) giving 6:1:93% of TFA:Methanol:DCM solution.

Mtt deprotection cocktail was added to the fully dried resin (400 μL), mixed, eluted by filtration over vacuum, then sequential aliquots of Mtt deprotection cocktail (4×400 μL) were added, mixed, incubated (5 min, RT), and eluted for a combined total incubation time of 20 min at RT.

Resin was filtered over vacuum, and washed (3× DCM, 400 μL; 1× DMA, 400 μL; 1× DMA with 2% DIEA, 400 μL; 3× DMA, 400 μL).

Step 6. Couple the Photocleavable Linker to Epsilon-Amino of Lysine

A solution was prepared containing Fmoc-PCL-OH (32 moles, 10 eq.), Oxyma (32 moles, 10 eq.), DIC (50 moles, 15.8 eq.), TMP (32 moles, 10 eq.) mixed in DMA (400 μL), incubated (1 min, RT), then added to dry resin inside the fritted spin-column, vortexed, and incubated (14 hr, 40° C.) to amidate the free ε-amine.

Resin was filtered over vacuum, and washed (2× DMA, 400 μL; 3× DCM, 400 μL; 1× DMA, 400 μL).

Step 7. Remove the Fmoc Protecting Group from the Previously Coupled Photocleavable Linker The pendent Fmoc was deprotected (5% Piperazine with 2% DBU in DMA, 400 μL; 2× 10 min at 40° C.).

Resin was filtered over vacuum, and washed (2× DMA, 400 μL; 3× DCM, 400 μL; 1× DMA, 400 μL).

Step 8. Couple the Fluorophore

A solution was prepared containing TAMRA (6 moles, 1.9 eq.), TMP (24 moles, 7.6 eq.), COMU (16 moles, 5 eq.), mixed in DMA (400 μL), incubated (1 min, RT), then added to dry resin inside the fitted spin-column, vortexed, and incubated with mixing (2 hr, 40° C., 800 RPM) to amidate the free amine.

Resin was filtered over vacuum, and washed (2× DMA, 400 μL; 3× DCM, 400 μL; 2× DMA, 400 μL; 2× DMSO), then incubated with mixing in DMSO (16 hr, 40° C.).

The following provides a broader account of the above-disclosed laboratory procedures.

Bi-functional linker attached to bead. Bi-functional linker was synthesized in solution and attached to an amine-functionalized beads. FIG. 11 discloses pathway of organic synthesis, starting with lysine. Lysine-Boc was than connected by TCO linker. The main part of the linker was took the form of polyethylene glycol (PEG) with a nitrogen at one end. Boc was a leaving group in this connecting reaction. The TCA that was used was actually a racemate of hydroxy-TCO. The hydroxyl group of this TCO derivative was connected to a carbon atom located four carbon atoms away from one side of the double bond (this is the same thing as being located three carbon atoms away from the other side of the double bond). As shown in FIG. 11, the first product in the multi-step synthesis took the form of Boc-lysine-linker-TCO. The hydroxyl group that was once part of hydroxy-TCO is still attached to the TCO group, where it is situated in between the aminated-polyethylene glycol group and the TCO group (FIG. 11).

The second set in the synthetic pathway involved treatment with HCl and addition of a photocleavable linker (PCL). The product of this second step was the same as the product of the first step, except with the Boc group replaced with the photocleavable linker. The lysine moiety takes a central position in the product of the second step. Regarding the lysine moiety, this lysine moiety has a free carboxyl group, and in the third step of the procedure, an aminated bead is connected to this free hydroxyl group, resulting in the synthesis of a bead-bound reagent, where the reagent takes the form of two branches, and where at the end of one branch is a TCO tag, and where at the end of the other branch is an aromatic ring bearing a cleavable bond. To attached a chemical monomer to the distal end of the photocleavable linker, first the Fmoc group is removed, and here the Fmoc group is replaced with a hydrogen atom.

Removing Fmoc. According to Isidro-Llobet et al, "Fmoc . . . is removed by bases mainly secondary amines, because they are better at capturing the dibenzofulvene generated during the removal" (Isidro-Llobet et al (2009) Chem. Rev. 109:2455-2504). Alternatively, Fmoc can be removed by catalytic hydrogenolysis with Pd/BaSO4, or by liquid ammonia and morpholine or piperidine.

Removal of Fmoc group followed by attaching a chemical monomer. Applicants then condensed a chemical monomer having a carboxylic acid group, where the result was generation of an amide bond. (This step not shown in any figure.)

Example 4. Cereblon-Based Assay for Active Compounds

Results from cell-based assays of compounds (cereblon-based assay). Reagents and methods for cell-based assay. Applicants used CCL-2 HeLa cells obtained from ATCC (American Type Culture Collection, Manasses, VA). Cell medium was Gibco DMEM high glucose medium buffered with HEPES. Atmosphere above cell culture was atmospheric air supplemented with 5% carbon dioxide, with the incubator at 37 degrees C. Cell medium was DMEM plus 10% fetal bovine serum, supplemented with GlutaMAX® (Gibco Thermofisher), and also supplemented with non-essential amino acids and penicillin plus streptomycin (Gibco Thermofisher, Waltham, MA). HeLa cells were transfected with a construct taking the form of LTR-CTCF-Promoter-IKZF1 (or IKZF3)-mNeon-P2A-mScar-LTR-CTCF. mScarlet is an element used as a positive control. mScarlet encodes red fluorescent protein called, "mScarlet" (see, Bindels et al (2017) Nature Methods. 14:53-56). The promoter is doxycycline inducicble promoter, which enables rapid onset induction and titration of the substrate. P2A is an element situated in between two other polypeptides. P2A functions, during translation, to product two separate polypeptides, thus allowing the mScar polypeptide to function as a positive control that produces red light, without being influenced by ubiquitination and degradation of the fusion protein consisting of IKZF1/Green Fluorescent Protein (GFP). mNeonGreen is derived from the lancelet *Branchiostoma lanceolatum* multimeric yellow fluorescence protein (Allele Biotechnology, San Diego, CA). P2A is a region that allows self-cleaving at a point in the P2A protein. More accurately, the P2A peptide causes ribosomes to skip the synthesis of the glycyl-prolyl peptide bond at the C-terminus of a 2A peptide, leading to the cleavage between a 2A peptide and its immediate downstream peptide (Kim, Lee, Li, Choi (2011) PLoS ONE. 6:e18556 (8 pages).

Demonstration of efficacy of cell-based assay for test compounds. The following demonstrates use of a cell-based assay for test compounds taking the form of lenalidomide and analogues of lenalidomide. FIGS. 5A-5H disclose results from HeLa cells that were transfected with lentiviral vector, where the vector expressed Green Fluorescent Protein (GFP) and a red fluorescent protein (mScarlet). Increasing the concentration of added lenalidomide resulted in progressively less green fluorescence, and elimination of green fluorescence at highest concentrations. But lenalidomide did not substantially decrease red fluorescence. Top: Expression of IKZF1/GFP fusion protein. Bottom: Expression of mScarlett control. Lenalidomide was added at zero, 0.1, 1.0, or 10 micromolar.

FIG. 6 disclose results from HeLa cells that were transfected with lentiviral vector, where the vector expressed Green Fluorescent Protein (GFP) and red fluorescent protein (mScarlet). Increasing concentration of added lenalidomide resulted in progressively less green fluorescence, and elimination of green fluorescence at highest concentrations. But lenalidomide did not substantially decrease red fluorescence. Top: Expression of IKZF3/GFP fusion protein. Bottom: Expression of mScarlett control. Lenalidomide was added at zero, 0.1, 1.0, or 10 micromolar.

To summarize the pathway where lenalidomide causes proteolysis of the fusion proteins, first lenalidomide is added to the HeLa cells. Then, the lenalidomide binds to the cereblon that naturally occurs in these cells. This cereblon occurs in a complex with E3 ubiquitin ligase. E3 ubiquitin ligase responds to the lenalidomide by tagging the recombinant IKZF1 fusion protein (or the recombinant IKZF3 fusion protein) with ubiquitin. The end-result is that the ubiquitin-tagged fusion protein is degraded in the cell's proteasome.

Coating the picowell plates. This describes solutions that are applied to the top surface of a picowell plate, but that do not necessarily enter and coat inside of picowells. This is also about solutions that are applied to the top surface of a picowell plate and that enter the picowells, and that coat the bottom surface of the picowells. Applicants added a solution of Pluronic® 127 (Sigma Aldrich, St. Louis, MO) to dry plastic. The result is a surface that is hydrophilic, and no longer hydrophobic. Then, the surface was washed with water. Then, phosphate buffered saline (PBS) was added, where this PBS enters inside the picowells. Moving air is applied by way of a vacuum, where the result is that it causes small bubbles in the picowells to expand, and where the bubbles are then replaced with the PBS, and where the end result is that much of the picowell gets filled with PBS. Then, PBS was replaced with vitronectin coating solution (AF-VMB-220) (PeproTech, Rocky Hill, NJ). Pluronics® 127 is: $H(OCH_2CH_2)_x$ $(OCH_2CHCH_3)_y(OCH_2CH_2)_zOH$. After applying the vitronectin coating solution, Applicants incubated for 30 min at 37 degrees C. to allow the coating solution to get into picowells. The Pluronic 127 coats the ridges that separate the picowells, and the vitronectin is at bottom of picowells. HeLa cells attach to vitronectin and when they attach to the vitronectin, they adhere to the bottom of the picowell.

HeLa cells were screened for successfully transfected cells by way of flow cytometry. Two criteria were used simultaneously for determining successful transfection. First, lenalidomide was added to cell media 2 days before sorting by flow cytometry. A positive cell was that which was red-plus and green-minus, where red-PLUS meant that the cells were transfected with the gene encoding mScar, and where green-MINUS meant that the lenalidomide had in fact promoted the ubiquitination and degradation of the fusion protein, IKZF1/mNeon (or the fusion protein, IKZF3/mNeon). Regarding doxycycline, doxycycline was used at 3 micromolar in order to induce expression of the lentiviral vector construct. A concentration/induction curve with doxycycline is shown by Go and Ho (2002) J. Gene Medicine. 4:258-270). After transfection with the lentivirus vector, the following condition was used to keep IKZF1 minimally expressed in growing cells. The condition was to leave doxycycline out of the medium, and also to use "insulating sequences" in the construct. The insulating sequences prevent read-through from promoters outside of the construct. Insulating sequences have been described (see, Anton et al (2005) Cancer Gene Therapy. 12:640-646; Carr et al (2017) PLoS ONE. 12:e0176013). Insulating sequences prevent promoters that are outside of the construct from driving expression of an open reading frame (ORF) that is part of the construct. To put cells into picowells, cells can be transferred to the top surface of a picowell plate, at a given ratio of, [number of cells]/[number of picowells]. The ratio can be, for example, about 1 cell/40 wells, about 1 cell/20 wells, about 1 cell/10 wells, about 2 cells/10 wells, about 4 cells/10 wells, about 8 cells/10 wells, about 16 cells/10 wells, about 32 cells/10 wells, about 50 cells/10 wells, about 100 cells/10 wells, and so on. The cells can be used for assays in picowells as soon as cells attach to the vitronectin that coats the bottom of the picowell.

Details of lentivirus construct and cell culture. This concerns onstructing reporter cell lines for IKZF1/3, culturing them in picowells, and assaying them with bulk lenalidomide. The plasmids carrying reporter construct were assembled from parts using Gibson assembly (see maps attached). Lentivirus with reporter construct, as well as UbC driven rtTA-M2.2 were made in LentiX HEK293T cells (Clontech, Palo Alto, CA) with $3^{rd}$ generation packaging system (chimeric CMV promoter and no tat protein). The plasmids were transfected via calcium precipitation method. Virus supernatant was harvested in the recommended LentiX media plus 1% bovine serum albumin (BSA), and filtered through 0.45 um low protein bind filters (Millipore). The host HeLa cells were obtained from ATCC, cultured in standard conditions. Viral supernatant was applied to subconfluent HeLa culture, after 24 hours changed to LentiX media with Doxicyclin. Two days before clone selection, lenalidomide was added to the culture. Clones were selected via fluorescence activated cell sorting (FACS), gated on both AlexaFluor 488 (negative) and Cy3 channels (positive). Clones were grown for 10 days without lenalidomide before assays. The most stable expression level clones are used for screening.

This describes experiment to seal cells with beads and lyse cells through porous beads. 96 well plate with picowell patterned bottom (MuWells) is treated with Pluronic F127 detergent (Sigma-Aldrich, St. Louis, MO) without vacuum applied to passivate upper part of the wells. After 30 min incubation, excess of detergent is washed away with phosphate buffered saline (PBS) or distilled $H_2O$. Wells are flushed with ethanol and dried in the biosafety cabinet with the air flow. Wells are wetted with PBS under strong vacuum to a completion, and PBS is replaced with Virtonectin coating reagent (Preprotech). The plate is incubated for 30 min at 37 C. Vitronectin coating reagent is removed and reporter cells are seeded at desirable density. From the moment of cell seeding, media stays in the dish throughout the assay. TentaGel® beads carrying the photocleavable compound could be seeded before vitronectin coating, or after cell seeding. PEG polymer beads are loaded on top of the culture in the excess over the well number. Spin the plate at 400 rcf for 1 min. Photo-release the compound off the beads using 365 nm LED light source for appropriate amount of time. Incubate in the CO2 incubator until the imaging (readout of the fluorescent reporters).

Constructs. FIG. 20 and FIG. 21 disclose the relevant constructs. Each of these figures discloses the sequence that is to be integrated into the HeLa cell genome, and each of the figures discloses the carrier sequence (the sequence belonging to lentivirus). Sequence belonging to lentivirus is from about one o'clock to about nine o'clock, where this sequenced is bracketed by two long terminal repeats (LTRs). Sequence from about nine o'clock to about one o'clock gets integrated into HeLa cell genome. In detail, first a plasmid is transfected into producer cells (HEK93T) (Clontech, Palo Alto, CA). The producer cells produce and then release lentivirus. The released lentivirus then infects HeLa cells and integrates nucleic acids into the HeLa cell genome.

Optics. For the present cell culture experiments, Applicants used EBQ100 Isolated mercury lamp connected to HBO 100 (Carl Zeiss Microscopy, GmbH, Germany), which was connected to an Axiovert 200-M Carl Zeiss microscope with Ludl Electronic Products stage (Ludl Electronic Products, Ltd., Hawthorne, NY). Applicants also used filter cubes with mercury lamp, where filter cubes controlled wavelength of excitation and also controlled wavelength of detecting emission. Images were captured with Basler ACA2440-35UM (Basler AG, 22926, Ahrensburg, Germany). Halogen lamp was used, as an alternative to mercury lamp. Microwell plates, picowell plates, and the like, were held in place with a plate holder and an "XY stage" with controller. XY stages and other precise positioning stages for optics use are available from, Newmark Systems, Inc., Rancho Santa Margarita, CA; Aerotech, Inc., Pittsburgh, PA, Physik Instrumente GmBH, 76228 Karlsruhe, Germany.

Example 5. Mdm2-Based Assay for Active Compounds

Modifying glass to contain an amino group. Silica substrates can be modified to contain an amino group, by way of one or more of a number of "functional silanes." These "functional silanes" are 3-aminopropyl-triethoxysilane (APTES), 3-aminopropyl-trimethoxysilane (APTMS), N-(2-aminoethyl)-3-aminopropyltriethoxysilane (AEAPTES), N-(2-aminoethyl)-3-aminopropyltrimethoxysilane (AEAPTMS), and N-(6-aminohexyl)aminomethyltriethoxysilane (AHAMTES). Reactions of these reagents with glass can be conducted in a vapor phase or in a solution phase (see, Zhu, Lerum, Chen (2012) Langmuir. 28:416-423).

Results from biochemical assays of compounds (MDM2-based assay). Laboratory methods. The following reagent was applied to a glass slide. The glass slide was modified to have amino groups. The reagent was NHS-PEG-mTET. NHS is N-hydroxy-succinimide. NHS is a type of activated ester. NHS is useful in bioconjugation reactions, such as surface activation of microbeads or of microarray slides (Klykov and Weller (2015) Analytical Methods. 7:6443-6448).

PEG is polyethylene glycol. mTET is methyltetrazine. This reagent was mixed with DMSO, and then a volume of 2 microliters was applied to the glass slide. The mixture was made by mixing 10 microliters of 50 mM NHS-PEG-mTET with 30 microliters DMSO. The NHS group reacts with the amino groups of the glass side, where the result is that the mTET group is affixed to the glass slide. The goal of the mTET was to create a covalent link between the slide and the bead.

TCO and tetrazine can mediate "click chemistry" reactions. Examples of these click chemistry reactions, is using antibodies that are functionalized with tetrazine to couple with DNA that is functionalized by TCO. Or using antibodies modified with TCO to couple with tetrazine-modified beads (see, van Buggenum et al (2016) Scientific Reports. 6:22675 (DOI:10.1038); Rahim et al (2015) Bioconjug. Chem. 18:352-360; Haun et al (2010) Nature Nanotechnol. 5:660-665).

In detail, the glass slide was prepared by applying a sheet of parafilm to the top of the slide, where the parafilm had an aperture cut out of the middle, where the drop of the above mixture was applied in the aperture directly to the glass slide. Before applying the mixture, the glass slide with the parafilm on top was heated at full heat for 90 seconds, in order to create a tight seal between the parafilm and the slide, in order to prevent seepage of liquids after applying the mixture to the open area (the aperture) in the parafilm. The glass slide, with the 2 microliter droplet sitting in the aperture cut into the Parafilm, was incubated overnight at room temperature. During the incubation, the glass slide was inside a petri dish, where the dish was covered with a glass cover that covered the top and sides of the petri dish. Before the overnight incubation, a square of Parafilm was placed over the drop and over the surrounding Parafilm, in order to prevent water from evaporating from the drop.

Inventive method to make complex of slide/bead/antibody. Applicants' method used beads that were functionalized by TCO. The TCO groups of the bead mediated covalent attachment of the methyltetrazine-functionalized slide to the bead. Also, the TCO groups of the bead mediated covalent attachment of the methyltetrazine-functionalized anti-p53 antibody to the bead.

Applicants surprisingly found that, if the first step is to contact slide and bead, then subsequent addition of antibody will NOT result in covalent attachment of the antibody to the bead. Also, Applicants surprisingly found that, if the first step is to contact bead with antibody, then subsequent transfer of this mixture to the slide will NOT result in covalent attachment of the bead to the slide. In a preferred method, all of these three reagents—the slide, the bead, and the antibody—are simultaneously brought into contact with each other. In another preferred embodiment, the bead and antibody are first mixed together to initiate covalent linking of the bead to the antibody, and then immediately or within a few minutes, this mixture is applied to the slide, where the result is covalent linking of the bead to the slide.

Nature of the enzyme-based screening assay. The assay takes the form of a glass slide with an attached bead. The bead contains attached antibodies that are specific for binding to the transcription factor, p53. This antibody can bind to human p53 and also to ubiquitinated human p53. So far, it can be seen that the assay method involves a sandwich between the following reagents:

Slide/Covalently bound bead/Bead-bound anti-p53 Ab/Ubiquitinated p53

The readout from this assay is ubiquitinated-p53, where the ubiquitinated-p53 is detected by a fluorescent antibody that is specific for ubiquitin. In detail, the antibody is a polyclonal antibody made in the goat, where the antibody is tagged with a fluorophore (AF488). FIG. 8 discloses the structure of AF488. This fluorescent antibody binds to ubiquitin. Thus, when ubiquitinated-p53 is detected, what exists is the following sandwich:

Slide/Covalently bound bead/Bead-bound bound anti-p53 Ab/Ubiquitinated p53/Fluorescent Ab

Example 6. Sequencing DNA in Picowells

Sequencing of bead-bound DNA barcodes was performed, where beads were situated in a picowell, one bead per picowell. The assay method involved interrogating each position on the bead-bound DNA barcode, one at a time, by way of transient binding of fluorescent nucleotides. Each bead contained about one hundred attomoles of coupled DNA barcode, where coupling was by click-chemistry. This number is equivalent to about sixty million oligonucleotides, coupled per bead. For each base on the DNA barcode, the assay involves adding all four fluorescent dNTPs at the same time. Without implying any limitation, the four fluorescent dNTPs were AF488-dGTP, CY3-dATP, TexasRed-dUTP, and CY5-dCTP. Fluorescent signals were captured, and then processed by ImageJ software (National Institutes of Health, NIH), to provide a corresponding numerical value. The data are from sequencing five consecutive nucleotides (all in a row) that was part of the bead-bound DNA barcode. The bead-bound DNA barcode included a DNA hairpin region. The bases in the DNA hairpin region annealed to itself, resulting in the formation of the hairpin, and where the 3'-terminal nucleotides in this DNA hairpin served as a sequencing primer. Sequencing by transient binding was initiated at this 3'-terminus. The sequencing assay was performed in triplicate, that is, using three different beads, where one DNA barcode sequence was used for each of the three beads. In other words, each of the three beads was expected to provide a sequencing read-out identical to that provided by the other two beads.

FIG. 28 discloses sequencing results, where sequencing was conducted on bead-bound DNA barcode. What is shown are results from interrogating the first base, the second base, the third base, the fourth base, and the fifth base. For each of these bases, what is separately shown, by way of separate histogram bars, is the fluorescent emission produced with interrogation with AF488-dGTP, CY3-dATP, TexasRed-dUTP, and CY5-dCTP, respectively. Each of the four histogram bars has different graphics: AF488-dGTP (black outline, gray interior), CY3-dATP (black outline, white interior), TexasRed-dUTP (solid black histogram bar), and CY5-dCTP (solid gray histogram bar). The bead diameter was 10-14 micrometers, after swelling in aqueous solution. The volume of the picowell was 12 picoliters.

The template sequence that was interrogated was: 5'-CT-CACATCCCATTTTCGCTTTAGT-3' (SEQ ID NO: 1). For this particular sequencing assay, five consecutive bases were interrogated, where the fluorescent dNTPs that gave the biggest fluorescent signal were fluorescent dGTP, dATP, dGTP, dUTP, and dGTP, which corresponds to a sequence on the template that is dC, dT, dC, dA, and dC. Thus, the sequencing results were 100% accurate. The results demonstrate that the bead-bound DNA barcodes can be sequenced, that is, when the DNA barcode is still bound to the bead. In other words, the bead-bound DNA barcodes are sequencable.

Example 7. Cell Barcoding

Introduction to the concept of barcoding. This introduces the concept of barcoding. A common barcoding technique is barcoding the transcriptome of a given single cell. FIG. 36 and FIG. 37 illustrate steps for procedures where the transcriptome is captured and amplified, in preparation for future sequencing. FIG. 36 shows lysis of cells to release mRNAs, followed by reverse transcription. FIG. 37 shows capture of mRNAs by way of immobilized poly(dT), followed by reverse transcription, and finally sequencing. Sequencing can be with Next Generation Sequencing (NGS).

Some or most of the messenger RNA (mRNA) molecules from a given cell can be tagged with a common barcode, where this tagging allows the researchers to determine, for any given mRNA sequence, the origin of that coding sequence in terms of a given cell. For example, where nucleic acids representing each of the separate transcriptomes from one hundred different single cells are mixed together, and where the nucleic acids from each of the 100 different single cell has its own barcode, then the following advantage will result. The advantage is that nucleic acids from all of the transcriptomes can be mixed together in one test tube, and then subjected to Next Generation Sequencing, where the barcode enables the user to identify which information is from the same cell.

The above advantage is described in a different way, as follows. In using mRNA barcoding, a given single cell is processed so that information from some or most of the mRNA molecules from that cell are converted to corresponding molecules of cDNA, where each of these cDNA molecules possesses exactly the same DNA barcode. This barcoding procedure can be repeated with ten, twenty, 100, several hundred, or over 1,000 different cells, where the cDNA molecules from each of these cells is distinguished by having a unique, cell-specific barcode. This method enables the researcher to conduct DNA sequencing, all in one sequencing run, from a pool of all of the barcoded cDNA molecules from all of the cells (all barcoded cDNA molecules mixed together, prior to sequencing) (see, Avital, Hashimshony, Yanai (2014) Genome Biology. 15:110).

Barcodes that tag nucleic acids compared with barcodes that tag the plasma membrane. Guidance is available for preparing libraries of chemicals, where each chemical, or where all members of each class of chemicals, is associated with a unique DNA barcode (see, Brenner and Lerner (1992) Proc. Nat'l. Acad. Sci. 89:5381-5383; Bose, Wan, Carr (2015) Genome Biology. 16:120. DOI 10.1186). With the above barcoding example in mind, the following provides another type of barcoding which can also be applied to a particular, single cell. The present disclosure provides cell-associated barcoding that takes the form of a tag that is stably attached to the cell's plasma membrane.

Option of at least two kinds of barcodes that get attached to the plasma membrane-bound. A barcode used for tagging the plasma membrane of given cell can include a first barcode that identifies the type of cell, and a second barcode that identifies a perturbant that was exposed to the cell. For example, the first barcode can identify the cell as originating from a healthy human subject, Human Subject No. 38 from Clinical Study No. 7, a human primary colorectal cancer cell line, a five-times passaged human primary colorectal cancer cell line, a multiple myeloma human subject with multiple myeloma, a treatment-naive Human Subject No. 23 with multiple myeloma, or from a treatment-experienced Human Subject No. 32 with multiple myeloma.

Also, the barcode can identify a "perturbant" that was given to that particular single cell (given either before or after barcoding). The "perturbant" can be an anti-cancer drug, a combination of anti-cancer drugs, a combinatorially generated compound, or a combination of an antibody drug and a small molecule drug. The barcoding can be used to keep track of a given single cell, and can be used to correlate that cell with subsequent behaviors such as activation or inhibition with one or more cell-signaling pathways, increased or decreased migration, apoptosis, necrosis, change in expression of one or more CD proteins (CD; cluster of differentiation), change in expression of one or more oncogenes, change in expression of one or more microRNAs (miRNAs). Expression can be in terms of, transcription rate, level of a given polypeptide in the cell, change in location of a given protein from cytosolic to membrane-bound, and so on.

Tagging cell-surface oligosaccharides of membrane-bound glycoproteins. Methods and reagents are available for connecting tags, such as DNA barcodes, to the plasma membrane of a living cell. Tagging can be accomplished with a reagent consisting of a covalent complex of a DNA barcode with a reactive moiety that attacks and covalently binds to oligosaccharide chains of membrane-bound glycoproteins. The literature establishes that hydrazide biocytin can be used to connect biotin to carbohydrates on membrane-bound glycoproteins. The present disclosure uses this reagent, except with the biotin replaced with a DNA barcode. The carbohydrate needs to be oxidized to form aldehydes. The hydrazide reacts with the aldehyde to form a hydrazine link. The sialic acid component on the oligosaccharides is easily oxidized with 1 mM Na meta-periodate (NaIO4). In conducting the oxidation step, and hydrazide-linking step, buffers with a primary amine group should be avoided. See, for example, "Instructions. EZ-LinkHydrazide Biocytin. Number 28020. ThermoScientific (2016) (4 pages), Bayer (1988) Analyt. Biochem. 170:271-281; Reisfeld (1987) Biochem. Biophys. Res. Commun. 142:519-526, Wollscheid, Bibel, Watts (2009) Nature Biotechnol. 27:378-386.

Another method for tagging the oligosaccharide moiety of glycoproteins on living cells, is to use periodate oxidation and aniline-catalyzed oxime ligation. This method uses mild periodate oxidation of sialic acids and then ligation with an aminoxy tag in the presence of aniline. In a variation of this method, galactose oxidase can be used to introduce aldehydes into terminal galactose residues and terminal N-acetylgalactosamine (GalNAc) residues of oligosaccharides. Galactose oxidase catalyzes the oxidation, at carbon-6, to generate an aldehyde. Following aldehyde generation, one can couple with aminoxybiotin using aniline-catalyzed ligation (see, Ramya, Cravatt, Paulson (2013) Glycobiology. 23:211-221). The present disclosure replaces the biotin with a DNA barcode and provides aniline-catalyzed ligation of an aminoxy-DNA barcode.

Tagging mediated by an antibody bound to the cell surface. The present disclosure provides methods and reagents for attaching barcodes to the plasma membrane of a cell, where attachment is mediated by an antibody that specifically binds to a membrane-bound protein. The antibody can be covalently modified with trans-cyclooctene (TCO) where this modification can be conducted with an overnight incubation at 4 degrees C. (see, Supporting Information (5 pages) for Devaraj, Haun, Weissleder (2009) Angew. Chem. Intl. 48:7013-7016). This covalent modification of antibody can be carried out with the reagent, trans-cyclooctene succinimidyl carbonate (Devaraj, Haun, Weissleder (2009) Angew. Chem. Intl. 48:7013-7016). The antibody-tetrazine complex can then be contacted with a cell, resulting in membrane-bound antibodies. The membrane-bound antibodies each bear a tetrazine moiety, which enables tagging of the antibody via click chemistry, such as, by exposing the antibodies to a DNA barcode-tetrazine complex.

Tetrazine can be introduced at free amino groups of the antibody, using the reagent, N-hydroxysuccinimide ester (NHS) (see, van Buggenum, Gerlach, Mulder (2016) Scientific Reports. 6:22675). Once the antibody contains one or more tetrazine groups, the antibody can be further modified by attaching a DNA barcode, by way of a reagent that is TCO-DNA barcode. With this modified antibody in hand, the antibody can then be used for a tagging living cell, where the antibody binds to a membrane-bound protein of the cell.

A complex of tetrazine-DNA barcode can be prepared. This complex can then be introduced into a cell medium, where the medium includes cells, and where the cells bear the attached antibody-TCO complex. Where the tetrazine-DNA barcode contacts the membrane-bound antibody-TCO complex, the result is a click chemistry reaction where the cells become tagged with the DNA barcode. This click chemistry reaction can be carried out for 30 minutes at 37 degrees C.

Preferred antibodies for use in the above procedure are those that bind tightly and specifically to membrane-bound proteins of the plasma membrane, where the membrane-bound protein occurs in high abundance, for example, at over 50,000 copies per cell membrane, and where the membrane-bound protein is stable on the cell surface and does not much recycle into the cell's interior, and where the membrane-bound membrane does not much shed into the culture medium.

Tagging membrane-bound proteins with azide followed by click chemistry with an octyne conjugate. Azide can be introduced on membrane-bound proteins of a living cell by way of the enzyme, lipoic acid ligase, followed by attachment of a fluorinated octyne compound that is conjugated to a DNA barcode. The conjugation of a fluorinated octyne compound to a fluorophore is described (see, Jewett and Bertozzi (2010) Chem. Soc. Rev. 39:1272-1279; Fernandez-Suarez, Bertozzi, Ting (2007) Nature Biotechnol. 25:1483-1487). To reiterate, "Ting and co-workers introduced azides into mammalian cell-surface proteins using . . . lipoic acid ligase . . . [t]he protein could then be labeled with a fluorinated cyclooctyne-conjugated fluorescent dye-conjugated fluorescent dye" (Jewett et al, supra).

Example 7. Caps Over Picowells

Capping picowells. Each picowell was capped with a sphere, one sphere to each picowell, where the sphere fits into the aperture (top opening) of the picowell. To apply the spheres to the picowell plate, the spheres are put into growth media and suspended, then applied to the top surface of the picowell plate, and the sphere allowed to settle. Then, the entire plate is placed in a centrifuge and spun at a low-gravity, in order to get a firm sitting of the spheres in the aperture of each picowell.

Active caps and passive caps. FIG. 18A shows an active cap inserted into the top of a picowell, and FIG. 18B shows a passive cap inserted into the top of a picowell. Preferably, the caps are made of material that is softer than the material used to make the picowell plate, where the result is slight deformation of the cap when it is pressed into the aperture of the picowell, and where the result is a snug fit that prevents leakage. In embodiments, the present disclosure provides one or more of active caps, passive caps, or both active caps and passive caps. Each cap may be free-standing and not connected to any other cap. In an alternative embodiment, to more caps may be connected together, for example, by way of a sheet of polymer that is capable of being layed upon the top surface of the plate, and where a plurality of caps protrude from the bottom of the sheet of polymer, and where the protruding caps are predeterminedly spaced in order to fit into each picowell. An active cap may be used instead of a bead that is capable of sitting on the floor of a microwell. The active cap contains many attached copies of substantially identical compounds, where each compound is attached to the active cap (shown here in the sample of a spherical bead), and where cleavage results in release of the compounds into the solution that resides in the microwell (FIG. 18A).

Regarding the passive cap, the passive cap is porous and it acts like a sponge. It absorbs products from biochemical reactions, and thus facilitates collection of products where the goal of the user is to determine the influence of a given compound on living, biological cells that are cultures in the picowell. In other words, the compound stimulates the cells to respond, where the response takes the form of increased (or decreased) expression of one or more metabolites, and where some of the metabolites diffuse towards the passive cap and are absorbed by the passive cap. The user can then collect the passive caps and analyze the metabolites that had absorbed to the passive cap (FIG. 18B).

Polymer mat that adheres to an array of caps. FIGS. 19A-19D illustrate a polymer mat that is capable of adhering to each cap in an array of porous caps. Once adhered, the polymer mat can be peeled away and removed, bringing with it each porous cap in the array. As a result, the polymer mat with the porous caps can be used for assays that measure metabolites or other chemicals that are associated with the porous cap.

To provide a step-wise example, each well in an array of many thousands of picowells can contain one bead, where each bead contains one type of compound, where the compound is attached via a cleavable linker. The picowell also contains a solution as well as cultured cells. The picowell is sealed with a porous cap, and where the porous cap contacts the solution and is able to capture (sample; absorb; absorb) metabolites that are released from the cultured cells. The metabolites can be metabolites of the compound, or the metabolites can take the form of cytokines, interleukins, products of intermediary metabolism, microRNA molecules, exosomes, and so on. Finally, a solution of polyacrylamide is poured over the picowell plate, and the polyacrylamide allowed to soak into the thousands of porous caps, and then solidify in the form of a mat that is firmly adhered to each and every one of the caps. The solified mat is then removed, where each cap is separately analyzed for absorbed metabolites.

In preferred embodiments, a polyacrylamide gel is used to crosslink the capping beads into the enmeshing layer or the mat. The protocol to create an 20% solution of polyacrylamide solution that can be poured over the picowell array to cure and enmesh the capping bead is as follows. Add 4 ml of a 40% bis-acrylamide solution and 2 ml of 1.5 M Tris pH 8.8 to 1.8 ml distilled deionized water. Just before pouring this mixture over the capped picowell array, 80 microliters of the free radical initializer ammonium persulfate (APS, 10% stock solution), and 8 microliter of the free radical stabilizer N,N,N',N'-tetramethylethylene-diamine (TEMED) are added to begin crosslinking of the gel. The gel layer is poured before complete crosslinking and allowed to fully crosslink over the capped picowell array. One fully cross-linked (stiff enough to be handled, or roughly 60 minutes of setting), the polyacrylamide layer may be peeled off using tweezers. It is found that the capping beads are lifted off the tops of the picowells and get attached to the polyacrylamide layer. This behavior can be observed for multiple bead types including polyacrylamide beads, Tentagel beads, polystyrene beads and silica beads.

Measuring efficacy of cap in preventing leaks. In embodiments, the efficacy of a cap can be determined by using the bead with the photocleavable linker. Images of a picowell, or of several picowells in one particular picowell array can be captured just before exposing picowells to UV light, and in the time frame after exposing picowells to UV light. For example, images can be captured at t=minus ten seconds and at t=10 seconds, 20 sec, 40 sec, 60 sec, 2 minutes, 4 min, 8 min, 15 min, 60 min, 90 min, 2 hours, 3 hours, and 4 hours. Excellent efficacy can be shown where the fluorescence of a given well at 2 hours is equal to at least 90%, at least 95%, at least 98%, or about 100% the fluorescence found at t=10 seconds, with subtraction of the background image taken at t=minus ten seconds. Images can also be taken of a region of the picowell plate outside of the picowell, for example, in the immediate vicinity of the cap. Excellent efficacy can be shown where the fluorescence of an area on the surface of the plate (outside of the picowell) and in the immediate vicinity of the cap is less than 1%, less than 0.5%, less than 0.1%, less than 0.05%, less than 0.01%, less than 0.005%, or less than 0.001%. This comparison may be made without regard to the volume of the fluid in the well, and without regard to the volume of any fluid situated on top of the plate and outside of the cap, and here, the comparison may simply take into account the entire visual field that is captured by the light detector. Alternatively, the comparison may be made with correction of the depth of the fluid (depth of picowell; depth of fluid on top of the picowell plate). Also alternatively, the comparison may take into account diffusion of any leaking fluorophore over the entire surface of the picowell plate.

How barcoding fits into the reagents and methods of the present disclosure. The following provides further embodiments of the reagents and methods of the present disclosure.

Reagents and capabilitites. A microscopic bead is provided. The microscopic bead can be covalently modified by a plurality of first linkers, each capable of coupling by way of solid-phase synthesis with monomers, where completion of the solid-phase synthesis creates a member of a chemical library. This member of the chemical library is bead-bound. The same microscopic bead can be covalently modified by a plurality of second linkers, each capable of being coupled with a plurality of DNA barcodes. This member of the DNA barcode is bead-bound.

Example 9. DNA Barcode of the Present Disclosure

This concerns a set of information that can be printed on paper, or stored in computer language, that provides a "DNA barcode" that correlates a DNA sequence with a chemical library member. This DNA barcode may be called a "legend" or a "key." The DNA barcode also provides nucleic acids that can identify a specific class of chemical compounds, such as analogs of a specific FDA-approved anti-cancer drugs, or that can identify the user's name, or that can identify a specific disease that is to be tested with the bead-bound chemical library.

Example 10. Lenalidomide Analogs

FIGS. 13, 14, and 15 disclose the conversion of lenalidomide to three different derivatives, each derivative bearing a carboxylic acid group. Each of these carboxylic acid groups can subsequently be used to condensed with the bead-linker complex. In this situation, where the carboxylic acid group is condensed to the bead-linker complex, it is attached at the position that was previously occupied by Fmoc.

Starting with a primary amine and converting it to a carboxylic acid (FIG. 13). Applicants take the approach of generating a library of compounds by converting a compound with a primary amine to a compound with a carboxyl group. FIG. 13 discloses starting with lenalidomide. Lenalidomide has a primary amine. To this is added, succinic anhydride in 4-dimethylaminopyridine (DMA) and acetonitrile (ACN). The succinic anhydride condenses with the primary amino group, resulting in lenalidomide bearing a carboxylic acid group. The term "cat." in the figure means, catalytic.

Subsequently, this carboxylic acid group can be linked to a bead. Thus, the resulting complex is: BEAD-succinic acid moiety-lenalidomide FIG. 14 discloses starting with linalidomide and adding t-butyl-bromoacetate, to give an intermediate. The intermediate is then treated with FmocOSu (o-succinimide), to produce a final product that is a carboxylic acid derivative of lenalidomide. The carboxylic acid moiety can then be condensed with a free amino group, for example, with the free amino group that once had an attached Fmoc group. Alternatively, the carboxylic acid can be condensed with the free amino group of a chemical monomer residing on the bead, where the result of the condensation is two chemical monomers attached to each other.

FIG. 15 discloses lenalidomide as the starting material. The lenalidomide is reacted with 3-carboxybenzaldehyde, where the aldehyde group condenses with the amino group, resulting in yet another type of carboxylic acid derivative of lenalidoimide.

FIG. 16A, FIG. 16B, and FIG. 16C discloses yet another approach of Applicants for generating a library of novel and unique bead-bound compounds, where compounds can be released from the bead, and then tested for activity in cell-based assays or in cell-free assays. Each of the three compounds is a lenalidomide analogue, where the primary amine is in a unique position of the benzene ring.

Example 11. Picowells Containing Cells Together with Beads that have a Coupled Response-Capture Element The present disclosure provides reagents, systems, and methods for assessing response of a cell to a compound, and where response that is measured takes the form of changes in the transcriptome. "Changes in the transcriptome" can refer, without implying any limitation, to change in amount each and every type of unique mRNA in the cell, and well as to change in amount of a pre-determined set of mRNA molecules in the cell. "Changes in transcriptome" includes change from below the lower limit of detection to becoming detectable, as well as change from being detectable to dropping below the lower limit of detection, where these changes are associated with release of the bead-bound compound.

Cells can be lysed by adding detergent or surfactant to the picowell array. For example, a volume of buffer containing detergent can be pipetted into a microwell that contains, within it, many thousands of picowells. The detergent can be allowed to diffuse into all of the picowells, causing lysis of the cells within, release of mRNA, and finally binding by the bead-bound "capture response element."

Cell lysis. Cells can be lysed by one or more cycles of freezing and thawing (Bose, Wan, Carr (2015) Genome Biology. 16:120. DOI 10.1186). Cells can also be lysed with perfluoro-1-octanol with shaking (Macosko, Basu, Satija (2015) Cell. 161:1202-1214; Ziegenhain (2017) Molecular Cell. 65:631-643; Eastburn, Sciambi, Abate (2014) Nucleic Acids Res. 42:e128). Also, cells can be lysed by a combination of a surfactant (Tween-20®) and a protease (Eastburn, Sciambi, Abate (2013) Anal. Chem. 85:8016-8021). Lysis of cells results in release of mRNA. The mRNA is captured by the bead that resides in the same picowell as the lysed cell (or cells). The bead contains a huge number of bead-bound polynucleotides, where each polynucleotide contains two nucleic acid, where the first nucleic acid contains a common DNA barcode and the second nucleic acid contains a "response capture element." Where the goal is indiscriminate capture of all mRNAs in the cell, the "response capture element" can take the form of poly(dT). This poly(dT) binds to the poly(A) tail of the mRNA molecules.

More cell lysis conditions. Cell lysis can be effected by exposure to detergent with a sodium salt, for example, 0.05% Triton X-100 with 15 mM NaCl, 25 mM NaCl, 50 mM NaCl, 75 mM NaCl, 100 mM NaCl, 0.1% Triton X-100 with 15 mM NaCl, 25 mM NaCl, 50 mM NaCl, 75 mM NaCl, 100 mM NaCl, 0.2% Triton X-100 with 15 mM NaCl, 25 mM NaCl, 50 mM NaCl, 75 mM NaCl, 100 mM NaCl, or 0.5% Triton X-100 with 15 mM NaCl, 25 mM NaCl, 50 mM NaCl, 75 mM NaCl, 100 mM NaCl, or with detergent with a potassium salt, such as, 0.05% Triton X-100 with 15 mM KCl, 25 mM KCl, 50 mM KCl, 75 mM KCl, 100 mM KCl, 0.1% Triton X-100 with 15 mM KCl, 25 mM KCl, 50 mM KCl, 75 mM KCl, 100 mM KCl, 0.2% Triton X-100 with 15 mM KCl, 25 mM KCl, 50 mM KCl, 75 mM KCl, 100 mM KCl, or 0.5% Triton X-100 with 15 mM KCl, 25 mM KCl, 50 mM KCl, 75 mM KCl, 100 mM KCl. Exposure can be for 10 min, 20 min, 40 min, or 60 min at about 4 degrees C., or at room temperature (23 degrees C.), and so on.

Present disclosure can assess influence of a compound on an expression profiles. A bead-bound capture element can take the form of one or more deoxyribonucleotides that can specifically hybridize to one or more mRNA molecules of interest, where the one or more mRNA molecules are associated with a specific disease. Expression profiles for various diseases are available, for example, for colon cancer (Llarena (2009) J. Clin. Oncol. 25:155 (e22182), ovarian cancer (Spentzos (2005) J. Clin. Oncol. 23:7911-7918), and lung adenocarcinoma (Takeuchi (2006) J. Clin. Oncol. 11:1679-1688). To give a similar example, what can also be characterized is the influence of a released compound on mRNAs associated with non-hepatic tumor cells that have metastasized to the liver (see, Barshack, Rosenwald, Bronfeld (2008) J. Clin. Oncol. 26:15 Suppl. 11026, Barshack (2010) Int. J. Biochem. Cell Biol. 42:1355-1362).

Capturing the transcriptome. Methods are available for capturing mRNA by hybridizing their polyA group to immobilized poly(dT) (see, Dubiley (1997) Nucleic Acids Res. 25:2259-2265; Hamaguchi, Aso, Shimada (1998) Clinical Chem. 44:2256-2263; D. S. Hage (2005) Handbook of Affinity Chromatography, $2^{nd}$ ed, CRC Press, page 549).

After capture of mRNA molecules released from the lysed cell (or cells), the bead-bound polynucleotide serves as a primer that supports reverse transcription from the mRNA, resulting in a bead-bound complementary DNA (cDNA), and where this bead-bound cDNA can be sequenced. Alternatively, the bead-bound cDNA can be released from the bead, where the bead-bound "response capture element" is coupled to the bead with a cleavable linker, such as with a photocleavable linker. If a photocleavable linker is used, cleaving conditions for releasing bead-bound compounds (compounds made from a chemical monomer library) but not also cleave the bead-bound "response capture element."

Where cells are exposed to a bead-bound compound or to a compound released from a bead, cells can be screened for a genetic response, for example, by characterizing any changes in the transcriptome with or without exposure to the compound. Also, cells can be screened for a phenotypic response, for example, apoptosis, change in activity of one or more cell-signaling proteins, or change in cell-surface expression of one or more CD proteins. CD is Cluster of Differentiation (See, Lal (2009) Mol. Cell Proteomics. 8:799-804; Belov (2001) Cancer Res. 61:4483-4489; LUIS/WHO Subcommittee on CD Nomenclature (1994) Bull.World Health Org. 72:807-808; TUTS-WHO Nobenclature Subcommittee (1984) Bull.World Health Org. 62:809-811). For some phenotypic response assays, the cells must not be lysed.

The present disclosure addresses the unmet need to partition different drugs to different cells, for example, by exposing a single cell to one type of drug where exposure occurs in a picowell.

The present disclosure also eliminates the need to prepare barcoded mRNA, where mRNA is released from a cell followed by preparing cDNA (in this type of barcode, all mRNA from a given cell receives the same barcode, when the transcriptosome is coverted to corresponding library of cDNA).

Parameters during cell incubation with the perturbant. For any given compound or some other type of perturbant, parameters that can be varied or controlled light, temperature, pH of cell medium, sound, concentration and exposure time to a reagent (reagent can be the compound released from the bead, an enzyme substrate, a cytokine, a compound that is already an established drug, a salt), mechanic agitation, an antibody against a cell-surface protein, and so on.

Barcoding the cell. Cells can be incubated with a bead-bound compound or with the compound following cleavage from a bead-bound cleavable linker. During or after incubation, cells can be barcoded with a membrane-bound barcode that identifies the purturbant. This membrane-bound barcode can be coupled to oligosaccharides of the cell membrane, polypeptides of the cell membrane, or phospholipids of the cell membrane.

Response capture elements other than poly(dT). Messenger RNA can be captured by way of the 5-prime 7-methylguanosine cap. This method is especially useful where there polyA tail is short (see, Blower, Jambhekar (2013) PLOS One. 8:e77700). Also, mRNA can be captured using immobilized DNA that is specific for a coding region of the mRNA. This method is called, "RNA exome capture," and variations of this name. According to Cieslik et al, "Unique to capture transcriptomics is an overnight capture reaction (RNA-DNA hybridization) using exon-targeting RNA probes" (Cieslik (2015) Genome Res. 25:1372-1381).

MicroRNA (miRNA). The present disclosure can assess the influence of a released bead-bound compound on expression profile of miRNAs in a given cell or, alternatively, on expression profiles of the population of mRNAs that are specifically bound by a given species of miRNA (Jain, Ghosh, Barh (2015) Scientific Reports. 5:12832). For example, the present disclosure provides a bead that contains: (1) Bead-bound compound; (2) Bead-bound DNA barcode; and (3) Bead-bound response capture element, where the response capture element either captures miRNA or where the response capture element includes a species of miRNA (as part of the response capture element). Expression profiles for microRNA have been found for various types of cancer, for example, breast cancer breast cancer (Tanja (2009) J. Clin. Oncol. 27:15 Suppl. 538).

Methods are available for capturing selected populations of mRNA from the entire transcriptome. Selectivity can be conferred by using one type of microRNA, such as miR-34a, as a bridging compound in a "pull-down" assay. In brief, "The transcripts pulled down with miR-34a were . . . enriched for their roles in growth factor signaling and cell cycle progression" (Lal, Thomas, Lieberman (2011) PLOS Genetics. 7:e1002363). The mRNA molecules that are captured are those that bind to the miR-34A.

Further methods for capturing mRNA and analyzing expression level is available (Bacher (2016) Genome Biology. 17:63; Svensson (2017) Nature Methods. 14:381; Miao and Zhang (2016) Quantitative Biol. 4:243; Gardini (2017) Nature Methods. 12:443). Cellular response taking the form of changes in enhancer RNA can be measured (see, Rahman (2017) Nucleic Acid Res. 45:3017).

The present invention is not to be limited by compositions, reagents, methods, systems, diagnostics, laboratory data, and the like, of the present disclosure. Also, the present invention is to not be limited by any preferred embodiments that are disclosed herein.

What is claimed is:

1. A bead complex comprising:
a bead;
a plurality of same compounds directly bound to the bead at a first position via a cleavable linker; and
directly bound to the bead at a second position different from the first position, in a sequential order:
a linker;
a primer directly bound to the linker;
an encoding region comprising a single-stranded DNA barcode, wherein the single-stranded DNA barcode is directly bound to the primer; and
a nucleic acid capturing group comprising a poly-T sequence, the nucleic acid capturing group being single-stranded and directly bound to the single-stranded DNA barcode, wherein:
the encoding region encodes a structure of each same compound of the plurality of same compounds or synthetic steps used to make the each corresponding same compound.

2. The bead complex of claim 1, wherein the cleavable linker comprises a photo-cleavable linker, an acid cleavable linker, a base cleavable linker, or a temperature cleavable linker.

3. The bead complex of claim 1, wherein the plurality of the same compounds each comprise multiple compound building blocks.

4. The bead complex of claim 3, wherein the encoding region encodes the synthetic steps used to make the each same compound.

5. The bead complex of claim 1, wherein the nucleic acid capturing group is configured to capture messenger RNA (mRNA).

6. The bead complex of claim 1, wherein the nucleic acid capturing group is configured to capture microRNA (miRNA).

7. A plurality of bead complexes comprising a first bead complex and a second bead complex, the first bead complex comprising:
a first bead;
a first plurality of same compounds directly bound to the first bead at a first position via a first cleavable linker; and
directly bound to the first bead at a second position different from the first position, in a sequential order:
a linker;
a first primer directly bound to the first linker;

a first encoding region comprising a first single-stranded DNA barcode, wherein the first single-stranded DNA barcode is directly bound to the first primer; and
a first nucleic acid capturing group comprising a first poly-T sequence, the first nucleic acid capturing group being single-stranded and directly bound to the first single-stranded DNA barcode, wherein:
the first encoding region encodes a structure of each first same compound of the first plurality of same compounds or synthetic steps used to make the each first same compound; and the second bead complex comprising:
a second bead;
a second plurality of second same compounds directly bound to the second bead at a third position via a second cleavable linker; and
directly bound to the second bead at a fourth position different from the third position, in a sequential order:
a second linker;
a second primer directly bound to the second linker;
a second encoding region comprising a second single-stranded DNA barcode, wherein the second single-stranded DNA barcode is directly bound to the first primer; and
a second nucleic acid capturing group comprising a second poly-T sequence, the second nucleic acid capturing group being single-stranded and directly bound to the second single-stranded DNA barcode, wherein:
the second encoding region encodes a structure of each second same compound of the second plurality of same compounds or synthetic steps used to make the each second same compound, the second plurality of second same compounds are different from the first plurality of first same compounds, and the second single-stranded DNA barcode is different from the first single-stranded DNA barcode.

8. The plurality of bead complexes of claim 7, wherein the first cleavable linker comprises a photo-cleavable linker, an acid cleavable linker, a base cleavable linker, or a temperature cleavable linker.

9. The plurality of bead complexes of claim 7, wherein the first plurality of the first same compounds comprise multiple compound building blocks.

10. The plurality of bead complexes of claim 7, wherein the first nucleic acid capturing group is configured to capture messenger RNA (mRNA).

11. The plurality of bead complexes of claim 7, wherein the first nucleic acid capturing group is configured to capture microRNA (miRNA).

12. The bead complex of claim 1, wherein the each same first compound comprises a benzimidazole compound, imidazolidinone compound, quinazolinone compound, isoindolinone compound, thiazole compound, or an imidazopyridine compound.

13. The bead complex of claim 1, wherein the each same first compound comprises a lenalidomide or a stereoisomer or an enantiomer thereof.

14. The bead complex of claim 1, wherein the plurality of same compounds are screened for activity of inhibiting or activating a protein or a cellular function.

15. The bead complex of claim 1, wherein the plurality of same compounds comprise non-nucleic acid molecules.

16. The bead complex of claim 1, wherein the plurality of same compounds comprise amino acids.

\* \* \* \* \*